United States Patent
Anderson et al.

(10) Patent No.: US 7,320,989 B2
(45) Date of Patent: *Jan. 22, 2008

(54) PYRIDINE, PYRIMIDINE, QUINOLINE, QUINAZOLINE, AND NAPHTHALENE UROTENSIN-II RECEPTOR ANTAGONISTS

(75) Inventors: Eric Anderson, Houston, TX (US); Brian Dupre, Houston, TX (US); Daxin Gao, Houston, TX (US); Raymond J. Kessler, Houston, TX (US); Wen Li, Santa Clara, CA (US); Chengde Wu, Pearland, TX (US)

(73) Assignee: Encysive Pharmaceuticals, Inc., Houston, TX (US)

( * ) Notice: Subject to any disclaimer, the term of this patent is extended or adjusted under 35 U.S.C. 154(b) by 47 days.

This patent is subject to a terminal disclaimer.

(21) Appl. No.: 10/924,181

(22) Filed: Aug. 23, 2004

(65) Prior Publication Data

US 2005/0054850 A1    Mar. 10, 2005

Related U.S. Application Data

(63) Continuation-in-part of application No. 10/783,916, filed on Feb. 20, 2004.

(60) Provisional application No. 60/451,089, filed on Feb. 28, 2003.

(51) Int. Cl.
*A61K 31/44* (2006.01)
*C07D 215/38* (2006.01)
*C07D 211/72* (2006.01)

(52) U.S. Cl. ............ 514/313; 546/159; 546/304; 514/353

(58) Field of Classification Search ........... 546/159, 546/304; 544/242; 514/256, 313, 352
See application file for complete search history.

(56) References Cited

U.S. PATENT DOCUMENTS 3,919,238 A  * 11/1975  Spencer et al. .............. 544/361
3,978,055 A     8/1976  Fauran et al. ................ 544/122

FOREIGN PATENT DOCUMENTS

| FR | 1503443 | * | 12/1966 |
|----|---------|---|---------|
| GB | 664262 | * | 1/1952 |
| WO | WO 02/062787 | | 8/2002 |
| WO | WO 02/089740 A2 | | 11/2002 |
| WO | WO 02/089785 A1 | | 11/2002 |
| WO | WO 02/089792 A1 | | 11/2002 |
| WO | WO 02/089793 A1 | | 11/2002 |
| WO | WO 02/090337 A1 | | 11/2002 |
| WO | WO 02/090348 A1 | | 11/2002 |
| WO | WO 02/090353 A1 | | 11/2002 |
| WO | WO 03/099773 A1 | | 12/2003 |
| WO | WO 2004/026836 A2 | | 4/2004 |

OTHER PUBLICATIONS

Cain et al, Journal of Medicinal Chemistry, vol. 21, No. 7, pp. 658-668, 1978.*
Elslager et al. "Synthesis and Antimalarial Effects of $N^2$-Aryl-$N^4$-[(dialkylamino)alkyl]-and $N^4$-Aryl-$N^2$[(dialkylamino)alkyl]-2,4-quinazolinediamines[1,2]" J.Med. Chem. 1981, 24, 127-140.

* cited by examiner

*Primary Examiner*—Zinna N. Davis
(74) *Attorney, Agent, or Firm*—Jones Day

(57) ABSTRACT

The present invention relates to urotensin II receptor antagonists, pharmaceutical compositions containing them and their use.

4 Claims, No Drawings

PYRIDINE, PYRIMIDINE, QUINOLINE, QUINAZOLINE, AND NAPHTHALENE UROTENSIN-II RECEPTOR ANTAGONISTS

CROSS-REFERENCE TO RELATED APPLICATIONS

The present application is a continuation-in-part of U.S. application Ser. No. 10/783,916, filed Feb. 20, 2004 which application claims the benefit of provisional application No. 60/451,089, filed Feb. 28, 2003.

FIELD OF THE INVENTION

The present invention relates to urotensin II receptor antagonists, pharmaceutical compositions containing them and their use.

BACKGROUND OF THE INVENTION

The integrated control of cardiovascular homeostasis is achieved through a combination of both direct neuronal control and systemic neurohormonal activation.

Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis are angiotensin-II, endothelin-1, and norepinephrine, all of which function via an interaction with specific G-protein coupled receptors (GPCR). Urotensin-II, represents an important member of this neurohumoral axis.

In the fish, this peptide has significant hemodynamic and endocrine actions in diverse end-organ systems and tissues:

both vascular and non-vascular (smooth muscle contraction) including smooth muscle preparations from the gastrointestinal tract and genitourinary tract. Both pressor and depressor activity has been described upon systemic administration of exogenous peptide.

osmoregulation effects which include the modulation of transepithelial ion ($Na^+$, $Cl^-$) transport.

Although a diuretic effect has been described, such an effect is postulated to be secondary to direct renovascular effects (elevated GFR); urotensin-II influences prolactic secretion and exhibits a lipolytic effect in fish (activating triacylglycerol lipase resulting in the mobilization of non-esterified free fatty acids) (Person, et al. Proc. Natl. Acad. Sci. (U.S.A.) 1980, 77, 5021; Conlon, et al. J. Exp. Zool. 1996, 275, 226); human urotensin-II has been found to be an extremely potent and efficacious vasoconstrictor; exhibited sustained contractile activity that was extremely resistant to wash out; and had detrimental effects on cardiac performance (myocardial contractility). Human urotensin-II was assessed for contractile activity in the rat-isolated aorta and was shown to be a very potent contractile agonist. Based on the in vitro pharmacology and in vivo hemodynamic profile of human urotensin-II, it plays a pathological role in cardiovascular diseases characterized by excessive or abnormal vasoconstriction and myocardial dysfunction. (Ames et al. Nature 1990, 401, 282.)

Compounds that antagonize the urotensin-II receptor may be useful in the treatment of congestive heart failure, stroke, ischemic heart disease (angina, myocardial ischemia), cardiac arrhythmia, hypertension (essential and pulmonary), COPD, fibrosis (e.g. pulmonary fibrosis), restenosis, atherosclerosis, dyslipidemia, asthma, neurogenic inflammation and metabolic vasculopathies all of which are characterized by abnormal vasoconstriction and/or myocardial dysfunction. Urotensin antagonists may provide end organ protection in hypersensitive cohorts in addition to lowering blood pressure.

Since urotensin-II and GPR 14 are both expressed within the mammalian CNS (Ames et al. Nature 1999, 401, 282), they also may be useful in the treatment of addiction, schizophrenia, cognitive disorders/Alzheimers disease, impulsivity, anxiety, stress, depression, pain, migraine, neuromuscular function, Parkinsons, movement disorders, sleep-wake cycle, and incentive motivation.

Functional urotensin-II receptors are expressed in rhabdomyosarcomas cell lines and therefore may have oncological indications. Urotensin may also be implicated in various metabolic diseases such as diabetes and in various gastrointestinal disorders, bone, cartilage, and joint disorders (e.g., arthritis and osteoporosis); and genito-urinary disorders. Therefore, these compounds may be useful for the prevention (treatment) of gastric reflux, gastric motility and ulcers, arthritis, osteoporosis and urinary incontinence.

SUMMARY OF THE INVENTION

In one aspect this invention provides for compounds and pharmaceutical compositions containing them.

In a second aspect, this invention provides for the use of these compounds as antagonists of urotensin II, and as inhibitors of urotensin II.

In another aspect, this invention provides for the use of these compounds for treating conditions associated with urotensin II imbalance.

In yet another aspect, this invention provides for the use of these compounds for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhage stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis atherosclerosis, dyslipidemia, addiction, schizophrenia, cognitive disorders/Alzheimers disease, impulsivity, anxiety, stress, depression, parkinsons, movement disorders, sleep-wake cycle, incentive motivation, pain, neuromuscular function, diabetes, gastric reflux, gastric motility disorders, ulcers and genitourinary diseases.

The urotensin antagonist may be administered alone or in conjunction with one or more other therapeutic agents, said agents being selected from the group consisting of endothelin receptor antagonists, angiotensin converting enzyme (ACE) inhibitors, A-II receptor antagonists, vasopeptidase inhibitors, diuretics, digoxin, and dual non-selective β-adrenoceptor and $_1$-adrenoceptor antagonists.

Other aspects and advantages of the present invention are described further in the following detailed description of the preferred embodiments thereof.

DETAILED DESCRIPTION OF THE INVENTION

The present invention provides for compounds of formula (I):

Formula (I)

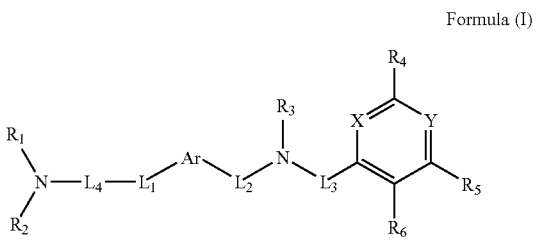

wherein Ar is selected from the group consisting of aryl, heteroaryl, benzoheteroaryl, pyridone, pyridazinone, and pyrimidone;

$R_1$ and $R_2$ are independently H, alkyl, cycloalkyl, bicyclic alkyl, adamantyl, aralkyl, aryl, $R_7CO$, or $R_8OCO$ or $R_1$ and $R_2$ along with N can form a cyclic or bicyclic heterocyclic ring system or $R_1$ and $L_1$ or $R_1$ and one carbon of $(CH_2)_n$ can form a 5, 6, or 7 membered ring;

$R_3$ is H, alkyl or aralkyl;

X and Y are independently C or N;

$R_4$, $R_5$, and Rr are independently selected from the group consisting of H, alkyl, aralkyl, aryl, heteroaryl, benzoheteroaryl, hydroxyl, halo, haloalkyl, alkoxy, aminocarbonyl and aminosulfonyl or $R_5$ and $R_6$ together can form a 5-6 membered aromatic ring or a 5-7 membered aliphatic ring;

$L_1$ is selected from the group consisting of a single bond, O, $NR_9$, CO, COO, OCO, $SO_2$, $NR_{10}CO$, $NR_{11}SO_2$, $NR_{12}CONR_{13}$, $NR_{14}SO_2NR_{15}$, $CH_2CHOHCH_2$, arene, heteroarene, pyridine, pyrimidone and pyridazinone;

$L_2$ and $L_3$ are independently selected from the group consisting of a single bond, $CH_2$, $NR_{16}$, CO and $SO_2$;

$L_4$ is $(Z)_n$, where each Z is independently $CH_2$, $CR_{17}R_{18}$, CO, $NR_{19}$, $CONR_{20}$ or $NR_{21}CO$, any two adjacent Zs may be replaced with a double or triple bond or $R_{17}$, $R_{18}$ or two $R_{17}$s can form a 5-8 membered aliphatic ring or $R_{17}$ and Ar can form a fused 5-8 membered aliphatic ring; n is an integer from 0 to 6;

$R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ are independently selected from the group consisting of H, alkyl, aryl and aralkyl, $R_{16}$ is also alkylsulfonyl or alkylsulfonyl or alkylcarbonyl or $R_{10}$ and CO and Ar can form pyridone, pyridazinone, and pyrimidone, and the pharmaceutically acceptable salts thereof.

Preferred structures of formula I are compounds of the formula:

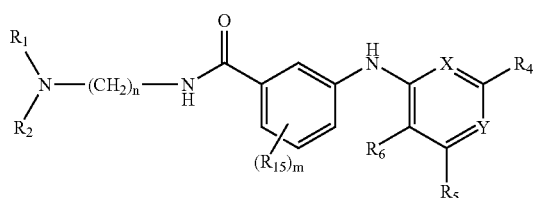

wherein each $R_{15}$ is independently H, alkyl, aralkyl, haloalkyl, aryl, heteroaryl, benzoheteroaryl, alkoxy, aminocarbonyl or aminosulfonyl; two of them can form a 5-6 membered aromatic rings or 5-7 membered aliphatic ring;

m is 0-3; and $R_1$, $R_2$, $R_4$, $R_5$, $R_6$, n, X and Y are as defined above, and the pharmaceutically acceptable salts thereof.

Preferred structures of formula I are also compounds of the formula:

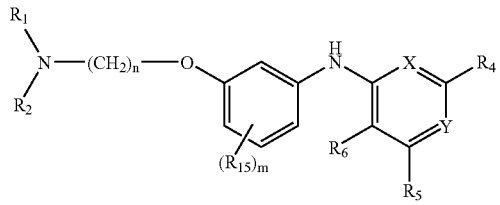

$R_1$, $R_2$, $R_4$, $R_5$, $R_6$, n and X are as defined in claim 1, and the pharmaceutically acceptable salts thereof.

The present invention is also directed to compounds of Formula (II):

Formula (II)

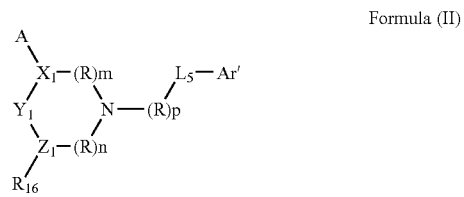

wherein A is a negatively ionizable group under physiological conditions;

$X_1$-$Y_1$-$Z_1$ is C, $C(R)_qC$ or $C(R)_qN$;

$L_5$ is $L_6Ar'L_7$ or $X_2Y_2Z_2$;

Ar' and Ar" are each independently aryl or heteroaryl;

$L_6$ and $L_7$ are each independently a bond, N, O, S, or $X_2Y_2Z_2$ where $X_2$ and $Z_2$ are each independently C, N or O and $Y_2$ is CO, SO, or $SO_2$;

R is $CR_{17}R_{18}$;

m, n, p and q are independently an integer from (0 to 6) provided that m and n cannot both be 0; and $R_{16}$, $R_{17}$ and $R_{18}$ are each independently H, alkyl, arakyl, aryl, heteroaryl, hydroxyl, alkoxy, aryloxy, amino, aminocarbonyl, aminosulfonyl provided that when A is $CO_2H$ and $X_1$—$Y_1$2 is C, then $X_2Y_2$2 is not NCON; and the pharmaceutically acceptable salts thereof.

Preferably, A is $CO_2H$, $CONHSO_2R_{19}$, $SO_2NHCOR_{20}$, tetrazole or other carboxylic isosteres where $R_{19}$ and $R_{20}$ have the same definition as $R_{16}$, $R_{17}$ and $R_{18}$.

Presently preferred cyclic and bicyclic ring systems include pyrrolidine, piperidine, azepane, azocane, piperazine, morpholine, diazepane, diazocane, imidazole, benzopyrrolidine, benzopiperidine, benzopiperazine, benzoimidazole, benzoazepine and tetrahedrobenzoazepine derivatives.

Presently preferred compounds of the present invention are:

{4-Chloro-3-[2-(3,4-dihydro-1H-isoquinolin-2-yl)ethoxy]phenyl}-(2-methylquinolin-4-yl)amine.

{3-[2-(4-Benzyl-piperidin-1-yl)ethoxy]phenyl}-(2-methylquinolin-4-yl)amine.

{4-Chloro-3-[2-(4-phenylpiperidin-1-yl)ethoxy]phenyl}-(2-methylquinolin-4-yl)amine.

{3-[2-(4-Benzylpiperazin-1-yl)ethoxy]phenyl}-(2-methylquinolin-4-yl)amine.

{3-[2-(Benzylmethylamino)ethoxy]phenyl}-(2-methylquinolin-4-yl)amine.

{3-[2-(4-Benzylpiperidin-1-yl)ethoxy]-5-trifluoromethylphenyl}-(2-methylquinolin-4-yl)amine.

{3-[3-(4-Benzylpiperidin-1-yl)propoxy]phenyl}-(2-methylquinolin-4-yl)amine.

{3-[2-(11-Methyl-1-phenylethylamino)ethoxy]phenyl}-(2-methylquinolin-4-yl)amine.

[3-(2-Benzylaminoethoxy)phenyl]-(2-methylquinolin-4-yl)amine.

1-(1-{2-[3-(2-Methylquinolin-4-ylamino)phenoxy]ethyl}-4-phenylpiperidin-4-yl)ethanone.

[3-(3-Benzylaminopropoxy)phenyl]-(2-methylquinolin-4-yl)amine.

{3-[2-(2-Benzylimidazol-1-yl)ethoxy]phenyl}-(2-methylquinolin-4-yl)amine.

(1-{2-[3-(2-Methylquinolin-4-ylamino)phenoxy]ethyl}piperidin-4-yl)diphenylmethanol.

4-Benzyl-1-{2-[3-(2-tert-butylquinolin-4-ylamino)phenoxy]ethyl}piperidin-4-ol.

4-Benzyl-1-{2-[3-(2-methylquinolin-4-ylamino)-5-trifluoromethylphenoxy]ethyl}piperidin-4-ol.

{3-[2-(4-Benzylpiperidin-1-yl)ethoxy]phenyl}-(2,6-dimethylpyrimidin-4-yl)amine.

{3-[2-(5-Benzyl-2,5-diazabicyclo[2.2.1]hept-2-yl)ethoxy]phenyl}-(2-methylquinolin-4-yl)amine.

{3-[2-(4-Benzylpiperazin-1-yl)ethoxy]-5-trifluoromethylphenyl}-(2-methylquinolin-4-yl)amine.

(2-Methylquinolin-4-yl)-{3-[2-(4-phenylpiperidin-1-yl)ethoxy]-5-trifluoromethyl phenyl}amine.

{3-[3-(1-Methyl-1-phenylethylamino)propoxy]phenyl}-(2-methylquinolin-4-yl)amine.

{3-[2-(5-Benzyl-2,5-diazabicyclo[2.2.1]hept-2-yl)ethoxy]-5-trifluoromethylphenyl}-(2-methylquinolin-4-yl)amine.

N-(2-{1-[2-(3-Fluorophenyl)ethyl]-6,7-dimethoxy-3,4-dihydro-1H-isoquinolin-2-yl}ethyl)-3-(2-methylquinolin-4-ylamino)benzamide.

N-[2-(6,7-Dimethoxy-3,4-dihydro-1H-isoquinolin-2-yl)ethyl]-3-(2-methylquinolin-4-ylamino)benzamide.

N-[2-(1,3-Dihydroisoindol-2-yl)ethyl]-3-(2-methylquinolin-4-ylamino)benzamide.

N-[2-(3,4-Dihydro-1H-isoquinolin-2-yl)ethyl]-2-methyl-5-(2-methylquinolin-4-ylamino)benzamide.

N-[2-(3,4-Dihydro-1H-isoquinolin-2-yl)ethyl]-2-hydroxy-5-(2-methylquinolin-4-ylamino)benzamide.

N-[2-(3,4-Dihydro-1H-isoquinolin-2-yl)ethyl]-3-(2-trifluoromethylquinolin-4-ylamino)benzamide.

N-[2-(3,4-Dihydro-1H-isoquinolin-2-yl)ethyl]-2,4,6-trimethyl-3-(2-methylquinolin-4-ylamino)benzamide.

2-[2-(3,4-Dihydro-1H-isoquinolin-2-yl)ethyl]-4-(2-methylquinolin-4-ylamino)-2,3-dihydroisoindol-1-one.

3-(2-Methylquinolin-4-ylamino)-N-[2-(1,3,4,5-tetrahydrobenzo[c]azepin-2-yl)ethyl]benzamide.

N-[2-(3,4-Dihydro-1H-isoquinolin-2-yl)ethyl]-2,5-bis(2-methylquinolin-4-ylamino)benzamide.

3  (2-Methylquinolin-4-ylamino)-N-[2-(octahydro-cis-isoquinolin-2-yl)ethyl]benzamide.

N-(2-Azepan-1-ylethyl)-3-(2-methylquinolin-4-ylamino)benzamide.

N-(2-Benzylaminoethyl)-3-(2-methylquinolin-4-ylamino)benzamide.

4-({2-[3-(2-Methylquinolin-4-ylamino)-benzoylamino]ethylamino}methyl)benzoic acid.

N-[2-(2,2-Dimethylpropylamino)ethyl]-3-(2-methylquinolin-4-ylamino)benzamide.

N-[2-(4-Benzylpiperazin-1-yl)ethyl]-3-(2-methylquinolin-4-ylamino)benzenesulfonamide.

{3-[5-(3,4-Dihydro-1H-isoquinolin-2-ylmethyl)isoxazol-3-yl]phenyl}-(2-methylquinolin-4-yl)amine.

{3-[3-(3,4-Dihydro-1H-isoquinolin-2-yl)propyl]-4-methylphenyl}-(2-methylquinolin-4-yl)amine.

$N^1$-[2-(3,4-Dihydro-1H-isoquinolin-2-yl)ethyl]-$N^7$-(2-methylquinolin-4-yl)-1,2,3,4-tetrahydronaphthalene-1,7-diamine.

[3'-(3,4-Dihydro-1H-isoquinolin-2-ylmethyl)biphenyl-4-yl]-(2-methylquinolin-4-yl)amine.

{3-[2-(4-Benzylpiperidin-1-yl)ethanesulfonyl]phenyl}-(2-methylquinolin-4-yl)amine.

N-[2-(4-Benzylpiperidin-1-yl)ethyl]-N'-(2-methylquinolin-4-yl)pyrimidine-4,6-diamine.

3-(4-Benzylpiperidin-1-yl)-1-[3-(2-methylquinolin-4-ylamino)phenyl]propan-1-one oxime.

{3-[3-(1-Methyl-1-phenylethylamino)propoxy]-5-trifluoromethylphenyl}-(2-methylquinolin-4-yl)amine.

{3-[2-(4-(4-Fluorophenyl)piperidin-1-yl)ethoxy]-5-trifluoromethylphenyl}(2-methylquinolin-4-yl)amine.

(3-{2-[2S,4S-5-(2,4,5-Trifluorobenzyl)-2,5-diazabicyclo[2.2.1]hept-2-yl]ethoxy}-5-trifluoromethylphenyl)(2-methyl quinolin-4-yl)amine.

[3-(3-Azepan-1-yl-propoxy)-5-trifluoromethyl-phenyl](2-methyl-quinolin-4-yl)amine.

{3-[3-(Adamantan-2-ylamino)-propoxy]-5-trifluoromethylphenyl}(2-methyl-quinolin-4-yl)amine.

{3-[3-(3,3-Dimethylpiperidin-1-yl)propoxy]-5-trifluoromethylphenyl}-(2-methylquinolin-4-yl)amine.

4-phenyl-1-{2-[3-(2-Methylquinolin-4-ylamino)-5-trifluoromethylphenoxy]ethyl}piperidine-4-carboxylic acid.

1-{2-[3-Fluoro-5-(2-methylquinolin-4-ylamino)phenoxy]ethyl}4-phenyl-piperidine-4-carboxylic acid.

The term "carbonyl" or "CO" as used herein, alone or in combination, includes derivatives such as oximes, ketals and cyclic ketals.

The term "alkyl" as used herein, alone or in combination, refers to $C_1$-$C_6$ straight or branched, substituted or unsubstituted saturated chain radicals derived from saturated hydrocarbons by the removal of one hydrogen atom, unless the term alkyl is preceded by a $C_x$-$C_y$ designation. Representative examples of alkyl groups include methyl, ethyl, n-propyl, iso-propyl, n-butyl, sec-butyl, iso-butyl, and tert-butyl among others.

The term "aryl", "arene" or "aromatic" as used herein alone or in combination, refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group which is an aromatic ring containing at least one endocyclic N, O or S atom such as furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-napthridinyl, pteridinyl, carbazolyl, acridinyl, phenazinyl, phenothiazinyl, phenoxyazinyl, pyrazolo[1,5-c]triazinyl and the like. "Aralkyl" and "alkylaryl" employ the term "alkyl" as defined above. Rings may be multiply substituted.

The term "aralkyl" as used herein, alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "cycloalkyl" as used herein refers to an aliphatic ring system having 3 to 10 carbon atoms and 1 to 3 rings, including, but not limited to, cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, diakylamino, hydroxyl, halo, mercapto, nitro, caroxaldehyde, carboxy, alkoxycarbonyl and carboxamide.

"Cycloalkyl" includes cis or trans forms. Furthermore, the substituents may either be in endo or exo positions in the bridged bycyclic systems.

The term "heteroaryl" or "heteroarene" as used herein, alone or in combination, refers to a 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "optical isomers" as used herein refers to compounds which differ only in the stereochemistry of at least one atom, including enantiomers, diastereomers and racemates.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylbeterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(O)—, —N—H—, —S—, —S(O)—, —O—, —C(O)O— or —S(O)O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in Advanced Organic Chemistry by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, sulfonyl and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfanyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio, carboxy lower alkyl, arylalkoxy, alkanoylamino, alkanoyl (lower alkyl) amino, lower alkylsufonylamino, arylsulfonylamino, alkylsulfonyl (lower alkyl) amino, arysulfonyl (lower alkyl) amino, lower alkylcarboxamide, di(lower alkyl)carboxamide, sulfonamide, lower alkylsulfonamide, di(lower alkyl sulfonamide, lower alkylsulfonyl, arylsulfonyl and alkyldithio.

As used herein, the term "composition" is intended to encompass a product comprising the specified ingredients in the specified amounts, a well as any product which results, directly or indirectly, from a combination of the specified ingredients in the specified amounts.

As used herein, the term "mammals" includes humans and other animals.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, dighiconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrastemal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) hurnectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or iastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The urotension antagonists of the present invention may be administered alone or in conjunction with one or more other therapeutic agents, said agents being selected from the group consisting of endothelin receptor antagonists, angiotensin coverting enzyme (ACE) inhibitors, A-II receptor antagonists, phosphodieterase inhibitors, vansopeptidase inhibitors, diuretics, digoxin, phosphodieterase inhibitors and dual non-selective β-anrenoceptor and $\xi_1$-adrenoceptor antagonists.

Preferably the composition is in unit dosage form, for example a tablet, capsule or metered aerosol dose, so that the patient may administer to themselves a single dose.

Each dosage unit for oral administration contains suitably from 0.0001 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1-400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.01 mg/Kg to 40 mg/Kg, of a compound of the Formula (I) or a pharmaceutically acceptable salt thereof calculated as the free acid. The daily dosage regimen for intranasal administration and oral inhalation is suitably about 10 to 500 mg/person. The active ingredient may be administered from 1 to 6 times a day, sufficient to exhibit the desired activity.

These compounds may be used for the treatment of congestive heart failure, stroke, ischemic heart disease (angina, myocardial ischemia), cardiac arrhythmia, hypertension (essential and pulmonary), renal disease (acute and chronic renal failure/end stage renal disease) along with peripheral vascular disease (male erectile dysfunction, diabetic retinopathy, intermittent claudication/ischemic limb disease) and ischemic/hemorrhagic stroke, COPD, restenosis, asthma, neurogenic inflammation, migraine, metabolic vasculopathies, bone/cartilage/joint disease, arthritis and other inflammatory diseases, fibrosis (e.g. pulmonary fibrosis), sepsis, atheroscloerosis, dyslipidemia, addiction, schizophrenia, cognitice disorders/Alzheimers disease, impulsivity, anxiety, stress, depression, pain, neuromuscular function, diabetes, gastric reflux, gastric motility disorders, ulcers and genitourinary diseases.

The urotension antagonists of the present invention may be administered alone or in conjunction with one or more other therapeutic agents, said agents being selected from the group consisting of endothelin receptor antagonists, angiotensin converting enzyme (ACE) inhibitors, A-II receptor antagonists, phosphodieterase inhibitors, vasopeptidase inhibitors, diuretics, digoxin, and dual non-selective β-adrenoceptor and $\delta_1$-adrenoceptor antagonists.

The biological activity of the compounds of Formula (I) are demonstrated by the following tests:

1) Inhibition of Human [$^{125}$I]-Urotensin-II Binding to Urotensin-II Receptor Binding of human [$^{125}$I]-urotensin-II to human urotensin-II receptor (UTR) was done using cell membranes from either TE-671 rhabdomyosarcoma cells or CHO cells stably expressing recombinant UTR, in a homogeneous Scintillation Proximity Assay (SPA).

The UTR cells membranes were pre-coupled overnight at 4° C. to WGA-PVT beads (Amersham RPNQ0001) at a ratio of 5-25 μg membrane to 0.5 mg beads/assay. Assay was performed in 96-well microtiter Optiplates (Packard 6005290) by mixing coupled beads and 0.1 nM [$^{125}$I U-II (2200 Ci/mmol, NEN NEX379), in a total volume of 100 μl 20 mM HEPES, 5 mM $MgCl_2$, pH 7.4. Test compounds were diluted in DMSO and were put in the assay at a final concentration of 1% DMSO. Incubation was done for 3 hours at 37° C. followed by reading in a TopCount scintillation microplate reader. Nonspecific binding was determined by adding 100 nM unlabeled human U-II (Phoenix Pharmaceuticals, 071-05) to the assay mixture. Analysis of the assay was performed using nonlinear least square fitting.

1) Inhibition of Human Urotensin-II-Induced $Ca^{2+}$ Mobilization in UTR Cells:

The function of urotensin-II was determined by measuring ligand-induced mobilization of intracellular $Ca^{2+}$ in a FlexStation scanning fluorometer (Molecular Devices). UTR cells were plated overnight at 50,000 cells/well in 96-well black/clear plates (Costar brand, Fisher 07-200-588). Cells were labeled with fluo-4AM dye (Molecular Probes, F-14201) in Hank's balanced salt solution (HBSS), 20 mM HEPES, 25 mM probenecid, pH 7.4, and then were washed with buffer. During the assay, cells were continuously monitored in the FlexStation and exposed to test compounds at a final concentration of 0.1% DMSO, followed by the addition of 1 nM human U-II. Fluorescence was read every 2 seconds for 2 minutes. The excitation and emission wavelengths used were 485 nm and 525 nm. Inhibition of the urotensin-II-induced signal was calculated using a nonlinear least square fitting program. Compounds of the present invention are active in these assays and have an $IC_{50}$ of <10 μM (Example 7 $IC_{50}$=6.5 μM).

The following Examples are illustrative but not limiting of the present invention:

EXAMPLE 1

N-(2-Dimethylamino-ethyl)-3-(2-methyl-quinolin-4-ylamino)-benzenesulfonamide

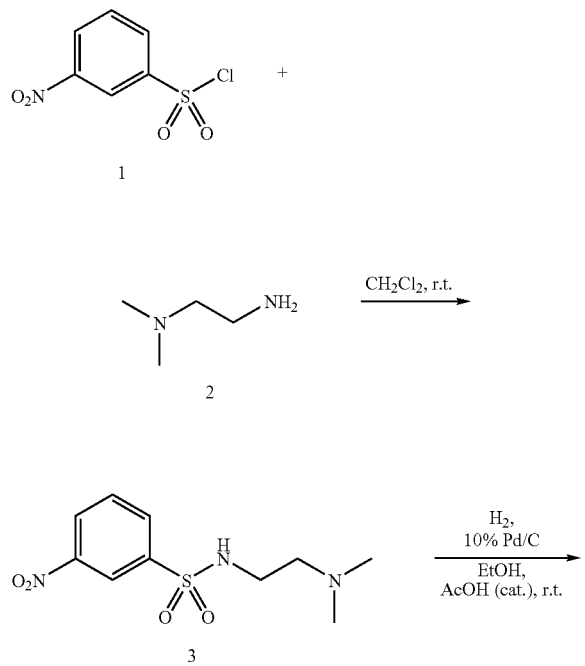

Step 1. N-(2-Dimethylamino-ethyl)-3-nitro-benzenesulfonamide (3).

To a solution of 3-nitrobenzenesulfonyl chloride (1, 1.0 g, 4.51 mmol) in anhydrous CH$_2$Cl$_2$ (9.0 mL) was added N,N-dimethyl-ethylenediamine (2, 0.5 mL, 4.55 mmol) dropwise. The resulting solution was stirred at room temperature overnight before it was diluted with EtOAc (80 mL). The organic mixture was washed with saturated NaHCO$_3$ (90 mL), brine (90 mL), and dried over MgSO$_4$. The solids were filtered and the filtrate was concentrated on a rotavap to give 3 as a foam (0.8 g) which was used in the next step without further purification.

Step 2. 3-Amino-N-(2-dimethylamino-ethyl)-benzenesulfonamide (4).

A solution of 3 (0.8 g) in ethanol (10 mL) was subjected to catalytic hydrogenation (10% Pd/C, Degussa, 0.8 g, 3 drops of AcOH, 1 atm.) overnight. To work up, the solids were filtered the filtrate was dried under vacuum to afford 4 as a solid (0.71 g) which was used in the next step without further purification.

Step 3. N-(2-Dimethylamino-ethyl)-3-(2-methyl-quinolin-4-ylamino)-benzenesulfonamide.

To a solution of 4 (0.3 g, 1.23 mmol) and 4-chloroquinaldine (5, 0.26 mL, 1.29 mmol) in ethanol (10 mL) were added 2 drops of conc. HCl. The resulting mixture was heated under reflux overnight before ethanol was removed under reduced pressure. The residue was basified with saturated NaHCO$_3$ (aq. 20 mL) and the basic solution was extracted with EtOAc (2×20 mL). The combined organic layers were dried over MgSO$_4$, the solids were filtered and the filtrate was concentrated on a rotavap. The residue was purified on Florisil® to give the title compound as an orange solid (15 mg).

EXAMPLE 2

N-(2-Dimethylamino-ethyl)-3-(2-methyl-quinolin-4-yl-amino)-benzamide

The title compound was synthesized in the same manner as for Example 1 except that 3-nitrobenzoyl chloride was used instead of 1 in Step 1. It was obtained as a pale yellow solid.

EXAMPLE 3

3-(2-Dimethylamino-ethoxy)-4-methyl-phenyl)-(2-methyl-quinolin-4-yl)-amine

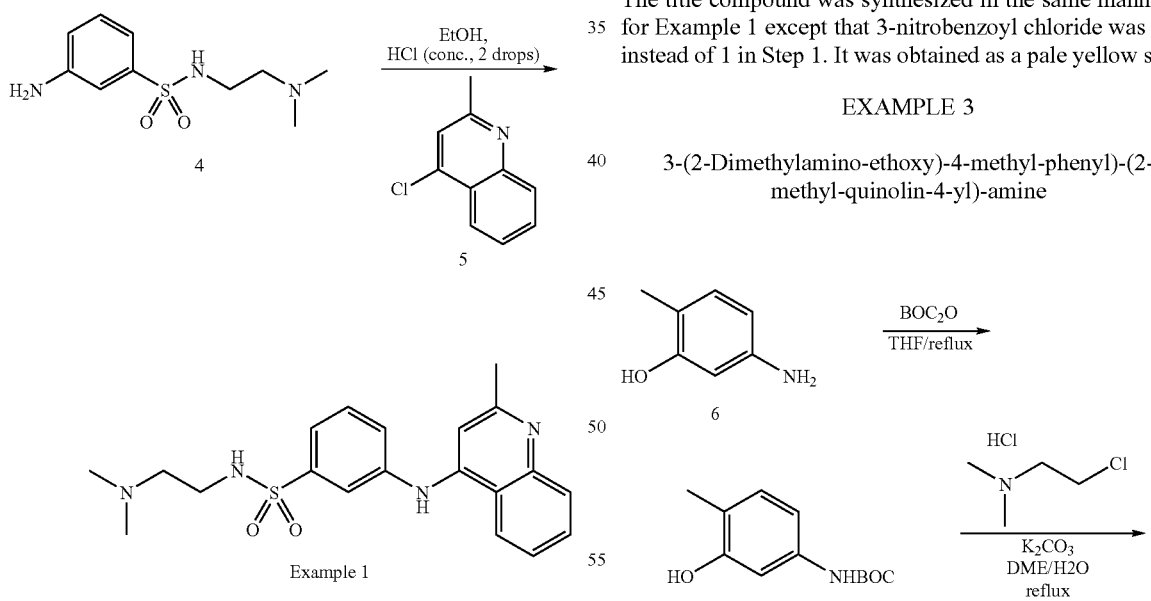

-continued

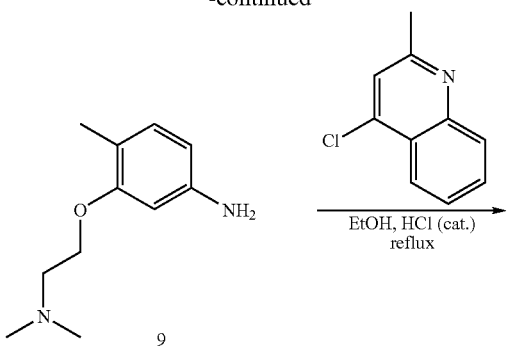

Example 3

Step 1. tert-Butyl(3-hydroxy-4-methyl-phenyl)-carbamate (7).

A solution of 5-amino-2-methylphenol (6, 1.0 g, 8.12 mmol) and di-tert-butyl dicarbonate (1.95 g, 8.93 mmol) in THF (25 mL) was heated under reflux overnight. After cooling to room temperature, the solution was diluted with EtOAc (75 mL) and the resulting mixture was washed with water (70 mL), 1N HCl (2×70 mL) and brine (70 mL). The organic layer was then dried over MgSO$_4$, the solids were filtered, and the filtrate was concentrated under reduced pressure. The desired product 7 was obtained as an oil (2.16 g) and was carried on to the next step without further purification.

Step 2. tert-Butyl(3-(2-dimethylamino-ethoxy)-4-methyl-phenyl)-carbamate (8).

A mixture of 7 (2.16 g, 9.68 mmol), 2-(dimethylamino)-ethyl chloride hydrochloride (1.53 g, 10.6 mmol) and K$_2$CO$_3$ (5.35 g, 3.87 mmol) in DME (28 mL)/H$_2$O (7 mL) was heated under reflux overnight. After cooling to room temperature, the solution was diluted with EtOAc (100 mL) and the resulting solution was washed with H$_2$O (2×100 mL) and brine (100 mL). The organic layer was dried over MgSO$_4$, the solids were filtered, and the filtrate was concentrated under reduced pressure. The residue was purified on silica gel to give 8 as an oil (1.15 g) which upon standing became a solid.

Step 3. 3-(2-Dimethylamino-ethoxy)-4-methylaniline (9).

A solution of 8 (1.15 g) in 6N HCl (10 mL) was heated at 60° C. for 4 hours. After cooling to room temperature, the solution was neutralized with 6N NaOH solution. The aqueous mixture was extracted with EtOAc (2×30 mL), the combined organic layers were washed with brine (1×50 mL) and dried over MgSO$_4$. The solids were filtered, and the filtrate was concentrated under reduced pressure to give the desired product as an oil (0.68 g).

Step 4. (3-(2-Dimethylamino-ethoxy)$_4$-methyl-phenyl)-(2-methyl-quinolin-4-yl)-amine.

To a solution of 9 (0.25 g, 1.29 mmol) and 5 (0.29 ml, 1.44 mmol) in EtOH (8 mL) were added 2 drops of conc. HCl. The mixture was heated under reflux overnight. After cooling to room temperature, EtOH was removed under reduced pressure. The residue was partitioned between sat. NaHCO$_3$ (aq.) and EtOAc (100 mL each) and the aquous layer was extracted with EtOAc (2×50 mL). The combined organic layers were dried over MgSO$_4$, the solids were filtered, and the filtrate was concentrated under reduced pressure. The residue was purified on Florisil® (50% EtOAc/Hexanes to 15% MeOH/EtOAc) to yield the title compound as a light yellow solid (0.25 g).

The compounds of Examples 4-11 were synthesized in the same manner as Example 3.

EXAMPLE 12

(3-Dimethylaminomethyl-phenyl)-(2-methyl-quinolin-4-yl)-amine

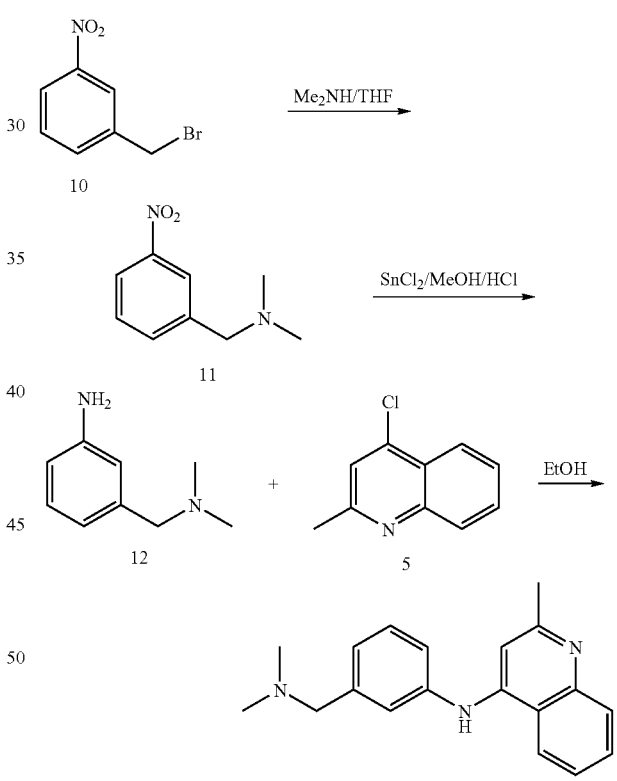

Example 12

Step 1. Dimethyl-(3-nitrobenzyl)-amine (11).

A solution of 3-nitrobenzyl bromide (10, 1.67 g, 7.73 mmol) and N,N-dimethylamine (4.25 mL, 2M in THF) in anhydrous THF (30 mL) was heated at 40° C. overnight. The reaction mixture was diluted with 1N HCl (30 mL, aq.), the aqueous layer separated, and extracted with EtOAc (30 mL). The pH of the aqueous layer was then adjusted to 9 using saturated Na$_2$CO$_3$ (aq.) and the aqueous layer was extracted with EtOAc (50 mL). The organic layer was washed with water (40 mL), brine (40 mL), and dried over Na$_2$SO$_4$. The solids were filtered and the filtrate was concentrated on a rotavap to give 11 (1.2 g).

Step 2. 3-Dimethylaminomethylaniline (12)

To a solution of 11 (1.2 g, 6.67 mmol) in methanol (100 mL) were sequentially added conc. HCl (10 mL) and SnCl$_2$ (5 g, 26.67 mmol). The reaction mixture was stirred at room temperature overnight before it was partitioned between water and EtOAc (200 mL each).

The organic layer was separated and washed with water (150 mL), brine (150 mL) and dried over Na$_2$SO$_4$. The solids were filtered and the filtrate was concentrated on a rotavap to give 12 (500 mg).

Step 3. (3-Dimethylaminomethyl-phenyl)-(2-methyl-quinolin-4-yl)-amine.

The title compound was synthesized in the same manner as shown in Step 3 of Example 1 and it was obtained as a yellowish solid (230 mg)

EXAMPLE 13

(4-Chloro-3-(2-(1-(2-(3,4-dimethoxy-phenyl)-ethyl)-6,7-dimethoxy-3,4-dihydro-1H-isoquinolin-2-yl)-ethoxy)-phenyl)-(2-methyl-quinolin-4-yl)-amine

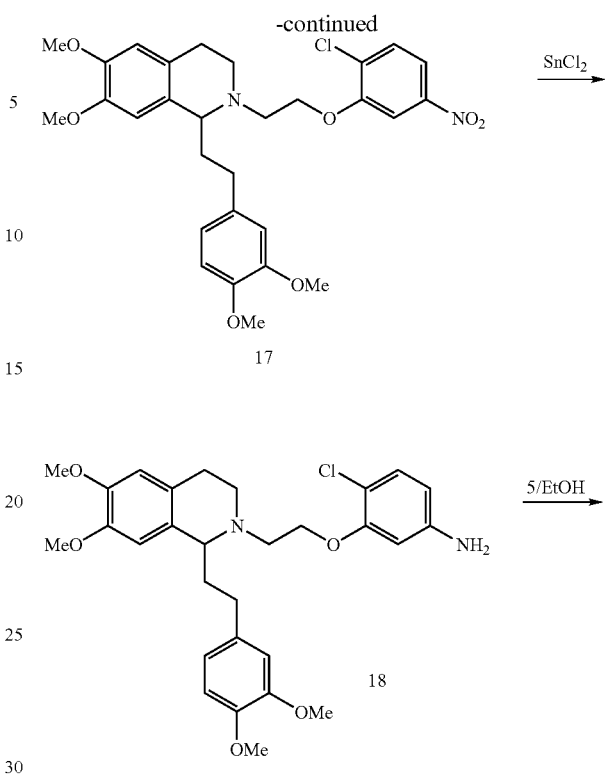

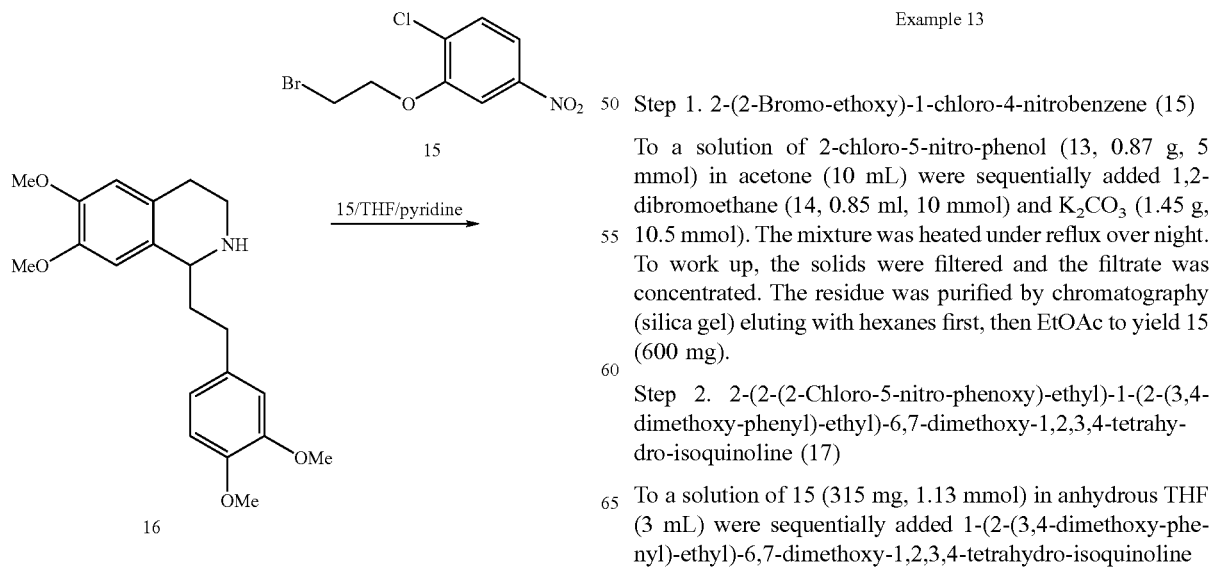

Example 13

Step 1. 2-(2-Bromo-ethoxy)-1-chloro-4-nitrobenzene (15)

To a solution of 2-chloro-5-nitro-phenol (13, 0.87 g, 5 mmol) in acetone (10 mL) were sequentially added 1,2-dibromoethane (14, 0.85 ml, 10 mmol) and K$_2$CO$_3$ (1.45 g, 10.5 mmol). The mixture was heated under reflux over night. To work up, the solids were filtered and the filtrate was concentrated. The residue was purified by chromatography (silica gel) eluting with hexanes first, then EtOAc to yield 15 (600 mg).

Step 2. 2-(2-(2-Chloro-5-nitro-phenoxy)-ethyl)-1-(2-(3,4-dimethoxy-phenyl)-ethyl)-6,7-dimethoxy-1,2,3,4-tetrahydro-isoquinoline (17)

To a solution of 15 (315 mg, 1.13 mmol) in anhydrous THF (3 mL) were sequentially added 1-(2-(3,4-dimethoxy-phenyl)-ethyl)-6,7-dimethoxy-1,2,3,4-tetrahydro-isoquinoline (16, Morimoto et al, Heterocycles 1996 43:2557; Brossi et al, Helv Chim Acta 1960 43:1459; Meyers et al, Tetrahedron Lett 1981 22:5115; Meyers et al, J Am Chem Soc 1983 105:117) (404 mg, 1.13 mmol) and pyridine (0.3 mL). The reaction mixture was heated under reflux for 2 days before it was partitioned between EtOAc and water (20 mL each). The organic layer was separated, washed with water (15 mL), brine (15 mL), and dried over $Na_2SO_4$. The solids were filtered and the filtrate was purified by chromatography (silica gel) eluting with hexanes:EtOAc (1:1) to give 17 (205 mg)

Step 3. 4-Chloro-3-(1-(2-(3,4-dimethoxy-phenyl)-ethyl)-6,7-dimethoxy-1,2,3,4-tetrahydro-isoquinolin-2-yl)-ethoxy) aniline (18)

To a solution of 17 (205 mg, 0.369 mmol) in methanol (10 mL) were sequentially added conc. HCl (0.5 mL) and $SnCl_2$ (280 mg, 1.48 mmol). The mixture was stirred at room temperature for 8 hours before it was diluted with water (100 mL) and the pH was adjusted to 10 using 2N NaOH. The mixture was extracted with EtOAc (150 mL) and the organic layer was washed with water and brine (100 mL each) and then dried over $Na_2SO_4$. The solids were filtered and the filtrate was concentrated on a rotavap to give 18 (170 mg).

Step 4. (4-Chloro-3-(2-(1-(2-(3,4-dimethoxy-phenyl)-ethyl)-6,7-dimethoxy-3,4-dihydro—The title compound was synthesized in the same manner as shown in Example 1/Step 3 using 5 and 18. It was obtained as a yellow solid (79 mg).

EXAMPLE 14

1-(4-Chloro-3-(2-dimethylamino-ethoxy)-phenyl)-3-(2-methyl-quinolin-4-yl)-urea

To a solution containing 4-aminoquinaldine (74 mg, 0.46 mmol) in anhydrous THF (5.0 Ml) was added triethylamine (0.2 Ml, 1.4 mmol). The solution was cooled to 0° C. followed by the addition of triphosgene (45.0 mg, 0.18 mmol). The reaction mixture was stirred at 0° C. for 10 minutes before the addition of a solution of 4-chloro-3-(2-dimethylamino-ethoxy)aniline (100.0 mg, 0.46 mmol, for its synthsis see Steps 1-3 for Example 1) in THF (2 Ml). The ice bath was removed and the mixture was heated at 65° C. for 2 hours before it was poured into a mixture of $CH_2Cl_2$/MeOH (20 Ml, 7:1 ratio). The resulting mixture was washed with 10% sodium bicarbonate (aq. 15.0 Ml). The organic layer was dried over $MgSO_4$ and concentrated.

The oily residue was chromatographed over silica gel (eluent: 20% MeOH in EtOAc) to give the desired product as an off-white solid (82.0 mg, 45% yield).

The compounds of Example 15 and 16 were synthesized in the same manner as for Example 2.

TABLE 1

| Example | Structure | Name | Physical Description | M + H |
|---|---|---|---|---|
| 1 | 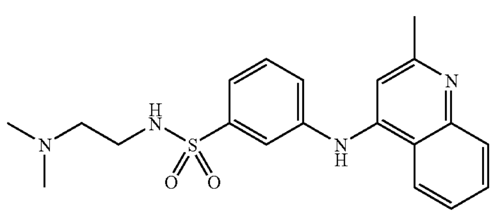 | N-(2-dimethylamino-ethyl)-3-(2-methyl-quinolin-4-ylamino)-benzenesulfonamide | orange solid | 385.27 |
| 2 | 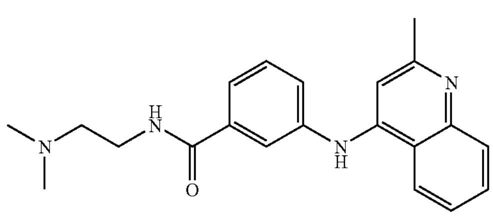 | N-(2-dimethylamino-ethyl)-3-(2-methyl-quinolin-4-ylamino)-benzamide | pale yellow solid | 349.29 |
| 3 | 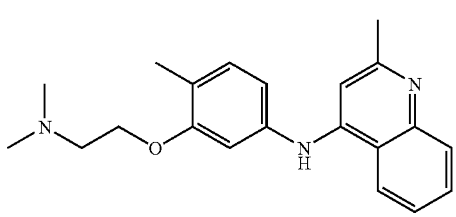 | (3-(2-dimethylamino-ethoxy)-4-methyl-phenyl)-(2-methyl-quinolin-4-yl)-amine | light yellow solid | 336.25 |

TABLE 1-continued

| Example | Structure | Name | Physical Description | M + H |
|---|---|---|---|---|
| 4 | 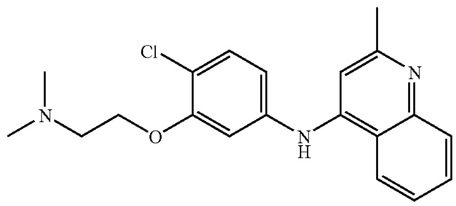 | (4-chloro-3-(2-dimethyl amino-ethoxy)-phenyl)-(2-methyl-quinolin-4-yl)-amine | yellow solid | 355.19 |
| 5 | 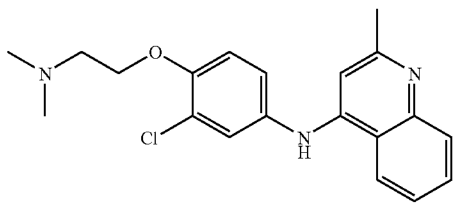 | (3-chloro-4-(2-dimethyl amino-ethoxy)-phenyl)-(2-methyl-quinolin-4-yl)-amine | yellow solid | 356.24 |
| 6 | 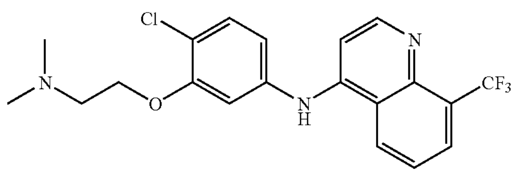 | (4-chloro-3-(2-dimethyl amino-ethoxy)-phenyl)-(8-trifluoromethyl-quinolin-4-yl)-amine | white solid | 410.18 |
| 7 | 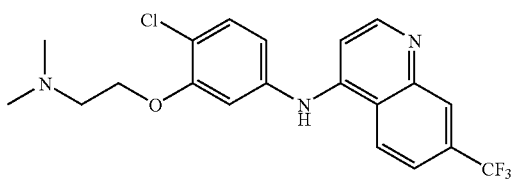 | (4-chloro-3-(2-dimethyl amino-ethoxy)-phenyl)-(7-trifluoromethyl-quinolin-4-yl)-amine | yellow solid | 410.12 |
| 8 | 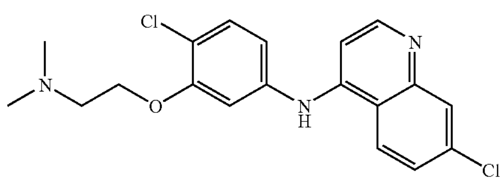 | (4-chloro-3-(2-dimethyl amino-ethoxy)-phenyl)-(7-chloro-quinolin-4-yl)-amine | yellow solid | 376.22 |
| 9 | 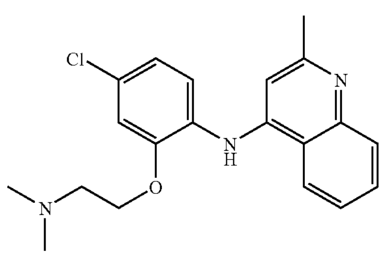 | (4-chloro-2-(2-dimethyl amino-ethoxy)-phenyl)-(2-methyl-quinolin-4-yl)-amine | yellow oil | 356.18 |
| 10 | 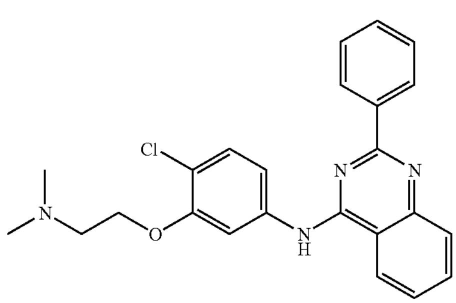 | (4-chloro-3-(2-dimethyl amino-ethoxy)-phenyl)-(2-phenyl-quinazolin-4-yl)-amine | yellow solid | 419.24 |

TABLE 1-continued

| Example | Structure | Name | Physical Description | M + H |
|---|---|---|---|---|
| 11 | 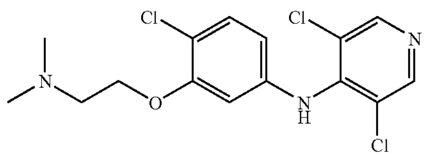 | (4-chloro-3-(2-dimethyl amino-ethoxy)-phenyl)-(3,5-dichloro-pyridin-4-yl)-amine | oil | 360.11 |
| 12 | 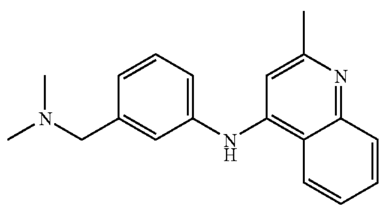 | (3-dimethyl aminomethyl-phenyl)-(2-methyl-quinolin-4-yl)-amine | yellowish solid | 291.27 |
| 13 | 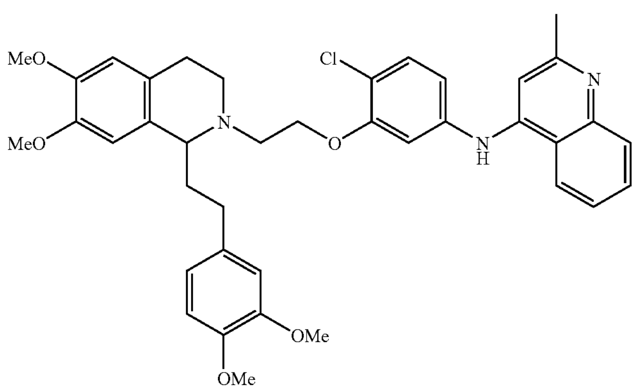 | (4-chloro-3-(2-(1-(2-(3,4-dimethoxy-phenyl)-ethyl)-6,7-dimethoxy-3,4-dihydro-1H-isoquinolin-2-yl)-ethoxy)-phenyl)-(2-methyl-quinolin-4-yl)-amine | yellow solid | 668.35 |
| 14 | 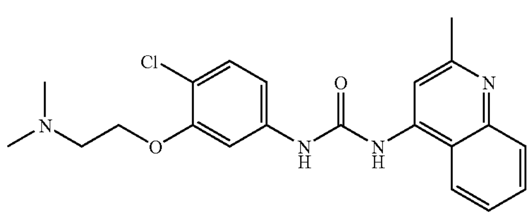 | 1-(4-chloro-3-(2-dimethyl amino-ethoxy)-phenyl)-3-(2-methyl-quinolin-4-yl)-urea | off-white solid | 399.23 |
| 15 | 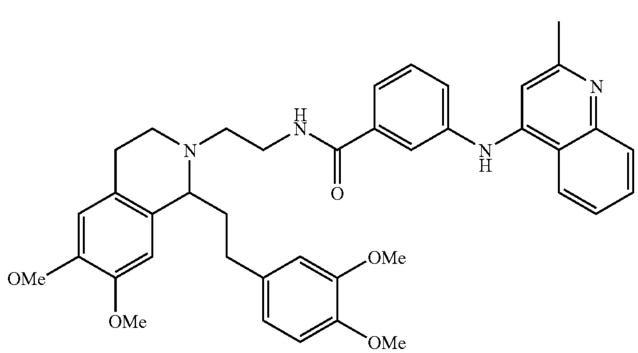 | N-(2-(1-(2-(3,4-dimethoxy-phenyl)-ethyl)-6,7-dimethoxy-3,4-dihydro-1H-isoquinolin-2-yl)-ethyl)3-(2-methyl-quinolin-4-yl)amino-benzamide | light yellow solid | 661.39 |

TABLE 1-continued

| Example | Structure | Name | Physical Description | M + H |
|---------|-----------|------|----------------------|-------|
| 16 | 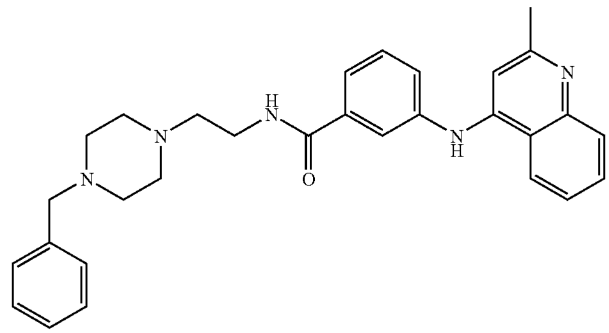 | N-(2-(4-benzyl-piperazin-1-yl)-ethyl)-3-(2-methyl-quinolin-4-yl)-amino-benzamide | light yellow foam | 480.37 |

The structures, chemical names, physical descriptions and M+H data for the compounds of Examples 17-76 are set forth in Table 2.

The compound of Example 17 was synthesized by methylating the compound of Example 3 using a standard method (NaH/DMF/MeI).

The compounds of Examples 18 and 19 were synthesized in the same manner as the compound of Example 3.

The compounds of Examples 20 to 32 were synthesized in the same manner as the compound of Example 13.

The compound of Example 33 was synthesized in the same manner as the compound of Example 13 except that 3-nitro-5-trifluoromethylphenol was used instead of 13. 3-Nitro-5-trifluoromethylphenol was synthesized by demethylating 3-nitro-5-trifluoromethylanisole using a standard method (BBr$_3$/CH$_2$Cl$_2$).

The compound of Example 34 was synthesized by hydrolysis of the compound of Example 32 using a standard method (NaOH/MeOH/THF).

The compounds of Examples 35 to 44 were synthesized in the same manner as the compound of Example 13.

The preparation of the compound of Example 45 is shown.

The compounds of Examples 46 to 54 were synthesized in the same manner as the compound of Example 13.

The preparation of the compound of Example 55 is shown.

The compounds of Examples 56 and 57 were synthesized in the same manner as the compound of Example 13.

The compound of Example 58 was synthesized in the same manner as the compound of Example 13 except that 4-chloro-2-tert-butylquinoline (C Wolf, R Lerebours: J Org Chem 2003, 68:7077-7084) was used instead of 4-chloro-2-methylquinoline.

The compound of Example 59 was synthesized in the same manner as the compound of Example 13.

The compound of Example 60 was synthesized by acylating the compound of Example 21 using a standard method (NaH/DMF/AcCl).

The compound of Example 61 was synthesized in the same manner as the compound of Example 13.

The compound of Example 62 was synthesized in the same manner as the compound of Example 33.

The compounds of Examples 63 to 65 were synthesized in the same manner as the compound of Example 13.

The compound of Example 66 was synthesized in the same manner as the compound of Example 13 and it was obtained as the dehydration product of the intended (1-{2-[3-(2-methylquinolin-4-ylamino)phenoxy]ethyl}piperidin-4-yl) diphenylmethanol.

The compound of Example 67 was synthesized in the same manner as the compound of Example 33.

The compound of Example 68 was synthesized by the hydrolysis of the compound of Example 65 (NaOH/MeOH/THF/65° C./2 days).

The compound of Example 69 was synthesized by the hydrolysis of the compound of Example 36 (NaOH/MeOW/THF).

The compounds of Examples 70 and 71 were synthesized in the same manner as the compound of Example 33.

The compounds of Examples 72 and 73 were synthesized in the same manner as the compound of Example 13.

The compound of Example 74 was synthesized in the same manner as the compound of Example 33.

The compounds of Examples 75 and 76 were synthesized in the same manner as the compound of Example 13.

EXAMPLE 45

{3-[2-(4-Benzenesulfonylpiperazin-1-yl)ethoxy]phenyl}-(2-methylquinolin-4-yl)amine

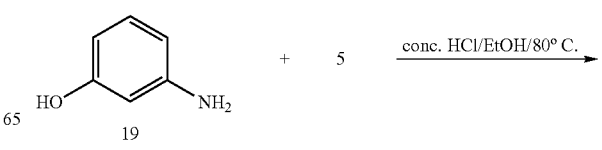

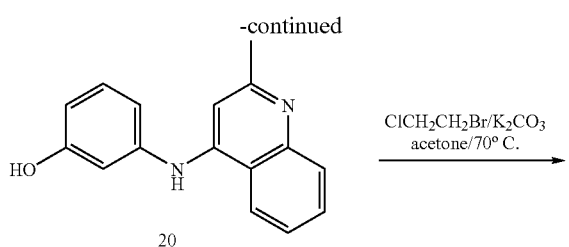

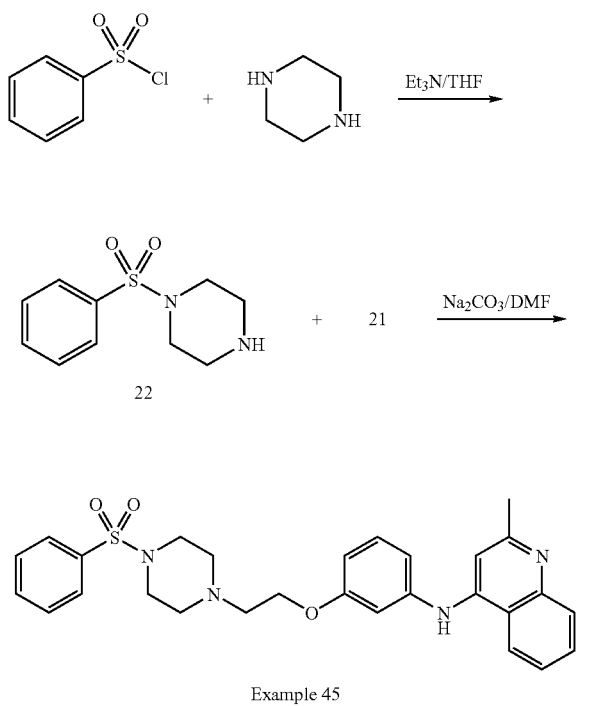

Example 45

Step 1. 3-(2-Methylquinolin-4-ylamino)phenol (20).

20 is prepared by the procedure of Example 1 Step 3.

Step 2. [3-(2-Chloroethoxy)phenyl]-(2-methylquinolin-4-yl)amine (21).

To a heterogeneous mixture of 20 (2.16 g, 6.90 mmol) in acetone (22 mL) were sequentially added 1-bromo-2-chloroethane (7.2 mL, 86.50 mmol) and potassium carbonate (3.00 g, 21.71 mmol). The reaction was stirred and heated at 70° C. for 17 hours before it was allowed to cool to room temperature and was filtered. The solids were rinsed with a 3:1 mixture of dichloromethane/methanol (25 mL×3), and the filtrate was isolated and evaporated to give the crude product. Column chromatography on silica (dichloromethane to 20/1 to 15/1 to 5/1 dichloromethane/methanol) gave 21 as a pale yellow solid (0.96 g, 35.5%).

Step 3. 1-Benzenesulfonylpiperazine (22).

To a solution of benzenesulfonyl chloride (1 g, 5.66 mmol) in THF (20 mL) were sequentially added triethylamine (1.97 mL, 14.15 mmol) and piperazine (2.92 g, 33.9 mmol). The reaction was stirred at room temperature for 1 hour before it was extracted with ethyl acetate and washed with water and brine. The ethyl acetate extracts were dried over anhydrous magnesium sulfate and concentrated. The residue was chromatographed on silica gel (1:1 hexanes/ethyl acetate to 10/1 dichloromethane/methanol) to give 22 as a yellow oil.

Step 4. {3-[2-(4-Benzenesulfonylpiperazin-1-yl)ethoxy]phenyl}-(2-methylquinolin-4-yl)amine.

To a solution of 21 (250 mg, 0.67 mmol) in DMF (5 mL) were sequentially added sodium carbonate (149 mg, 1.41 mmol), and 22 (183 mg, 0.808 mmol). The reaction was placed under a $N_2$ atmosphere and heated at 90° C. for 16 hours. After cooling to room temperature, the reaction mixture was extracted with ethyl acetate and washed with water and brine. The ethyl acetate extracts were dried over anhydrous magnesium sulfate and evaporated. The residue was purified via reversed phase HPLC to yield the title compound as a pale yellow solid (20 mg, 6%).

EXAMPLE 55

{3-[2-(2-Benzylimidazol-1-yl)ethoxy]phenyl}-(2-methylquinolin-4-yl)amine

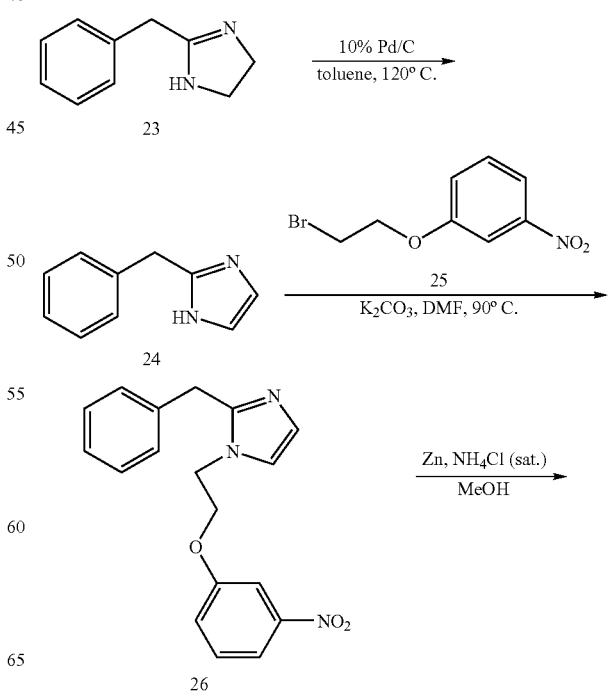

-continued

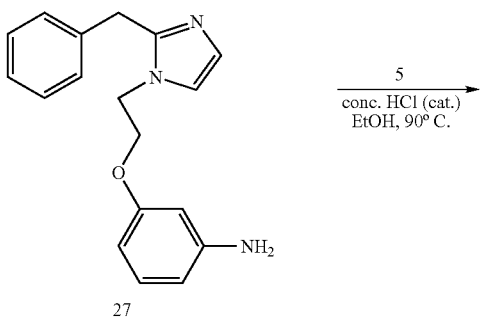

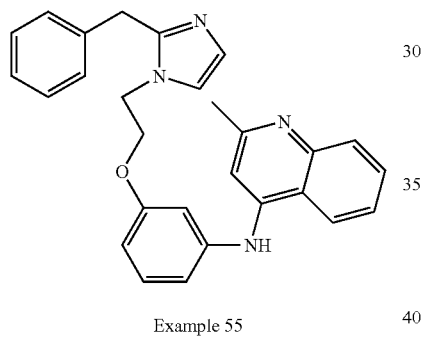

Example 55

Step 1. 2-Benzyl-1H-imidazole (24).

A mixture of 23 (0.78 g, 4.8 mmol) and 10% Pd/C (0.78 g) in toluene (25 mL) was heated at 120° C. for 48 hours. It was allowed to cool to room temperature and the solids were filtered off. The filtrate was concentrated in vaccuo and the residue was purified on silica gel column to give 24 (0.16 g, 21%).

Step 2. 2-Benzyl-1-[2-(3-nitrophenoxy)ethyl]-1H-imidazole (26).

26 is prepared from 24 and 25 by the procedure of Example 45 Step 4.

Step 3. 3-[2-(2-Benzylimidazol-1-yl)ethoxy]phenylamine (27).

27 is prepared from 26 by the procedure of Example 110 Step 4.

Step 4. {3-[2-(2-Benzylimidazol-1-yl)ethoxy]phenyl}-(2-methylquinolin-4-yl)amine.

The title compound is prepared by the procedure of Example 1 Step 3.

EXAMPLE 67

Methyl 4-benzyl-1-{2-[3-(2-methylquinolin-4-ylamino)-5-trifluoromethylphenoxy]ethyl}piperidine-4-carboxylate

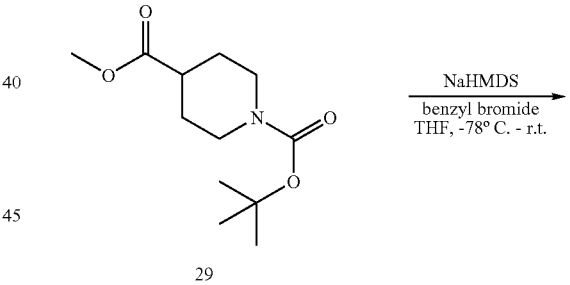

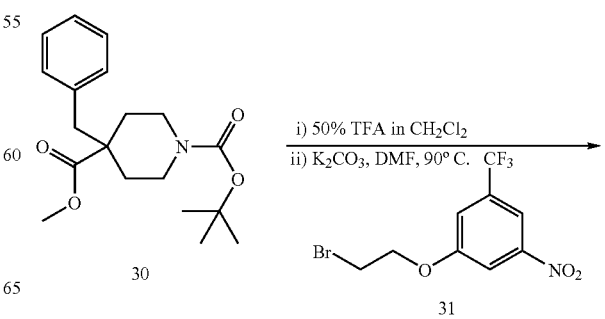

-continued

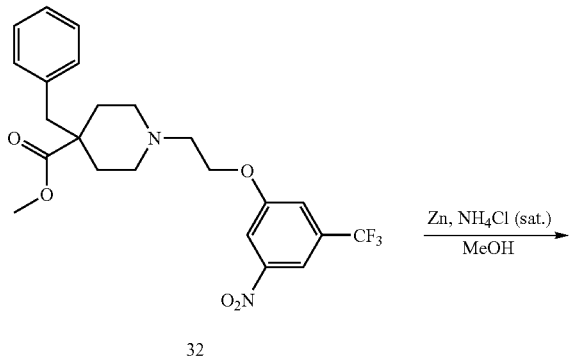

Zn, NH₄Cl (sat.) / MeOH →

33 conc. HCl (cat.) / EtOH, 95° C. →
5

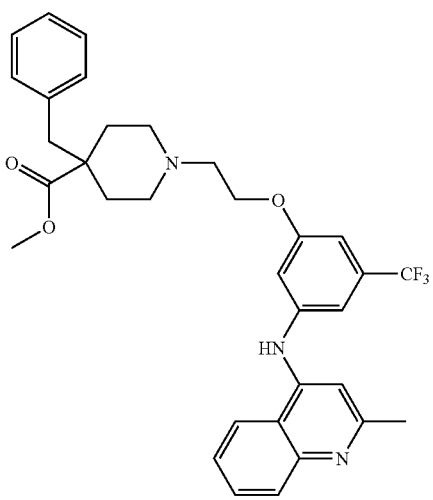

Example 67

Step 1. 1-tert-Butyl 4-methyl piperidine-1,4-dicarboxylate (29).

To a solution of methyl isonipecotate (28) (2.84 g, 19.84 mmol) and DMAP (cat.) in anhydrous $CH_2Cl_2$ (25 mL) at 0° C. was added di-tert-butoxycarbonate (5.20 g, 23.82 mmol).

The mixture was heated under reflux for 5 hours before it was allowed to cool to room temperature and diluted with dichloromethane (100 mL). After washing with 1 N HCl (2×100 mL) and water (100 mL), the organic layer was dried over $Na_2SO_4$, and concentrated to provide 29 (4.64 g, 97%).

Step 2. 1-tert-Butyl 4-methyl 4-benzylpiperidine-1,4-dicarboxylate (30).

To a solution of 29 (4.64 g, 19.08 mmol) in anhydrous THF (20 mL) at −78° C. was added NaHMDS (1.0 M in THF, 22.90 mL, 22.90 mmol) slowly. It was stirred at −78° C. for 30 minutes before the addition of benzyl bromide (3.91 g, 22.87 mmol). The cold bath was removed and the reaction was allowed to warm to room temperature and stirred overnight.

The mixture was diluted with EtOAc (150 mL) and washed with water (2×100 mL) and brine (100 mL). The organic layer was dried ($Na_2SO_4$), concentrated in vacuo, and the residue was purified by flash column chromatography to afford 30 (4.5 g, 71%).

Step 3. Methyl 4-benzylpiperidine-4-carboxylate

A solution of 30 (4.5 g, 13.5 mmol) in TFA (25 mL) and $CH_2Cl_2$ (25 mL) was stirred at room temperature for 40 minutes. The mixture was concentrated and the residue diluted with EtOAc (100 mL). Upon sequential washings with 1 N NaOH (2×100 mL) and water (100 mL), the organic solution was dried ($Na_2SO_4$) and concentrated to dryness to afford the desired product as a yellow solid (2.9 g, 92%).

Step 4. Methyl 4-benzyl-1-[2-(3-nitro-5-trifluoromethylphenoxy)ethyl]piperidine-4-carboxylate (32).

32 is prepared from 30 and 31 by the procedures of Example 45 Step 4.

Step 5. Methyl 1-[2-(3-amino-5-trifluoromethylphenoxy)ethyl]-4-benzylpiperidine-4-carboxylate (33).

33 is prepared by the procedure of Example 110 Step 4.

Step 6. Methyl 4-benzyl-1-{2-[3-(2-methylquinolin-4-ylamino)-5-trifluoromethylphenoxy]ethyl}piperidine-4-carboxylate.

The title compound is prepared from 33 by the procedure of Example 1 Step 3.

TABLE 2

| Example | Structure | Chemical name | Physical description[a] | [M + H]+ |
|---|---|---|---|---|
| 17 | 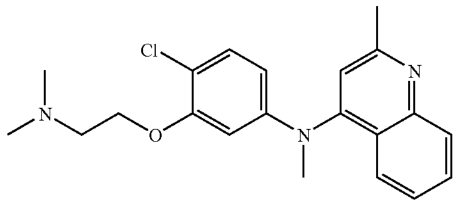 | [4-Chloro-3-(2-dimethylamino-ethoxy)phenyl]-methyl-(2-methylquinolin-4-yl)amine | yellow solid[b] | 370.34 |
| 18 | 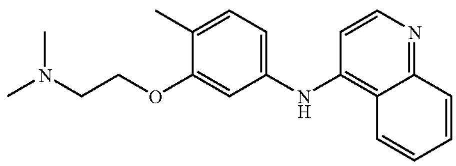 | [3-(2-Dimethylamino-ethoxy)-4-methylphenyl]-quinolin-4-ylamine | pale yellow solid | 322.24 |
| 19 | 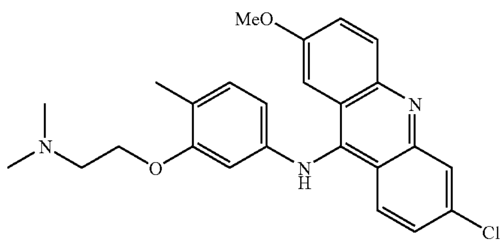 | (6-Chloro-2-methoxyacridin-9-yl)-[3-(2-dimethylamino-ethoxy)-4-methylphenyl]amine | orange-yellow solid[b] | 436.27 |
| 20 | 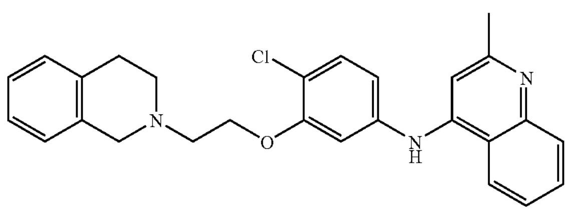 | {4-Chloro-3-[2-(3,4-dihydro-1H-isoquinolin-2-yl)ethoxy]phenyl}-(2-methylquinolin-4-yl)amine | yellowish solid | 444.20 |
| 21 | 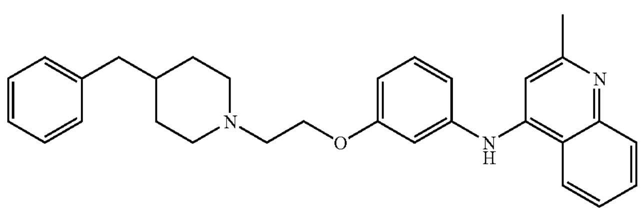 | {3-[2-(4-Benzyl-piperidin-1-yl)ethoxy]phenyl}-(2-methyl quinolin-4-yl)amine | yellow solid | 452.34 |
| 22 | 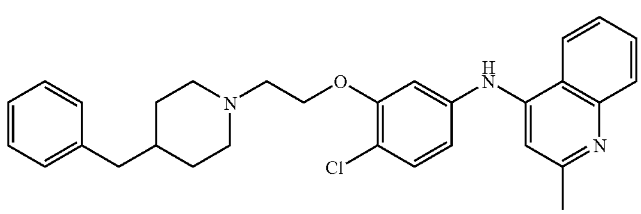 | {3-[2-(4-Benzyl-piperidin-1-yl)ethoxy]-4-chlorophenyl}-(2-methylquinolin-4-yl)amine | off-white solid | 486.30 |
| 23 | 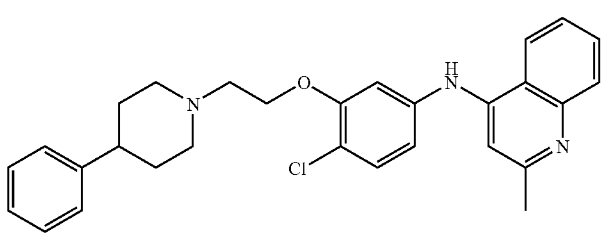 | {4-Chloro-3-[2-(4-phenyl piperidin-1-yl)ethoxy]phenyl}-(2-methylquinolin-4-yl)amine | white solid[b] | 472.22 |

TABLE 2-continued

| Example | Structure | Chemical name | Physical description[a] | [M + H]+ |
|---|---|---|---|---|
| 24 | 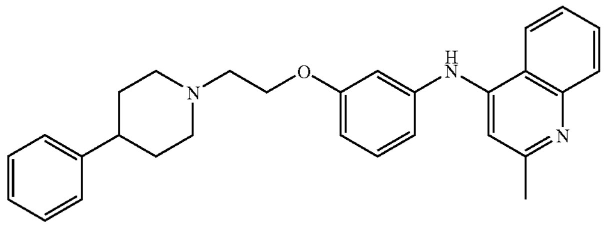 | (2-Methylquinolin-4-yl)-{3-[2-(4-phenyl-piperidin-1-yl)ethoxy]phenyl}amine | brown solid[b] | 438.26 |
| 25 | 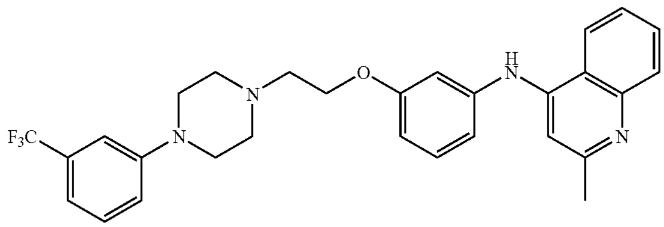 | (2-Methylquinolin-4-yl)-(3-{2-[4-(3-trifluoromethyl-phenyl)piperazin-1-yl]ethoxy}phenyl)amine | brown solid | 551.31[c] |
| 26 | 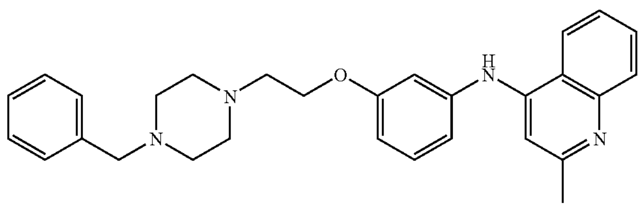 | {3-[2-(4-Benzylpiperazin-1-yl)ethoxy]phenyl}-(2-methylquinolin-4-yl)amine | yellow solid[b] | 453.29 |
| 27 | 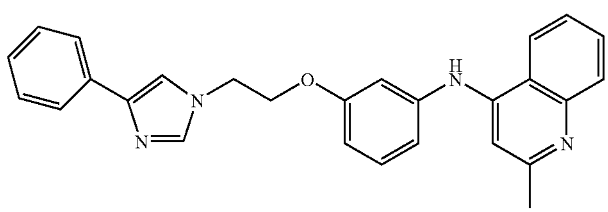 | (2-Methylquinolin-4-yl)-{3-[2-(4-phenylimidazol-1-yl)ethoxy]phenyl}amine | yellow solid | 420.32 |
| 28 | 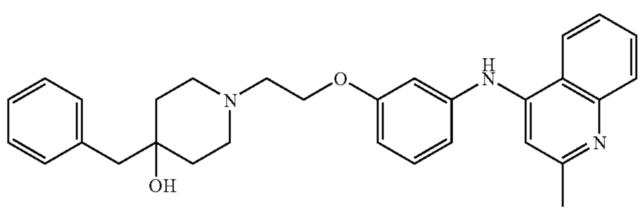 | 4-Benzyl-1-{2-[3-(2-methyl quinolin-4-ylamino)phenoxy]ethyl}piperidin-4-ol | yellow solid | 468.27 |
| 29 | 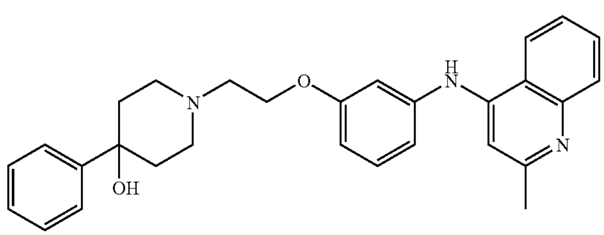 | 1-{2-[3-(2-Methylquinolin-4-yl amino)phenoxy]ethyl}-4-phenylpiperidin-4-ol | yellow solid | 454.23 |
| 30 | 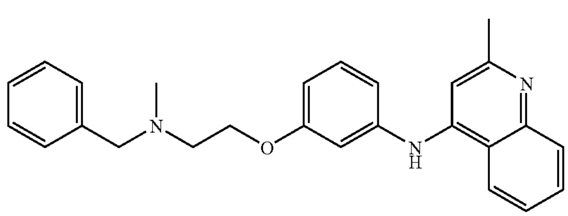 | {3-[2-(Benzylmethylamino)ethoxy]phenyl}-(2-methyl quinolin-4-yl)amine | yellow solid | 398.24 |

TABLE 2-continued

| Example | Structure | Chemical name | Physical description[a] | [M + H]+ |
|---|---|---|---|---|
| 31 | 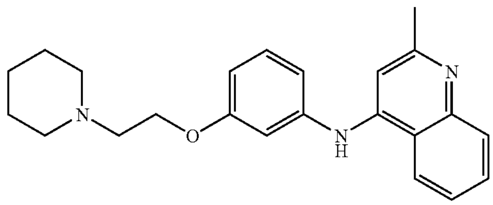 | (2-Methylquinolin-4-yl)-[3-(2-piperidin-1-yl ethoxy)phenyl]amine | yellow solid | 362.23 |
| 32 | 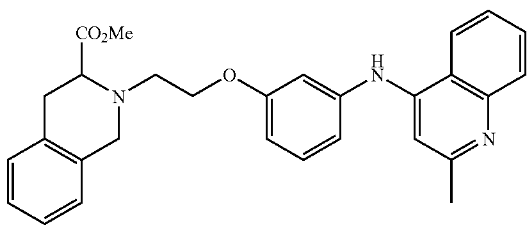 | Methyl 2-{2-[3-(2-methyl quinolin-4-ylamino)phenoxy] ethyl}-1,2,3,4-tetrahydro isoquinoline-3-carboxylate | white solid[b] | 468.23 |
| 33 | 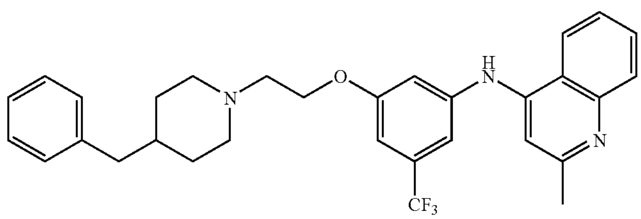 | {3-[2-(4-Benzylpiperidin-1-yl) ethoxy]-5-trifluoromethyl phenyl}-(2-methylquinolin-4-yl) amine | yellow solid | 520.25 |
| 34 | 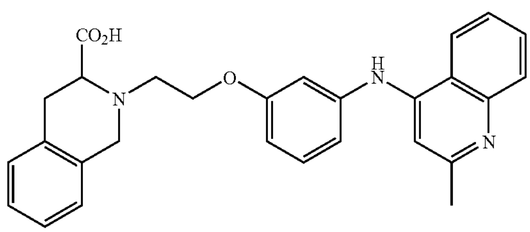 | 2-{2-[3-(2-Methylquinolin-4-yl amino)phenoxy]ethyl}-1,2,3,4-tetrahydroisoquinoline-3-carboxylic acid | yellow solid[e] | 454.22 |
| 35 | 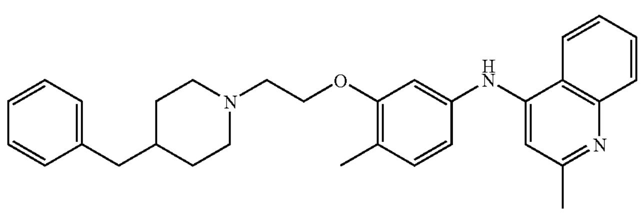 | {3-[2-(4-Benzylpiperidin-1-yl) ethoxy]-4-methylphenyl}-(2-methylquinolin-4-yl)amine | yellow solid | 466.31 |
| 36 | 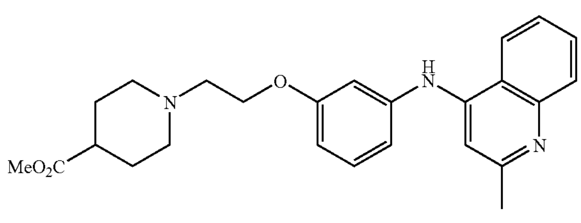 | Methyl 1-{2-[3-(2-methyl quinolin-4-ylamino)phenoxy] ethyl}piperidine-4-carboxylate | yellow solid | 420.26 |
| 37 | 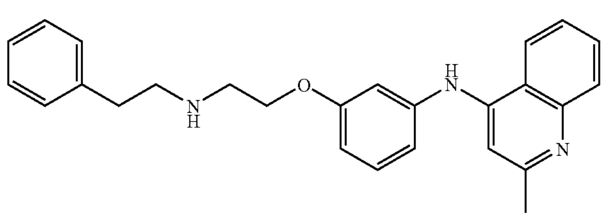 | (2-Methylquinolin-4-yl)-[3-(2-phenethylaminoethoxy) phenyl]amine | yellow solid[b] | 398.26 |

TABLE 2-continued

| Example | Structure | Chemical name | Physical description[a] | [M + H]+ |
|---|---|---|---|---|
| 38 | 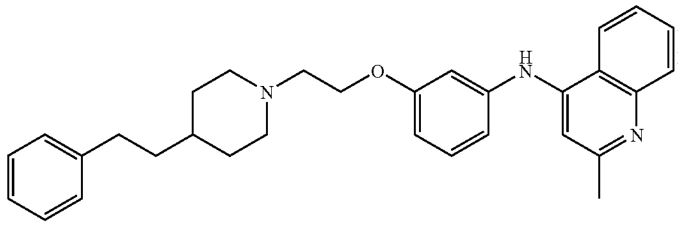 | (2-Methylquinolin-4-yl)-{3-[2-(4-phenethylpiperidin-1-yl)-ethoxy]phenyl}amine | yellow solid[b] | 467.29 |
| 39 | 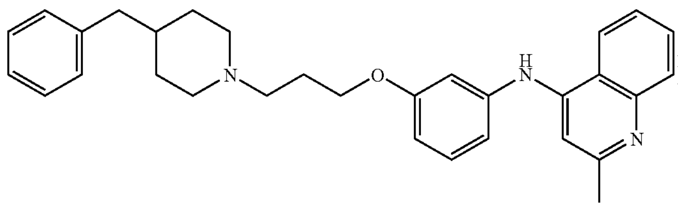 | {3-[3-(4-Benzylpiperidin-1-yl)propoxy]phenyl}-(2-methyl quinolin-4-yl)amine | yellow solid | 466.37 |
| 40 | 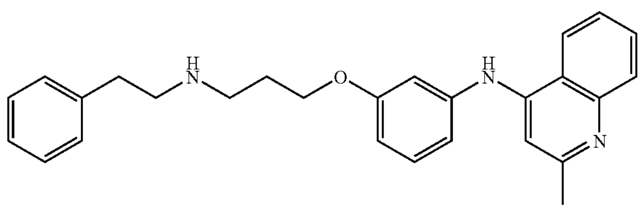 | (2-Methylquinolin-4-yl)-[3-(3-phenethylamino propoxy)phenyl]amine | yellow solid | 412.33 |
| 41 | 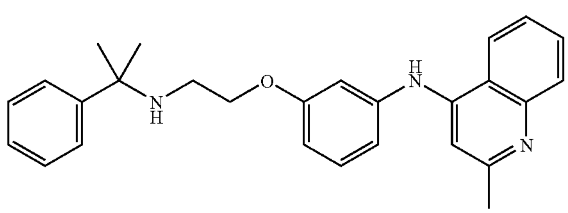 | {3-[2-(1-Methyl-1-phenyl ethylamino)ethoxy] phenyl}-(2-methylquinolin-4-yl)amine | yellow solid | 412.20 |
| 42 | 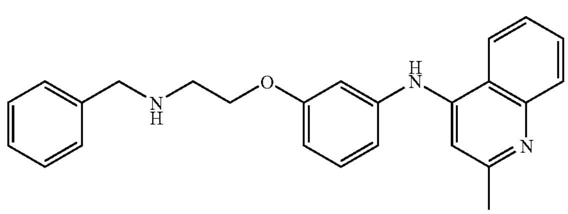 | [3-(2-Benzylaminoethoxy) phenyl]-(2-methyl quinolin-4-yl)amine | pale yellow solid | 384.25 |
| 43 | 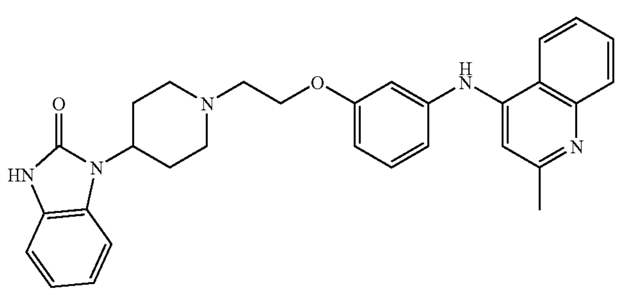 | 1-(1-{2-[3-(2-Methylquinolin-4-ylamino)phenoxy]ethyl} piperidin-4-yl)-1,3-dihydro-benzoimidazol-2-one | pale yellow solid | 494.28 |

TABLE 2-continued

| Example | Structure | Chemical name | Physical description[a] | [M + H]+ |
|---|---|---|---|---|
| 44 | 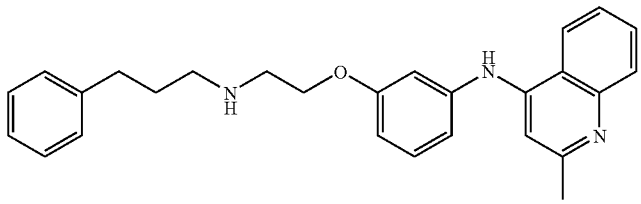 | (2-Methylquinolin-4-yl)-{3-[2-(3-phenylpropylamino)ethoxy]phenyl}amine | yellow solid[b] | 412.29 |
| 45 | 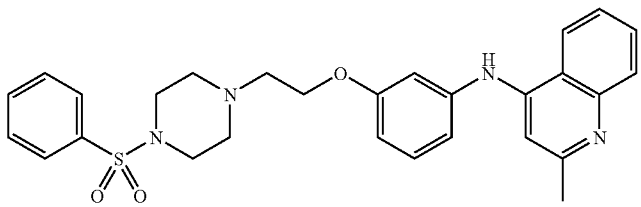 | {3-[2-(4-Benzenesulfonyl piperazin-1-yl)ethoxy]phenyl}-(2-methylquinolin-4-yl)amine | yellow solid[b] | 503.34 |
| 46 | 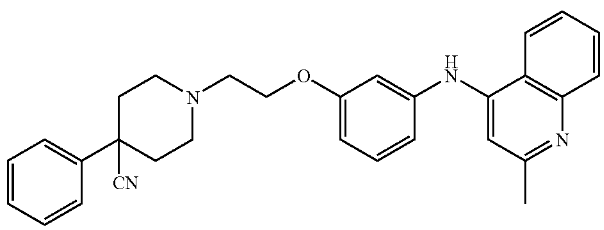 | 1-{2-[3-(2-Methylquinolin-4-yl amino)phenoxy]ethyl}-4-phenylpiperidine-4-carbonitrile | yellow solid | 463.32 |
| 47 | 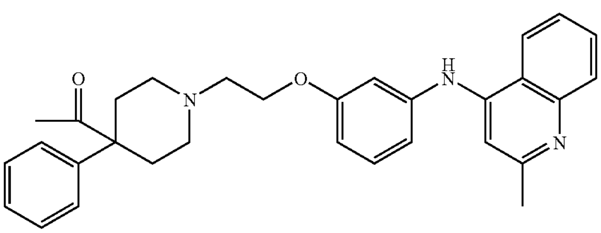 | 1-(1-{2-[3-(2-Methylquinolin-4-ylamino)phenoxy]ethyl}-4-phenylpiperidin-4-yl)ethanone | yellow solid | 480.32 |
| 48 | 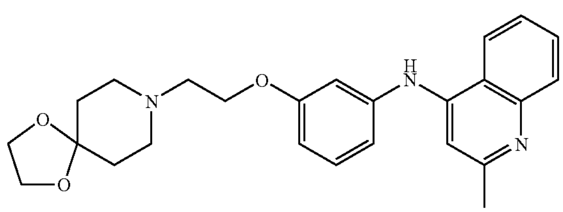 | {3-[2-(1,4-Dioxa-8-aza spiro[4.5]dec-8-yl)ethoxy]phenyl}-(2-methyl quinolin-4-yl)amine | pale yellow solid[b] | 420.26 |
| 49 | 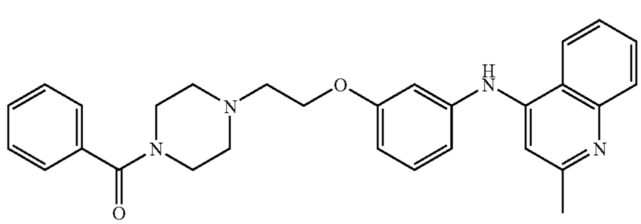 | 1-Benzoyl-4-{2-[3-(2-methyl quinolin-4-ylamino)phenoxy]ethyl}piperazine | yellow solid[b] | 467.33 |
| 50 | 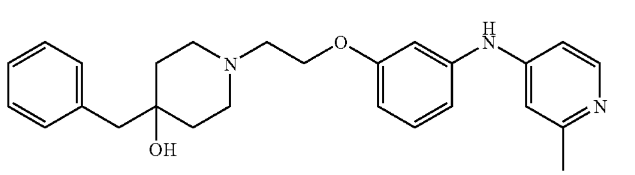 | 4-Benzyl-1-{2-[3-(2-methyl pyridin-4-ylamino)phenoxy]ethyl}piperidin-4-ol | white solid | 418.28 |

TABLE 2-continued

| Example | Structure | Chemical name | Physical description[a] | [M + H]+ |
|---|---|---|---|---|
| 51 | 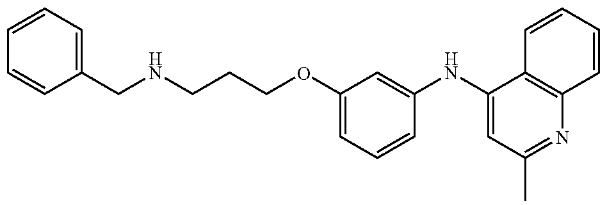 | [3-(2-Benzylaminopropoxy)phenyl]-(2-methylquinolin-4-yl)amine | yellow solid | 398.26 |
| 52 | 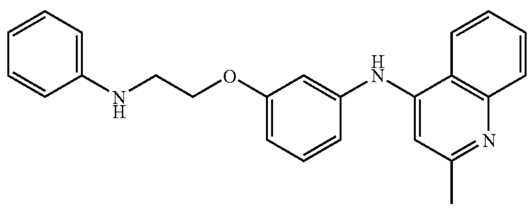 | (2-Methylquinolin-4-yl)-[3-(2-phenylaminoethoxy)phenyl]amine | yellow solid | 370.26 |
| 53 | 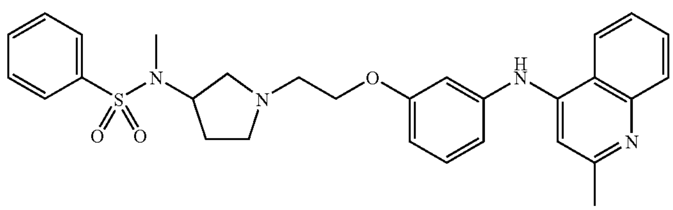 | N-Methyl-N-(1-{2-[3-(2-methylquinolin-4-ylamino)phenoxy]ethyl}pyrrolidin-3-yl)benzenesulfonamide | pale yellow solid | 517.28 |
| 54 | 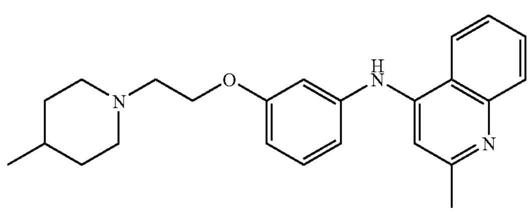 | {3-[2-(4-Methylpiperidin-1-yl)ethoxy]phenyl}-(2-methylquinolin-4-yl)amine | pale yellow solid | 376.25 |
| 55 | 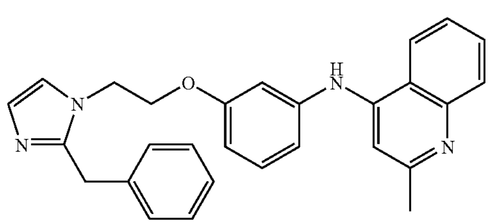 | {3-[2-(2-Benzylimidazol-1-yl)ethoxy]phenyl}-(2-methylquinolin-4-yl)amine | off-white foam[b] | 435.29 |
| 56 | 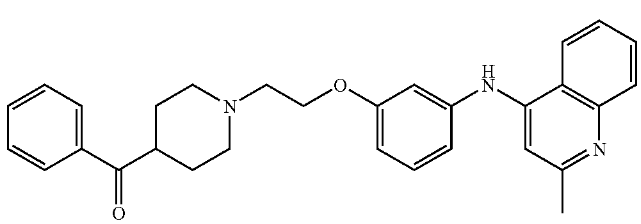 | (1-{2-[3-(2-Methylquinolin-4-ylamino)phenoxy]ethyl}piperidin-4-yl)phenylmethanone | off-white solid[b] | 466.29 |

TABLE 2-continued

| Example | Structure | Chemical name | Physical description[a] | [M + H]+ |
|---|---|---|---|---|
| 57 | 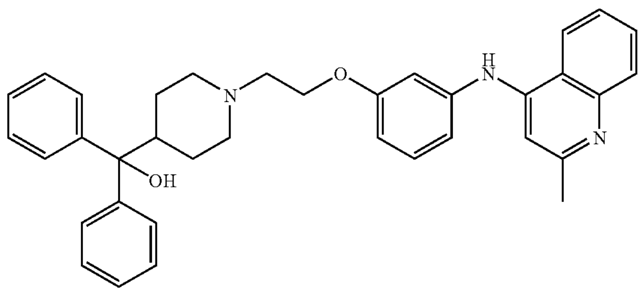 | (1-{2-[3-(2-Methylquinolin-4-ylamino)phenoxy]ethyl}piperidin-4-yl)diphenylmethanol | yellow solid | 544.30 |
| 58 | 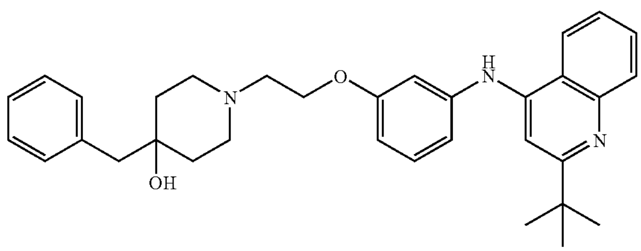 | 4-Benzyl-1-{2-[3-(2-tert-butyl quinolin-4-ylamino)phenoxy]ethyl}piperidin-4-ol | yellow solid | 510.39 |
| 59 | 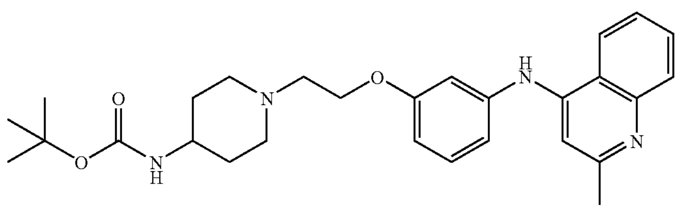 | tert-Butyl (1-{2-[3-(2-methyl quinolin-4-ylamino)phenoxy]ethyl}piperidin-4-yl)carbamate | pale yellow solid | 477.25 |
| 60 | 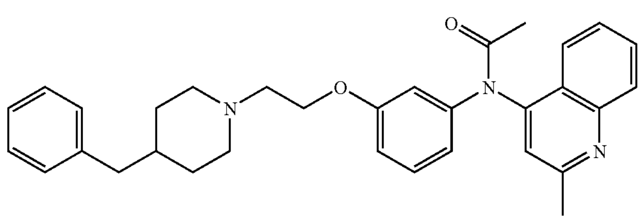 | N-{3-[2-(4-Benzylpiperidin-1-yl)ethoxy]phenyl}-N-(2-methyl quinolin-4-yl)acetamide | pale yellow solid[b] | 494.19 |
| 61 | 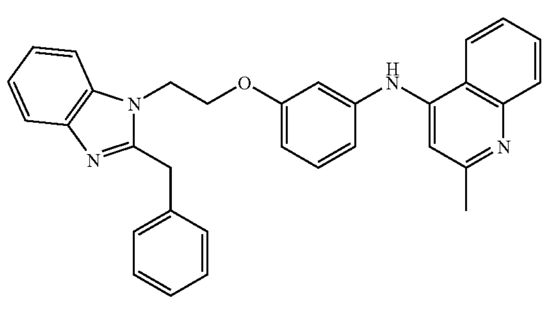 | {3-[2-(2-Benzylbenzo imidazol-1-yl)ethoxy]phenyl}-(2-methylquinolin-4-yl)amine | white solid | 485.29 |
| 62 | 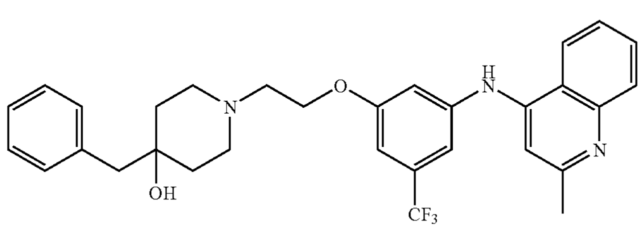 | 4-Benzyl-1-{2-[3-(2-methyl quinolin-4-ylamino)-5-trifluoromethylphenoxy]ethyl}piperidin-4-ol | yellow solid | 536.28 |

TABLE 2-continued

| Example | Structure | Chemical name | Physical description[a] | [M + H]+ |
|---|---|---|---|---|
| 63 | 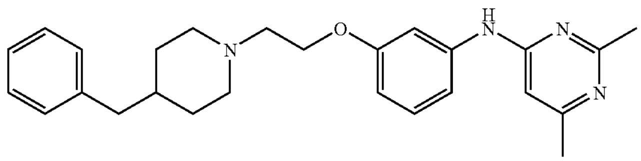 | {3-[2-(4-Benzylpiperidin-1-yl)ethoxy]phenyl}-(2,6-dimethyl pyrimidin-4-yl)amine | white solid[b] | 417.29 |
| 64 | 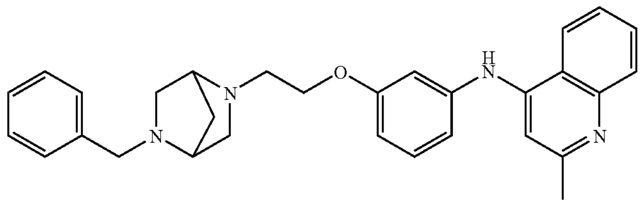 | {3-[2-(5-Benzyl-2,5-diaza bicyclo[2.2.1]hept-2-yl)ethoxy]phenyl}-(2-methyl quinolin-4-yl)amine | white amorphous solid[b] | 465.24 |
| 65 | 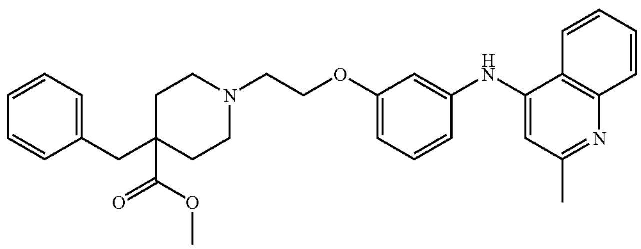 | Methyl 4-benzyl-1-{2-[3-(2-methylquinolin-4-ylamino)phenoxy]ethyl}piperidine-4-carboxylate | yellow powder | 510.25 |
| 66 | 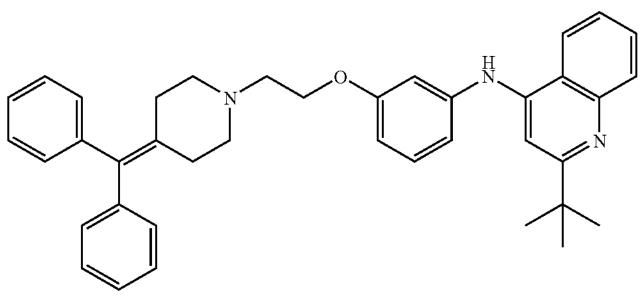 | {3-[2-(4-Benzhydrylidene piperidin-1-yl)ethoxy]phenyl}-(2-tert-butylquinolin-4-yl)amine | yellow amorphous solid | 568.33 |
| 67 | 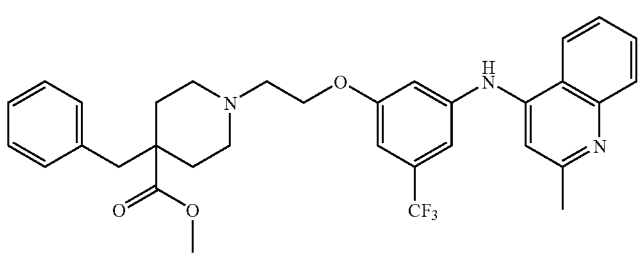 | Methyl 4-benzy-1-{2-[3-(2-methylquinolin-4-ylamino)-5-trifluoro-methylphenoxy]ethoxy}piperidine-4-carboxylate | pale yellow solid | 578.24 |
| 68 | 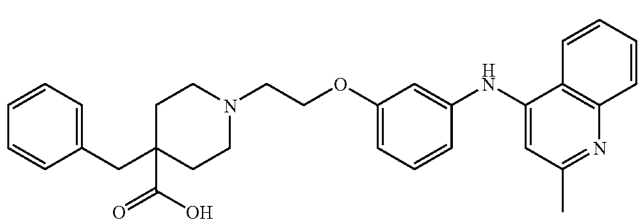 | 4-Benzyl-1-{2-[3-(2-methyl quinolin-4-ylamino)phenoxy]ethyl}piperidine-4-carboxylic acid | yellow powder | 496.25 |

TABLE 2-continued

| Example | Structure | Chemical name | Physical description[a] | [M + H]+ |
|---|---|---|---|---|
| 69 | 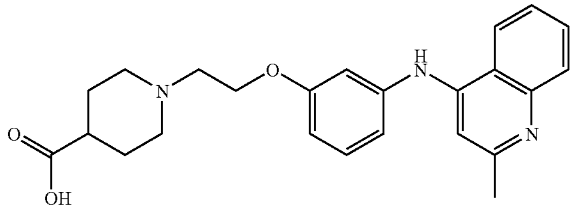 | 1-{2-[3-(2-Methylquinolin-4-yl amino)phenoxy]ethyl} piperidine-4-carboxylic acid | yellow solid[e] | 406.13 |
| 70 | 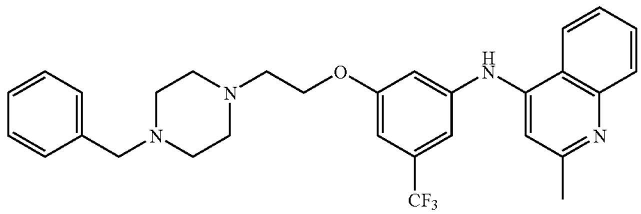 | {3-[2-(4-Benzylpiperazin-1-yl) ethoxy]-5-trifluoromethyl penyl}-(2-methyl quinolin-4-yl)amine | yellow solid | 521.23 |
| 71 | 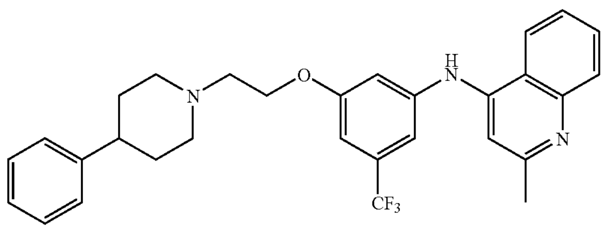 | (2-Methylquinolin-4-yl)-{3-[2-(4-phenylpiperidin-1-yl) ethoxy]-5-trifluoromethyl phenyl}amine | yellow solid | 506.23 |
| 72 | 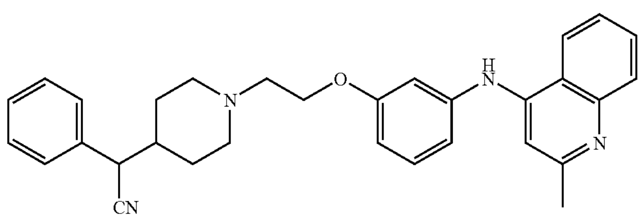 | (1-{2-[3-(2-Methylquinolin-4-yl amino)phenoxy]ethyl} piperidin-4-yl)phenyl acetonitrile | yellow solid | 477.30 |
| 73 | 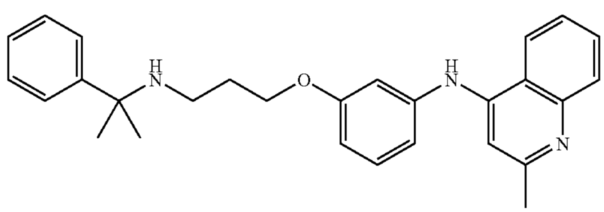 | {3-[3-(1-Methyl-1-phenyl ethylamino)propoxy] phenyl}-(2-methyl-quinolin-4-yl)amine | yellow solid | 426.15 |
| 74 | 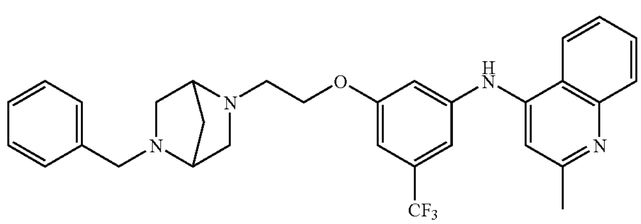 | {3-[2-(5-Benzyl-2,5-diaza bicyclo[2.2.1]hept-2-yl) ethoxy]-5-trifluoromethyl phenyl}-(2-methyl quinolin-4-yl)amine | yellow solid[f] | 533.26 |
| 75 | 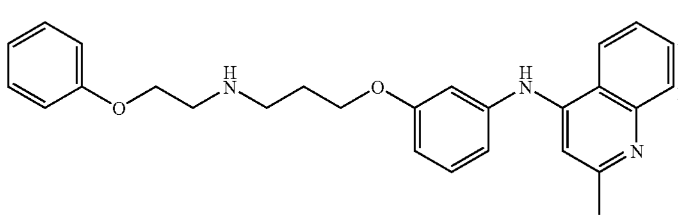 | (2-Methylquinolin-4-yl)-{3-[3-(2-phenoxyethylamino) propoxy]phenyl}amine | pale yellow solid | 428.27 |

TABLE 2-continued

| Example | Structure | Chemical name | Physical description[a] | [M + H]+ |
|---|---|---|---|---|
| 76 | 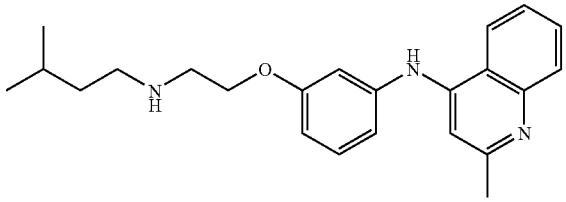 | {3-[2-(3-Methylbutylamino)ethoxy]phenyl}-(2-methyl quinolin-4-yl)amine | yellow oil[b] | 364.23 |

[a]DiHCl salt unless otherwise noted
[b]Parent compound
[c]+CO2
[e]sodium salt
[f]TriHCl salt The compound of Example 77 was synthesized by benzylation of the compound of Example 2 using a standard method (NaH/BnBr/DMF). The synthesis of Example 2 is the same as for Example 1 except that 3-nitrobenzoyl chloride was used instead of 3-nitrobenzenesulfonyl chloride.

The compounds of Examples 78 to 101 were synthesized in the same manner as the compound of Example 2.

The compound of Example 102 was synthesized by demethylation of the compound of Example 99 using a standard method (BBr$_3$/CH$_2$Cl$_2$).

The compound of Example 103 was synthesized in the same manner as the compound of Example 2.

The compound of Example 104 was synthesized in the same manner as the compound of Example 2 except that the last step was a standard coupling with 2,4-dimethoxybenzenesulfonyl chloride.

The compound of Example 105 was synthesized in the same manner as the compound of Example 2.

The structures, chemical names and physical descriptions for the compounds of Examples 77-173 are set forth in Table 3.

The compound of Example 106 was synthesized by demethylation of the compound of Example 103 using a standard method (BBr$_3$/CH$_2$Cl$_2$).

The compound of Example 107 was synthesized in the same manner as the compound of Example 2 using 2,4,6-trimethyl-3-nitrobenzoyl chloride instead of 3-nitrobenzoyl chloride. 2,4,6-Trimethyl-3-nitrobenzoyl chloride was synthesized by treatment of 2,4,6-trimethyl-3-nitrobenzoic acid (C Wu et al: J Med Chem 1999, 42:4485-4499) with POCl$_3$.

The compounds of Examples 108 and 109 were synthesized in the same manner as the compound of Example 2.

The preparation of the compound of Example 110 is shown.

The compound of Example 111 was synthesized in the same manner as the compound of Example 79 except that 2,3,4,5-tetrahydro-1H-benzo[c]azepine (A I Meyers, R H Hutchings: Tetrahedron 1993, 49:1807-1820) was used instead of 1,2,3,4-tetrahydro-isoquinoline.

The compound of Example 112 is shown.

The compound of Example 113 was synthesized in the same manner as the compound of Example 110.

The preparation of Example 114 is shown.

The compound of Example 115 was synthesized in a 3-step sequence: coupling of 36 with 2-amino-5-nitrobenzoic acid (EDCI/HOBT/DIPEA/DMF), then steps 4 and 5 of Example 45.

The compounds of Examples 116 to 118 were synthesized in the same manner as the compound of Example 2.

The compound of Example 119 was synthesized in the same manner as the compound of Example 79 except that 7-phenyl-1,2,3,4-tetrahydroisoquinoline was used instead of 1,2,3,4-tetrahbydroisoquinoline 7-Phenyl-1,2,3,4-tetrahydroisoquinoline was synthesized by a standard Suzuki coupling between phenylboronic acid and 7-bromo-1,2,3,4-tetrahydroisoquinoline (GE Stokker: Tetrahedron Lett 1996:5453-5456).

The compound of Example 120 was synthesized in the same manner as the compound of Example 79 except that 7-fluoro-1,2,3,4-tetrahydroisoquinoline (GE Stokker: Tetrahedron Lett 1996:5453-5456) was used instead of 1,2,3,4-tetrahydroisoquinoline.

The compounds of Examples 121 to 122 were synthesized in the same manner as the compound of Example 120.

The compound of Example 123 was synthesized in the same manner as the compound of Example 2.

The compound of Example 124 was synthesized in the same manner as the compound of Example 120.

The compound of Example 125 was synthesized in the same manner as the compound of Example 79 except that the last step was a Buchwald coupling (Buchwald et al: Tetrahedron Lett 1995 36:3609) with 5-bromo-m-xylene instead of the acid catalyzed coupling with 5.

The compound of Example 126 was synthesized in the same manner as the compound of Example 2.

The compounds of Examples 127 and 128 were synthesized in the same manner as the compound of Example 120.

The compounds of Examples 129 and 130 were synthesized in the same manner as the compound of Example 2.

The compound of Example 131 was synthesized in the same manner as the compound of Example 120.

The compound of Examples 132 to 135 were synthesized in the same manner as the compound of Example 2.

The compound of Example 136 was synthesized in the same manner as the compound of Example 120.

The compounds of Examples 137 to 140 were synthesized in the same manner as the compounds of Example 2.

The compound of Example 141 was synthesized by a Buchwald coupling (Buchwald et al: Tetrahedron Lett 1995 36:3609) between 3-bromo-N-[2-(3,4-dihydro-1H-isoquinolin-2-yl)ethyl]benzamide and 4-amino-2-dimethylaminopyridine (Hnschberger A et al, Tetrahedron 2000, 56:1361-1367).

The compound of Example 142 was synthesized in the same manner as the compound of Example 125.

The compound of Example 143 was synthesized in the same manner as the compound of Example 2.

The preparation of Example 144 is shown.

The compounds of Examples 145 and 146 were synthesized in the same manner as the compound of Example 2.

The compound of Example 147 was synthesized in the same manner as the compound of Example 144.

The compound of Example 148 was synthesized in the same manner as the compound of Example 2.

The compound of Example 149 was synthesized in the same manner as the compound of Example 141.

The compound of Example 150 was synthesized in the same manner as the compound of Example 2.

The compound of Example 151 was synthesized in the same manner as the compound of Example 144.

The compound of Example 152 was synthesized by hydrolysis (1 eq NaOH/THF/MeOH/H$_2$O) of methyl 4-({2-[3-(2-methyl quinolin-4-ylamino)benzoylamino]ethylamino}-methyl)benzoate which was synthesized in the same manner as for Example 144.

The compound of Example 153 was synthesized in the same manner as the compound of Example 2.

The compound of Example 154 was synthesized by hydrolysis (1 eq NaOH/THF/MeOH/H$_2$O) of the compound of Example 151.

The compound of Example 155 was synthesized in the same manner as the compound of Example 141.

The compound of Example 156 was synthesized in the same manner as the compound of Example 2.

The compound of Example 157 was synthesized in the same manner as the compound of Example 151 and during the reductive amination step the lactam ring was formed.

The compound of Example 158 was synthesized in the same manner as the compound of Example 12 except that 2-bromo-2-methyl-N-(3-nitrobenzyl)propionamide and 40 were used instead of 3-nitrobenzyl bromide and dimethylamine, respectively. 2-Bromo-2-methyl-N-(3-nitrobenzyl)propionamide was synthesized by a standard coupling (HOBt/EDCI/DIPEA/DMF) of 2-bromo-2-methylpropionic acid and 3-nitroaniline.

The compounds of Examples 159 to 161 were synthesized in the same manner as the compound of Example 2.

The compounds of Examples 162 to 168 were synthesized in the same manner as the compound of Example 144.

The preparation of the compound of Example 169 is shown.

The compounds of Examples 170 to 173 were synthesized in the same manner as the compound of Example 144.

EXAMPLE 110

2-[2-(3,4-Dihydro-1H-isoquinolin-2-yl)ethyl]-4-(2-methylquinolin-4-ylamino)-2,3-dihydroisoindol-1-one

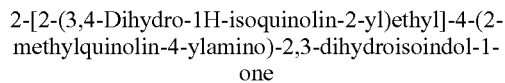

34

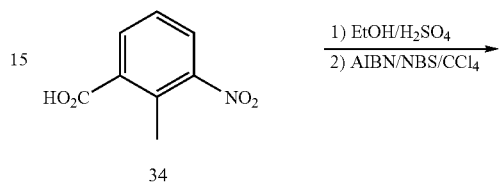

35

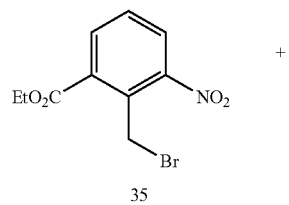

36

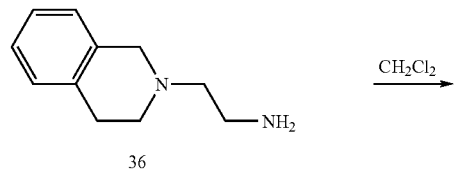

37

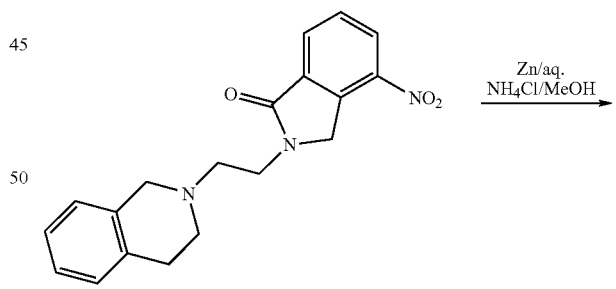

38

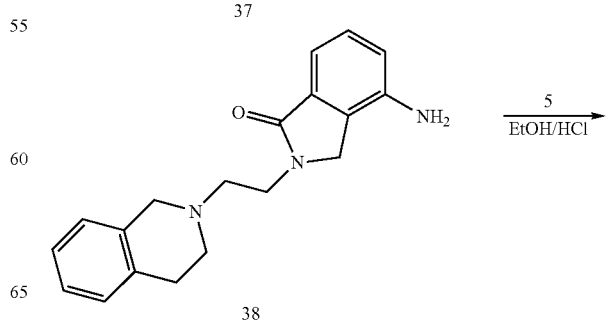

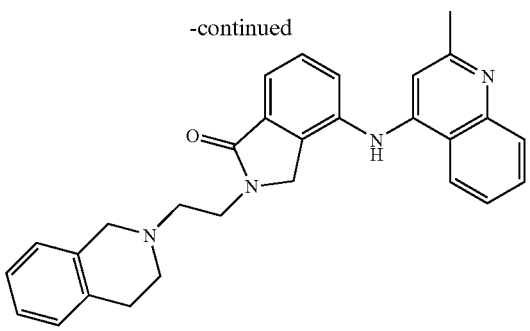

Example 110

Step 1. Ethyl 2-methyl-3-nitrobenzoate.

To a solution of 2-methyl-3-nitrobenzoic acid (34) (3.4 g, 18.8 mmol) in EtOH (60 mL) was added conc $H_2SO_4$ (1 mL) dropwise. The resulting solution was heated at 75° C. for 72 hours before the solvent was evaporated. The residue was basified with saturated aq. $NaHCO_3$ and extracted with EtOAc, washed with water, brine. The organic layer was dried over $MgSO_4$ and concentrated to give the desired ethyl ester (3.9 g, ~quantitative).

Step 2. Ethyl 2-bromomethyl-3-nitrobenzoate (35).

To a solution of ethyl 2-methyl-3-nitrobenzoate (3.9 g, 18.6 mmol) in $CCl_4$ (56 mL) were sequentially added AIBN (0.61 g, 20% mol) and NBS (3.5 g, 19.5 mmol). The mixture was heated at 80° C. for 72 hours before it was allowed to cool to room temperature. The resulting precipitate was filtered through a plug of silica gel, washed with dichloromethane, and the filtrate was concentrated to give a 1:1 mixture of 35 (3.1 g, 58%) and the starting material.

Step 3. 2-[2-(3,4-Dihydro-1H-isoquinolin-2-yl)ethyl]-4-nitro-2,3-dihydroisoindol-1-one (37).

To a solution of 2-(3,4-dihydro-1H-isoquinolin-2-yl)ethylamine (36) (0.36 g, 2.0 mmol) in dichloromethane (4 mL) was added the bromide 35 (0.75 g, 2.6 mmol) in dichloromethane (5 mL) at 0° C. The mixture was allowed to warm to room temperature and stirred for 16 hours before it was poured into saturated $NaHCO_3$ (aq. 50 mL) and extracted with dichloromethane (2×50 mL). The combined organic layers were washed with water (70 mL), brine (70 mL), dried over $MgSO_4$, and concentrated on a rotavap. The residue was chromatographed on silica gel eluting with 3:1 to 1:1 hexanes/EtOAc to give 37 (0.39 g, 57%).

Step 4. 4-Amino-2-[2-(3,4-dihydro-1H-isoquinolin-2-yl)ethyl]-2,3-dihydroisoindol-1-one (38).

To a solution of 37 (0.38 g, 1.1 mmol) in methanol (6 mL) was added a solution of ammonium chloride (0.13 g, 2.42 mmol) in water (1.5 mL). Zinc powder (0.49 g, 7.4 mmol) was then added portionwise and the resulting mixture was stirred for 2 hours. The solids were filtered and washed with methanol, the filtrate was basified with saturated sodium bicarbonate (aq.), and the resulting mixture was extracted with EtOAc. The organic layer was dried over $MgSO_4$ and concentrated to give 38 (0.31 g, 88%).

Step 5. 2-[2-(3,4-Dihydro-1H-isoquinolin-2-yl)ethyl]-4-(2-methylquinolin-4-ylamino)-2,3-dihydroisoindol-1-one.

The title compound was prepared from 38 by the procedure of Example 1 Step 3.

EXAMPLE 112

N-[2-(3,4-Dihydro-1H-isoquinolin-2-yl)-1,1-dimethylethyl]-3-(2-methylquinolin-4-ylamino)benzamide

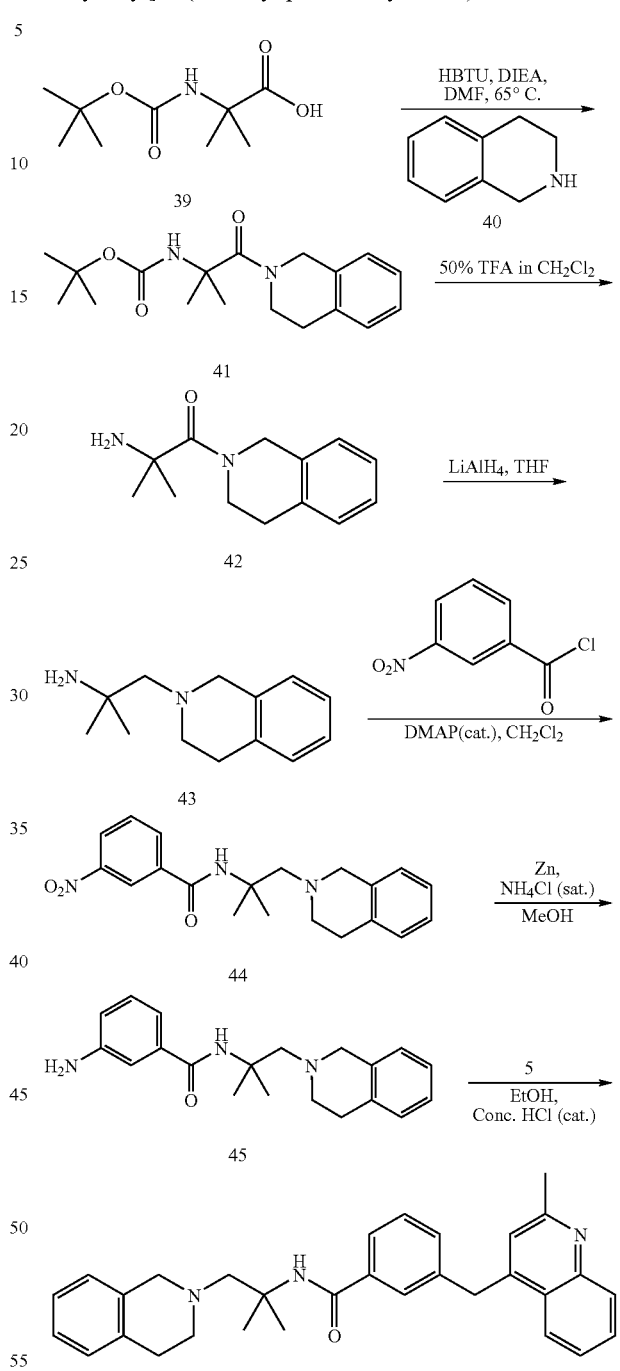

Example 112

Step 1. tert-Butyl [2-(3,4-dihydro-1H-isoquinolin-2-yl)-1,1-dimethyl-2-oxoethyl]carbamate (41).

To a solution of 39 (0.28 g, 1.38 mmol), 1,2,3,4-tetrahydroisoquinoline (40) (0.18 g, 1.38 mmol) and diisopropylethylamine (0.50 g, 3.85 mmol) in anhydrous DMF (5 mL) was added HBTU (0.72 g, 1.90 mmol). The mixture was heated at 65° C. overnight before it was allowed to cool to room temperature, and diluted with EtOAc (100 mL). The resulting solution was sequentially washed with 1N HCl (2×100 mL), 1N NaOH (2×100 mL) and brine (100 mL).

The residue after drying (Na₂SO₄) and concentration of the organic layer was purified on silica gel column to give 41 (0.36 g, 82%).

Step 2. 2-Amino-1-(3,4-dihydro-1H-isoquinolin-2-yl)-2-methylpropan-1-one (42).

A solution of 41 (0.36 g, 1.1 mmol) in TFA (5 mL) and CH₂Cl₂ (5 mL) was stirred at room temperature for 40 minutes. The mixture was concentrated in vacuo and the residue was dissolved in EtOAc (50 mL). Upon sequential washings with 1 N NaOH (2×50 mL) and brine (50 mL), the organic solution was dried (Na₂SO₄) and concentrated to afford 42 (0.20 g, 77%).

Step 3. 2-(3,4-Dihydro-1H-isoquinolin-2-yl)-1,1-dimethylethylamine (43).

To a solution of 42 (0.20 g, 0.91 mmol) in anhydrous THF (4 mL) at 0° C. was added LiAlH₄ (1.0 M in THF, 3.0 mL, 3.0 mmol). The resulting mixture was heated under reflux overnight before it was allowed to cool to room temperature. Excess LiAlH4 was destroyed with slow addition of Na₂SO₄ 10H₂O at 0° C. until gas evolution ceased. The solids were filtered off and the filtrate was concentrated to give 43 (0.14 g, 79%).

Step 4. N-[2-(3,4-Dihydro-1H-isoquinolin-2-yl)-1,1-dimethylethyl]-3-nitrobenzamide (44).

To a solution of 3-nitrobenzoylchloride (0.14 g, 0.75 mmol) and 43 (0.15 g, 0.76 mmol) in anhydrous CH₂Cl₂ (7 mL) was added DMAP (10 mg). The reaction was stirred at room temperature overnight before it was diluted with EtOAc (100 mL). Upon sequential washings with 1 N NaOH (2×100 mL), water (200 mL), the organic mixture was dried (Na₂SO₄) and concentrated under reduced pressure to give 44 (0.31 g, 100%) as a thick dark oil.

Step 5. 3-Amino-N-[2-(3,4-dihydro-1H-isoquinolin-2-yl)-1,1-dimethylethyl]benzamide (45).

45 was prepared from 44 by the procedure of Example 110 Step 4.

Step 6. N-[2-(3,4-Dihydro-1H-isoquinolin-2-yl)-1,1-dimethylethyl]-3-(2-methylquinolin-4-ylamino)benzamide.

The title compound was prepared from 45 by the procedure of Example 1 Step 3.

EXAMPLE 114

N-[2-(3,4-Dihydro-1H-isoquinolin-2-yl)-2-methylpropyl]-3-(2-methylquinolin-4-ylamino)benzamide

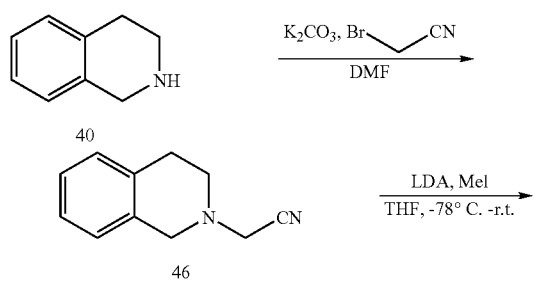

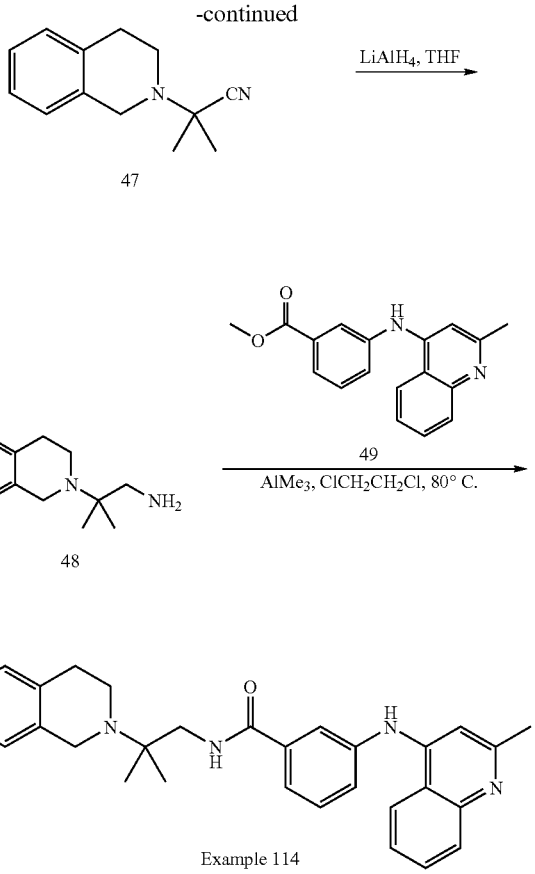

Step 1. (3,4-Dihydro-1H-isoquinolin-2-yl)acetonitrile (46).

46 was prepared from 40 by the procedure of Example 13 Step 2.

Step 2. 2-(3,4-Dihydro-1H-isoquinolin-2-yl)-2-methylpropionitrile (47).

To a solution of 46 (1.27 g, 7.38 mmol) in anhydrous THF (20 mL) was slowly added LDA (2.0 M in THF, 8.1 mL, 16.2 mmol) at −78° C. The resulting mixture was stirred at −78° C. for 30 minutes before the addition of iodomethane (4.20 g, 29.6 mmol). The cold bath was removed and the reaction was allowed to warm up to room temperature and stirred overnight. To work up, the mixture was diluted with EtOAc (150 mL), the resulting solution washed with 1 N NaOH (2×100 mL) and brine (100 mL). The organic layer was dried (Na₂SO₄), concentrated, and the residue purified on a silica gel column to afford 47 (0.38 g, 26%).

Step 3. 2-(3,4-Dihydro-1H-isoquinolin-2-yl)-2-methylpropylamine (48).

48 was prepared from 47 by the procedure of Example 112 Step 3.

Step 4. N-[2-(3,4-Dihydro-1H-isoquinolin-2-yl)-2-methylpropyl]-3-(2-methylquinolin-4-ylamino)benzamide.

48 and 49 were reacted in the presence of AlMe₃ and ClCH₂CH₂Cl at 80° by the procedure of Lipton, M E; Basha, A; Weinreb, M: *Organic Syntheses*, 1988, 6, 492-495.

EXAMPLE 144

N-(2-Benzylaminoethyl)-3-(2-methylquinolin-4-ylamino)benzamide

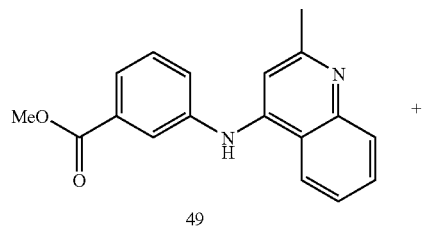

EXAMPLE 169

3-(2-Methylquinolin-4-ylamino)-N-[2-(4-phenyl-3,4-dihydro-1H-isoquinolin-2-yl)ethyl]benzamide

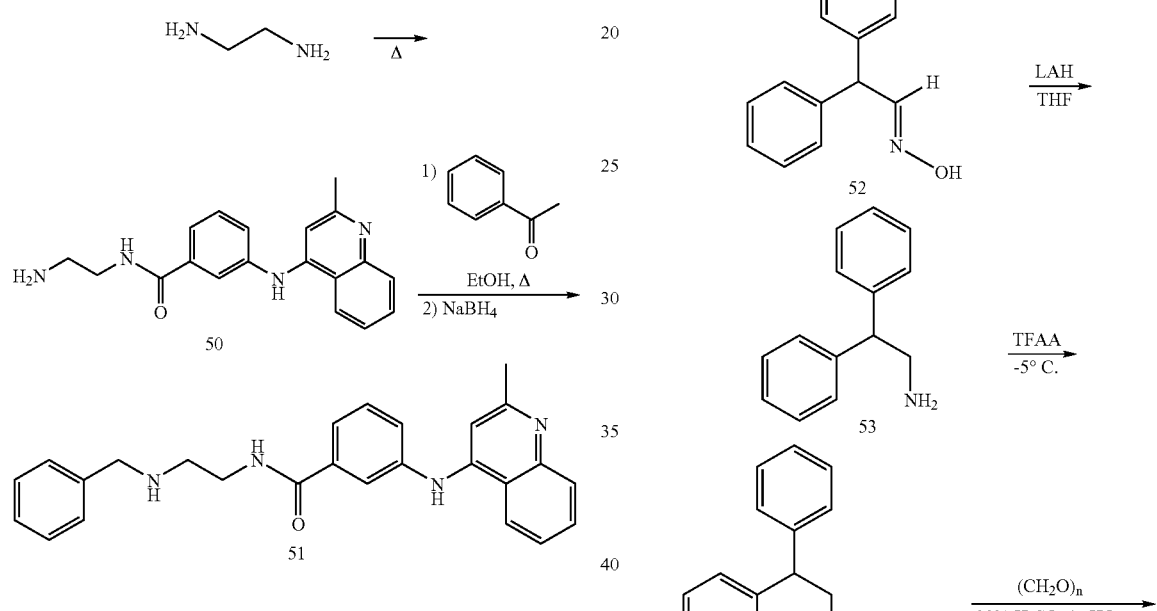

Step 1. N-(2-Aminoethyl)-3-(2-methylquinolin-4-ylamino)benzamide (50).

A mixture of methyl ester 49 (2.0 g, 6.8 mmol) and ethylenediamine (30 mL) was heated at 110° C. for 2 hours before it was poured into ice water (300 mL). The precipitate was filtered and dried under high vaccum to give 50 (2.0 g, 91%) as an off-white solid, which was used without further purification.

Step 2. N-(2-Benzylaminoethyl)-3-(2-methylquinolin-4-ylamino)benzamide.

A solution of amine 50 (0.22 g, 0.68 mmol) and benzaldehyde (0.07 mL, 0.08 mmol) in EtOH (3.0 mL) was heated at reflux overnight before it was allowed to cool to room temperature. Sodium borohydride (0.04 g, 0.80 mmol) was added and the reaction was stirred at room temperature for 1 hour. The mixture was mixed with 2N NaOH (3.0 mL), brine (2.0 mL), and extracted with 7:3 $CH_2Cl_2$/MeOH (3×5.0 mL). The combined organic layers were dried ($K_2CO_3$) and concentrated under reduced pressure. The residue was purified by flash chromatrography ($SiO_2$, gradient elution, 3:1 hexanes/EtOAc to 7:3 $CH_2Cl_2$/MeOH) to yield the desired product (0.15 g, 62%) as a pale yellow solid.

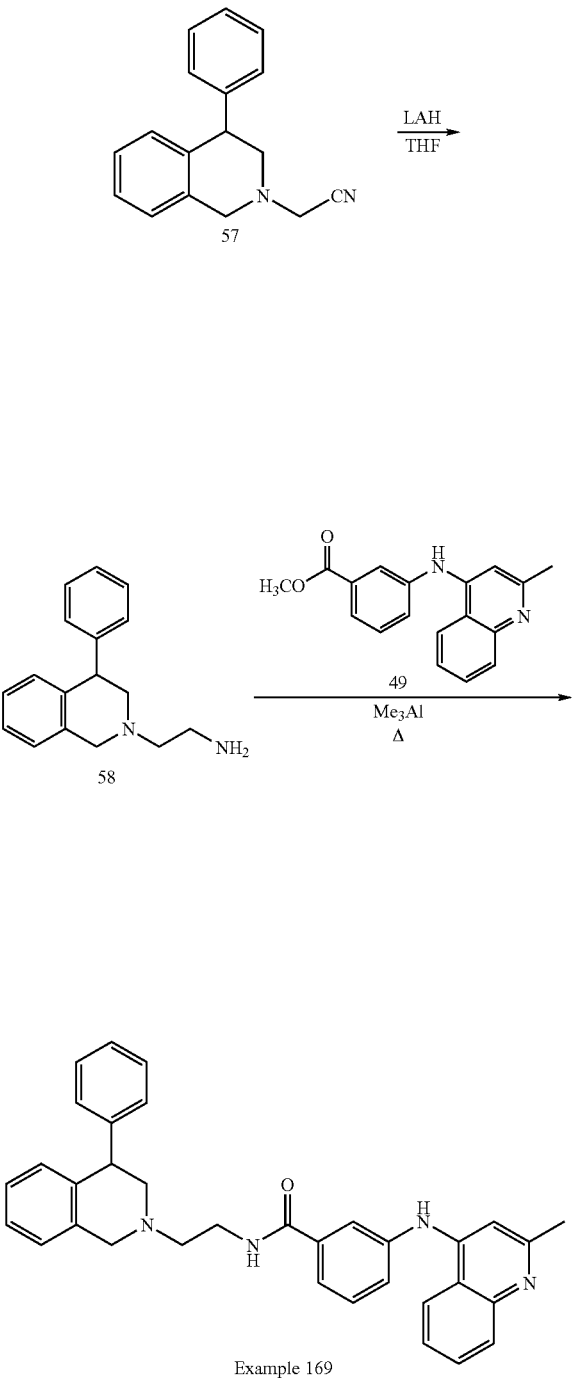

Example 169 pressure. The residue was washed with water (50 mL) and extracted with EtOAc (3×50 mL). The combined organic layers were dried (MgSO$_4$) and concentrated under reduced pressure to give 52 (4.0 g, 93%).

Step 2. 2,2-Diphenylethylamine (53).

To a solution of oxime 52 (4.0 g, 18.9 mmol) in THF (50 mL) was added LiAlH$_4$ (1.0 M solution in THF, 28.3 mL, 28.3 mmol) at 0° C. and the mixture was stirred at room temperature for 4 hours. Sodium sulfate decahydrate was added and the reaction was stirred for an additional hour. The solids were filtered and the filtrate was concentrated under reduced pressure to give 53 (3.14 g, 84%) as a yellow oil.

Step 3. N-(2,2-Diphenylethyl)-2,2,2-trifluoroacetamide (54).

To neat TFAA (14.9 g, 63.6 mmol) at −5° C. was added amine 53 (3.14 g, 15.9 mmol) dropwise over a 10 minute period and the resulting mixture was stirred for 2 hours. The crude mixture was poured into ice water and extracted with ethyl acetate (3×60 mL). The combined organic layers were dried (MgSO$_4$) and concentrated under reduced pressure. Purification by recrystallization (hexanes/ethyl acetate) provided 54 (1.5 g, 32%) as a yellow solid.

Step 4. 4-Pheny-1-trifluoroacetyl-3,4-dihydro-1H-isoquinoline (55).

Compound 54 (1.5 g, 5.11 mmol) and paraformaldehyde (1.2 g, 7.67 mmol) were added in small portions simultaneously to a solution of H$_2$SO$_4$ (4 mL) in HOAc (16 mL). The reaction mixture was stirred for 12 hours and then poured into ice water. The aqueous mixture was extracted with ethyl acetate (3×50 mL) and the combined organic layers were dried (MgSO$_4$) and concentrated under reduced pressure to yield 55 (1.0 g, 66%) a yellow solid.

Step 5. 4-Phenyl-1,2,3,4-tetrahydroisoquinoline (56).

To a solution of 55 (0.9 g, 2.94 mmol) in MeOH (10 mL) were added water (2 mL), KOH (0.33 g, 5.89 mmol), and the reaction was stirred at room temperature for 12 hours. The mixture was washed with a saturated sodium chloride solution and extracted with 7:3 CH$_2$Cl$_2$/MeOH (3×10 mL). The combined organic layers were dried (K$_2$CO$_3$) and concentrated under reduced pressure to give 56 (0.70 g. 100%) as a yellow oil.

Step 6. (4-Phenyl-3,4-dihydro-1H-isoquinolin-2-yl)acetonitrile (57).

57 was prepared from 56 by the procedure of Example 13 Step 2.

Step 7. 2-(4-Phenyl-3,4-dihydro-1H-isoquinolin-2-yl)ethylamine (58).

58 was prepared from 57 by the procedure of Example 112 Step 3.

Step 8. 3-(2-Methylquinolin-4-ylamino)-N-[2-(4-phenyl-3,4-dihydro-1H-isoquinolin-2-yl)ethyl]benzamide.

The title compound was prepared by reacting 58 with 49 by the procedure of Lipton, MF; Basha, A; Weinreb, M: *Organic Syntheses*, 1988, 6, 492-495.

Step 1. Diphenylacetaldehyde oxime (52).

To a solution of diphenylacetaldehyde (51) (4.0 g, 20.3 mmol) in EtOH (50 mL) were sequentially added hydroxylamine hydrochloride (1.41 g, 20.3 mmol) and 2 N NaOH (aq. 5 mL). The reaction was stirred at room temperature overnight followed by removal of EtOH under reduced

TABLE 3

| Example | Structure | Chemical name | Physical description[a] | [M + H]+ |
|---------|-----------|---------------|-------------------------|----------|
| 77 | 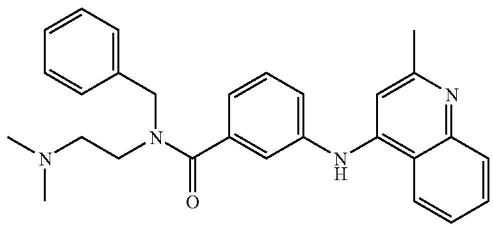 | N-Benzyl-N-(2-dimethyl aminoethyl)-3-(2-methylquinolin-4-yl amino)-benzamide | yellow solid[b] | 439.28 |
| 78 | 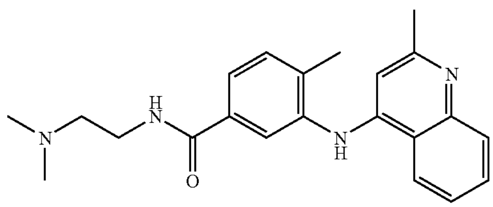 | N-(2-Dimethylaminoethyl)-4-methyl-3-(2-methylquinolin-4-yl amino)benzamide | Light yellow solid[d] | 363.32 |
| 79 | 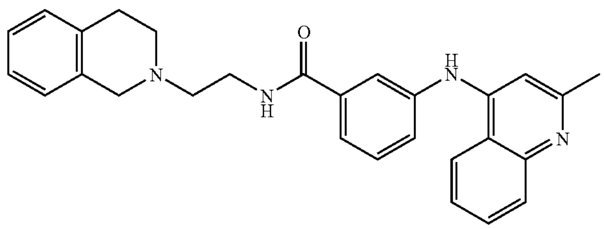 | N-[2-(3,4-Dihydro-1H-isoquinolin-2-yl)ethyl]-3-(2-methyl quinolin-4-ylamino)benzamide | Light yellow solid | 437.22 |
| 80 | 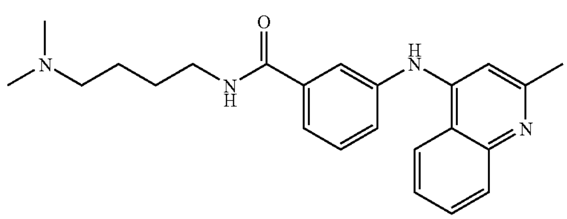 | N-(4-Dimethylaminobutyl)-3-(2-methylquinolin-4-ylamino) benzamide | yellowish solid[b] | 377.26 |
| 81 | 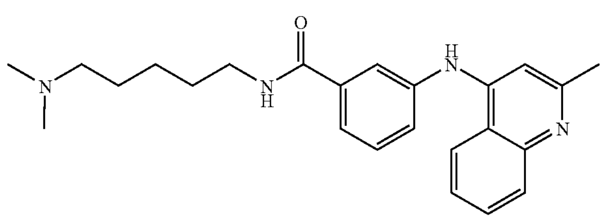 | N-(5-Dimethylaminopentyl)-3-(2-methylquinolin-4-ylamino)benzamide | yellow oil[b] | 391.28 |
| 82 | 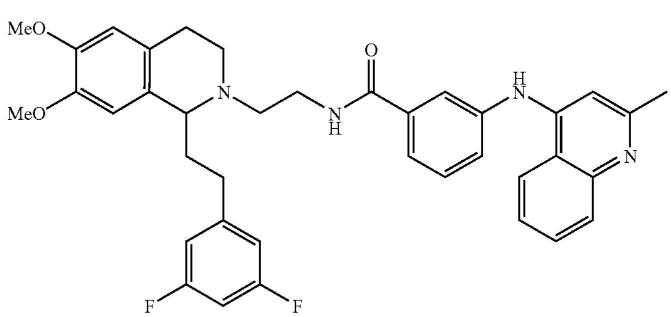 | N-(2-{1-[2-(3,5-Difluorophenyl)ethyl]-6,7-dimethoxy-3,4-dihydro-1H-isoquinolin-2-yl}ethyl)-3-(2-methyl quinolin-4-ylamino)benzamide | off-white solid[b] | 637.31 |

TABLE 3-continued

| Example | Structure | Chemical name | Physical description[a] | [M + H]+ |
|---|---|---|---|---|
| 83 | 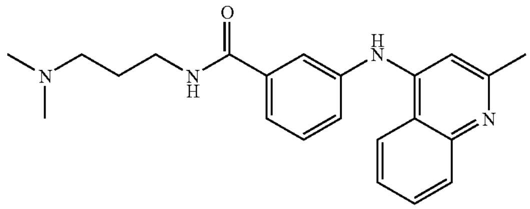 | N-(3-Dimethylaminopropyl)-3-(2-methylquinolin-4-ylamino)benzamide | yellow solid | 363.31 |
| 84 | 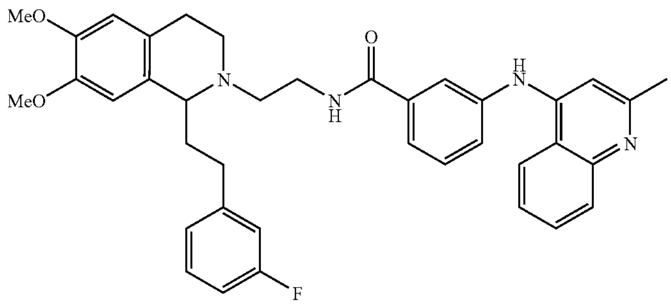 | N-(2-{1-[2-(3-Fluorophenyl)ethyl]-6,7-dimethoxy-3,4-dihydro-1H-isoquinolin-2-yl}ethyl)-3-(2-methylquinolin-4-ylamino)benzamide | white solid[d] | 619.38 |
| 85 | 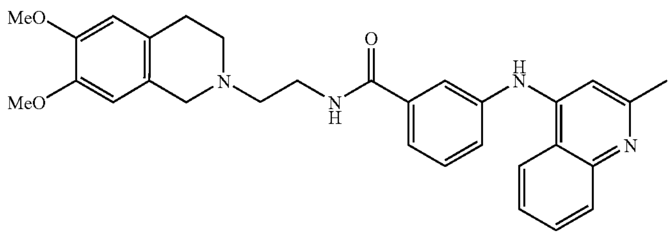 | N-[2-(6,7-Dimethoxy-3,4-dihydro-1H-isoquinolin-2-yl)ethyl]-3-(2-methylquinolin-4-ylamino)benzamide | yellow foam[b] | 497.34 |
| 86 | 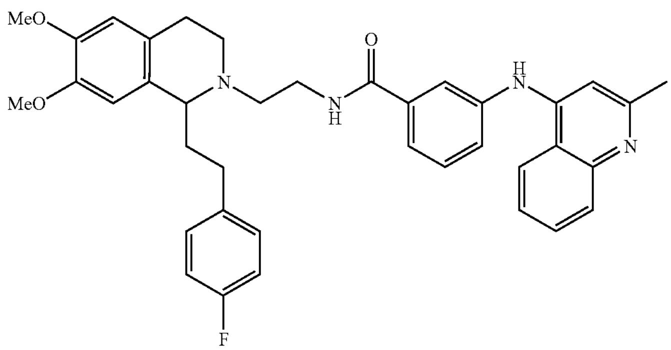 | N-(2-{1-[2-(4-Fluorophenyl)ethyl]-6,7-dimethoxy-3,4-dihydro-1H-isoquinolin-2-yl}ethyl)-3-(2-methylquinolin-4-ylamino)benzamide | yellow solid | 619.37 |
| 87 | 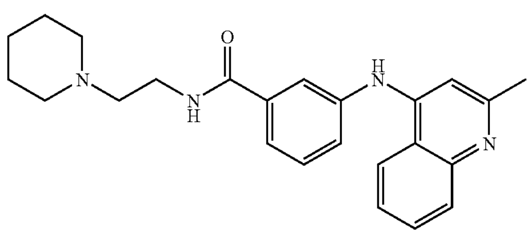 | 3-(2-Methylquinolin-4-ylamino)-N-(2-piperidin-1-ylethyl)benzamide | yellowish solid | 389.32 |
| 88 | 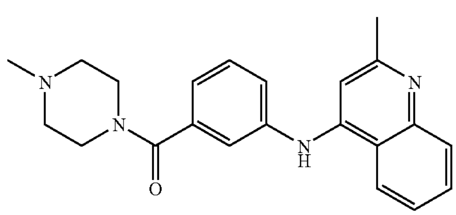 | 1-Methyl-4-[3-(2-methylquinolin-4-ylamino)benzoyl]piperazine | yellow solid | 361.32 |

TABLE 3-continued

| Example | Structure | Chemical name | Physical description[a] | [M + H]+ |
|---------|-----------|---------------|-------------------------|----------|
| 89 | 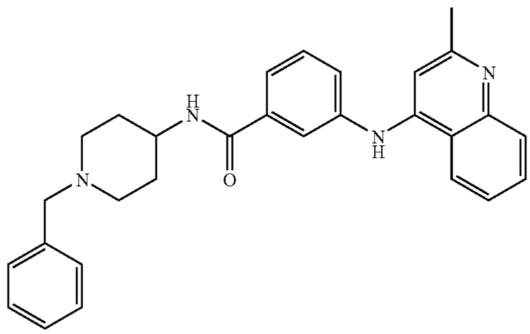 | N-(1-Benzylpiperidin-4-yl)-3-(2-methylquinolin-4-ylamino)benzamide | yellow solid | 451.41 |
| 90 | 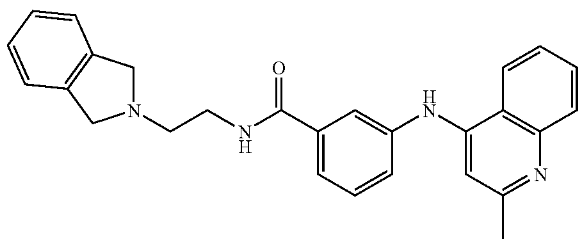 | N-[2-(1,3-Dihydroisoindol-2-yl)ethyl]-3-(2-methylquinolin-4-ylamino)benzamide | off-white solid | 423.35 |
| 91 | 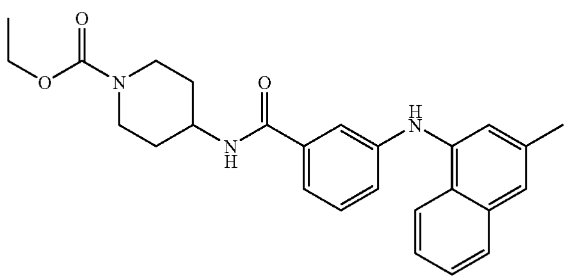 | Ethyl 4-[3-(2-methylquinolin-4-ylamino)benzoylamino]piperidine-1-carboxylate | yellow solod | 433.40 |
| 92 | 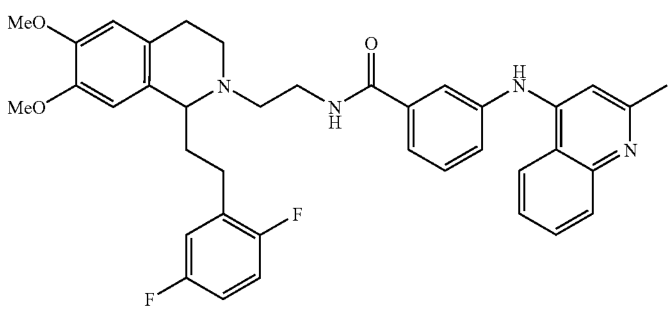 | N-(2-{1-[2-(2,5-Difluorophenyl)ethyl]-6,7-dimethoxy-3,4-dihydro-1H-isoquinolin-2-yl}ethyl)-3-(2-methylquinolin-4-ylamino)benzamide | white solid | 637.39 |
| 93 | 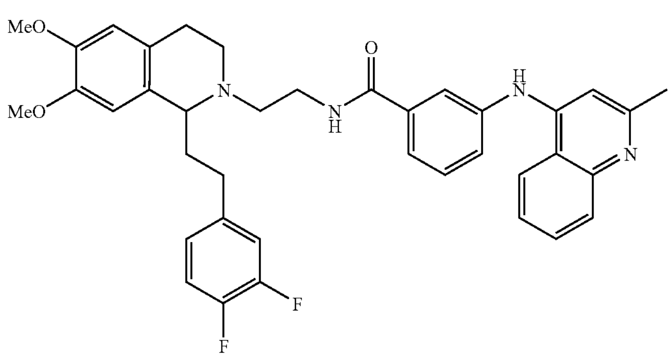 | N-(2-{1-[2-(3,4-Difluorophenyl)ethyl]-6,7-dimethoxy-3,4-dihydro-1H-isoquinolin-2-yl}ethyl)-3-(2-methylquinolin-4-ylamino)benzamide | yellow solid | 637.33 |

TABLE 3-continued

| Example | Structure | Chemical name | Physical description[a] | [M + H]+ |
|---|---|---|---|---|
| 94 | 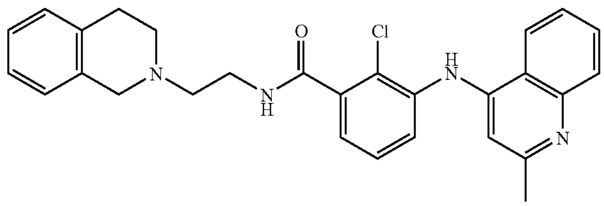 | 2-Chloro-N-[2-(3,4-dihydro-1H-isoquinolin-2-yl)ethyl]-3-(2-methyl-quinolin-4-ylamino)benzamide | white solid | 471.29 |
| 95 | 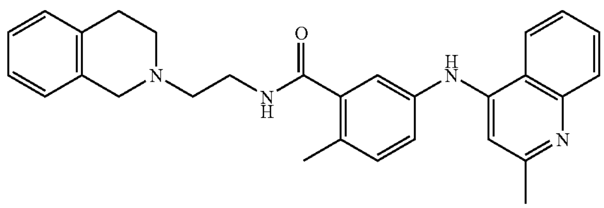 | N-[2-(3,4-Dihydro-1H-isoquinolin-2-yl)ethyl]-2-methyl-5-(2-methyl quinolin-4-ylamino)benzamide | white solid | 451.37 |
| 96 | 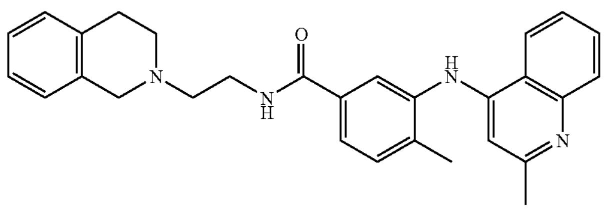 | N-[2-(3,4-Dihydro-1H-isoquinolin-2-yl)ethyl]-4-methyl-3-(2-methyl quinolin-4-ylamino)benzamide | off-white solid | 451.34 |
| 97 | 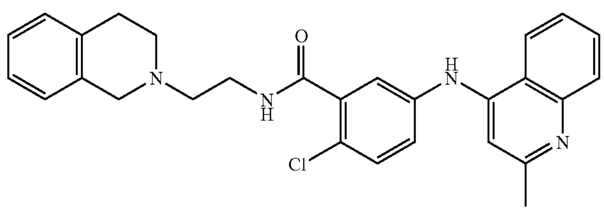 | 2-Chloro-N-[2-(3,4-dihydro-1H-isoquinolin-2-yl)ethyl]-5-(2-methyl quinolin-4-ylamino)benzamide | yellow solid | 471.38 |
| 98 | 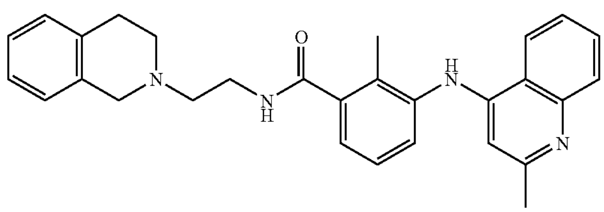 | N-[2-(3,4-Dihydro-1H-isoquinolin-2-yl)ethyl]-2-methyl-3-(2-methyl quinolin-4-ylamino)benzamide | yellowish solid | 451.25 |
| 99 | 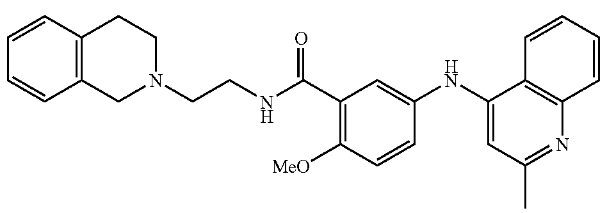 | N-[2-(3,4-Dihydro-1H-isoquinolin-2-yl)ethyl]-2-methoxy-5-(2-methyl quinolin-4-ylamino)benzamide | yellow solid | 467.33 |
| 100 | 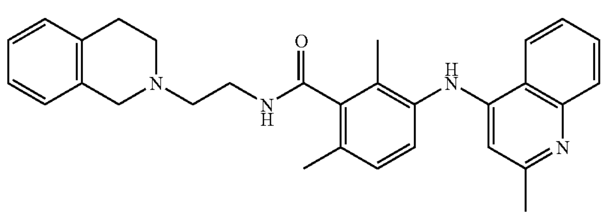 | N-[2-(3,4-Dihydro-1H-isoquinolin-2-yl)ethyl]-2,6-dimethyl-3-(2-methyl quinolin-4-ylamino)benzamide | white solid | 465.37 |

TABLE 3-continued

| Example | Structure | Chemical name | Physical description[a] | [M + H]+ |
|---|---|---|---|---|
| 101 | 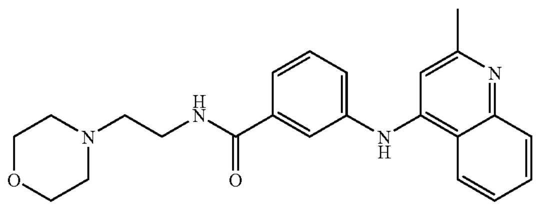 | 3-(2-Methylquinolin-4-ylamino)-N-(2-morpholin-4-ylethyl)benzamide | yellow solid[b] | 391.32 |
| 102 | 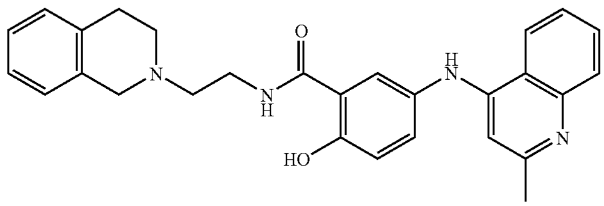 | N-[2-(3,4-Dihydro-1H-isoquinolin-2-yl)ethyl]-2-hydroxy-5-(2-methyl quinolin-4-ylamino)benzamide | yellow solid | 453.29 |
| 103 | 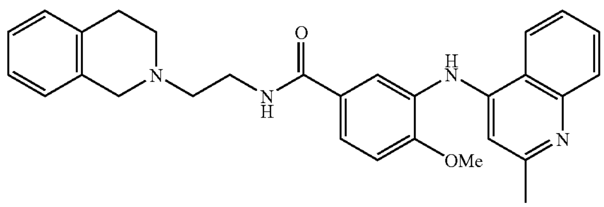 | N-[2-(3,4-Dihydro-1H-isoquinolin-2-yl)ethyl]-4-methoxy-3-(2-methyl quinolin-4-ylamino)benzamide | yellow solid | 467.34 |
| 104 | 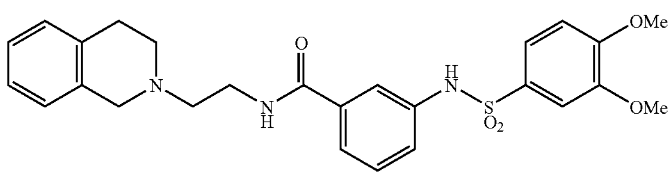 | N-[2-(3,4-Dihydro-1H-isoquinolin-2-yl)ethyl]-3-(3,4-dimethoxy benzenesulfonylamino)benzamide | off-white solid[b] | 496.26 |
| 105 | 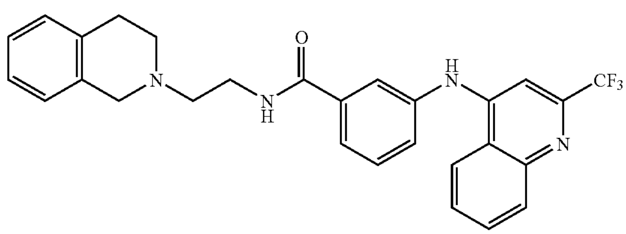 | N-[2-(3,4-Dihydro-1H-isoquinolin-2-yl)ethyl]-3-(2-trifluoromethyl quinolin-4-ylamino)benzamide | yellow solid | 491.22 |
| 106 | 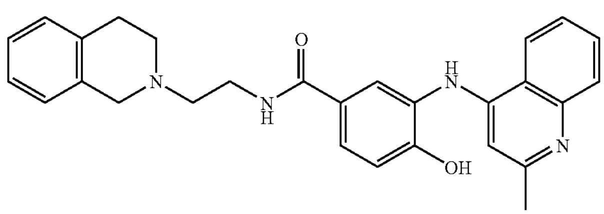 | N-[2-(3,4-Dihydro-1H-isoquinolin-2-yl)ethyl]-4-hydroxy-3-(2-methyl quinolin-4-ylamino)benzamide | yellow solid | 453.20 |
| 107 | 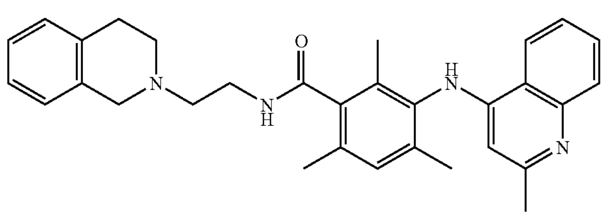 | N-[2-(3,4-Dihydro-1H-isoquinolin-2-yl)ethyl]-2,4,6-trimethyl-3-(2-methylquinolin-4-ylamino)benzamide | pink solid | 479.27 |

TABLE 3-continued

| Example | Structure | Chemical name | Physical description[a] | [M + H]+ |
|---|---|---|---|---|
| 108 | 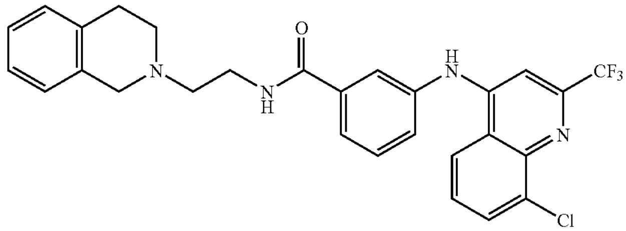 | 3-(8-Chloro-2-trifluoromethyl quinolin-4-ylamino)-N-[2-(3,4-dihydro-1H-isoquinolin-2-yl)ethyl]benzamide | yellow solid | 525.21 |
| 109 | 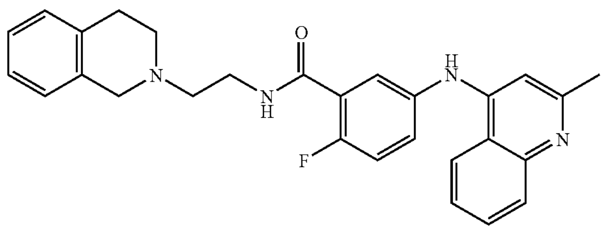 | N-[2-(3,4-Dihydro-1H-isoquinolin-2-yl)ethyl]-2-fluoro-5-(2-methyl quinolin-4-ylamino)benzamide | white solid | |
| 110 | 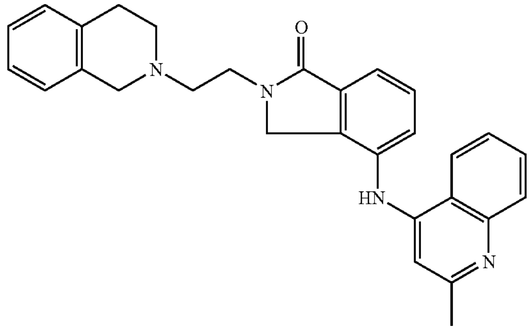 | 2-[2-(3,4-Dihydro-1H-isoquinolin-2-yl)ethyl]-4-(2-methylquinolin-4-yl amino)-2,3-dihydroisoindol-1-one | off-white solid | 449.21 |
| 111 | 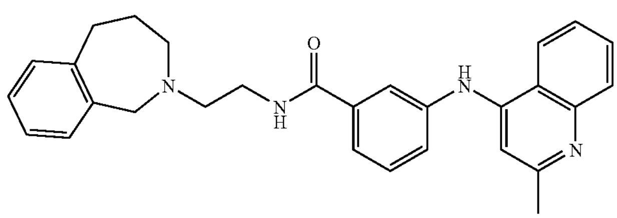 | 3-(2-Methylquinolin-4-ylamino)-N-[2-(1,3,4,5-tetrahydrobenzo[c]azepin-2-yl)ethyl]benzamide | yellow solid | 451.23 |
| 112 | 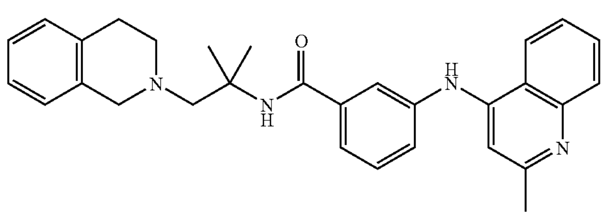 | N-[2-(3,4-Dihydro-1H-isoquinolin-2-yl)-1,1-dimethylethyl]-3-(2-methyl quinolin-4-ylamino)benzamide | light yellow solid | 465.25 |
| 113 | 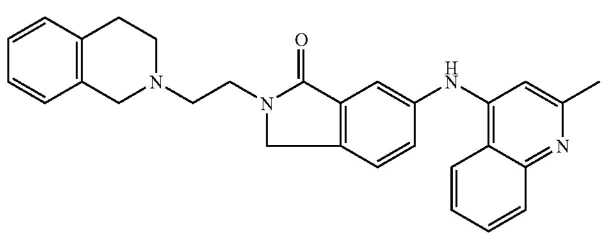 | 2-[2-(3,4-Dihydro-1H-isoquinolin-2-yl)ethyl]-6-(2-methyl-quinolin-4-yl amino)-2,3-dihydroisoindol-1-one | yellow solid | 449.26 |

TABLE 3-continued

| Example | Structure | Chemical name | Physical description[a] | [M + H]+ |
|---|---|---|---|---|
| 114 | 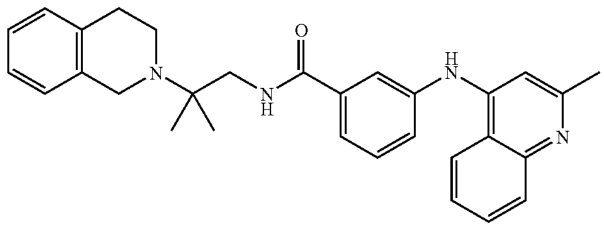 | N-[2-(3,4-Dihydro-1H-isoquinolin-2-yl)-2-methylpropyl]-3-(2-methyl quinolin-4-ylamino)benzamide | light yellow solid | 465.23 |
| 115 | 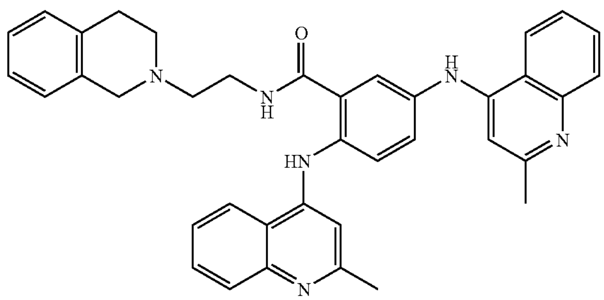 | N-[2-(3,4-Dihydro-1H-isoquinolin-2-yl)ethyl]-2,5-bis(2-methyl quinolin-4-ylamino)benzamide | yellowish solid | 452.18 |
| 116 | 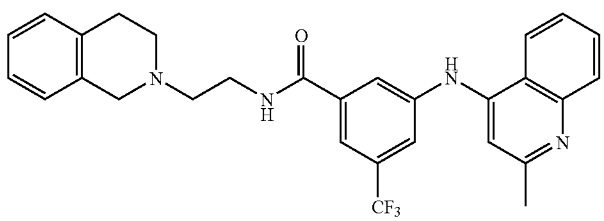 | N-[2-(3,4-Dihydro-1H-isoquinolin-2-yl)ethyl]-3-(2-methylquinolin-4-yl amino)-5-trifluoromethylbenzamide | off-white solid | 505.19 |
| 117 | 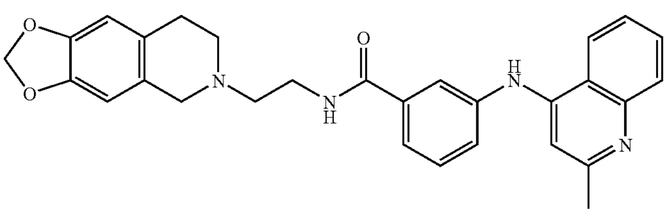 | N-[2-(7,8-Dihydro-5H-[1,3]dioxolo[4,5-g]isoquinolin-6-yl)ethyl-3-(2-methylquinolin-4-ylamino) benzamide | pale yellow solid | 481.20 |
| 118 | 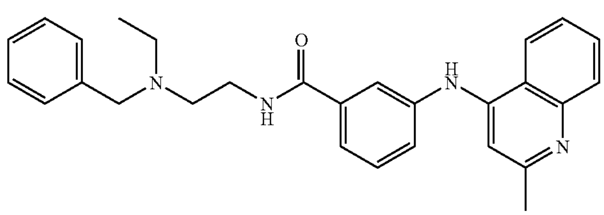 | N-[2-(Benzylethylamino) ethyl]-3-(2-methylquinolin-4-ylamino) benzamide | pale yellow solid | 439.18 |
| 119 | 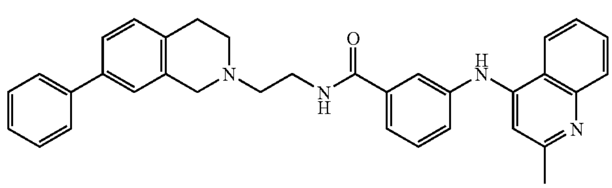 | 3-(2-Methylquinolin-4-ylamino)-N-[2-(7-phenyl-3,4-dihydro-1H-isoquinolin-2-yl)ethyl]benzamide | yellow solid | 513.29 |

TABLE 3-continued

| Example | Structure | Chemical name | Physical description[a] | [M + H]+ |
|---|---|---|---|---|
| 120 | 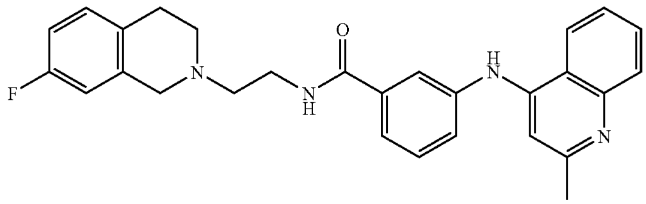 | N-[2-(7-Fluoro-3,4-dihydro-1H-isoquinolin-2-yl)ethyl]-3-(2-methyl quinolin-4-ylamino)benzamide | yellow solid | 455.18 |
| 121 | 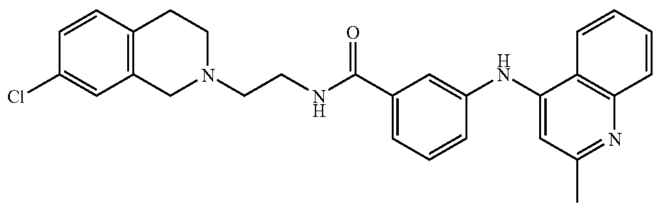 | N-[2-(7-Chloro-3,4-dihydro-1H-isoquinolin-2-yl)ethyl]-3-(2-methyl quinolin-4-ylamino)benzamide | off-white solid | 471.16 |
| 122 | 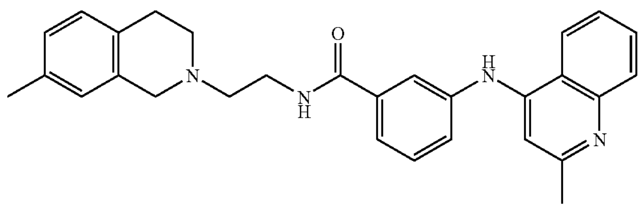 | N-[2-(7-Methyl-3,4-dihydro-1H-isoquinolin-2-yl)ethyl]-3-(2-methyl quinolin-4-ylamino)benzamide | yellow solid | 451.22 |
| 123 | 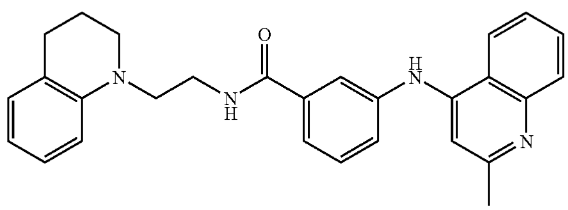 | N-[2-(3,4-Dihydro-2H-quinolin-1-yl)ethyl]-3-(2-methylquinolin-4-yl amino)benzamide | yellow solid | 437.25 |
| 124 | 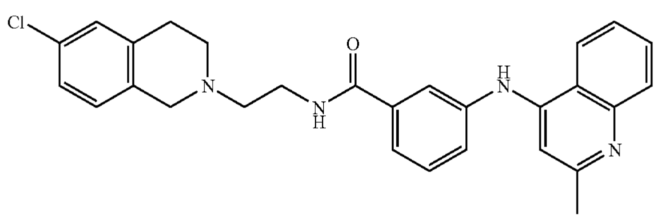 | N-[2-(6-Chloro-3,4-dihydro-1H-isoquinolin-2-yl)ethyl]-3-(2-methyl quinolin-4-ylamino)benzamide | off-white solid | |
| 125 | 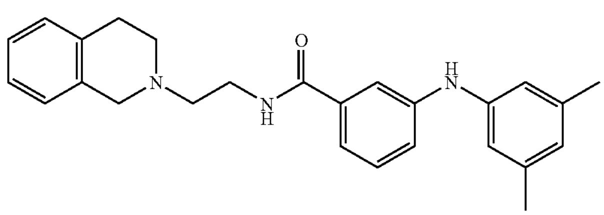 | N-[2-(3,4-Dihydro-1H-isoquinolin-2-yl)ethyl]-3-(3,5-dimethyl-phenylamino)benzamide | white solid[b] | 400.18 |
| 126 | 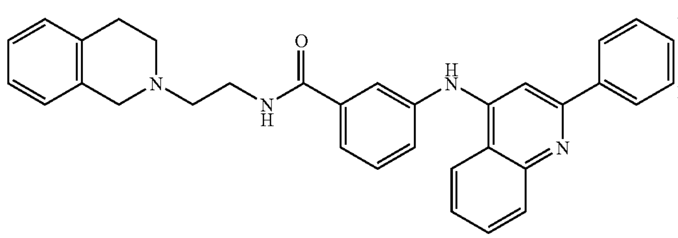 | N-[2-(3,4-Dihydro-1H-isoquinolin-2-yl)ethyl]-3-(2-phenylquinolin-4-yl amino)benzamide | yellow solid | 499.24 |

TABLE 3-continued

| Example | Structure | Chemical name | Physical description[a] | [M + H]+ |
|---|---|---|---|---|
| 127 | 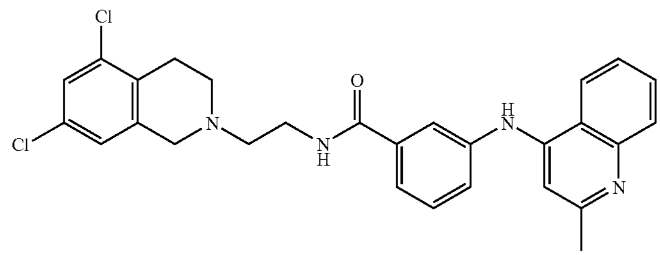 | N-[2-(5,7-Dichloro-3,4-dihydro-1H-isoquinolin-2-yl)ethyl]-3-(2-methyl quinolin-4-ylamino)benzamide | yellow solid[b] | 505.08 |
| 128 | 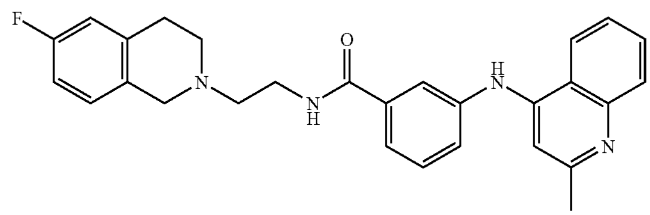 | N-[2-(6-Fluoro-3,4-dihydro-1H-isoquinolin-2-yl)ethyl]-3-(2-methyl quinolin-4-ylamino)benzamide | yellow solid | 455.25 |
| 129 | 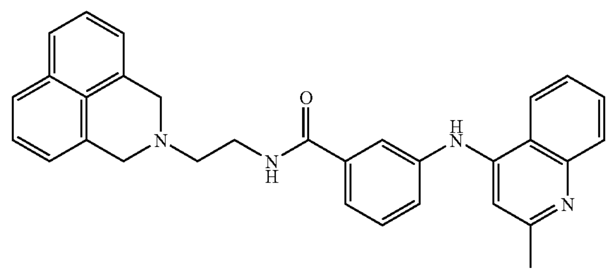 | N-[2-(1H,3H-Benzo[de]isoquinolin-2-yl)ethyl]-3-(2-methylquinolin-4-yl amino)benzamide | yellow solid | 773.20 |
| 130 | 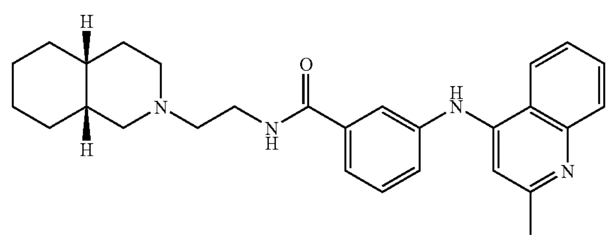 | 3-(2-Methylquinolin-4-ylamino)-N-[2-(octahydro-cis-isoquinolin-2-yl)ethyl]benzamide | yellow solid | 443.26 |
| 131 | 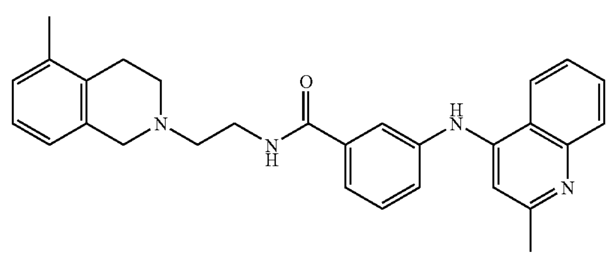 | N-[2-(5-Methyl-3,4-dihydro-1H-isoquinolin-2-yl)ethyl]-3-(2-methyl quinolin-4-ylamino)benzamide | yellow solid | 451.24 |
| 132 | 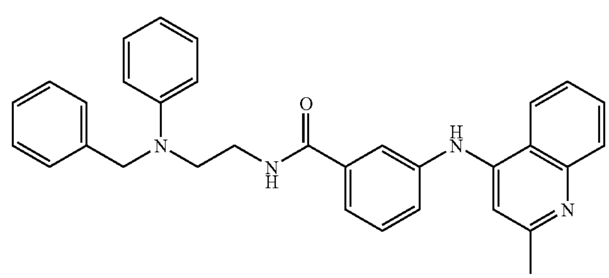 | N-[2-(Benzylphenylamino)ethyl]-3-(2-methylquinolin-4-ylamino)benzamide | pale yellow solid[b] | 487.24 |

TABLE 3-continued

| Example | Structure | Chemical name | Physical description[a] | [M + H]+ |
| --- | --- | --- | --- | --- |
| 133 | 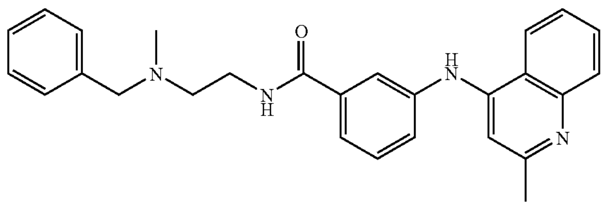 | N-[2-(Benzylmethylamino) ethyl]-3-(2-methylquinolin-4-ylamino)benzamide | pale yellow solid | 425.21 |
| 134 | 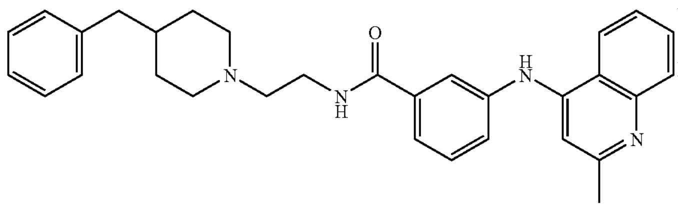 | N-[2-(4-Benzylpiperidin-1-yl)ethyl]-3-(2-methylquinolin-4-ylamino)benzamide | yellow solid | 479.24 |
| 135 | 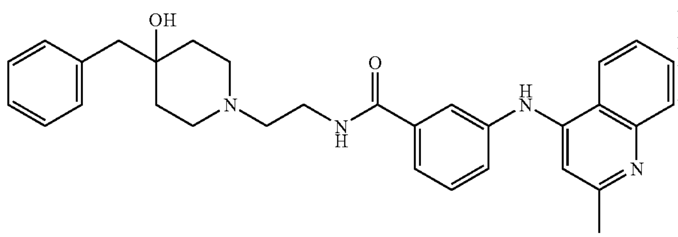 | N-[2-(4-Benzyl-4-hydroxy piperidin-1-yl)ethyl]-3-(2-methyl quinolin-4-ylamino)benzamide | yellow solid | 495.20 |
| 136 | 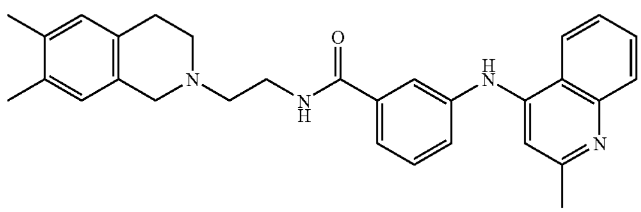 | N-[2-(6,7-Dimethyl-3,4-dihydro-1H-isoquinolin-2-yl)ethyl]-3-(2-methyl quinolin-4-ylamino)benzamide | yellow solid | |
| 137 | 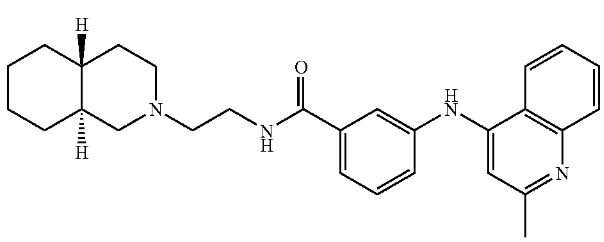 | 3-(2-Methylquinolin-4-ylamino)-N-[2-(octahydro-trans-isoquinolin-2-yl)ethyl]benzamide | brown solid | 443.31 |
| 138 | 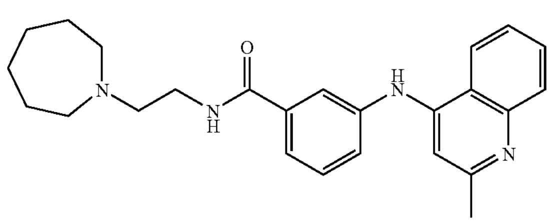 | N-(2-Azepan-1-ylethyl)-3-(2-methylquinolin-4-ylamino)benzamide | yellow solid | 403.23 |

TABLE 3-continued

| Example | Structure | Chemical name | Physical description[a] | [M + H]+ |
|---|---|---|---|---|
| 139 | 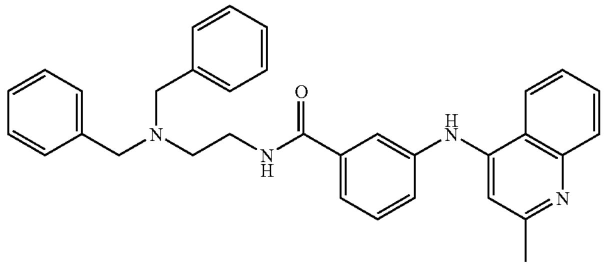 | N-(2-Dibenzylaminoethyl)-3-(2-methylquinolin-4-ylamino)benzamide | yellow solid | 501.26 |
| 140 | 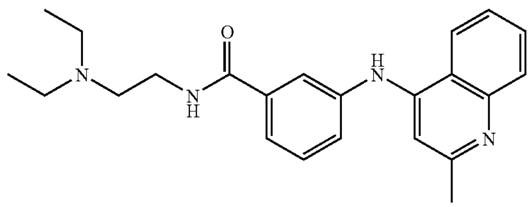 | N-(2-Diethylaminoethyl)-3-(2-methylquinolin-4-ylamino)benzamide | yellow solid | 378.09 |
| 141 | 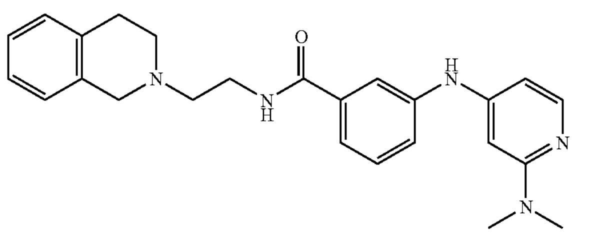 | N-[2-(3,4-Dihydro-1H-isoquinolin-2-yl)ethyl]-3-(2-dimethylamino pyridin-4-ylamino)benzamide | pale orange solid | 416.26 |
| 142 | 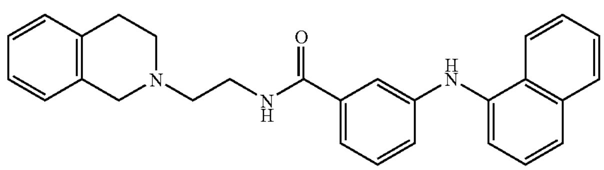 | N-[2-(3,4-Dihydro-1H-isoquinolin-2-yl)ethyl]-3-(naphthalen-1-yl amino)benzamide | brown solid[d] | 422.23 |
| 143 | 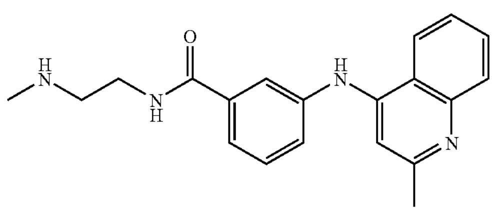 | N-(2-Methylaminoethyl)-3-(2-methyl quinolin-4-ylamino)benzamide | pale yellow solid[b] | 335.21 |
| 144 | 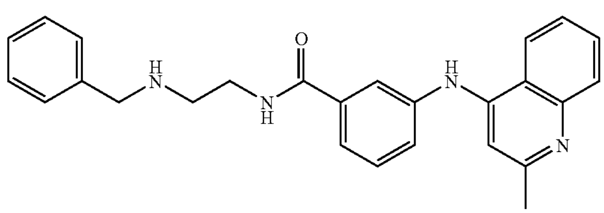 | N-(2-Benzylaminoethyl)-3-(2-methyl quinolin-4-ylamino)benzamide | yellow solid | 411.24 |
| 145 | | N-(1-Benzylpyrrolidin-3-yl)-3-(2-methylquinolin-4-ylamino)benzamide | yellow solid | 437.28 | ns
TABLE 3-continued

| Example | Structure | Chemical name | Physical description[a] | [M + H]+ |
|---|---|---|---|---|
| 146 | 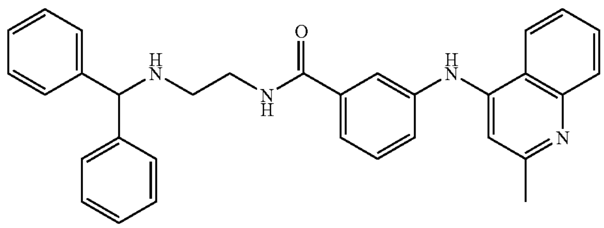 | N-[2-(Benzhydrylamino)ethyl]-3-(2-methylquinolin-4-ylamino)benzamide | off-white solid | 487.18 |
| 147 | 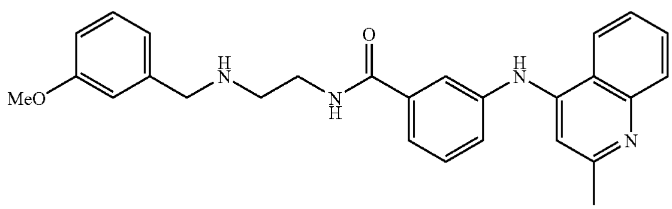 | N-[2-(3-Methoxybenzylamino)ethyl]-3-(2-methylquinolin-4-yl amino)benzamide | pale yellow solid | 441.26 |
| 148 | 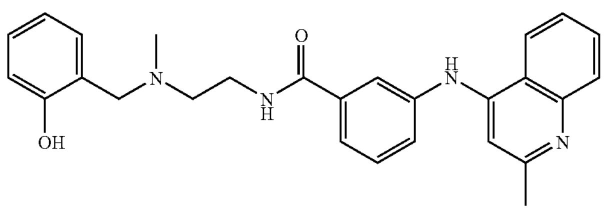 | N-{2-[(2-Hydroxybenzyl)methylamino]ethyl}-3-(2-methyl quinolin-4-ylamino)benzamide | pale yellow solid[b] | 441.11 |
| 149 | 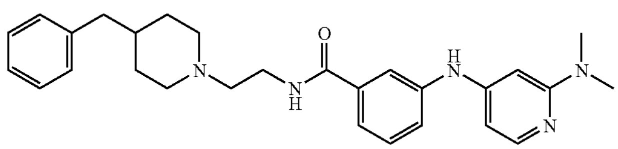 | N-[2-(4-Benzylpiperidin-1-yl)ethyl]-3-(2-dimethylamino pyridin-4-ylamino)benzamide | orange solid | 458.26 |
| 150 | 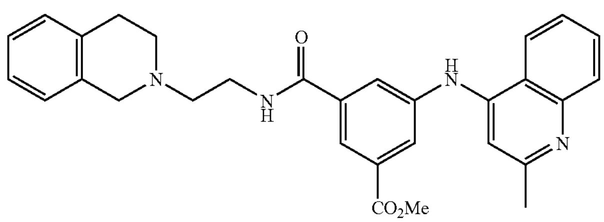 | MethylN-[2-(3,4-dihydro-1H-isoquinolin-2-yl)ethyl]-5-(2-methylquinolin-4-ylamino)isophthalamate | off-white solid | 495.23 |
| 151 | 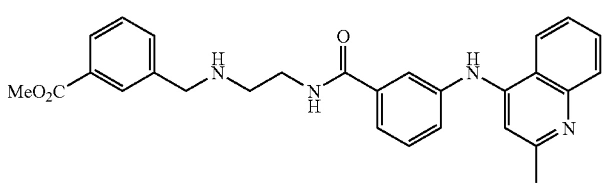 | Methyl3-({2-[3-(2-methyl quinolin-4-ylamino)benzoylamino]ethylamino}-methyl)benzoate | pale yellow solid | 469.29 |
| 152 | 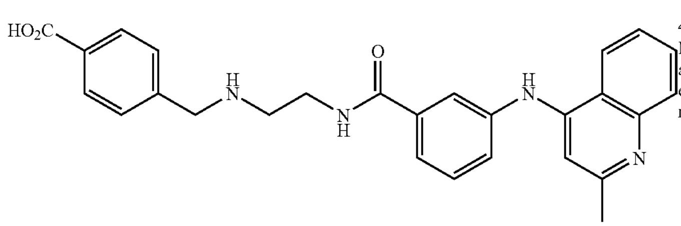 | 4-({2-[3-(2-Methylquinolin-4-yl amino)-benzoylamino]ethylamino}methyl)benzoic acid | pale yellow solid[e] | 455.30 |

TABLE 3-continued

| Example | Structure | Chemical name | Physical description[a] | [M + H][+] |
|---|---|---|---|---|
| 153 | 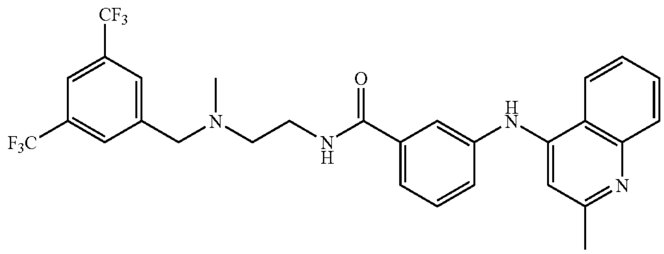 | N-{2-[(3,5-Bis-trifluoromethyl benzyl)methylamino] ethyl}-3-(2-methylquinolin-4-ylamino)benzamide | pale yellow solid | 561.28 |
| 154 | 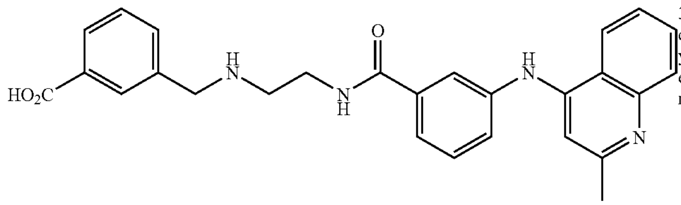 | 3-({2-[3-(2-Methyl quinolin-4-ylamino)benzoylamino] ethylamino}-methyl)benzoic acid | pale yellow solid[e] | 455.27 |
| 155 | 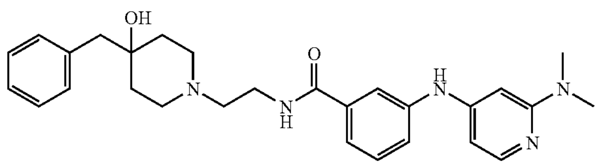 | N-[2-(4-Benzyl-4-hydroxy piperidin-1-yl)ethyl]-3-(2-dimethyl aminopyridin-4-ylamino)benzamide | pale yellow solid | 474.28 |
| 156 | 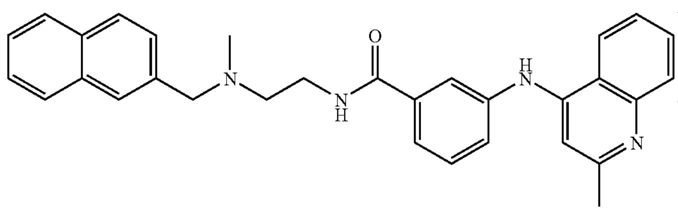 | N-[2-(Methylnaphthalen-2-ylmethyl amino)ethyl]-3-(2-methyl quinolin-4-ylamino)benzamide | yellow solid | 475.24 |
| 157 | 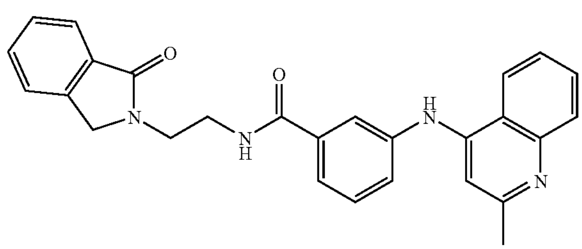 | 3-(2-Methylquinolin-4-ylamino)-N-[2-(1-oxo-1,3-dihydro isoindol-2-yl)-ethyl]benzamide | off-white solid[d] | 437.24 |
| 158 | 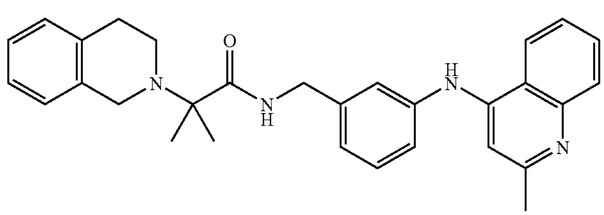 | 2-(3,4-Dihydro-1H-isoquinolin-2-yl)-N-[3-(2-methylquinolin-4-ylamino) benzyl]isobutyramide | yellow solid | 465.28 |

TABLE 3-continued

| Example | Structure | Chemical name | Physical description[a] | [M + H]+ |
|---|---|---|---|---|
| 159 | 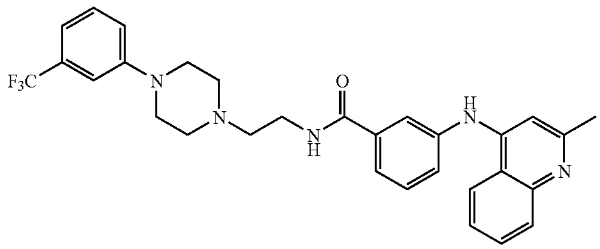 | 3-(2-Methylquinolin-4-ylamino)-N-{2-[4-(3-trifluoromethylphenyl)piperazin-1-yl]-ethyl}benzamide | light yellow solid | 534.30 |
| 160 | 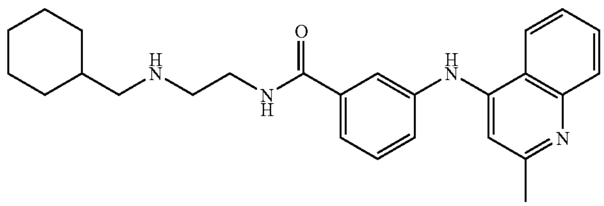 | N-[2-(Cyclohexylmethylamino)ethyl]-3-(2-methylquinolin-4-ylamino)benzamide | pale yellow solid | 417.29 |
| 161 | 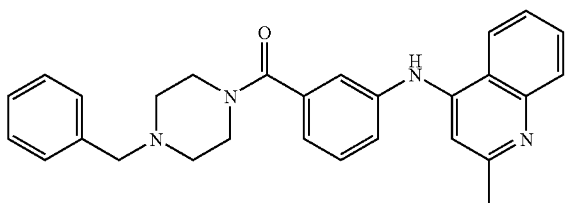 | 1-Benzyl-4-[3-(2-methylquinolin-4-ylamino)benzoyl]piperazine | brown solid | 437.30 |
| 162 | 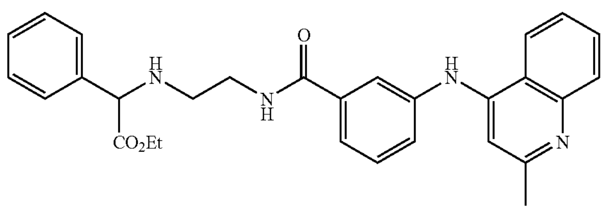 | Ethyl {2-[3-(2-methylquinolin-4-ylamino)benzoylamino]ethylamino}phenylacetate | pale yellow solid | 483.25 |
| 163 | 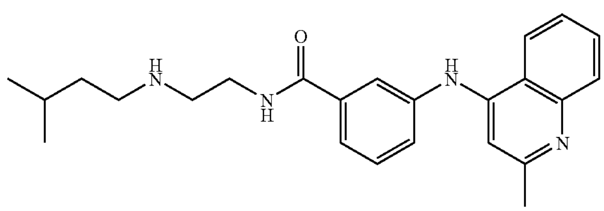 | N-[2-(3-Methylbutylamino)ethyl]-3-(2-methylquinolin-4-ylamino)benzamide | pale yellow solid | 391.23 |
| 164 | 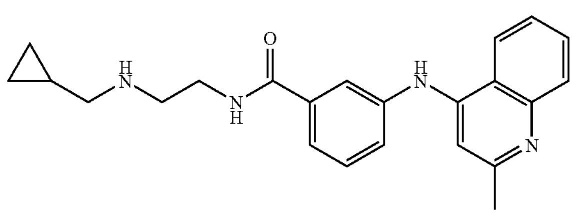 | N-[2-(Cyclopropylmethylamino)ethyl]-3-(2-methylquinolin-4-ylamino)benzamide | pale yellow solid | 374.27 |
| 165 | 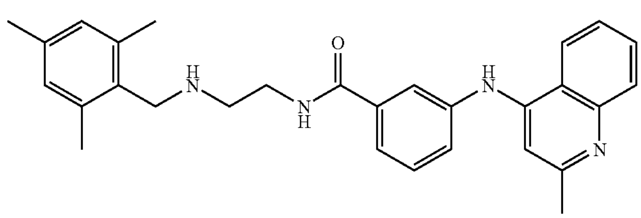 | 3-(2-Methylquinolin-4-ylamino)-N-[2-(2,4,6-trimethylbenzylamino)ethyl]benzamide | pale yellow solid | 453.25 |

TABLE 3-continued

| Example | Structure | Chemical name | Physical description[a] | [M + H]+ |
|---|---|---|---|---|
| 166 | 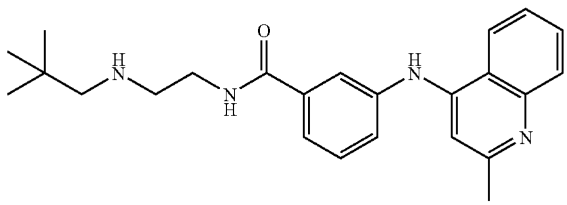 | N-[2-(2,2-Dimethylpropylamino)ethyl]-3-(2-methylquinolin-4-yl amino)benzamide | pale yellow solid | 391.27 |
| 167 | 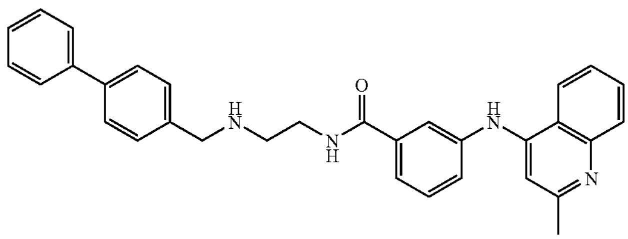 | N-{2-[(Biphenyl-4-ylmethyl)amino]ethyl}-3-(2-methylquinolin-4-yl amino)benzamide | pale yellow solid | 487.20 |
| 168 | 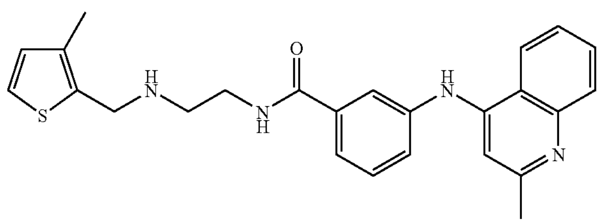 | 3-(2-Methylquinolin-4-ylamino)-N-{2-[(3-methylthiophen-2-yl methyl)amino]-ethyl}benzamide | pale yellow solid | 431.11 |
| 169 | 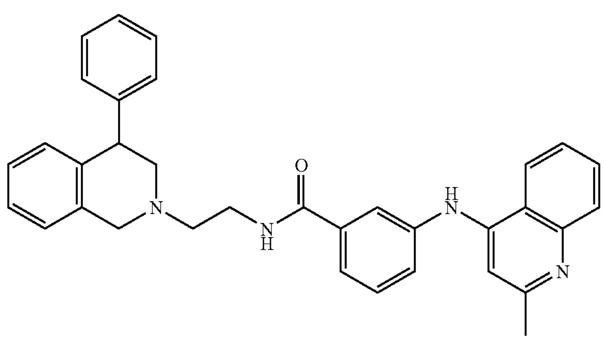 | 3-(2-Methylquinolin-4-ylamino)-N-[2-(4-phenyl-3,4-dihydro-1H-isoquinolin-2-yl)ethyl]benzamide | off-white solid | 513.26 |
| 170 | 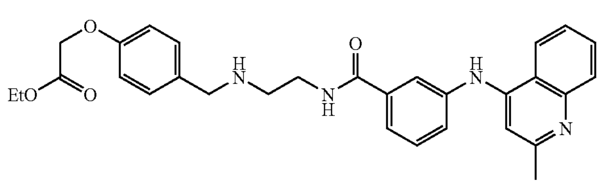 | Ethyl [4-({2-[3-(2-methylquinolin-4-yl amino)benzoylamino]ethylamino}methyl)phenoxy]acetate | off-white solid[b] | 513.15 |
| 171 | 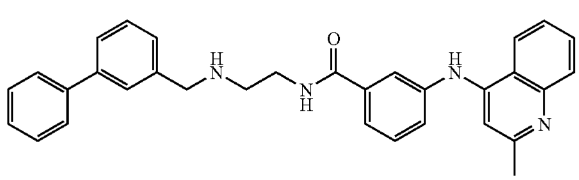 | N-{2-[(Biphenyl-3-ylmethyl)amino]ethyl}-3-(2-methylquinolin-4-yl amino)benzamide | off-white solid[b] | 487.26 |

TABLE 3-continued

| Example | Structure | Chemical name | Physical description[a] | [M + H]+ |
|---|---|---|---|---|
| 172 | 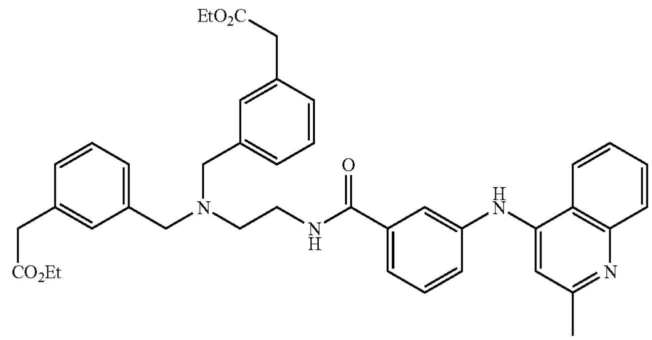 | Ethyl {3-[((3-ethoxycarbonylmethyl benzyl)-{2-[3-(2-methylquinolin-4-ylamino) benzoylamino]ethyl} amino)methyl]phenyl} acetate | pale yellow solid[b] | 673.34 |
| 173 | 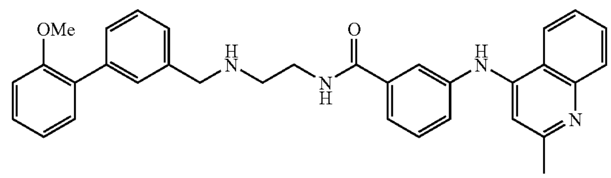 | N-{2-[(2'-Methoxybiphenyl-3-yl methyl)amino]ethyl}-3-(2-methyl quinolin-4-ylamino)benzamide | pale yellow solid[b] | 517.29 |

[a]DiHCl salt unless otherwise noted.
[b]Paren compound
[d]HCl salt
[e]Na salt

The compound of Example 174 was synthesized in the same manner as the compound of Example 1.

The compound of Example 175 was synthesized in the same manner as the compound of Example 177.

The preparation of the compounds of Examples 176 and 177 are shown.

The compound of Example 178 was synthesized in the same manner as the compound of Example 1.

The preparation of the compound of Example 179 is shown.

The compound of Example 180 was synthesized in the same manner as the compound of Example 179.

The preparation of the compound of Example 181 is shown.

The compound of Example 182 was synthesized in the same manner as the compound of Example 178 except that N-[2-(3,4-dihydro-1H-isoquinolin-2-yl)ethyl]-3-nitrobenzenesulfonamide was methylated using a standard method (NaH/MeI/DMF) before carried on to the next step.

The preparation of the compounds of Examples 183 and 184 are shown.

The compound of Example 185 was synthesized in the same manner as the compound of Example 184.

The preparation of the compound of Example 186 is shown.

The compounds of Examples 187 and 188 were synthesized in the same manner as the compound of Example 184.

The preparation of the compounds of Examples 189 to 191 are shown.

The compounds of Examples 192 to 194 were synthesized in the same manner as the compound of Example 186.

The compound of Example 195 was synthesized in the same manner as the compound of Example 190.

The compound of Example 196 was synthesized in the same manner as the compound of Example 186.

The compound of Example 197 was synthesized in the same manner as the compound of Example 191.

The preparation of the compound of Example 198 is shown.

The compound of Example 199 was synthesized in the same manner as the compound of Example 198.

The compound of Example 200 was synthesized in the same manner as the compound of Example 191.

The compound of Example 201 was synthesized via reduction (see Example 112 step 3) of the compound of Example 134.

The preparation of the compounds of Examples 202 and 203 are shown.

The compound of Example 204 was synthesized in the same manner as the compound of Example 198.

The compounds of Examples 205 and 206 were synthesized in the same manner as the compound of Example 2.

The compound of Example 207 was synthesized via reduction (see Example 112 step 3) of the compound of Example 144.

The preparation of the compounds of Examples 208 to 210 are shown.

The compound of Example 211 was synthesized in the same manner as the compound of Example 210.

The structures, chemical names, physical descriptions and M+H data for the compounds of Examples 174-211 are set forth in Table 4.

EXAMPLE 176

N-(2-Dimethylaminoethyl)-N'-(2-methylquinolin-4-yl)phenylene-1,3-diamine

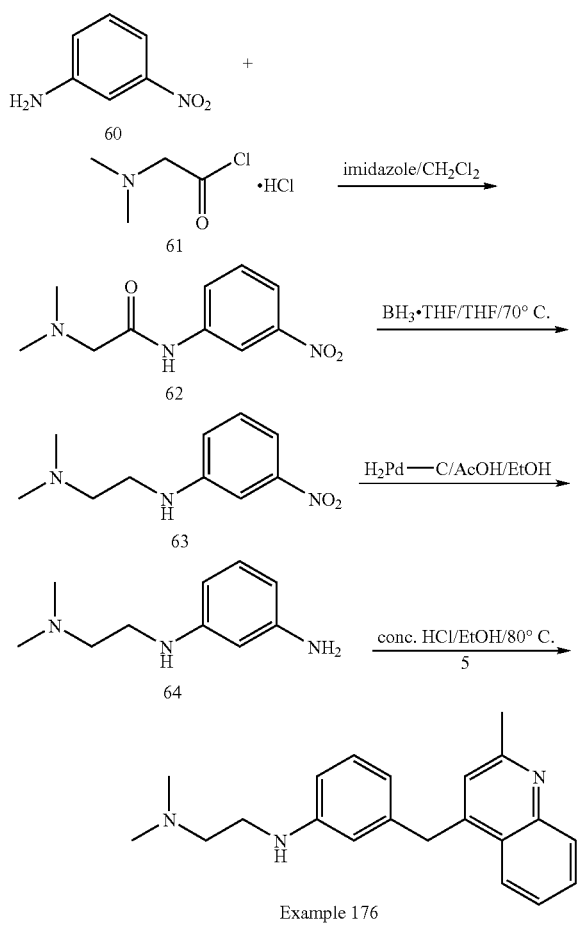

Example 176

Step 1. 2-Dimethylamino-N-(3-nitrophenyl)acetamide (62).

To a heterogeneous mixture of 61 (186 mg, 1.18 mmol) in dichloromethane (6 mL) were sequentially added imidazole (281 mg, 4.13 mmol) and a solution of 60 (214 mg, 1.55 mmol) in dichloromethane (6 mL). The reaction was stirred at room temperature for 16 hours before is it was extracted with ethyl acetate (40 mL, 30 mL) and washed with water (30 mL). The ethyl acetate extracts were dried over anhydrous magnesium sulfate and concentrated. The residue was chromatographed on silica gel (1:1 hexanes/ethyl acetate to 10:1 dichloromethane/methanol) to give 62 as a yellow oil.

Step 2. N,N-Dimethyl-N'-(3-nitrophenyl)ethane-1,2-diamine (63).

To a solution of 62 (482 mg, 2.05 mmol) in THF (2.8 mL) under a $N_2$ atmosphere was added $BH_3$.THF (1.0 M solution in THF, 2.8 mL, 2.80 mmol). The reaction was heated at 70° C. for 1.5 hours before it was allowed to cool to room temperature.

The mixture was treated with 2 N HCl (aq. 3 mL) (moderate bubbling) and then the solvent was evaporated. The aqueous residue was extracted with chloroform (2×40 mL) and washed with sat. $NaHCO_3$ (aq.), water, and brine (20 mL each). The chloroform extracts were dried over anhydrous magnesium sulfate and concentrated. The residue was chromatographed on Florisil® (1:1 hexanes/ethyl acetate to 10:1 dichloromethane/methanol) to afford 63 as a yellow oil (124 mg, 28.9%).

Step 3. N-(2-Dimethylaminoethyl)benzene-1,3-diamine (64).

64 is prepared from 63 by the procedure of Example 1 Step 2.

Step 4. N-(2-Dimethylaminoethyl)-N'-(2-methylquinolin-4-yl)phenylene-1,3-diamine The title compound is prepared from 64 by the procedure of Example 1 Step 3.

EXAMPLE 177

[3-(3-Dimethylaminopropyl)phenyl]-(2-methylquinolin-4-yl)amine

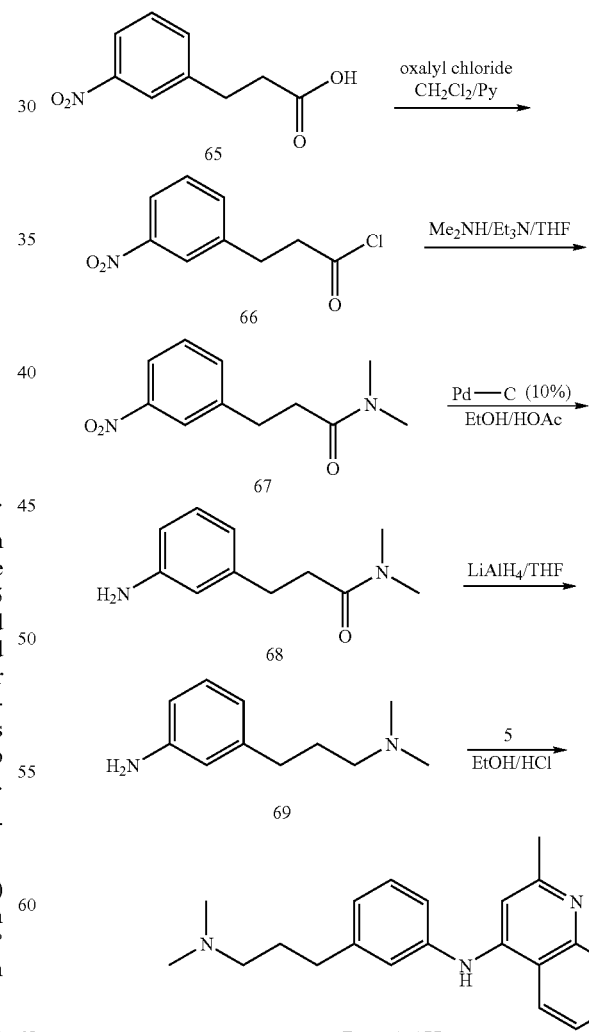

Example 177

Step 1. N,N-Dimethyl-3-(3-nitrophenyl)propionamide (67).

To a suspension of 65 (2.04 g, 10.45 mmol) in anhydrous dichloromethane (15 mL) under nitrogen were sequentially added anhydrous pyridine (2 drops) and oxalyl chloride (2 M in $CH_2Cl_2$, 11.5 mL, 23 mmol) dropwise. The resulting mixture was heated at 50° C. for 1.5 hours before it was concentrated. The residue was dissolved in anhydrous THF (20 mL) under nitrogen followed by the sequential addition of triethylamine (1.16 mL, 11.55 mmol) and dimethylamine (2 M in THF, 7.87 mL, 15.68 mmol). The reaction was stirred at room temperature overnight before it was diluted with EtOAc (150 mL), and washed with water (150 mL) and brine (150 mL). The organic layer was dried over $Na_2SO_4$ and evaporated under reduced pressure to give 67 as a yellowish oil (977 mg, 43%).

Step 2. 3-(3-Aminophenyl)-N,N-dimethylpropionamide (68).

68 was prepared from 67 by the procedure of Example 1 Step 2.

Step 3. 3-(3-Dimethylaminopropyl)phenylamine (69).

69 was prepared from 68 by the procedure of Example 112 Step 3.

Step 4. [3-(3-Dimethylaminopropyl)phenyl]-(2-methylquinolin-4-yl)amine.

The title compound is prepared from 69 by the procedure of Example 1 Step 3.

EXAMPLE 179

[3'-(3,4-Dihydro-1H-isoquinolin-2-ylmethyl)biphenyl-3-yl]-(2-methylquinolin-4-yl)amine

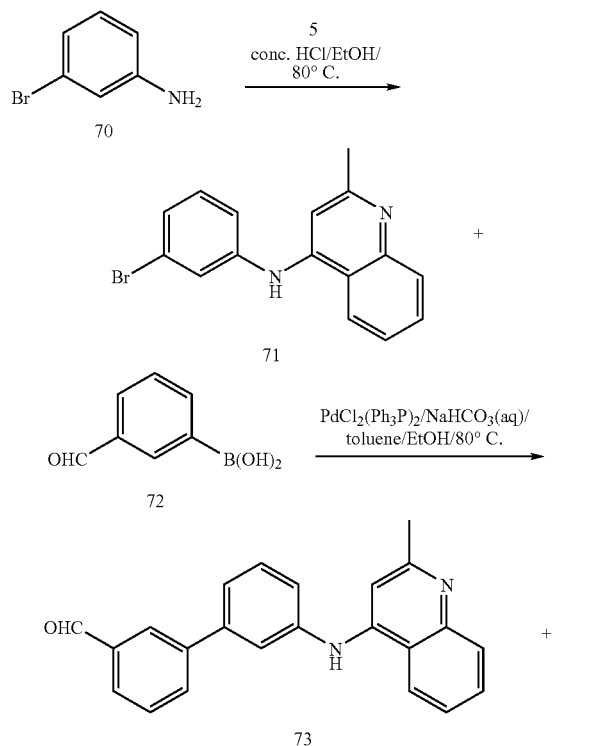

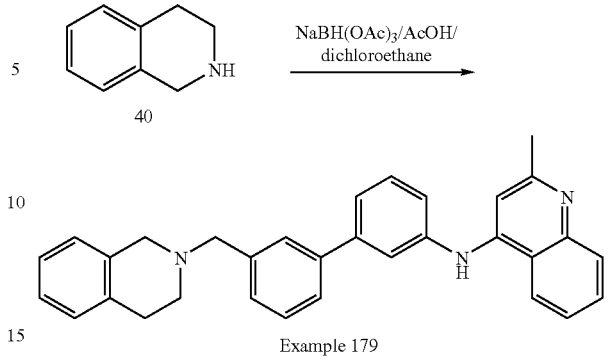

Example 179

Step 1. (3-Bromophenyl)-(2-methylquinolin-4-yl)amine (71).

71 is prepared from 70 by the procedure of Example 1 Step 3.

Step 2. 3'-(2-Methylquinolin-4-ylamino)biphenyl-3-carbaldehyde (73).

To a suspension of 71 (294 mg, 0.94 mmol) in toluene (9.6 mL) under $N_2$ were sequentially added saturated $NaHCO_3$ (aq. 3.8 mL), a solution of 72 (199 mg, 1.33 mmol) in EtOH (6.7 mL), and $PdCl_2(Ph_3P)_3$ (32 mg, 0.046 mmol). The reaction was heated at 80° C. for 21 hours before it was allowed to cool to room temperature. The reaction mixture was extracted with ethyl acetate (40 mL) and washed with water (15 mL), brine (15 mL). The ethyl acetate extracts were dried over anhydrous magnesium sulfate and concentrated. The residue was chromatographed on silica gel (dichloromethane to 20:1 dichloromethane/methanol) to give 73 as a yellow solid (219 mg, 68.9%).

Step 3.3'-(3,4-Dihydro-1H-isoquinolin-2-ylmethyl)biphenyl-3-yl]-(2-methylquinolin-4-yl)amine.

To a solution of 73 (102 mg, 0.301 mmol) in dichloroethane (3.0 mL) under $N_2$ was added 40 (0.04 mL, 0.315 mmol). The reaction was stirred for 24 minutes before the sequential addition of $NaBH(OAc)_3$ (94 mg, 0.444 mmol) and AcOH (0.02 mL, 0.349 mmol). The reaction was stirred for 19 hours and then extracted with ethyl acetate (2×30 mL). The ethyl acetate extracts were washed with 2 N NaOH (aq. 15 mL), brine (15 mL), dried ($MgSO_4$), and concentrated. The residue was chromatographed on silica gel (dichloromethane to 30:1 to 20:1dichloromethane/methanol) to give the desired product as a yellow solid (75 mg, 55%).

EXAMPLE 181

2-Dimethylaminoethyl 3-(2-methylquinolin-4-ylamino)benzoate

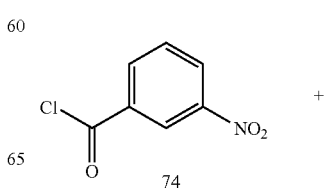

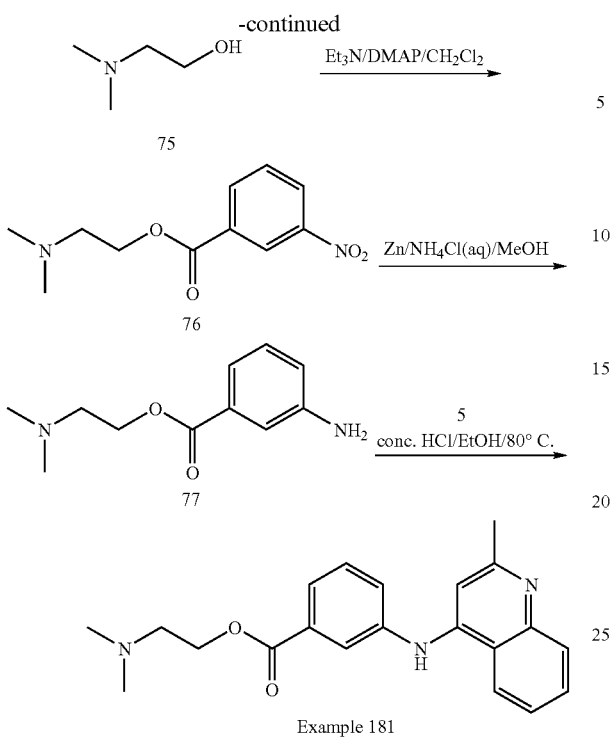

Example 181

Step 1. 2-Dimethylaminoethyl 3-nitrobenzoate (76).

To a solution of 74 (835 mg, 4.50 mmol) in dichloromethane (50 mL) were sequentially added triethylamine (0.63 mL, 6.75 mmol), a solution of 75 (800 mg, 8.97 mmol) in dichloromethane (10 mL) and a catalytic amount of DMAP. The reaction was stirred for 16 hours before it was extracted with dichlormethane. The dichloromethane extracts were washed with water and brine, dried (MgSO$_4$), and concentrated to give the crude product 76.

Step 2. 2-Dimethylaminoethyl 3-aminobenzoate (77).

77 was prepared from 76 by the procedure of Example 110 Step 4.

Step 3. 2-Dimethylaminoethyl 3-(2-methylquinolin-4-ylamino)benzoate.

The title compound was prepared from 77 by the procedure of Example 1 Step 3.

EXAMPLE 183

{3-[5-(3,4-Dihydro-1H-isoquinolin-2-ylmethyl)isoxazol-3-yl]phenyl}-(2-methyl-quinolin-4-yl)amine

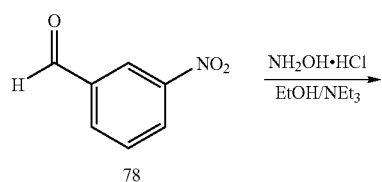

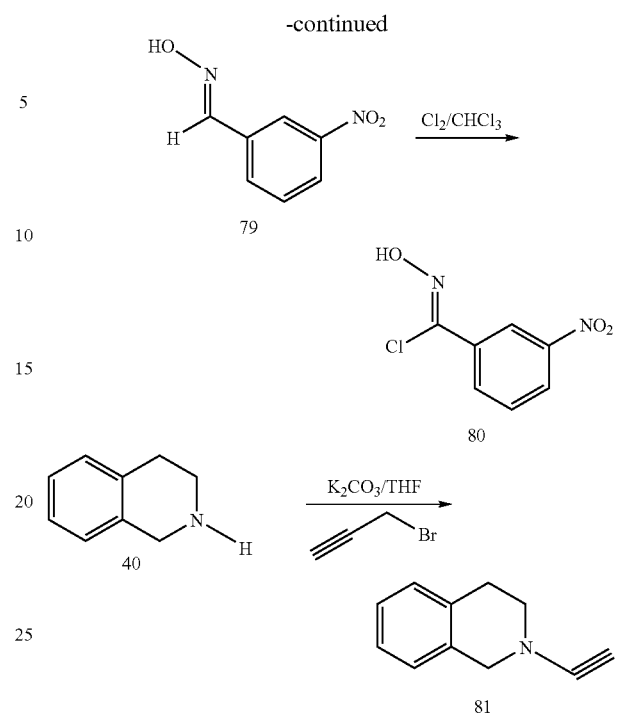

Example 183

Step 1. 3-Nitrobenzaldehyde oxime (79).

To a solution of 78 (6.04 g, 40 mmol) in ethanol (135 mL) were sequentially added hydroxylamine hydrochloride (2.92 g, 42 mmol) and triethylamine (4.6 g, 54 mmol). The mixture was heated at reflux overnight and concentrated under reduced pressure. The residue was mixed with ethyl acetate (100 mL) and washed with water (3×100 mL), brine (100 mL).

The ethyl acetate solution was dried (MgSO$_4$) ard concentrated under reduced pressure to give 79 (5.67 g, ~100%).

Step 2. 3-Nitrobenzonitrile oxide hydrogen chloride (80).

To a solution of 79 (1.66 g, 10 mmol) in chloroform (50 mL) was introduced chlorine gas at −5° C. over 15 minutes. The color of the reaction mixture changed from colorless to light blue, green, and finally yellow. After an additional 15 minutes, the reaction mixture was concentrated under reduced pressure to give 80 (2.0 g, 100%) as a yellow oil.

Step 3. 2-Propargyl-1,2,3,4-tetrahydroisoquinoline (81).

See Example 13 Step 2.

Step 4. 2-[3-(3-Nitrophenyl)isoxazol-5-ylmethyl]-1,2,3,4-tetrahydroisoquinoline (82).

A solution of 80 (0.2 g, 1.0 mmol) and 81 (0.2 g, 1.17 mmol) in toluene (5 mL) was heated at reflux for 4 hours. The reaction was cooled and mixed with 0.5 N NaOH (5 mL), then extracted with ethyl acetate (2×10 mL). The organic material was combined, dried ($K_2CO_3$) then concentrated under reduced pressure. The residue was purified by flash chromatography ($SiO_2$, gradient elution, hexane to 3:1 hexane/ethyl acetate) to give 82 (228 mg, 68%) as a yellow oil.

Step 5. 3-[5-(3,4-Dihydro-1H-isoquinolin-2-ylmethyl)isoxazol-3-yl]phenylamine (83).

83 was prepared from 82 by the procedure of Example 12 Step 2.

Step 6. {3-[5-(3,4-Dihydro-1H-isoquinolin-2-ylmethyl)isoxazol-3-yl]phenyl}-(2-methyl-quinolin-4-yl)amine.

The title compound was prepared from 83 by the procedure of Example 1 Step 3.

EXAMPLE 184

{3-[3-(3,4-Dihydro-1H-isoquinolin-2-yl)propyl]phenyl}-(2-methylquinolin-4-yl)amine Step 1. 2-Allyl-1,2,3,4-tetrahydroisoquinoline (84).

84 was prepared from 40 by the procedure of Example 13 Step 2.

Step 2. 2-[3-(3-Nitrophenyl)propyl]-1,2,3,4-tetrahydroisoquinoline (85).

To a solution of 84 (488 mg, 2.82 mmol) in anhydrous THF (3 mL) was added 9-BBN (0.5 M in THF, 5.64 mL, 2.82 mmol) under $N_2$. The mixture was stirred at room temperature for 3 hours to give mixture I.

To a solution of 1-bromo-3-nitrobenzene (518 mg, 2.56 mmol) in anhydrous THF (8 mL) were sequentially added $PdCl_2(dppf)$ (63 mg, 0.0077 mmol) and sodium methoxide (416 mg, 7.68 mmol) to mixture II.

To mixture II was added dropwise mixture I under $N_2$ and the resulting mixture was heated at 75° C. for 17 hours. Upon cooling to room temperature, the reaction mixture was filtered, and the filtrate diluted with EtOAc (150 mL). The organic solution was washed with water (100 mL) and brine (100 mL), dried over $Na_2SO_4$, and concentrated under reduced pressure. The residue was purified through column flash chromatography (silica gel) eluting with 8:1 hexanes/EtOAc to give 85 as an orange oil (226 mg, 27%).

Step 3. 3-[3-(3,4-Dihydro-1H-isoquinolin-2-yl)propyl]phenylamine (86).

86 was prepared from 85 by the procedure of Example 110 Step 4.

Step 4. {3-[3-(3,4-Dihydro-1H-isoquinolin-2-yl)propyl]phenyl}-(2-methylquinolin-4-yl)amine.

The title compound was prepared from 86 by the procedure of Example 1 Step 3.

EXAMPLE 186

1-[2-(3,4-Dihydro-1H-isoquinolin-2-yl)ethyl]-3-[3-(2-methylquinolin-4-ylamino)phenyl]urea

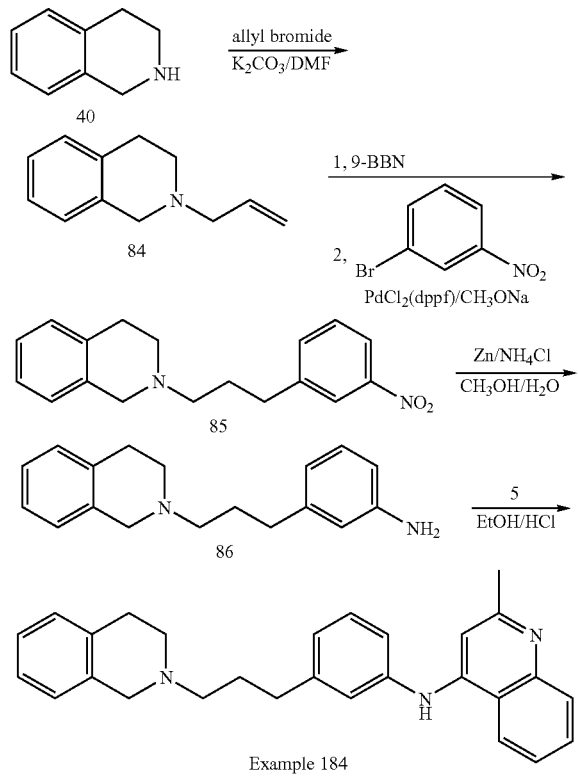

Example 184

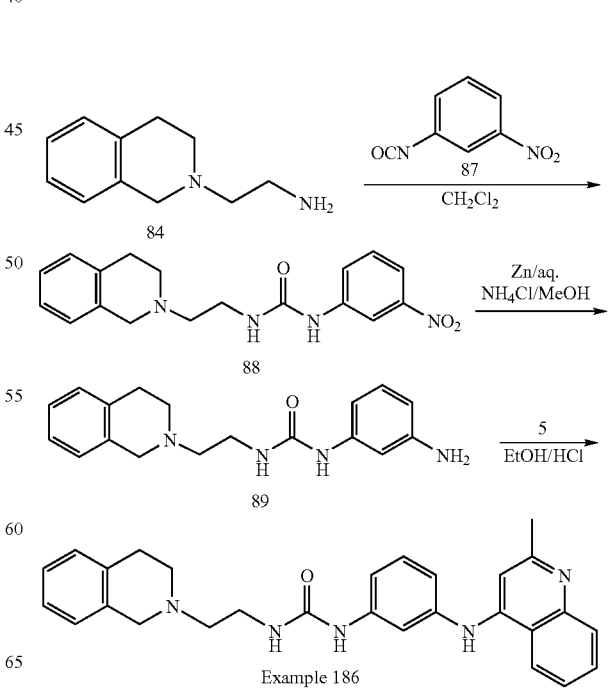

Example 186

Step 1. 1-[2-(3,4-Dihydro-1H-isoquinolin-2-yl)ethyl]-3-(3-nitrophenyl)urea (88).

To a solution of 36 (0.35 g, 2.0 mmol) in dichloromethane (10 mL) was added 3-nitrophenyl isocyanate (87) (0.35 g, 2.0 mmol). The mixture was stirred at room temperature overnight before it was partitioned between water (100 mL) and dichloromethane (100 mL). The organic layer was washed with 88 (0.56 g, 82%).

Step 2. 1-(3-Aminophenyl)-3-[2-(3,4-dihydro-1H-isoquinolin-2-yl)ethyl]urea (89).

89 is prepared from 88 by the procedure of Example 110 Step 4.

Step 3. 1-[2-(3,4-Dihydro-1H-isoquinolin-2-yl)ethyl]-3-[3-(2-methylquinolin-4-ylamino)phenyl]urea.

The title compound is prepared from 89 by the procedure of Example 1 Step 3.

EXAMPLE 189

{3-[5-(3,4-Dihydro-1H-isoquinolin-2-ylmethyl)-[1,3,4]oxadiazol-2-yl]phenyl}-(2-methylquinolin-4-yl)amine

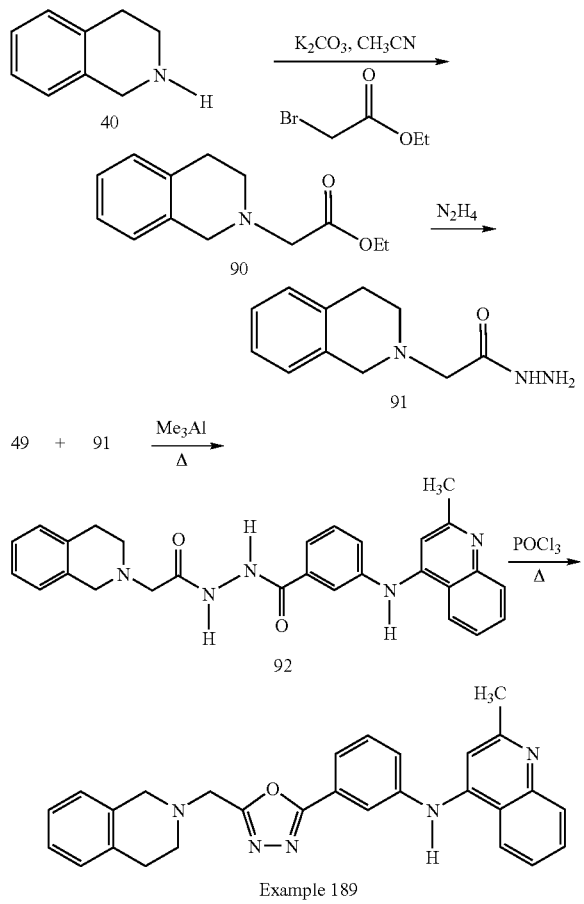

Example 189

Step 1. Ethyl(3,4-dihydro-1H-isoquinolin-2-yl)acetate (90).

To a solution of 40 (1.33 g, 10.0 mmol) in acetonitrile (50 mL) were sequentially added potassium carbonate (5.53 g, 40.0 mmol) and ethyl bromoacetate (1.67 g, 10.0 mmol). The reaction mixture was stirred at room temperature overnight, then partitioned between EtOAc (200 mL) and water (150 mL). The organic layer was dried (MgSO$_4$) and concentrated under reduced pressure to give 90 (2.1 g, 99%).

Step 2. (3,4-Dihydro-1H-isoquinolin-2-yl)acetic hydrazide (91).

A solution of 90 (2.0 g, 9.12 mmol) and hydrazine (5.1 g, 91 mmol) in ethanol (30 mL) was heated at reflux overnight. The mixture was concentrated under reduced pressure to give 91 (1.87 g ~100%) which was used without further purification.

Step 3. 3-(2-Methylquinolin-4-ylamino)-N'-(2-3,4-dihydro-1H-isoquinolin-2-yl-acetyl)benzoic hydrazide (92).

To a solution of 91 (205 mg, 1.0 mmol) in xylene (5 mL) was added trimethyl aluminum (2 M solution in hexanes, 0.75 mL, 1.5 mmol). The mixture was stirred under nitrogen for 10 minutes before the addition of methyl 3-(2-methylquinolin-4-ylamino)benzoate (49) (150 mg, 0.5 mmol). The reaction was heated at reflux overnight, quenched with water (2 mL), basified to pH 9 (2 N NaOH), and extracted with 7:3 CH$_2$Cl$_2$/MeOH. The organic layer was dried (K$_2$CO$_3$) and concentrated under reduced pressure, and the residue was purified by flash chromatography (SiO$_2$, gradient elution) to give 92 as a pale yellow oil (147 mg, 63%).

Step 4. {3-[5-(3,4-Dihydro-1H-isoquinolin-2-ylmethyl)-[1,3,4]oxadiazol-2-yl]phenyl}-(2-methylquinolin-4-yl)amine.

A mixture of 92 (195 mg, 0.42 mmol) in phosphorous oxychloride (0.5 mL) was heated overnight before mixing cautiously with ice water (2 mL). The mixture was extracted with 7:3 CH$_2$Cl$_2$/MeOH, and the organic layer was dried (MgSO$_4$) and concentrated under reduced pressure. The residue was purified by flash chromatography (SiO$_2$, gradient elution) to give the desired product as a pale yellow solid (69 mg, 37%).

EXAMPLE 190

{3-[3-(3,4-Dihydro-1H-isoquinolin-2-yl)prop-1-ynyl]phenyl}-(2-methylquinolin-4-yl)amine

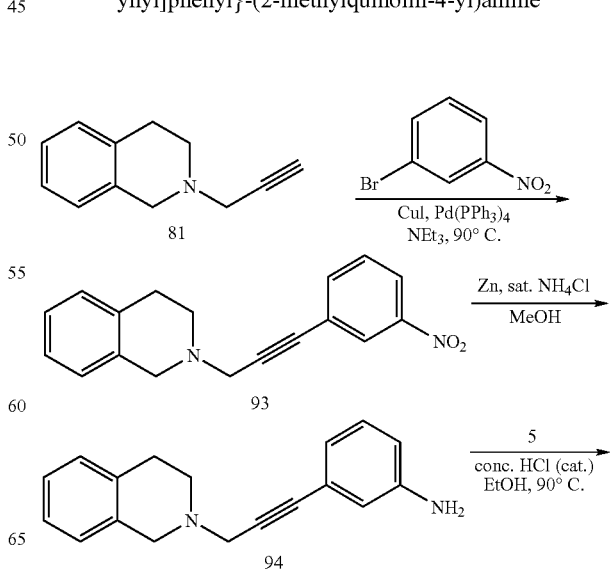

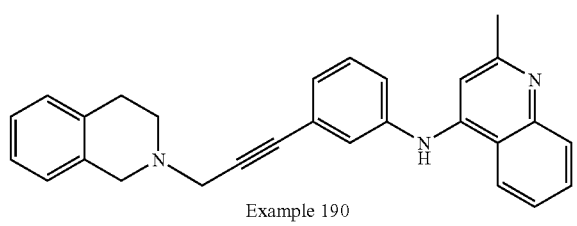

Example 190

Step 1. 2-[3-(3-Nitrophenyl)prop-2-ynyl]-1,2,3,4-tetrahydroisoquinoline (93).

To a solution of 81 (2.06 g, 10.2 mmol) in anhydrous triethylamine (30 mL) were sequentially added 1-bromo-3-nitrobenzene (1.83 g, 10.67 mmol), CuI (0.39 g, 2.05 mmol) and Pd(PPh$_3$)$_4$ (1.17 g, 1.0 mmol). The mixture was heated at 90° C. for 1 hour before it was filtered through Celite® and the filtrate was diluted with EtOAc (150 mL). The resulting solution was washed with water (100 mL), brine (100 mL), dried over Na$_2$SO$_4$ and concentrated. The residue was purified via flash silica gel chromatography to provide 93 (1.97 g, 66%).

Step 2. 3-[3-(3,4-Dihydro-1H-isoquinolin-2-yl)prop-1-ynyl]phenylamine (94).

94 was prepared from 93 by the procedure of Example 110 Step 4.

Step 3. {3-[3-(3,4-Dihydro-1H-isoquinolin-2-yl)prop-1-ynyl]phenyl}-(2-methylquinolin-4-yl)amine.

The title compound was prepared from 94 by the procedure of Example 1 Step 3.

EXAMPLE 191

N$^1$-[2-(3,4-Dihydro-1H-isoquinolin-2-yl)ethyl]-N$^7$-(2-methylquinolin-4-yl)-1,2,3,4-tetrahydronaphthalene-1,7-diamine

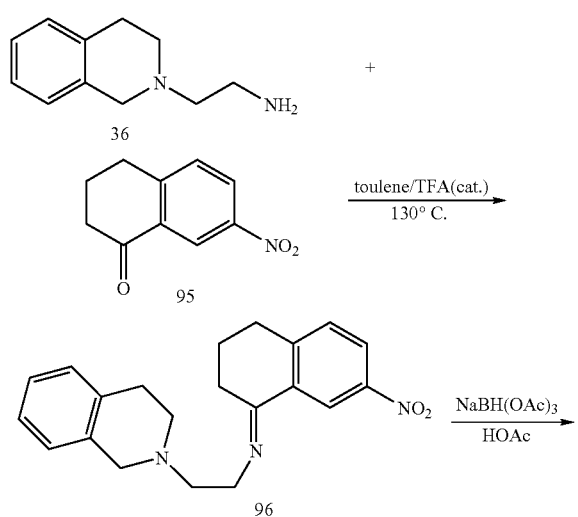

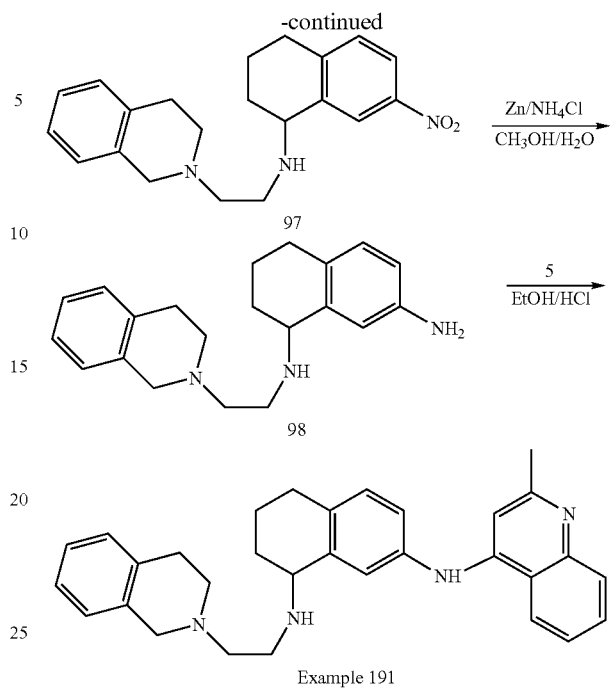

Example 191

Step 1. [2-(3,4-Dihydro-1H-isoquinolin-2-yl)ethyl]-(7-nitro-3,4-dihydro-2H-naphthalen-1-ylidene)amine (96).

To a solution of 36 (964 mg, 5.48 mmol) and 7-nitro-3,4-dihydro-2H-naphthalen-1-one (95) (1.05 g, 5.48 mmol) in toluene (30 mL) was added a catalytic amount of TFA. The reaction was heated at 130° C. overnight before it was allowed to cool to room temperature and diluted with EtOAc (100 mL). The organic solution was sequentially washed with saturated NaHCO$_3$ (aq. 100 mL), brine (100 mL), dried over Na$_2$SO$_4$, and concentrated to give 96 as a brown oil (1.8 g, 94%).

Step 2. [2-(3,4-Dihydro-1H-isoquinolin-2-yl)ethyl]-(7-nitro-1,2,3,4-tetrahydro-naphthalen-1-yl)amine (97).

To a solution of 96 (1.42 g, 4.07 mmol) in anhydrous dichloroethane (10 mL) were sequentially added acetic acid (267 mg, 4.48 mmol) and NaBH(OAc)$_3$ (1.12 g, 5.29 mmol) under N$_2$. The reaction was stirred at room temperature for 2 hours before it was quenched by slow addition of water (100 mL). The mixture was extracted with dichloromethane (100 mL) and the organic layer was sequentially washed with water (100 mL), saturated aq. NaHCO$_3$ (100 mL), and water (100 mL). The residue, from drying (Na$_2$SO$_4$) and concentrating the organic layer, was chromatographed on silica gel (EtOAc to 5:1 EtOAc/CH$_3$OH) to yield 97 as a brown oil (755 mg, 53%).

Step 3. N$^1$-[2-(3,4-Dihydro-1H-isoquinolin-2-yl)ethyl]-1,2,3,4-tetrahydronaphthalene-1,7-diamine (98).

98 was prepared from 97 by the procedure of Example 110 Step 4.

Step 4. N$^1$-[2-(3,4-Dihydro-1H-isoquinolin-2-yl)ethyl]-N$^7$-(2-methylquinolin-4-yl)-1,2,3,4-tetrahydronaphthalene-1,7-diamine.

The title compound was prepared from 98 by the procedure of Example 1 Step 3.

EXAMPLE 198

[2'-(3,4-Dihydro-1H-isoquinolin-2-ylmethyl)biphenyl-3-yl]-(2-methylquinolin-4-yl)amine

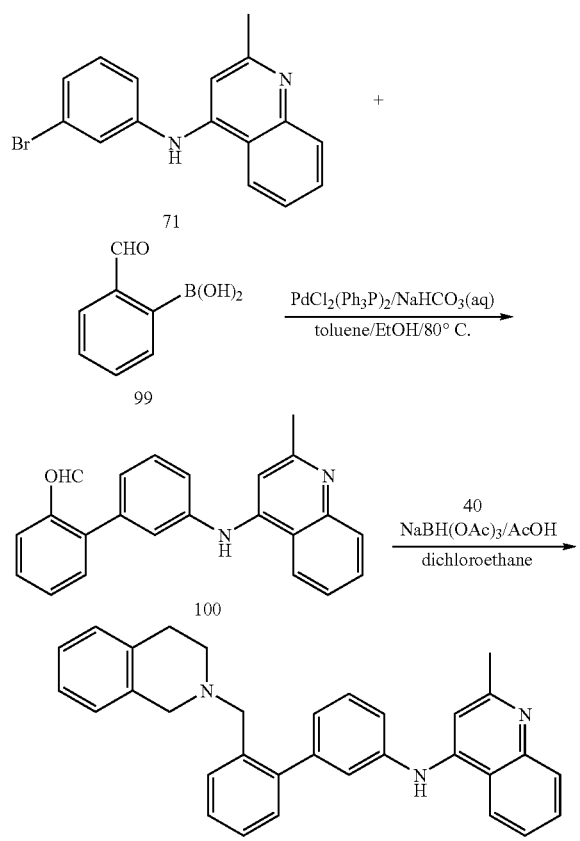

Example 198

Step 1. 3'-(2-Methylquinolin-4-ylamino)biphenyl-2-carbaldehyde (100).

To a stirred suspension of 71 (411 mg, 1.31 mmol) in toluene (12.8 mL) under N₂ were sequentially added saturated NaHCO₃ (aq. 0.5 mL), a solution of 99 (303 mg, 2.02 mmol) in EtOH (8.9 mL), and PdCl₂(Ph₃P)₃ (52 mg, 0.07 mmol). The reaction was heated at 80° C. for 41 hours before it was allowed to cool to room temperature and extracted with ethyl acetate (50 mL). The ethyl acetate extracts were washed with water (30 mL), brine (30 mL), dried (MgSO₄), and concentrated. The residue was chromatographed on silica gel (dichloromethane to 20:1 dichloromethane/methanol) to give 100 as a yellow solid (166 mg, 37.4%).

Step 2. [2'-(3,4-Dihydro-1H-isoquinolin-2-ylmethyl)biphenyl-3-yl]-(2-methylquinolin-4-yl)amine.

To a solution of 100 (166 mg, 0.49 mmol) and 40 (0.06 mL, 0.473 mmol) in dichloroethane (4.9 mL) were sequentially added NaBH(OAc)₃ (155 mg, 0.73 mmol) and HOAc (0.03 mL, 0.52 mmol). The reaction was stirred for 48 hours and then extracted with dichloromethane (2×30 mL). The dichloromethane extracts were washed with 2 N NaOH (aq. 15 mL), brine (15 mL), dried (MgSO₄), and concentrated. The residue was chromatographed on silica gel (ethyl acetate) to give desired product as a yellow solid (51 mg, 23.7%).

EXAMPLE 202

{3-[2-(4-Benzylpiperidin-1-yl)ethanesulfonyl]phenyl}-(2-methylquinolin-4-yl)amine

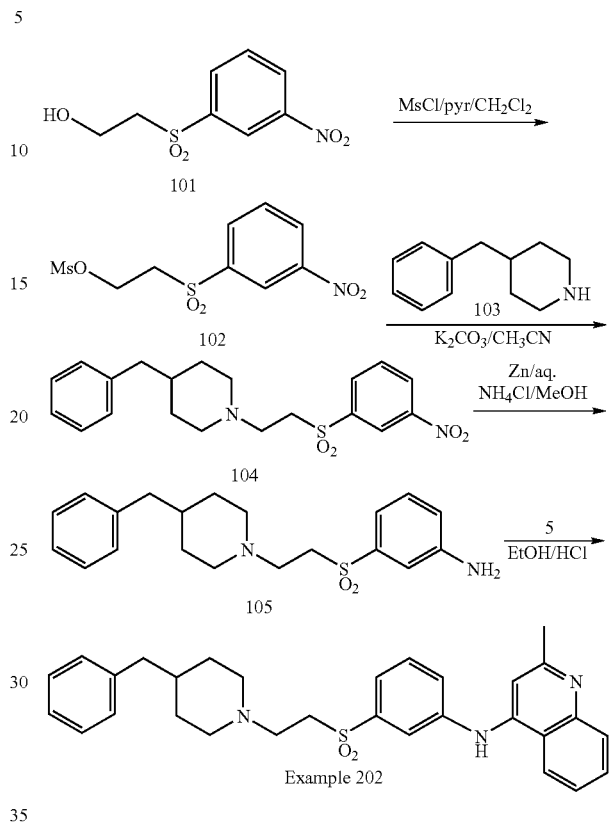

Example 202

Step 1. 2-(3-Nitro-benzenesulfonyl)ethyl methanesulfonate (102).

To a solution of 2-(3-nitrobenzenesulfonyl)ethanol (101) (5.0 g, 21.6 mmol) in dichloromethane (31.5 mL) and pyridine (7 mL) was added methanesulfonyl chloride (4.9 g, 43 mmol). The mixture was stirred at room temperature overnight before it was partitioned between dichloromethane (200 mL) and 0.5 N HCl (200 mL). The organic layer was dried over MgSO₄ and concentrated on a rotavap to give 102 (4.78 g, 71%).

Step 2. 4-Benzyl-1-[2-(3-nitrobenzenesulfonyl)ethyl]piperidine (104).

A mixture of 102 (1.0 g, 3.2 mmol), 4-benzylpiperidine (103) (0.62 g, 3.5 mmol), and potassium carbonate (1.1 g, 8.0 mmol) in acetonitrile (10 ml) was heated at 70° C. overnight. It was allowed to cool to room temperature and partitioned between EtOAc (150 mL) and water (150 mL). The organic layer was washed with water (100 ml), brine (100 ml), dried over MgSO₄, and concentrated. The residue was chromatographed on silica gel (8:1 to 4:1 to 2:1 hexanes/EtOAc) to give 104 (0.26 g, 21%).

Step 3. 3-[2-(4-Benzylpiperidin-1-yl)ethanesulfonyl]phenylamine (105).

See Example 110 Step 4.

Step 4. {3-[2-(4-Benzylpiperidin-1-yl)ethanesulfonyl]phenyl}-(2-methylquinolin-4-yl)amine.

The title compound was prepared from 105 by the procedure of Example 1 Step 3.

EXAMPLE 203

(3-{[2-(4-Benzylpiperidin-1-yl)ethylamino]methyl}phenyl)-(2-methylquinolin-4-yl)amine

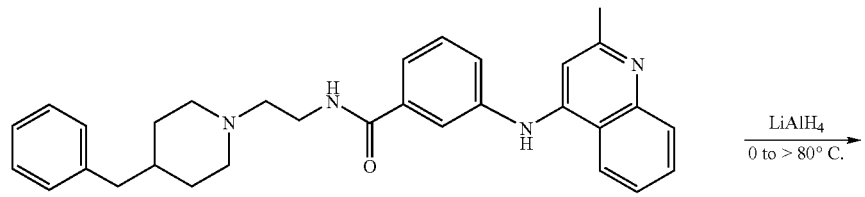

Example 134

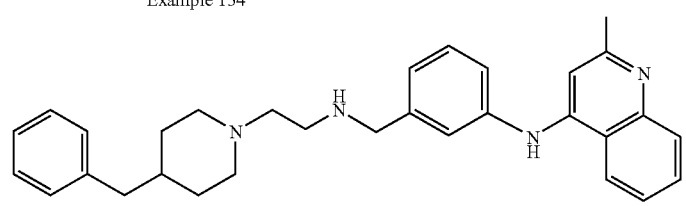

Example 203

To a solution of Example 134 (0.62 g, 1.30 mmol) in THF (20 mL) was added LiAlH$_4$ (1 M in THF, 4.0 mL, 3.90 mmol) at 0° C. The mixture was warmed to room temperature and then heated at 80° C. for 16 hours. The reaction was allowed to cool to room temperature and quenched with Na$_2$SO$_4$·10H$_2$O. The resulting slurry was filtered, rinsed with ethyl acetate, and the filtrate concentrated. The residue was chromatographed on silica gel (dichloromethane to 10:1 to 5:1 dichloromethane/methanol) to give the desired product as a yellow solid (170 mg, 28.3%).

EXAMPLE 208

N-[2-(4-Benzylpiperidin-1-yl)ethyl]-N'-(2-methylquinolin-4-yl)pyrimidine-4,6-diamine

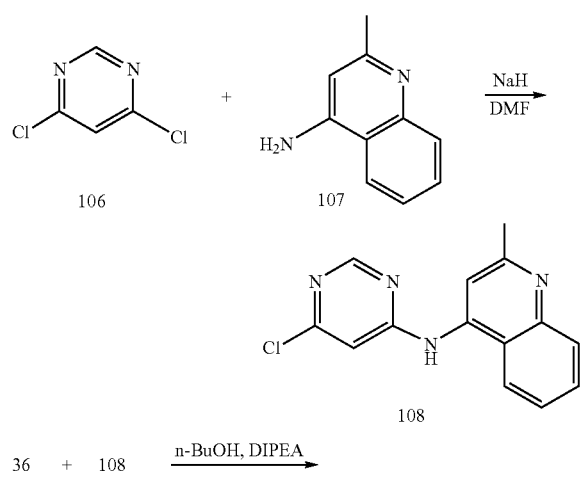

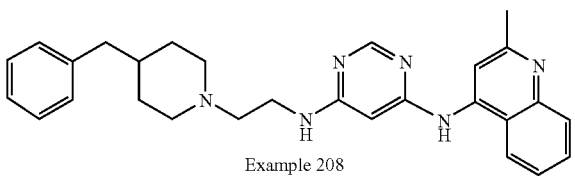

Example 208

Step 1. (6-Chloropyrimidin-4-yl)-(2-methylquinolin-4-yl)amine (108).

To a solution of 4-amino-2-methylquinoline (107) (1.0 g, 6.7 mmol) in anhydrous DMF (60 mL) was added NaH (60% in mineral oil, 0.32 g, 8.0 mmol). The mixture was stirred for 1 hour followed by the addition of 4,6-dichloropyrimidine (106) (1.0 g, 6.7 mmol). The reaction was heated at 90° C. overnight before it was poured into ice water (100 mL). The mixture was extracted with ether (3×100 mL) and the combined organic layers were dried (MgSO$_4$), concentrated under reduced pressure. The residue was purified by flash chromatrography (SiO$_2$, gradient elution, hexanes to 3:1 hexanes/ethyl acetate to 7:3 CH$_2$Cl$_2$/MeOH) to provide 108 (80 mg, 5%) as a white solid.

Step 2. N-[2-(4-Benzylpiperidin-1-yl)ethyl]-N'-(2-methylquinolin-4-yl)pyrimidine-4,6-diamine.

To a solution of diamine 36 (0.05 g, 0.21 mmol) in n-BuOH (2 mL) were sequentially added 108 (0.05 g, 0.18 mmol) and diisopropylethylamine (37 mg, 0.27 mmol). The mixture was heated at 100° C. overnight before the volatiles were removed under reduced pressure. The residue was purified by flash chromatography (SiO$_2$, gradient elution, 3:1 hexanes/ethyl acetate to 7:3 CH$_2$Cl$_2$/MeOH) to yield the desired product (20 mg, 25%) as a yellow oil.

EXAMPLE 209

3-(4-Benzylpiperidin-1-yl)-1-[3-(2-methylquinolin-4-ylamino)phenyl]propan-1-one

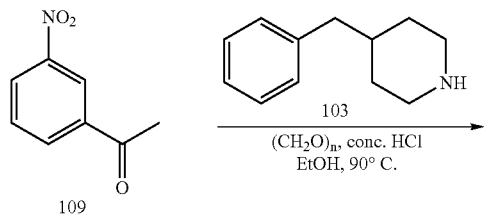

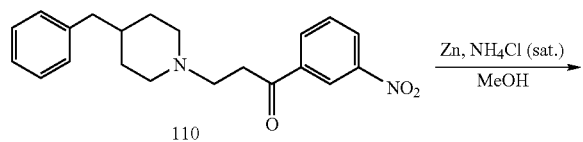

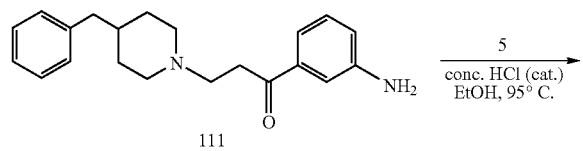

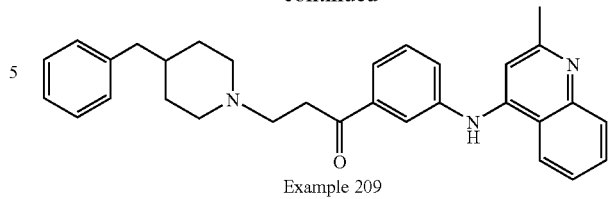

Example 209

Step 1. 3-(4-Benzylpiperidin-1-yl)-1-(3-nitrophenyl)propan-1-one (110).

To a solution of 3-nitroacetophenone (109) (0.60 g, 3.63 mmol) and 4-benzylpiperidine (103) (0.64 g, 3.63 mmol) in absolute ethanol (5 mL) was added concentrated hydrochloric acid (0.30 mL, 3.60 mmol). The mixture was heated under reflux and paraformaldehyde (0.32 g, 10.96 mmol) was added in four portions over a period of 40 minutes. The resulting mixture was heated under reflux overnight before it was allowed to cool to room temperature and diluted with EtOAc (100 mL). Following sequential washings with 1 N NaOH (2×100 mL), water (100 mL), and brine (100 mL), the organic solution was dried ($Na_2SO_4$) and concentrated. The residue was purified via flash silica gel chromatography to provide 110 (0.26 g, 20%) as a dark syrup.

Step 2. 1-(3-Amino-phenyl)-3-(4-benzyl-piperidin-1-yl)-propan-1-one (111).

111 was prepared from 110 by the procedure of Example 110 Step 4.

Step 3. 3-(4-Benzylpiperidin-1-yl)-1-[3-(2-methylquinolin-4-ylamino)phenyl]propan-1-one.

The title compound was prepared from 111 by the procedure of Example 1 Step 3.

EXAMPLE 210

3-(4-Benzylpiperidin-1-yl)-1-[3-(2-methylquinolin-4-ylamino)phenyl]propan-1-one O-methyloxime

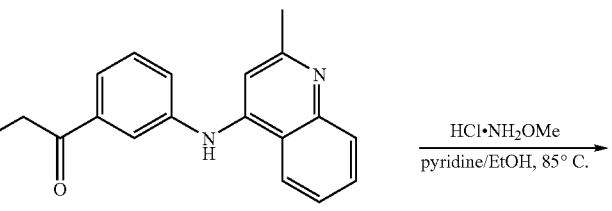
Example 209

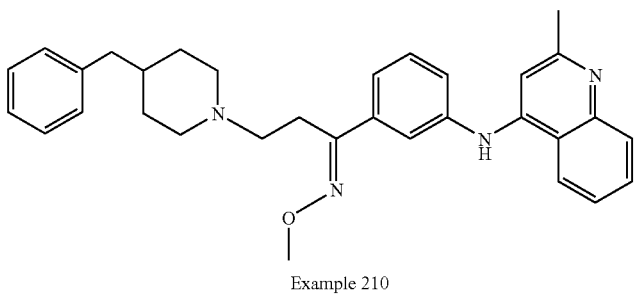
Example 210

A mixture of Example 209 (0.40 g, 0.86 mmol), ethoxyamine hydrochloric acid (0.22 g, 2.63 mmol,) and pyridine (0.19 g, 2.47 mmol) in anhydrous ethanol (3.0 mL) was heated under reflux overnight. The reaction was allowed to cool to room temperature and diluted with EtOAc (100 mL). Upon sequential washings with 1 N NaOH (2×100 mL) and brine (100 mL), the organic solution was dried over Na$_2$SO$_4$ and evaporated to dryness. The resulting residue was purified via flash silica gel chromatography to give the desired product (100 mg, 24%) as a white foam.

TABLE 4

| Example # | Structure | Chemical Name | Physical Description[a] | [M + H]+ |
|---|---|---|---|---|
| 174 | 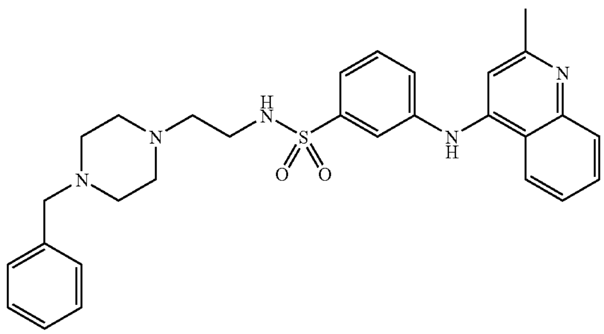 | N-[2-(4-Benzylpiperazin-1-yl)ethyl]-3-(2-methylquinolin-4-yl amino)benzenesulfonamide | pale yellow solid[b] | 516.39 |
| 175 | 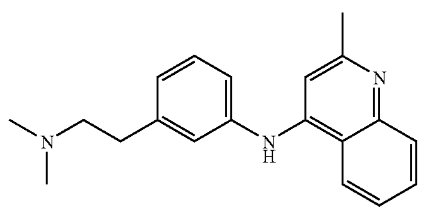 | [3-(2-Dimethylaminoethyl)phenyl]-(2-methyl quinolin-4-yl)amine | yellowish solid[b] | 306.27 |
| 176 | 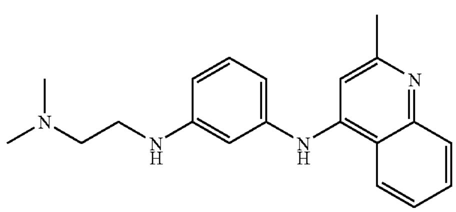 | N-(2-Dimethylaminoethyl)-N'-(2-methylquinolin-4-yl) phenylene-1,3-diamine | yellow solid[b] | 321.29 |
| 177 | 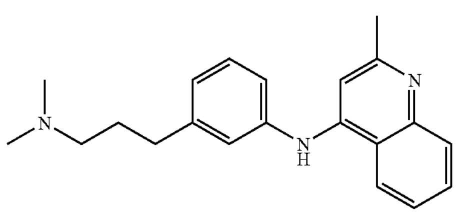 | [3-(3-Dimethylaminopropyl)phenyl]-(2-methyl quinolin-4-yl)amine | yellow solid | 320.35 |
| 178 | 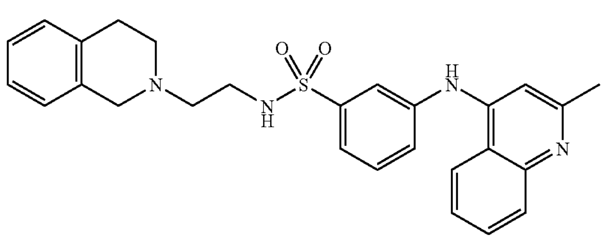 | N-[2-(3,4-Dihydro-1H-isoquinolin-2-yl)ethyl]-3-(2-methylquinolin-4-ylamino) benzenesulfonamide | yellow solid | 222.14 |

TABLE 4-continued

| Example # | Structure | Chemical Name | Physical Description[a] | [M + H]+ |
|---|---|---|---|---|
| 179 | 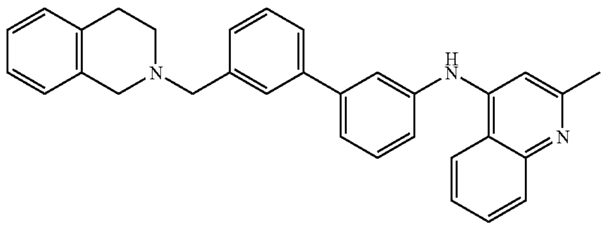 | [3'-(3,4-Dihydro-1H-isoquinolin-2-ylmethyl)biphenyl-3-yl]-(2-methylquinolin-4-yl)amine | yellow solid | 456.18 |
| 180 | 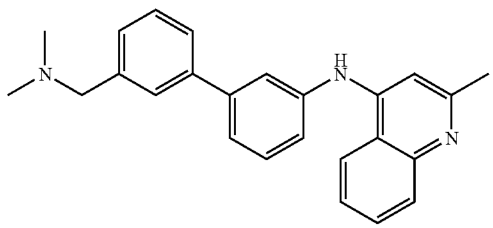 | (3'-Dimethylaminomethyl biphenyl-3-yl)-(2-methylquinolin-4-yl)amine | yellow solid[b] | 368.00 |
| 181 | 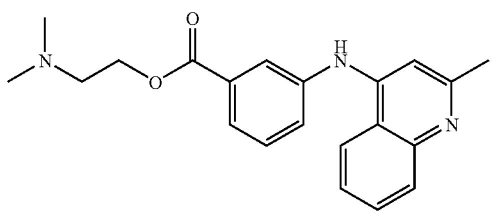 | 2-Dimethylaminoethyl 3-(2-methylquinolin-4-ylamino) benzoate | yellow solid | |
| 182 | 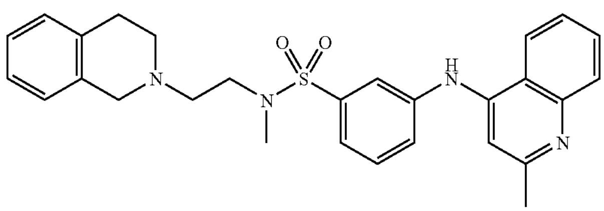 | N-[2-(3,4-Dihydro-1H-isoquinolin-2-yl)-ethyl]-N-methyl-3-(2-methyl quinolin-4-ylamino) benzenesulfonamide | yellow solid | 487.21 |
| 183 | 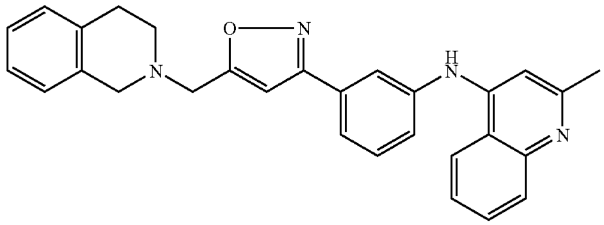 | {3-[5-(3,4-Dihydro-1H-isoquinolin-2-ylmethyl)isoxazol-3-yl]phenyl}-(2-methylquinolin-4-yl)amine | pale yellow solid[b] | 447.21 |
| 184 | 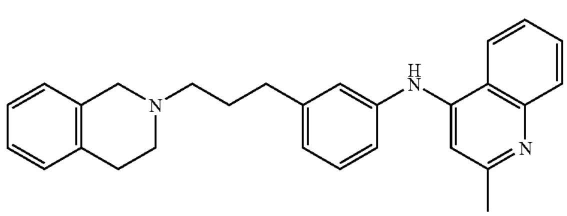 | {3-[3-(3,4-Dihydro-1H-isoquinolin-2-yl)propyl]phenyl}-(2-methyl quinolin-4-yl)amine | yellow solid | 408.29 |
| 185 | 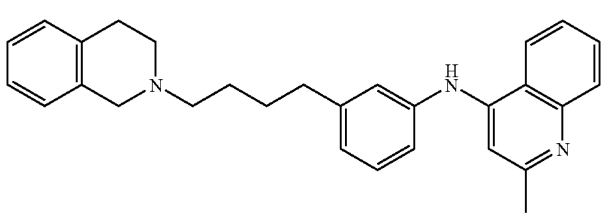 | {3-[4-(3,4-Dihydro-1H-isoquinolin-2-yl)butyl]phenyl}-(2-methyl quinolin-4-yl)amine | yellow solid | 422.30 |

TABLE 4-continued

| Example # | Structure | Chemical Name | Physical Description[a] | [M + H]+ |
|---|---|---|---|---|
| 186 | 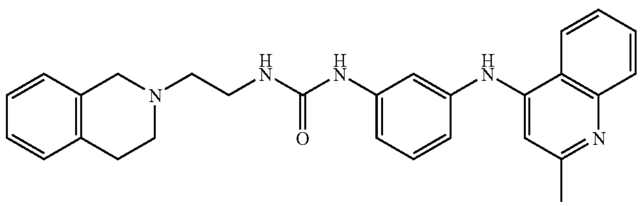 | 1-[2-(3,4-Dihydro-1H-isoquinolin-2-yl)ethyl]-3-[3-(2-methyl quinolin-4-ylamino)phenyl]urea | yellow solid | 452.08 |
| 187 | 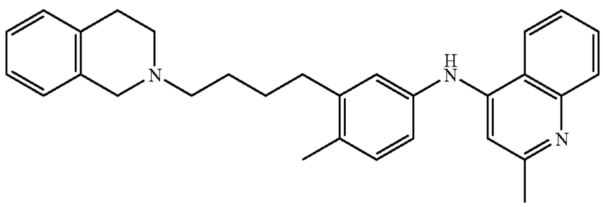 | {3-[4-(3,4-Dihydro-1H-isoquinolin-2-yl)butyl]-4-methylphenyl}-(2-methylquinolin-4-yl)amine | yellow solid | 436.31 |
| 188 | 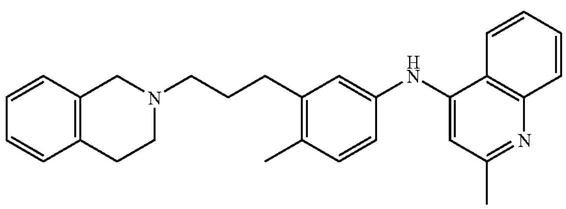 | {3-[3-(3,4-Dihydro-1H-isoquinolin-2-yl)propyl]-4-methylphenyl}-(2-methylquinolin-4yl)amine | yellow solid | 422.30 |
| 189 | 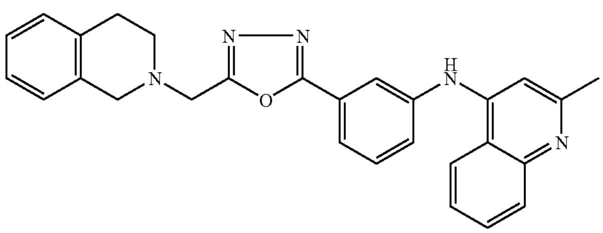 | {3-[5-(3,4-Dihydro-1H-isoquinolin-2-ylmethyl)-[1,3,4]oxadiazol-2-yl]phenyl}-(2-methylquinolin-4-yl)amine | pale yellow solid[b] | 448.20 |
| 190 | 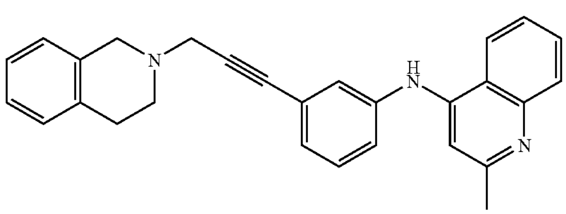 | {3-[3-(3,4-Dihydro-1H-isoquinolin-2-yl)prop-1-ynyl]phenyl}-(2-methylquinolin-4-yl)amine | off-white solid | 401.19 |
| 191 | 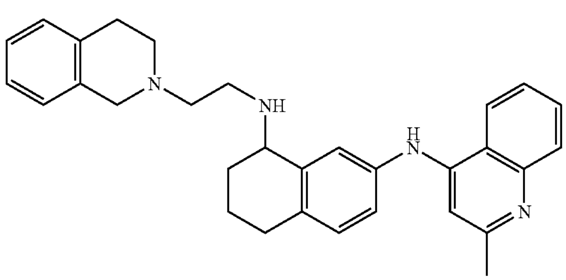 | N$^1$-[2-(3,4-Dihydro-1H-isoquinolin-2-yl)ethyl]-N$^7$-(2-methylquinolin-4-yl)-1,2,3,4-tetrahydro naphthalene-1,7-diamine | yellow solid | 463.20 |

TABLE 4-continued

| Example # | Structure | Chemical Name | Physical Description[a] | [M + H]+ |
|---|---|---|---|---|
| 192 | 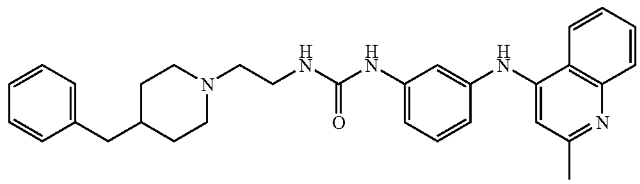 | 1-[2-(4-Benzylpiperidin-1-yl)ethyl]-3-[3-(2-methylquinolin-4-ylamino)phenyl]urea | green solid | 494.14 |
| 193 | 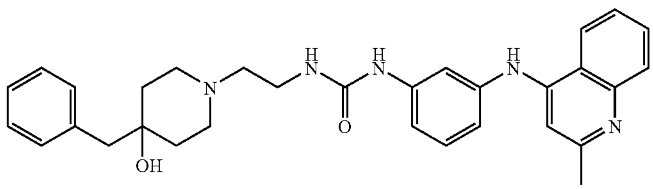 | 1-[2-(4-Benzyl-4-hydroxypiperidin-1-yl)ethyl]-3-[3-(2-methylquinolin-4-ylamino)-phenyl]urea | light brown solid | 510.18 |
| 194 | 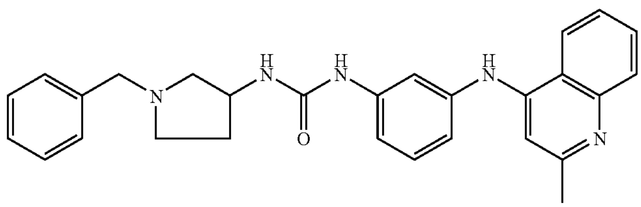 | 1-(1-Benzylpyrrolidin-3-yl)-3-[3-(2-methylquinolin-4-ylamino)phenyl]urea | pale yellow solid | 452.25 |
| 195 | 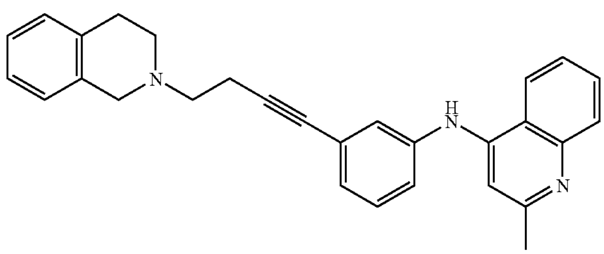 | {3-[4-(3,4-Dihydro-1H-isoquinolin-2-yl)but-1-ynyl]phenyl}-(2-methylquinolin-4-yl)amine | pale yellow solid[b] | 418.31 |
| 196 | 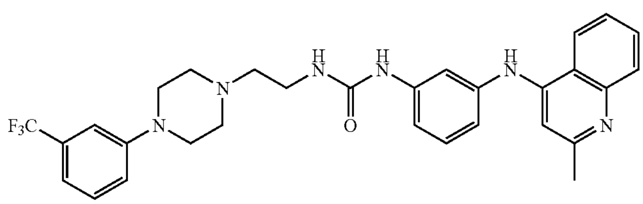 | 1-[3-(2-Methylquinolin-4-ylamino)phenyl]-3-{2-[4-(3-trifluoromethylphenyl)piperazin-1-yl]ethyl}urea | yellow solid[f] | 549.15 |
| 197 | 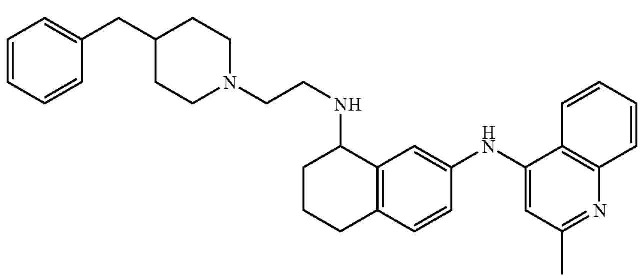 | N[1]-[2-(4-Benzylpiperidin-1-yl)ethyl]-N[7]-(2-methylquinolin-4-yl)-1,2,3,4-tetrahydronaphthalene-1,7-diamine | yellow solid[b] | 505.24 |
| 198 | 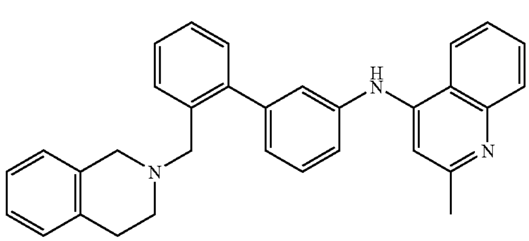 | [2'-(3,4-Dihydro-1H-isoquinolin-2-ylmethyl)biphenyl-3-yl]-(2-methylquinolin-4-yl)amine | yellow solid | 456.24 |

TABLE 4-continued

| Example # | Structure | Chemical Name | Physical Description[a] | [M + H]+ |
|---|---|---|---|---|
| 199 | 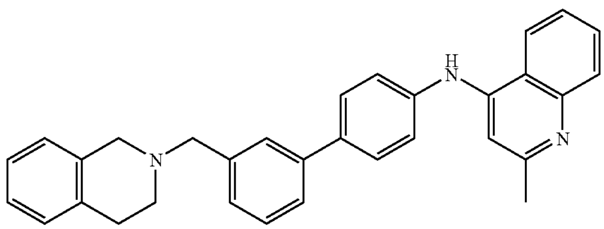 | [3'-(3,4-Dihydro-1H-isoquinolin-2-ylmethyl)biphenyl-4-yl]-(2-methylquinolin-4-yl)amine | yellow solid | 456.34 |
| 200 | 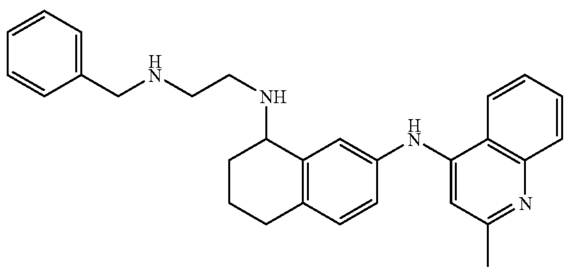 | N[1]-(2-Benzylaminoethyl)-N[7]-(2-methylquinolin-4-yl)-1,2,3,4-tetrahydronaphthalene-1,7-diamine | brownish oil[b] | 437.18 |
| 201 | 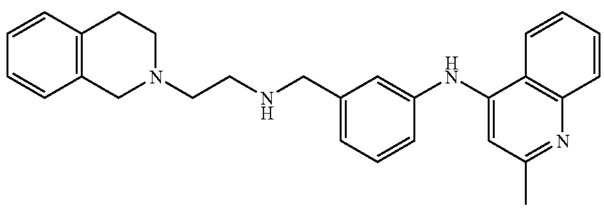 | (3-{[2-(3,4-Dihydro-1H-isoquinolin-2-yl)ethylamino]methyl}phenyl)-(2-methyl-quinolin-4-yl)amine | yellow solid[b] | 423.29 |
| 202 | 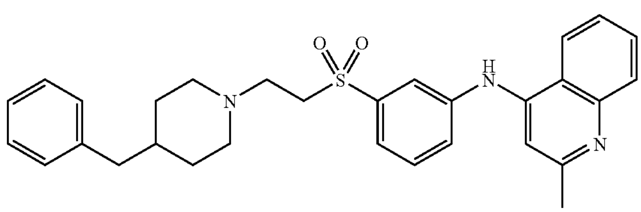 | {3-[2-(4-Benzylpiperidin-1-yl)ethanesulfonyl]-phenyl}-(2-methylquinolin-4-yl)amine | yellow solid | 500.27 |
| 203 | 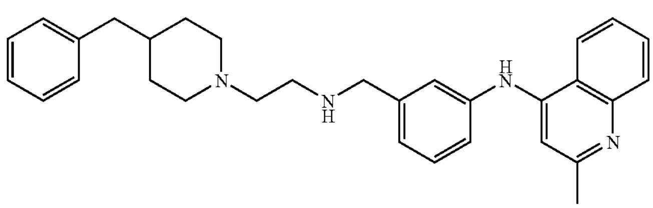 | (3-{[2-(4-Benzylpiperidin-1-yl)ethylamino]methyl}phenyl)-(2-methylquinolin-4-yl)amine | yellow solid | 465.28 |
| 204 | 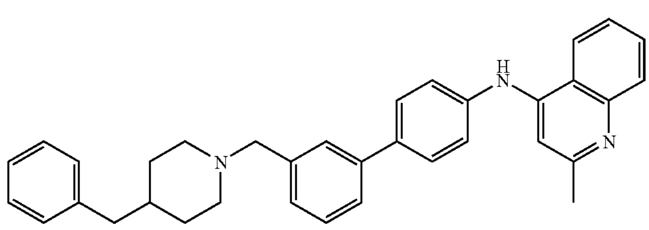 | [3'-(4-Benzylpiperidin-1-ylmethyl)biphenyl-4-yl]-(2-methylquinolin-4-yl)amine | pale yellow solid | 498.37 |

TABLE 4-continued

| Example # | Structure | Chemical Name | Physical Description[a] | [M + H]+ |
|---|---|---|---|---|
| 205 | 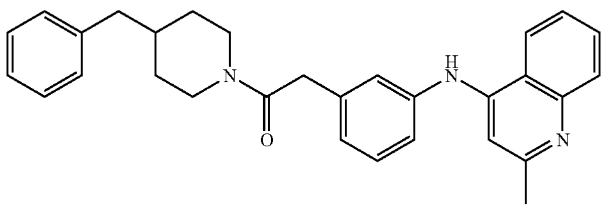 | 4-Benzyl-1-{[3-(2-methyl quinolin-4-ylamino) phenyl]acetyl}piperidine | yellow solid[b] | 450.35 |
| 206 | 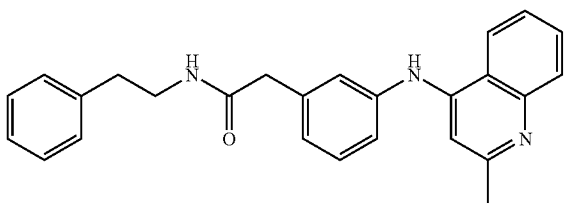 | 2-[3-(2-Methylquinolin-4-yl amino)phenyl]-N-phenethyl acetamide | yellow solid[b] | 396.30 |
| 207 | 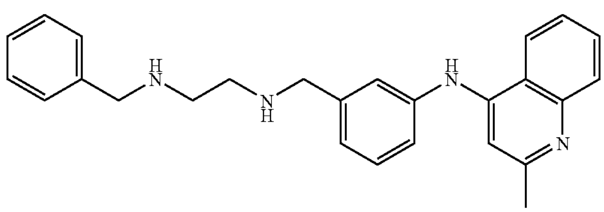 | N-Benzyl-N'-[3-(2-methyl quinolin-4-ylamino)benzyl] ethane-1,2-diamine | pale yellow solid | 397.24 |
| 208 | 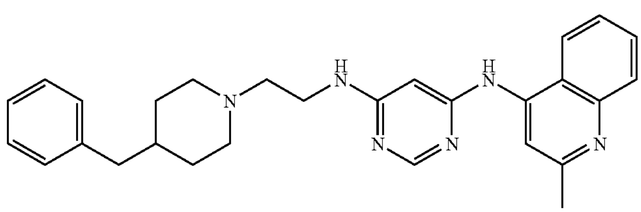 | N-[2-(4-Benzylpiperidin-1-yl) ethyl]-N'-(2-methylquinolin-4-yl)pyrimidine-4,6-diamine | off-white solid[b] | 453.29 |
| 209 | 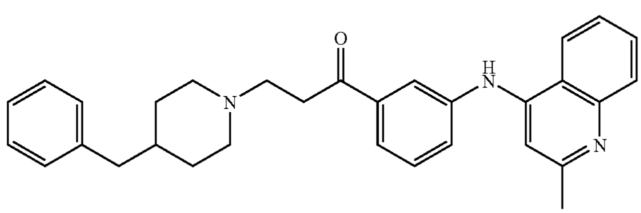 | 3-(4-Benzylpiperidin-1-yl)-1-[3-(2-methylquinolin-4-ylamino) phenyl]propan-1-one | yellow solid | 464.26 |
| 210 | 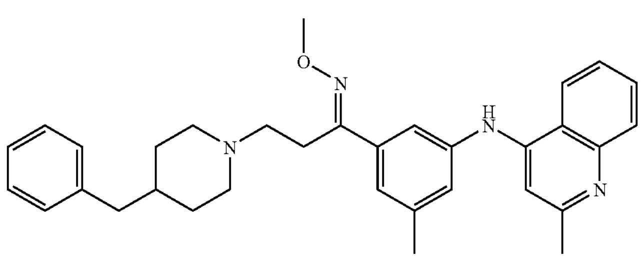 | 3-(4-Benzylpiperidin-1-yl)-1-[3-(2-methylquinolin-4-ylamino) phenyl]propan-1-one O-methyl oxime | pale yellow solid | 493.28 |

TABLE 4-continued

| Example # | Structure | Chemical Name | Physical Description[a] | [M + H]+ |
|---|---|---|---|---|
| 211 | 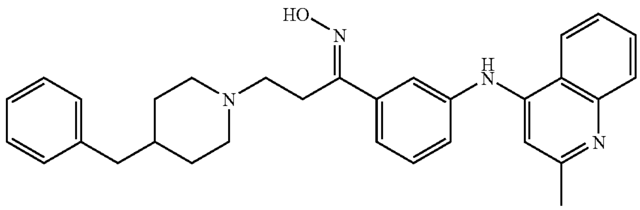 | 3-(4-Benzylpiperidin-1-yl)-1-[3-(2-methylquinolin-4-ylamino)phenyl]propan-1-one oxime | white solid | 479.28 |

[a]DiHCl salt unless otherwise noted.
[b]Parent compound
[f]TriHCl salt

The compounds of Examples 212 and 213 were synthesized in the same manner as for Example 67.

The compounds of Examples 214 and 221 were synthesized in the same manner and the synthesis for Example 214 is illustrated as follows:

EXAMPLE 214

(2-Methylquinolin-4-yl)(3-{2-[(3-methylthiophen-2-ylmethyl)amino]ethoxy}phenyl)amine

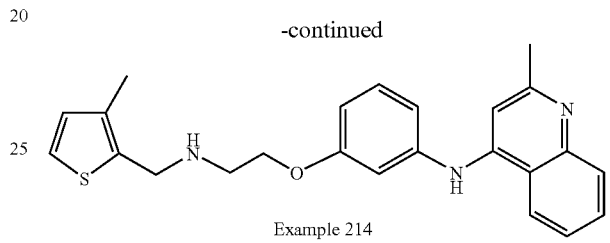

Example 214

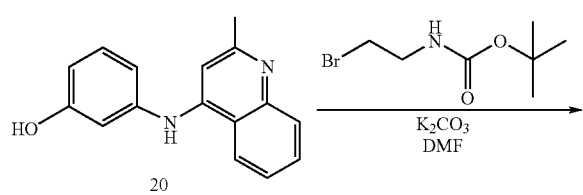

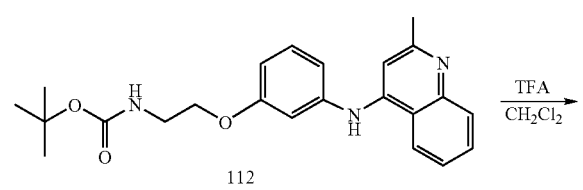

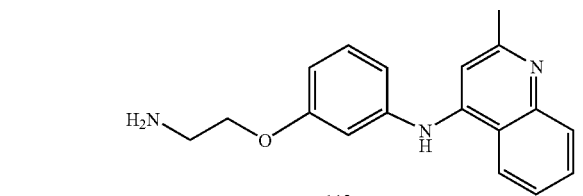

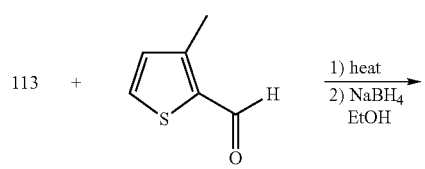

Step 1. tert-Butyl {2-[3-(2-methylquinolin-4-ylamino)phenoxy]ethyl}carbamate.

To a solution of 20 (1.0 g, 3.9 mmol) in DMF (15 ml) were sequentially added potassium carbonate (0.6 g, 4.7 mmol) and tert-butyl(2-bromoethyl)carbamate (0.9 g, 3.9 mmol). The is reaction mixture was stirred at 80° C. overnight before it was mixed with water (20 ml), saturated NaCl solution (5.0 ml), and extracted with 7:3 $CH_2Cl_2$/MeOH (3×20 ml). The organic layers were combined, dried ($K_2CO_3$), and then concentrated under reduced pressure.

The residue was purified by flash chromatography ($SiO_2$, gradient elution, 9:1 to 8:2 A/B, A: 3:1 hexanes/ethyl acetate, B: 7/3 $CH_2Cl_2$/MeOH) to yield the desired product 112 as a colorless oil (0.18 g, 12%).

Step 2. [3-(2-Aminoethoxy)phenyl](2-methylquinolin-4-yl)amine.

To a solution of 112 (0.18 g, 0.45 mmol) in $CH_2Cl_2$ (5.0 ml) was added trifluoroacetic acid (0.35 ml, 4.5 mmol) and the reaction mixture was stirred at room temperature overnight. The reaction mixture was mixed with water (5.0 ml), saturated NaCl solution (3.0 ml), made basic with 2N NaOH (3.0 ml), and extracted with 7:3 $CH_2Cl_2$/MeOH (3×5.0 ml). The organic materials were combined, dried ($K_2CO_3$), and then concentrated under reduced pressure to give amine 113 as a white solid (0.11 g, 85%).

Step 3. (2-Methylquinolin-4-yl)(3-{2-[(3-methylthiophen-2-ylmethyl)amino]ethoxy}phenyl)amine.

Amine 113 (0.10 g, 0.34 mmol) and 3-methyl-thiophene-2-carboxaldehyde (0.03 ml, 0.34 mmol) were mixed and heated under vacuum with a heat gun for 5 minutes or until bubbling stops. The reaction mixture was allowed to cool to room temperature under vacuum. To a solution of this mixture in EtOH (4 ml) was added sodium borohydride (0.03 g, 0.85 mmol) in portions, and the resulting mixture was stirred at room temperature for 1 hour. The reaction was treated with water (4 ml), saturated NaCl solution (3.0 ml), made basic with 2N NaOH (2.0 ml), and extracted with 7:3 CH$_2$Cl$_2$/MeOH (3×5.0 ml). The organic layers were combined, dried (K$_2$CO$_3$), and then concentrated under reduced pressure. The residue was purified by reverse phase HPLC (10-50% aqueous acetonitrile) to yield the desired product as an off-white solid (0.01 g, 4%).

EXAMPLE 222

2-{3-[3-(2-Methylquinolin-4-ylamino)-5-trifluoromethylphenoxy]propyl}isoindole-1,3-dione

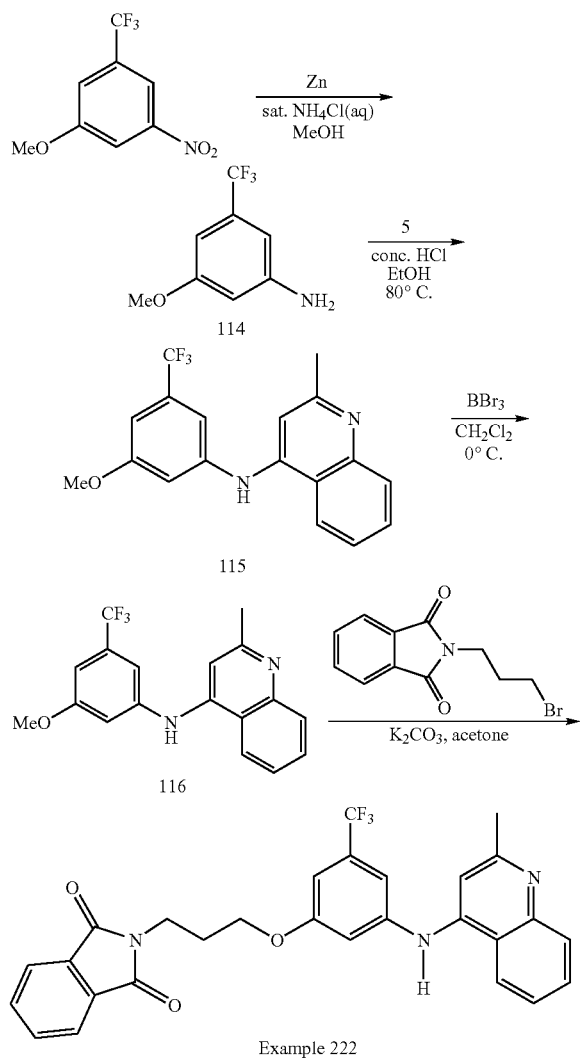

Example 222

Step 1. 3-Methoxy-5-trifluoromethylphenylamine.

To a solution of 1-methoxy-3-nitro-5-trifluoromethylbenzene (10.0 g, 45.22 mmol) in methanol (100 mL) were sequentially added sat. aq. NH$_4$Cl (100 ml) and zinc (19.31 g, 295.35 mmol) at room temperature. The resulting mixture was stirred at room temperature for 3 hours before the reaction was filtered through Celite®, rinsed with methanol (2×100 mL), and the filtrate was evaporated. The residue was extracted with ethyl acetate (200 mL), washed with water (50 mL), and brine (50 mL). The organic layer was dried over MgSO$_4$ and concentrated on a rotavap to give the desired product 114 as a yellow solid (7.63 g, 88% yield).

Step 2. (3-Methoxy-5-trifluoromethylphenyl)(2-methylquinolin-4-yl)amine.

To a solution of 114 (7.61 g, 39.81 mmol) in EtOH (80 ml) were sequentially added 4-chloroquinaldine (5) (7.07 g, 39.83 mmol) and conc. HCl (0.25 ml) at room temperature. The resulting mixture was heated at 80° C. for 1 hour before the reaction was allowed to cool to room temperature and filtered. The solids were rinsed with diethyl ether (6×50 mL) and air-dried under house vacuum to afford the desired product 115 as a pale purple solid (12.73 g, 87%).

Step 3. 3-(2-Methylquinolin-4-ylamino)-5-trifluoromethylphenol.

To a suspension of 115 (12.70 g, 38.22 mmol) in dichloromethane (109 ml) was added BBr$_3$ (50 g, 199.57 mmol) over 3 min. at 0° C. The resulting mixture was stirred at 0° C. for 3 hours before the reaction was quenched with methanol (40 ml) over 3 minutes. The mixture was stirred an additional 5 minutes and filtered. The solids were rinsed with MeOH (3×50 ml) and air-dried under house vacuum to afford the desired product 116 as a pale yellow solid (9.76 g, 71% yield).

Step 4. 2-{3-[3-(2-Methylquinolin-4-ylamino)-5-trifluoromethylphenoxy]propyl}isoindole-1,3-dione.

To a solution of 116 (3.0 g, 8.46 mmol) and N-3-bromopropylphthalimide (2.27 g, 8.46 mmol) in acetone (50 ml) was added potassium carbonate (2.57 g, 18.6 mmol). The mixture was heated under reflux for 2 days before the solvent was removed under reduced pressure.

The residue was partitioned between water (75 ml) and 7:3 methylene chloride/methanol (50 ml), and the organic layer was separated, dried (MgSO$_4$), and concentrated. The residue was recrystallized from hot ethyl acetate to give the desired product as white crystals (3.01 g, 72%).

The compounds of Examples 223 and 224 were synthesized in the same manner as Example 214.

EXAMPLE 225

{3-[3-(1,3-Dihydroisoindol-2-yl)propoxy]-5-trifluoromethylphenyl}(2-methylquinolin-4-yl)amine To a solution of the product of Example 222 (81.3 mg, 0.16 mmol) in THF (2 ml) at 0° C. was added dropwise a solution of lithium aluminum hydride (0.8 ml of a 1 M solution in THF). The reaction was stirred for 3 hours while the bath temperature rose to ambient temperature. Powdered sodium sulfate decahydrate (300 mg) was added in portions at 0° C. and the resulting mixture was stirred for 2 hours before it was filtered through a pad of Celite®. The filtrate was concentrated under reduced pressure and the residue purified by flash chromatography (SiO$_2$, gradient 3:1 hexane/ethyl acetate to 7:3 methylene chloride/methanol) to give the desired product as a yellow solid (55 mg, 72%). It was converted to the diHCl salt (X) by the sequential addition of acetonitrile (1 mL), 0.1N HCl (2.3 mL) and followed by lyopholization.

The compounds of Examples 226 and 227 were synthesized in the same manner as Example 214.

The compounds of Examples 228 and 229 were synthesized in the same manner as Example 45.

The compound of Example 230 was synthesized in the same manner as Example 67.

| Example # | structure | chemical name | physical description[a] | [M + H]+ |
|---|---|---|---|---|
| 212 | 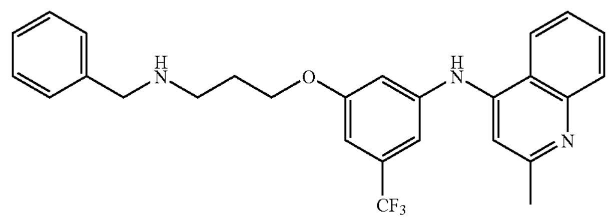 | [3-(3-benzylaminopropoxy)-5-trifluoromethylphenyl]-(2-methylquinolin-4-yl)amine | white solid | 466.20 |
| 213 | 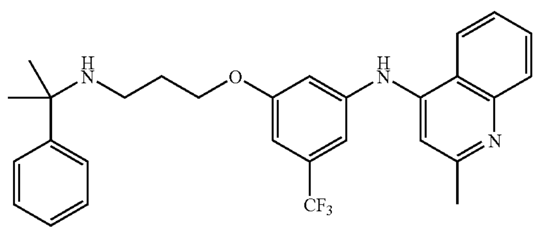 | {3-[3-(1-methyl-1-phenylethylamino)propoxy]-5-trifluoromethylphenyl}-(2-methylquinolin-4-yl)amine | yellow solid | 494.07 |
| 214 | 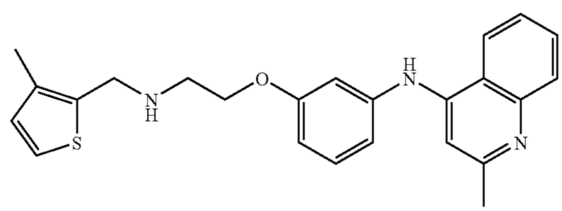 | (2-methylquinolin-4-yl)-(3-{2-[(3-methylthiophen-2-ylmethyl)amino]ethoxy}phenyl)amine | pale yellow solid | 404.18 |
| 215 | 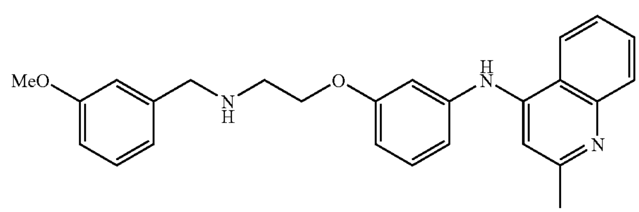 | {3-[2-(3-methoxybenzylamino)ethoxy]phenyl}(2-methylquinolin-4-yl)amine | pale yellow solid | 414.25 |
| 216 | 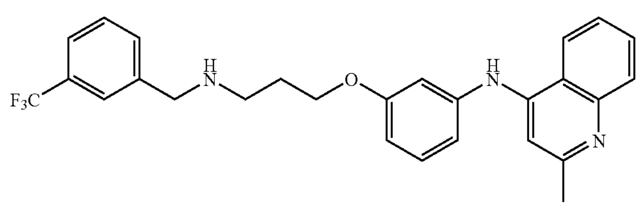 | (2-methylquinolin-4-yl){3-[3-(3-trifluoromethylbenzylamino)propoxy]phenyl}amine | pale yellow solid | 466.29 |
| 217 | 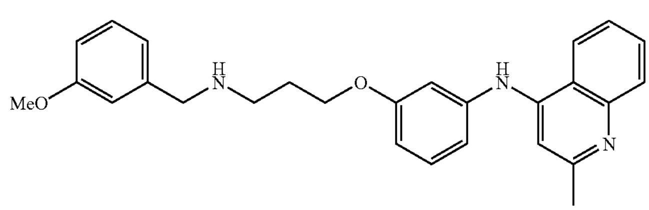 | {3-[3-(3-methoxybenzylamino)propoxy]phenyl}(2-methylquinolin-4-yl)amine | white solid | 428.29 |

-continued

| Example # | structure | chemical name | physical description[a] | [M + H]+ |
|---|---|---|---|---|
| 218 | 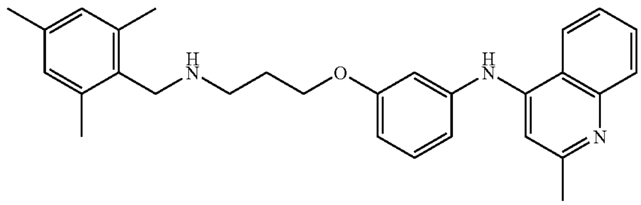 | (2-methyl quinolin-4-yl){3-[3-(2,4,6-trimethylbenzylamino)propoxy]phenyl}amine | pale yellow solid | 440.22 |
| 219 | 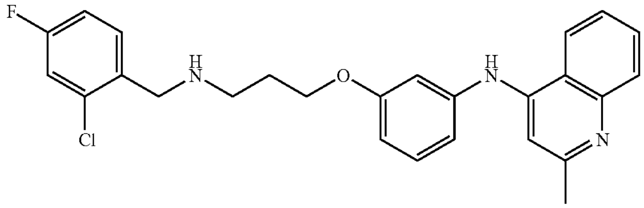 | {3-[3-(2-chloro-4-fluorobenzylamino)propoxy]phenyl}(2-methyl quinolin-4-yl)amine | pale yellow solid | 450.18 |
| 220 | 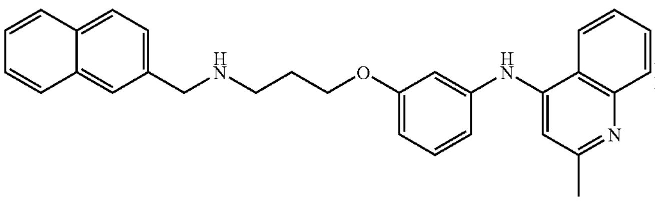 | (2-methylquinolin-4-yl)(3-{3-[(naphthalen-2-yl methyl)amino]propoxy}phenyl)amine | off-white solid | 448.27 |
| 221 | 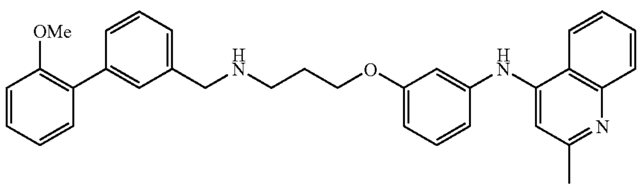 | (3-{3-[(2'-methoxybiphenyl-3ylmethyl)amino]propoxy}phenyl)(2-methyl quinolin-4yl)amine | pale yellow solid[b] | 504.29 |
| 222 | 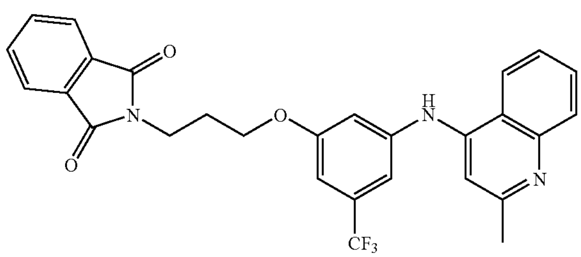 | 2-{3-[3-(2-methylquinolin-4-ylamino)-5-trifluoromethyl phenoxy]propyl}isoindole-1,3-dione | white solid[b] | 506.30 |
| 223 | 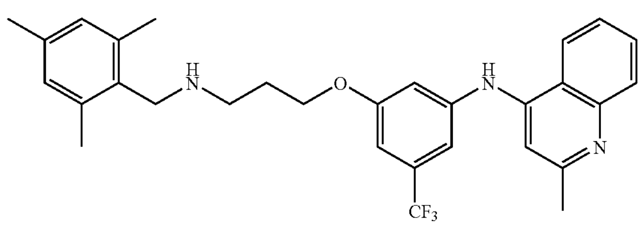 | (2-methyl quinolin-4-yl){3-trifluoromethyl-5-[3-(2,4,6-trimethyl benzylamino)propoxy]phenyl}amine | white solid | 508.36 |
| 224 | 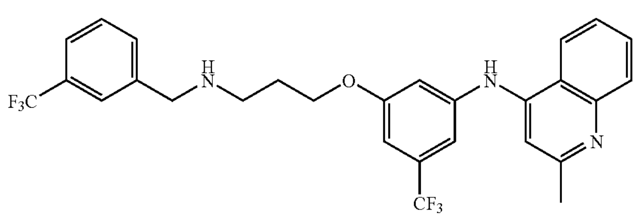 | (2-methyl quinolin-4-yl){3-trifluoromethyl-5-[3-(3-trifluoromethyl benzylamino)propoxy]phenyl}amine | white solid | 534.30 |

-continued

| Example # | structure | chemical name | physical description[a] | [M + H]+ |
|---|---|---|---|---|
| 225 | 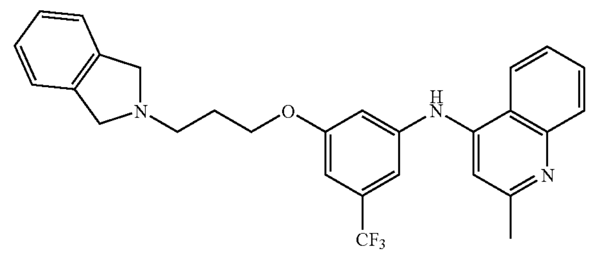 | {3-[3-(1,3-dihydroisoindol-2-yl)propoxy]-5-trifluoromethylphenyl}(2-methylquinolin-4-yl)amine | green solid | 478.37 |
| 226 | 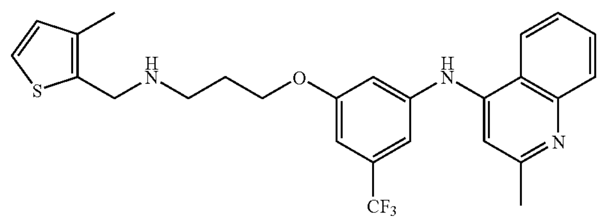 | (2-methylquinolin-4-yl){3-[3-(3-methylthien-2-yl)methylamino)propoxy]-5-trifluoromethylphenyl}amine | white solid | 486.35 |
| 227 | 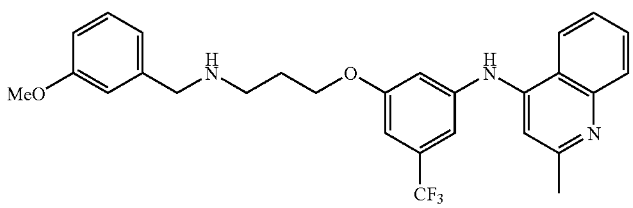 | {3-[3-(3-methoxybenzylamino)propoxy]-5-trifluoromethylphenyl}(2-methylquinolin-4-yl)amine | white solid[b] | 496.39 |
| 228 | 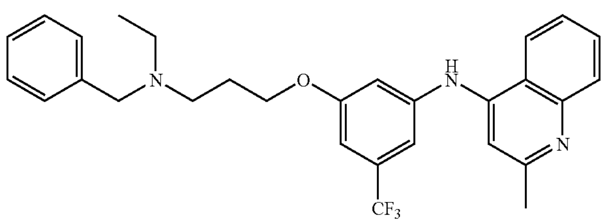 | {3-[3-(benzylethylamino)propoxy]-5-trifluoromethylphenyl}(2-methyl-quinolin-4-yl)amine | pale yellow solid[b] | 494.23 |
| 229 | 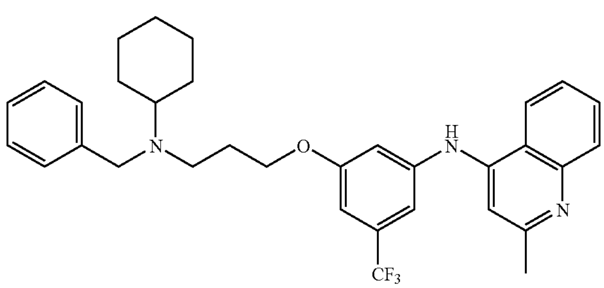 | {3-[3-(benzylcyclohexylamino)propoxy]-5-trifluoromethylphenyl}(2-methyl-quinolin-4-yl)amine | pale yellow solid[b] | 548.44 |
| 230 | 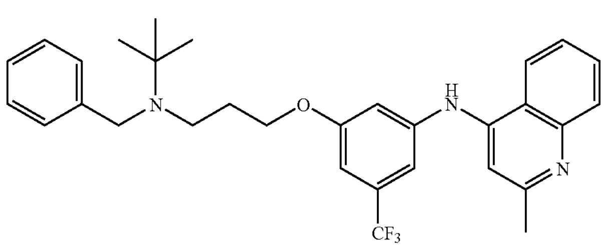 | {3-[3-(benzyl-tert-butylamino)propoxy]-5-trifluoromethylphenyl}(2-methyl-quinolin-4-yl)amine | pale yellow solid | 466.39 |

[a]diHCl salt unless otherwise noted
[b]parent compound
[c]sodium salt
[d]triHCl salt The compounds of Examples 231 to 234 were synthesized in the same manner as for Example 238.

The compounds of Examples 235 and 236 were synthesized in the same manner and the synthesis is illustrated for Example 235 as follows:

EXAMPLE 235

{3-[2-(4-Benzyl-4-methoxypiperidin-1-yl)ethoxy]phenyl}(2-methylquinolin-4-yl)amine

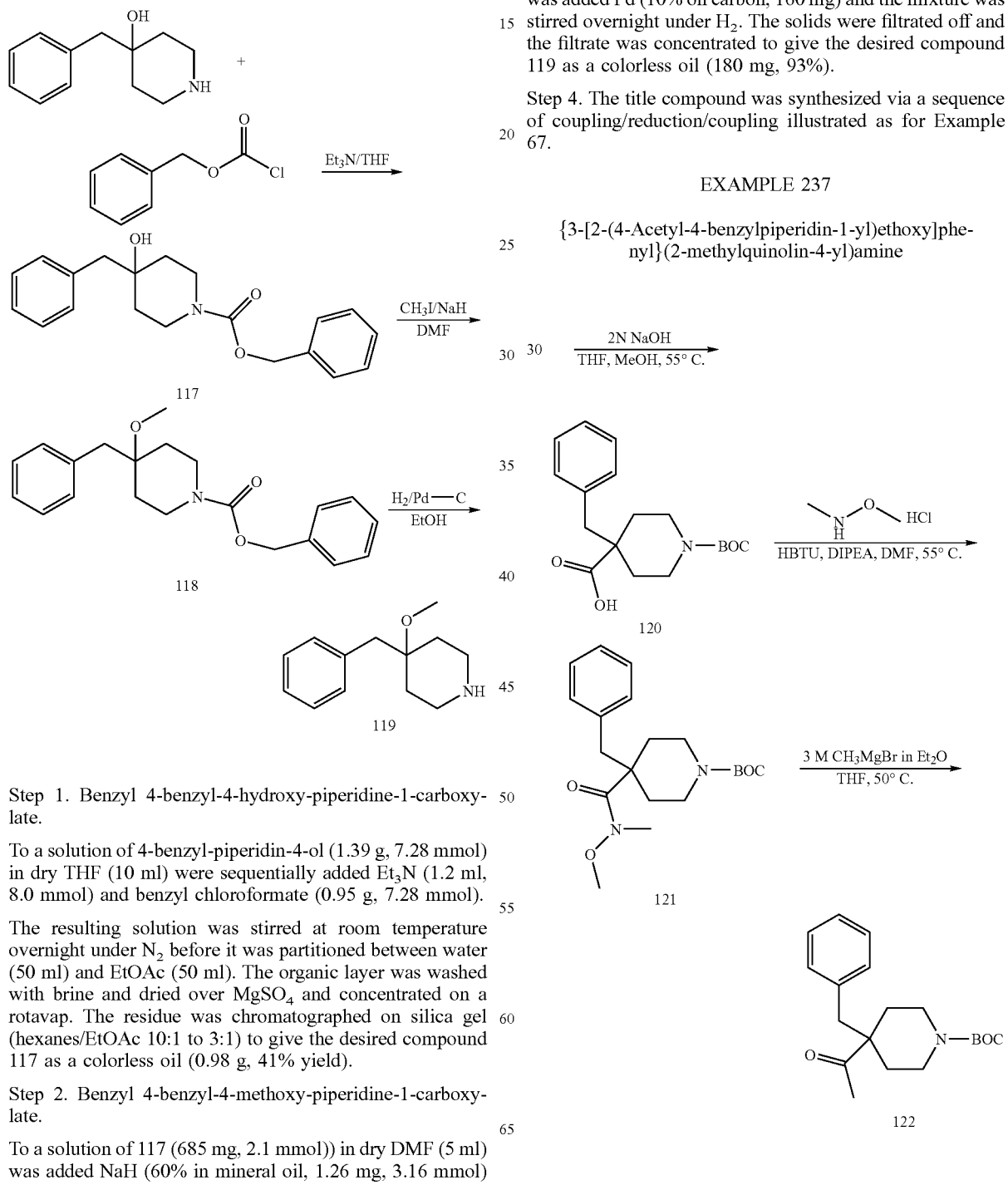

Step 1. Benzyl 4-benzyl-4-hydroxy-piperidine-1-carboxylate.

To a solution of 4-benzyl-piperidin-4-ol (1.39 g, 7.28 mmol) in dry THF (10 ml) were sequentially added Et$_3$N (1.2 ml, 8.0 mmol) and benzyl chloroformate (0.95 g, 7.28 mmol). The resulting solution was stirred at room temperature overnight under N$_2$ before it was partitioned between water (50 ml) and EtOAc (50 ml). The organic layer was washed with brine and dried over MgSO$_4$ and concentrated on a rotavap. The residue was chromatographed on silica gel (hexanes/EtOAc 10:1 to 3:1) to give the desired compound 117 as a colorless oil (0.98 g, 41% yield).

Step 2. Benzyl 4-benzyl-4-methoxy-piperidine-1-carboxylate.

To a solution of 117 (685 mg, 2.1 mmol)) in dry DMF (5 ml) was added NaH (60% in mineral oil, 1.26 mg, 3.16 mmol) at 0° C. It was stirred for 15 minutes before the addition of iodomethane (299 mg, 2.1 mmol). The reaction was stirred overnight and quenched with methanol (1 ml). The mixture was partitioned between water (30 ml) and EtOAc (30 ml) and the organic layer was washed with brine, dried over MgSO$_4$, and concentrated on a rotavap.

The residue was chromatographed on silica gel (hexanes/EtOAc 4:1) to give the desired compound 118 as a colorless oil (0.75 g, ~100% yield)

Step 3. 4-Benzyl-4-methoxypiperidine.

To a solution of 118 (321 mg, 0.95 mmol)) in EtOH (10 ml) was added Pd (10% on carbon, 160 mg) and the mixture was stirred overnight under H$_2$. The solids were filtrated off and the filtrate was concentrated to give the desired compound 119 as a colorless oil (180 mg, 93%).

Step 4. The title compound was synthesized via a sequence of coupling/reduction/coupling illustrated as for Example 67.

EXAMPLE 237

{3-[2-(4-Acetyl-4-benzylpiperidin-1-yl)ethoxy]phenyl}(2-methylquinolin-4-yl)amine

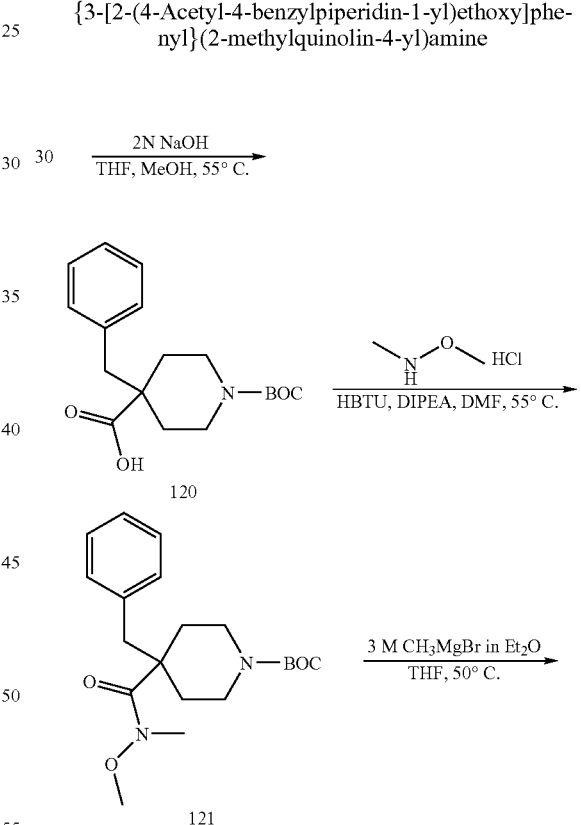

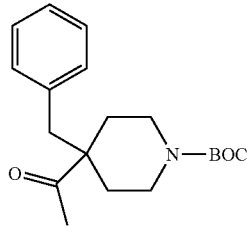

Step 1. 4-Benzyl-1-tert-butoxycarbonylpiperidine-4-carboxylic acid.

To the solution of 30 (2.42 g, 7.26 mmol) in TBF (22 ml) was added 2 N NaOH (11 ml) at room temperature. MeOH (~5 ml) was added dropwise to this mixture until the mixture became homogeneous. The reaction was stirred overnight before the addition of NaOH pellets (2.03 g, 50.75 mmol). The resulting mixture was heated at 55° C. for 3 days, allowed to cool to room temperature, diluted with water (100 ml), washed with Et$_2$O (50 ml×2), and cidified with 2N HCl. The desired product 120 was collected on a filter paper as a white solid (2.0 g, 86%).

Step 2. 4-Benzyl-1-tert-butoxycarbonyl-4-(methoxymethylcarbamoyl)piperidine.

The same procedure as shown for Example 112, step 1 was used.

Step 3. 4-Acetyl-4-benzyl-1-tert-butoxycarbonylpiperidine.

To the solution of 121 (0.15 g, 0.42 mmol) in anhydrous THF (2 ml) was added CH$_3$MgBr (3.0 M in Et$_2$O, 0.63 ml, 1.89 mmol) dropwise at 0° C. The resulting mixture was stirred at 0° C. for 1 hour and at 500° C. for 3 hours before the reaction was quenched with sat. NH$_4$Cl.

The mixture was extracted with EtOAc (3×50 ml) and the combined organic layers were washed with brine (50 ml), dried over Na$_2$SO$_4$ and concentrated on a rotavap. The residue was chromatographed on silica gel to afford the desired product 122 as a colorless oil. (75 mg, 56%).

Step 4. {3-[2-(4-Acetyl-4-benzylpiperidin-1-yl)ethoxy]phenyl}(2-methylquinolin-4-yl)amine.

The title compound was synthesized via a sequence of deprotection/coupling/reduction/coupling as illustrated for Example 67 (steps 3-5).

EXAMPLE 238

{3-[2-(4-Benzyl-4-(morpholin-4-ylcarbonyl))piperidin-1-yl)ethoxy]phenyl}(2-methylquinolin-4-yl) amine The title compound was synthesized from the product of Example 68 using the same procedure as shown for Example 112, step 1.

EXAMPLE 239

4-(3-Methylbenzyl)-1-{2-[3-(2-methylquinolin-4-ylamino)phenoxy]ethyl}piperidin-4-ol

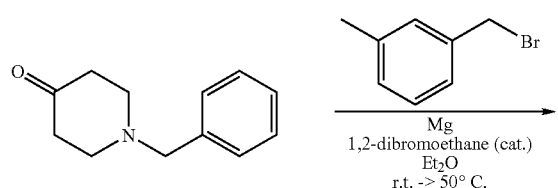

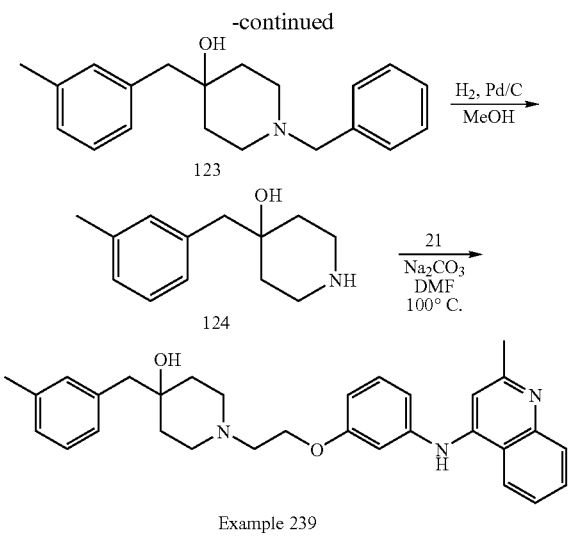

Example 239

Step 1. 1-Benzyl-4-(3-methylbenzyl)piperidin-4-ol.

To a solution of 3-methylbenzyl bromide (2.343 g, 12.66 mmol) in ether (53 mL) in a flame-dried flask was added magnesium (789 mg, 10.63 mmol) at room temperature. The resulting mixture was stirred for 35 minutes, and then to the mixture was added 1-benzylpiperidin-4-one (2.012 g, 10.63 mmol). The resulting mixture was stirred at room temperature for 1 hour before it was quenched with sat. NH$_4$Cl (aq) (40 mL). The mixture was extracted with ether (30 mL, 50 mL) and washed with sat. NH$_4$Cl (aq) (40 mL), brine (40 mL). The organic layer was dried over MgSO$_4$, concentrated on a rotavap, and the residue chromatographed on silica gel (1:1 to >1:3 hexanes/ethyl acetate) to afford the desired product 123 as a pale yellow oil (969 mg, 31%).

Step 2. 4-(3-Methylbenzyl)piperidin-4-ol.

To a solution of 123 (958 mg, 3.243 mmol) in methanol (16.3 mL) was added 10% palladium on carbon (884 mg, 0.831 mmol) at room temperature. The resulting mixture was placed under a H$_2$ atmosphere and stirred at room temperature for 90 hours before the reaction was filtered through Celite®. The Celite® was rinsed with methanol (5×10 mL), and the filtrate was concentrated on a rotavap to give desired product 124 as a pale yellow oil (700 mg, quantitative yield).

Step 3. 4-(3-Methylbenzyl)-1-{2-[3-(2-methylquinolin-4-ylamino)phenoxy]ethyl}piperidin-4-ol.

To a solution of 124 (253 mg, 0.809 mmol) in DMF (5.3 mL) were sequentially added 21 (161 mg, 0.784 mmol) and Na$_2$CO$_3$ (217 mg, 2.047 mmol) at room temperature. The resulting solution was heated at 100° C. for 17 hours before the reaction was diluted with EtOAc (40 mL). The mixture was extracted with ethyl acetate (2×40 mL) and washed with water (2×30 mL). The organic layer was dried over MgSO$_4$, concentrated on a rotavap, and the residue was chromatographed on silica gel (10:1 ethyl acetate/methanol to >8:1 dichloromethane/methanol) to afford the desired product as a yellow solid (89 mg, 24%).

The compound of Example 240 was synthesized in the same manner as for Example 238.

The compound of Example 241 was synthesized in the same manner as for Example 67 (Steps 3-5).

The compounds of Examples 242 and 243 were synthesized in the same manner as for Example 71.

EXAMPLE 244

4-(4-Methylbenzyl)-1-{2-[3-(2-methylquinolin-4-ylamino)-5-trifluoromethylphenoxy]ethyl}piperidin-4-ol Step 1. 4-(4-Methyl-benzyl)-piperidin-4-ol.

See Example 239, Steps 2-3.

Step 2. 4-(4-Methylbenzyl)-1-{2-[3-(2-methylquinolin-4-ylamino)-5-trifluoromethylphenoxy]ethyl}piperidin-4-ol.

See Example 67, Steps 3-5.

The compounds of Examples 245 and 246 were synthesized in the same manner as for example 71

The compound of Example 247 was synthesized in the same manner as for Example 238.

The compound of Example 248. 4-(2-Chlorobenzyl)-1-{2-[3-(2-methylquinolin-4-ylamino)-5-trifluoromethylphenoxy]ethyl}piperidin-4-ol.

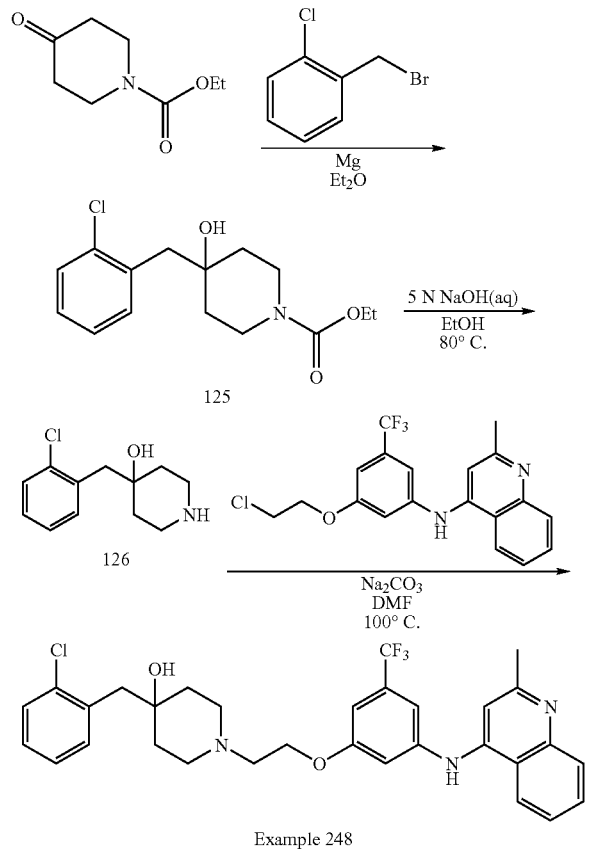

Example 248

Step 1. [3-(2-Chloroethoxy)-5-trifluoromethylphenyl)](2-methylquinolin-4-yl)amine (127).

The same procedure as Step 1 of Example 239 was used except that compound 116 was used instead of 20.

Step 2. Ethyl 4-(2-chlorobenzyl)-4-hydroxypiperidine-1-carboxylate.

The same procedure as Step 2 for Example 239 was used except that ethyl carbamate was utilized as the protecting group instead of a benzyl group.

Step 3. 4-(2-Chlorobenzyl)piperidin-4-ol.

To a solution of 125 (1.28 g, 4.30 mmol) in ethanol (22 mL) was added aq. 5 N NaOH (8.60 mL) at room temperature. The resulting mixture was heated at 80° C. for 94 hours before the reaction was diluted with ethyl acetate (20 mL). The mixture was extracted with ethyl acetate (2×50 mL), and washed with water (20 mL). The organic layer was dried over $MgSO_4$ and concentrated on a rotavap to afford the desired product 126 as a yellow solid (730 mg, 75%).

Step 4. 4-(2-Chlorobenzyl)-1-{2-[3-(2-methylquinolin-4-ylamino)-5-trifluoromethylphenoxy]ethyl}piperidin-4-ol.

See Step 4 of Example 239.

The compound of Example 249 was synthesized in the same manner as for Example 248.

The compounds of Examples 250 to 253 were synthesized in the same manner as for Example 71.

The compounds of Examples 254 and 255 were synthesized in the same manner as for Example 248.

EXAMPLE 256

{3-[2-(4-Phenylpiperidin-1-yl)ethoxy]-5-trifluoromethylphenyl}(2-isopropylquinolin-4-yl)amine Step 1. 4-Chloro-2-isopropylquinoline.

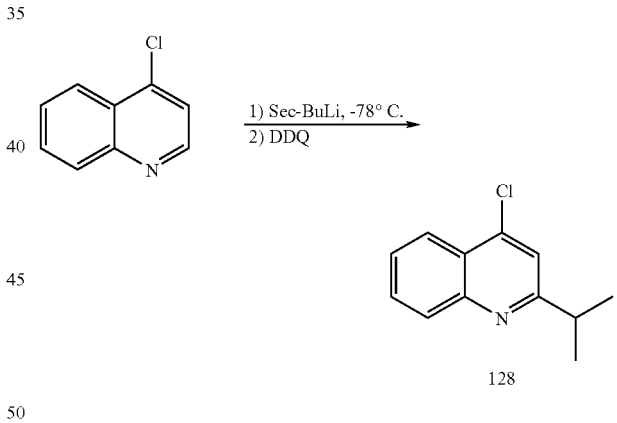

To a solution of 4-chloroquinoline (1.06 mg, 6.48 mmol) in dry THF (35 ml) was added dropwise sec-BuLi (11.6 ml, 0.7 M in pentane, 8.1 mmol) at −78° C. over 10 minutes. The resulting solution was stirred for 4 hours at −78° C. before it was quenched with sat. aq. $NH_4Cl$ (5 ml). The mixture was extracted with EtOAc (100 ml), washed with water (100 ml), and brine (100 ml). The organic layer was dried over $MgSO_4$ and concentrated on a rotavap to give crude product (3.3 g) as a brown oil. To a solution of the brown oil (3.3 g) in acetone (7 ml) was added a solution of CAN (7 g) in water (30 ml). The resulting mixture was stirred for 1 hour before it was extracted with DCM (100 ml) and washed with water (100 ml). The organic layer was dried over $MgSO_4$ and concentrated on a rotavap. The residue was chromatographed on silica gel (hexanes/EtOAc 3:1) to give the desired compound 128 as a brown oil (670 mg, 50%).

Step 2. {3-[2-(4-Phenylpiperidin-1-yl)ethoxy]-5-trifluoromethylphenyl}(2-isopropylquinolin-4-yl)amine.

The titled compound was synthesized in the same manner as for Example 71 using 128.

The compounds of Examples 257 and 258 were synthesized in the same manner as for Example 248.

The compound of Example 259. (4-Benzyl-1-{2-[3-(2-methylquinolin-4-ylamino)-5-trifluoromethylphenoxy]ethyl}piperidin-4-yl)methanol.

To a solution of Example 67 (0.19 g, 0.33 mmol) in THF (5 ml) was added lithium aluminum hydride (650 ml, 0.66 mmol) at 0° C. The mixture was stirred at room temperature overnight before it was quenched with Na$_2$SO$_4$ 10H$_2$O (pellets) until no more bubbles were observed.

The mixture was then diluted with ethyl acetate, the solids filtered, and the filtrate washed with water (50 ml), brine (50 ml). The organic layer was dried over MgSO$_4$ and concentrated on a rotovap to give the desired product as a yellow solid (0.1 g, 67%).

EXAMPLE 260

(2-Methylquinolin-4-yl)-{3-[3-(4-phenylpiperidin-1-yl)propoxy]-5-trifluoromethylphenyl}amine Step 1. 1-(3-Bromopropoxy)-3-nitro-5-trifluoromethylbenzene.

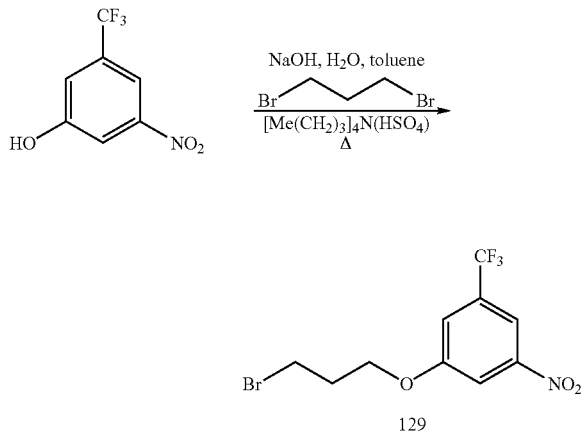

To a solution of 3-nitro-5-trifluoromethylphenol (6.2 g, 29.94 mmol) in toluene (100 ml) were sequentially added a solution of sodium hydroxide (2.4 g, 59.87 mmol) in water (60 ml), 1,3-dibromopropane (9.1 ml, 89.81 mmol), and tetrabutylammonium hydrogensulfate (1.0 g, 3.0 mmol). The resulting mixture was heated at 90° C. overnight before it was partitioned between water and toluene. The aqueous layer was extracted with ethyl acetate (2×50 ml).

The combined organic layers were washed with water (200 ml), brine (150 ml), dried over MgSO$_4$ and concentrated on a rotavap. The residue was chromatographed on silica gel with hexanes/ethyl acetate (100:1 to 50:1 to 20:1) to afford the desired product 129 as yellow oil (8.80 g, 90% yield).

Step 2. (2-Methylquinolin-4-yl)-{3-[3-(4-phenylpiperidin-1-yl)propoxy]-5-trifluoromethylphenyl}amine.

The title compound was synthesized in the same manner as for Example 71 using 129.

The compound of Example 261 was synthesized in the same manner as for Example 259.

EXAMPLE 262

{3-[2-(4,4-Diphenylpiperidin-1-yl)ethoxy]-5-trifluoromethylphenyl}(2-methylquinolin-4-yl)amine Step 1. 4,4-Diphenylpiperidine.

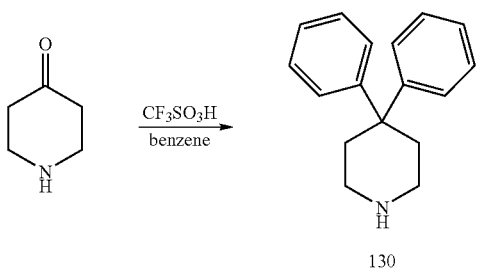

To a solution of piperidone (0.5 g, 5.04 mmol) in dry benzene (5 ml) was added trifluoromethanesulfonic acid (5 ml). The resulting solution was stirred at room temperature overnight before it was poured into ice, basified with 2N NaOH (30 ml), extracted with ethyl acetate (3×30 ml), and washed with water (100 ml), brine (50 ml). The organic layer was dried over MgSO$_4$ and concentrated on a rotavap to give the desired product 130 (0.80 g, 67% yield).

Step 2. {3-[2-(4,4-Diphenylpiperidin-1-yl)ethoxy]-5-trifluoromethylphenyl}(2-methylquinolin-4-yl)amine.

The title compound was synthesized in the same manner as for Example 71 using 130.

The compounds of Examples 263 to 265 were synthesized in the same manner as for Example 71.

EXAMPLE 266

4-Benzyl-1-{2-[5-(2-methylquinolin-4-ylamino)biphenyl-3-yloxy]ethyl}piperidin-4-ol

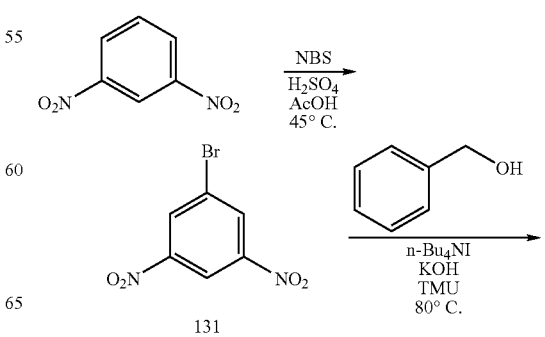

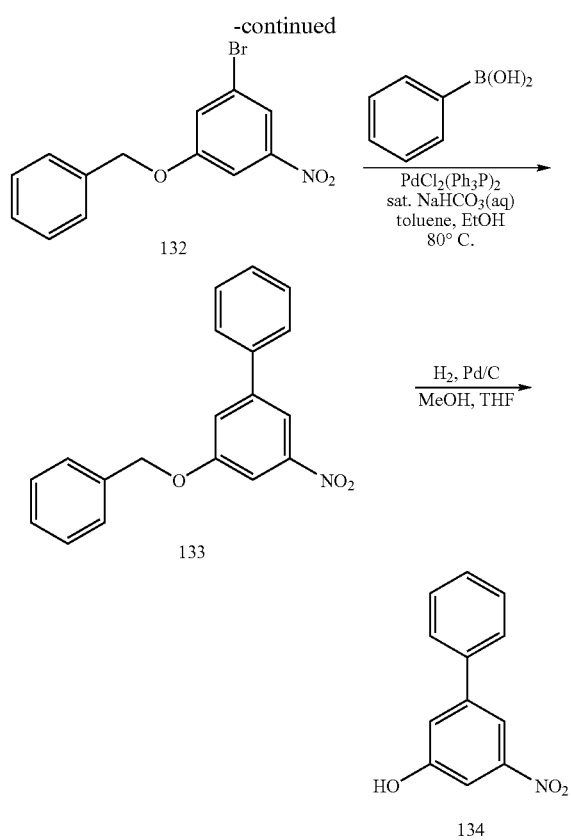

Step 1. 1-Bromo-3,5-dinitrobenzene.

To a solution of 1,3-dinitrobenzene (14.98 g, 88.93 mmol) in trifluoroacetic acid (50 mL) were sequentially added H₂SO₄ (20 mL) and N-bromosuccinimide (23.85 g, 134.00 mmol) at room temperature. The resulting mixture was heated at 45° C. for 65 hours before the reaction was poured into iced water (300 mL). The mixture was extracted with dichloromethane (2×100 mL). The organic layer was dried over MgSO₄, concentrated on a rotavap, the residue was recrystallized, and the mother liquor was concentrated to give impure desired product.

The product was then chromatographed on silica gel (20:1 hexanes/ethyl acetate) to afford the desired 131 as a pale orange-yellow solid (1.28 g, 6%).

Step 2. 1-Benzyloxy-3-bromo-5-nitrobenzene.

To a solution of 131 (1.26 g, 5.09 mmol) in 1,1,3,3-tetramethylurea (12.7 mL) were sequentially added benzyl alcohol (606 mg, 5.61 mmol), KOH (409 mg, 7.289 mmol), and tetrabutylammonium iodide (184 mg, 0.50 mmol) at room temperature. The resulting mixture was heated at 80° C. for 23 hours before the reaction was diluted with ether (50 mL).

The mixture was extracted with ether (75 mL, 50 mL) and washed with water (2×50 mL).

The organic layer was dried over MgSO₄, concentrated on a rotavap, and the residue chromatographed on silica gel (20:1 hexanes/ethyl acetate) to afford the desired product 132 as a yellow oil (993 mg, 63%).

Step 3. 5-Benzyloxy-3-nitrobiphenyl.

See Example 179, Step 2.

Step 4. 5-Aminobiphenyl-3-ol.

To a solution of 133 (982 mg, 3.19 mmol) in toluene (21 mL) were added sequentially a solution of phenylboronic acid (519 mg, 3.82 mmol) in ethanol (13 mL), sat. aq. NaHCO₃ (8.4 mL), and dichlorobis(triphenylphosphine)palladium(II) (110 mg, 0.16 mmol). The resulting mixture was placed under a nitrogen atmosphere and heated at 80° C. for 18 hours before the reaction was diluted with ethyl acetate (50 mL). The mixture was extracted with ethyl acetate (50 mL) and washed with water (2×30 mL). The organic layer was dried over MgSO₄, concentrated on a rotavap, and the residue was chromatographed on silica gel (20:1 hexanes/ethyl acetate) to afford the desired product 134 as a yellow solid (523 mg, 54%).

Step 5. 5-(2-Methylquinolin-4-ylamino)biphenyl-3-ol.

See Example 1, Step 3.

Step 6. [5-(2-Chloroethoxy)biphenyl-3-yl](2-methylquinolin-4-yl)amine.

See Example 239, Step 1.

Step 7. 4-Benzyl-1-{2-[5-(2-methylquinolin-4-ylamino)biphenyl-3-yloxy]ethyl}piperidin-4-ol.

See Example 239, Step 4.

EXAMPLE 267

1-{2-[3-(2-Methylquinolin-4-ylamino)-trifluoromethylphenoxy]ethyl}-N-phenylpiperidine-4-carboxamide

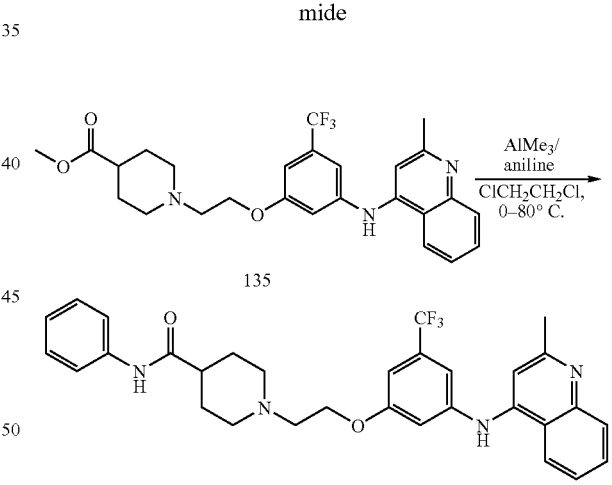

Example 267

Step 1. Methyl 1-{2-[3-(2-methylquinolin-4-ylamino)-5-trifluoromethylphenoxy]ethyl}piperidine-4-carboxylate.

Compound 135 was synthesized in the same manner as for Example 71.

Step 2. 1-{2-[3-(2-Methylquinolin-4-ylamino)-trifluoromethylphenoxy]ethyl}-N-phenylpiperidine-4-carboxamide.

A mixture of aniline (0.041 g, 0.44 mmol) and AlMe₃ (2.0 M in heaxanes, 0.2 ml, 0.40 mmol) in anhydrous dichloroethane (5 ml) was stirred at 0° C. for 20 minutes before the addition of 135 (0.10 g, 0.21 mmol). The resulting mixture was heated at 80° C. overnight before it was partitioned between water (30 ml) and EtOAc (80 ml). The organic layer was washed with 0.5 N NaOH (2×50 ml), water (50 ml) and brine (50 ml), dried over Na₂SO₄ and concentrated on a rotavap. The residue was chromatographed on silica gel to afford the desired product as yellow solid (0.092 g, 82%).

EXAMPLE 268

4-Benzyl-1-{2-[3-chloro-5-(2-methylquinolin-4-ylamino)phenoxy]ethyl}piperidin-4-ol

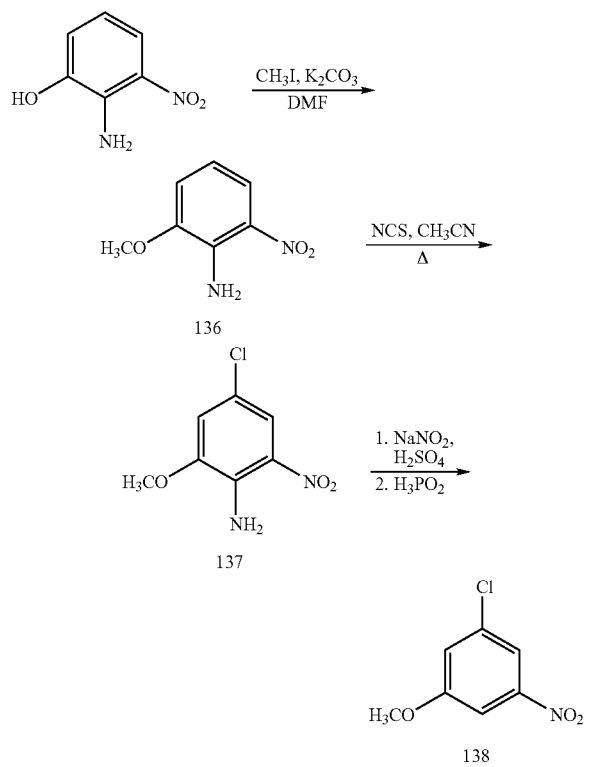

Step 1. 2-Methoxy-6-nitrophenylamine.

To a solution of 2-amino-3-nitrophenol (5 g, 32.4 mmol) in DMF (165 ml) were sequentially added potassium carbonate (9.0 g, 65 mmol) and methyl iodide (2.2 ml, 35 mmol). The mixture was heated at 50° C. overnight before it was cooled to room temperature, mixed with water (300 ml), and extracted with ethyl acetate (3×50 ml). The extracts were combined, washed with water (150 ml), brine (80 ml), and dried (MgSO₄). Removal of the solvent under reduced pressure gave a dark orange solid that was triturated with 1:1 hexane/ether. The solids were collected by filtration to give product 136 as orange needles (4.1 g, 76%).

Step 2. 4-Chloro-2-methoxy-6-nitrophenylamine.

Aniline 136 from the previous step (3.74 g, 22.2 mmol) was dissolved in acetonitrile (100 ml) and N-chlorosuccinimide (3.07 g, 23 mmol) was added. The mixture was heated under reflux overnight then concentrated under reduced pressure. The residue was recrystallized from ethyl acetate to give product 137 as orange needles 3.05 g (69%).

Step 3. 1-chloro-3-methoxy-5-nitrobenzene.

4-Chloro-2-methoxy-6-nitroaniline (137) (14 g, 69 mmol) was dissolved in glacial acetic acid (115 ml) and treated with concentrated sulfuric acid (110 ml). The solution was cooled in an ice bath and a cold solution of sodium nitrite (5.03 g, 73 mmol) in water (20 ml) was added slowly to keep the reaction temperature below 5° C. After the addition was complete, the reaction was stirred for an additional 15 minutes before the addition of hypophosphorous acid (70 ml of a 50% solution in water, 0.9 M). The mixture was stirred at room temperature overnight and recooled with an ice bath. The solids were collected by filtration, washed with water, then dried under vacuum to give 3-chloro-5-nitro anisole (138) as a light salmon-colored solid 7.43 g, 57%).

Step 4. 4-Benzyl-1-{2-[3-chloro-5-(2-methylquinolin-4-ylamino)phenoxy]ethyl}piperidin-4-ol.

The title compound was synthesized in the same manner as for Example 239.

Example 269 was synthesized in the same manner as for Example 248, final step.

| Example # | structure | chemical name | physical description[a] | [M + H]⁺ |
|---|---|---|---|---|
| 231 | 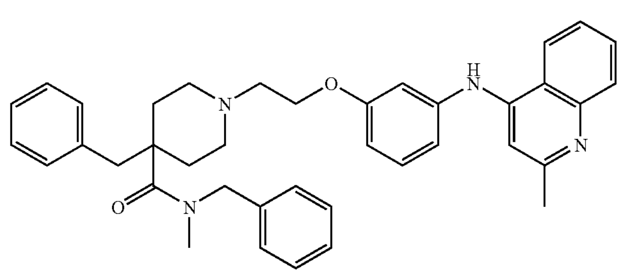 | N-benzyl-4-benzyl-1-{2-[3-(2-methylquinolin-4-ylamino)phenoxy]ethyl}-N-methyl piperidine-4-carboxamide | light yellow solid | 599.29 |

-continued

| Example # | structure | chemical name | physical description[a] | [M + H]+ |
|---|---|---|---|---|
| 232 | 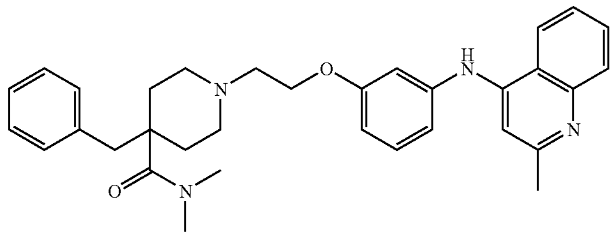 | 4-benzyl-1-{2-[3-(2-methylquinolin-4-ylamino)phenoxy]ethyl}-N,N-dimethyl piperidine-4-carboxamide | yellow foam[b] | 523.22 |
| 233 | 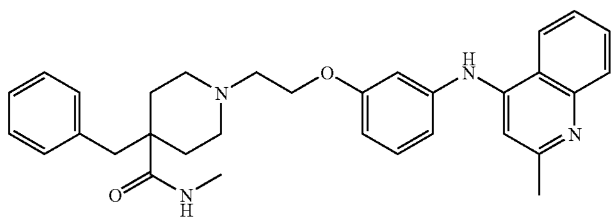 | 4-benzyl-1-{2-[3-(2-methylquinolin-4-ylamino)phenoxy]ethyl}-N-methyl piperidine-4-carboxamide | yellow solid | 509.32 |
| 234 | 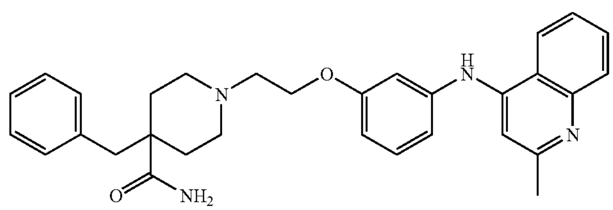 | 4-benzyl-1-{2-[3-(2-methylquinolin-4-ylamino)phenoxy]ethyl} piperidine-4-carboxamide | light yellow solid | 495.30 |
| 235 | 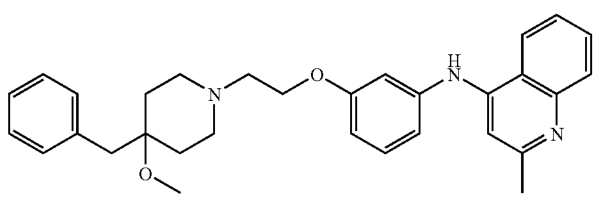 | {3-[2-(4-benzyl-4-methoxy piperidin-1-yl)ethoxy]phenyl}(2-methylquinolin-4-yl)amine | yellow solid | 482.29 |
| 236 | 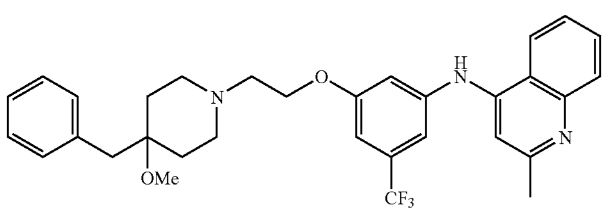 | {3-[2-(4-benzyl-4-methoxypiperidin-1-yl)ethoxy]-5-trifluoromethylphenyl}(2-methylquinolin-4-yl)amine | yellowish solid | 275.60[e] |
| 237 | 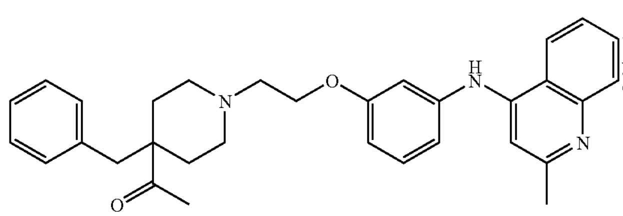 | {3-[2-(4-acetyl-4-benzylpiperidin-1-yl)ethoxy]phenyl}(2-methylquinolin-4-yl)amine | yellow solid | 494.35 |

-continued

| Example # | structure | chemical name | physical description[a] | [M + H]+ |
|---|---|---|---|---|
| 238 | 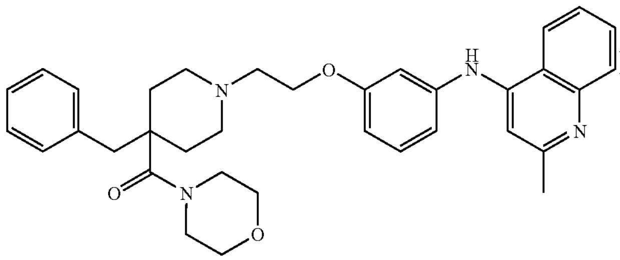 | {3-[2-(4-benzyl-4-(morpholin-4-ylcarbonyl))piperidin-1-yl)ethoxy]phenyl}(2-methylquinolin-4-yl)amine | yellow solid | 565.57 |
| 239 | 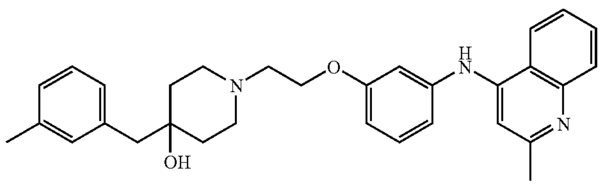 | 4-(3-methylbenzyl)-1-{2-[3-(2-methylquinolin-4-ylamino)phenoxy]ethyl}piperidin-4-ol | yellow solid | 482.48 |
| 240 | 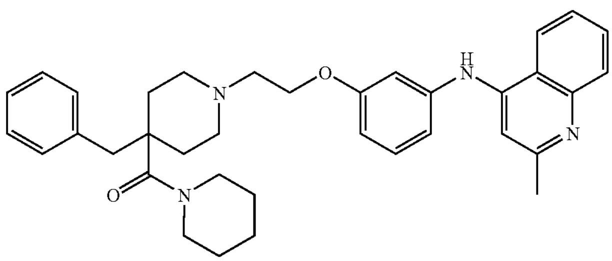 | {3-[2-(4-benzyl-4-(piperidin-1-ylcarbonyl))piperidin-1-yl)ethoxy]phenyl}(2-methylquinolin-4-yl)amine | yellow solid | 563.59 |
| 241 | 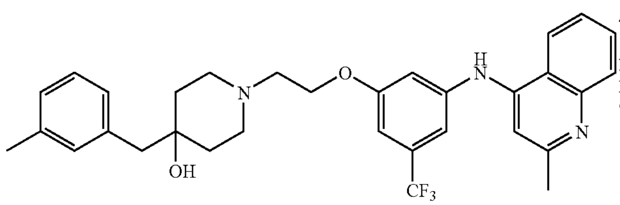 | 4-(3-methylbenzyl)-1-{2-[3-(2-methylquinolin-4-ylamino)-5-trifluoromethylphenoxy]ethyl}piperidin-4-ol | pale yellow solid | 550.24 |
| 242 | 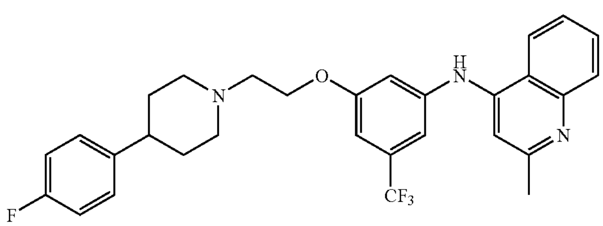 | {3-[2-(4-(4-fluorophenyl)piperidin-1-yl)ethoxy]-5-trifluoromethylphenyl}(2-methylquinolin-4-yl)amine | pale yellow solid | 524.35 |
| 243 | 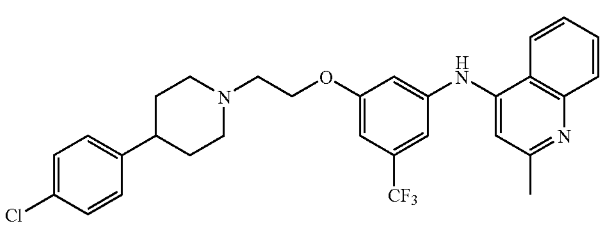 | {3-[2-(4-(4-chlorophenyl)piperidin-1-yl)ethoxy]-5-trifluoromethylphenyl}(2-methylquinolin-4-yl)amine | light yellow solid | 540.16 |

-continued

| Example # | structure | chemical name | physical description[a] | [M + H]+ |
|---|---|---|---|---|
| 244 | 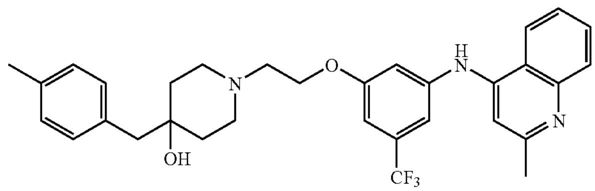 | 4-(4-methylbenzyl)-1-{2-[3-(2-methylquinolin-4-ylamino)-5-trifluoromethylphenoxy]ethyl}piperidin-4-ol | pale yellow solid [b] | 550.46 |
| 245 | 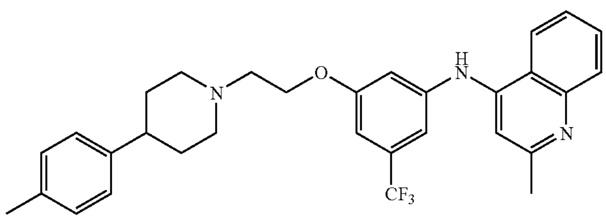 | {3-[2-(4-(4-methylphenyl)piperidin-1-yl)ethoxy]-5-trifluoromethylphenyl}(2-methylquinolin-4-yl)amine | yellow solid | 520.20 |
| 246 | 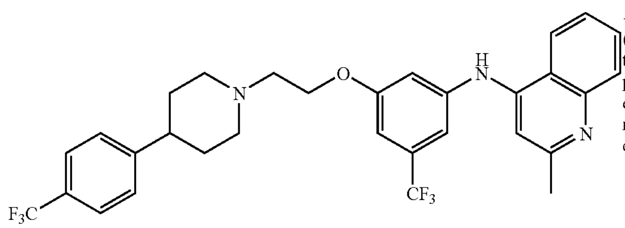 | {3-trifluoromethyl-5-[2-(4-(4-trifluoromethylphenyl)piperidine-1-yl)ethoxy]phenyl}(2-methylquinolin-4-yl)amine | yellow solid | 574.15 |
| 247 | 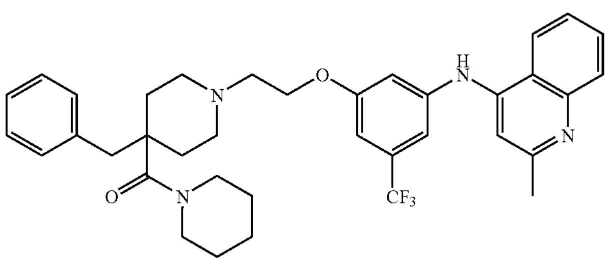 | {3-[2-(4-benzyl-4-(piperidin-1-ylcarbonyl))piperidin-1-yl)ethoxy]-5-trifluoromethylphenyl}(2-methylquinolin-4-yl)amine | light yellow solid | 631.56 |
| 248 | 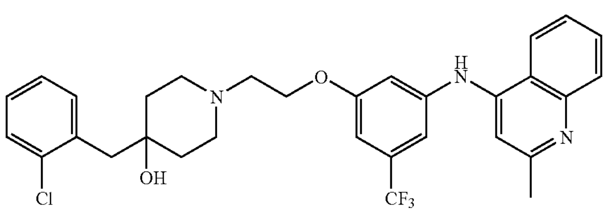 | 4-(2-chlorobenzyl)-1-{2-[3-(2-methylquinolin-4-ylamino)-5-trifluoromethylphenoxy]ethyl}piperidin-4-ol | pale yellow solid | 570.18 |
| 249 | 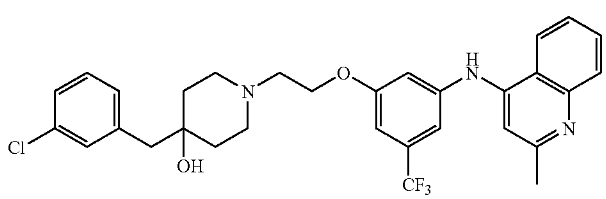 | 4-(3-chlorobenzyl)-1-{2-[3-(2-methylquinolin-4-ylamino)-5-trifluoromethylphenoxy]ethyl}piperidin-4-ol | pale yellow solid [b] | 570.41 |
| 250 | 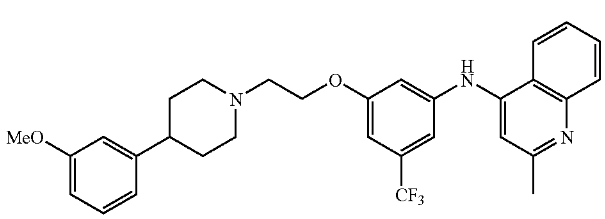 | {3-[2-(4-(3-methoxyphenyl)piperidin-1-yl)ethoxy]-5-trifluoromethylphenyl}(2-methylquinolin-4-yl)amine | light yellow solid | 536.45 |

| Example # | structure | chemical name | physical description[a] | [M + H]+ |
|---|---|---|---|---|
| 251 | 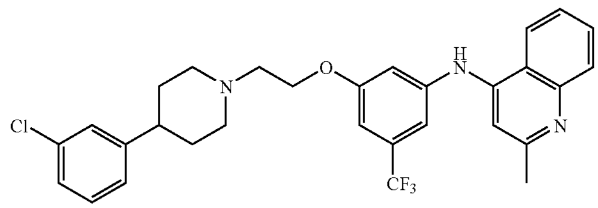 | {3-[2-(4-(3-chlorophenyl)piperidin-1-yl)ethoxy]-5-trifluoromethylphenyl}(2-methylquinolin-4-yl)amine | pale yellow solid | |
| 252 | 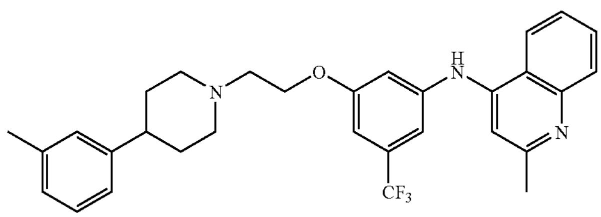 | {3-[2-(4-(3-methylphenyl)piperidin-1-yl)ethoxy]-5-trifluoromethylphenyl}(2-methylquinolin-4-yl)amine | pale yellow solid | |
| 253 | 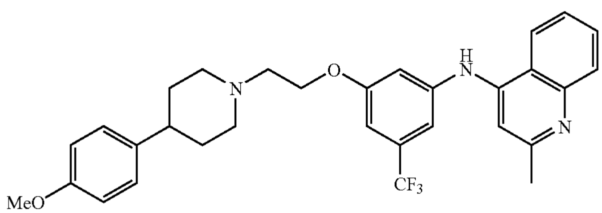 | {3-[2-(4-(4-methoxyphenyl)piperidin-1-yl)ethoxy]-5-trifluoromethylphenyl}(2-methylquinolin-4-yl)amine | light yellow solid | 536.38 |
| 254 | 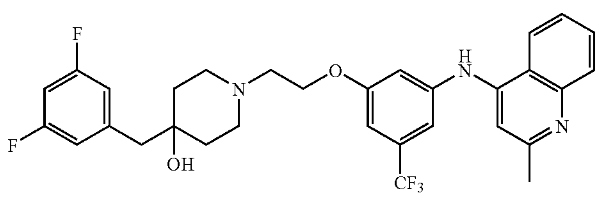 | 4-(3,5-difluorobenzyl)-1-[2-[3-(2-methylquinolin-4-ylamino)-5-trifluoromethyl phenoxy]ethyl}piperidin-4-ol | pale yellow solid[b] | 572.42 |
| 255 | 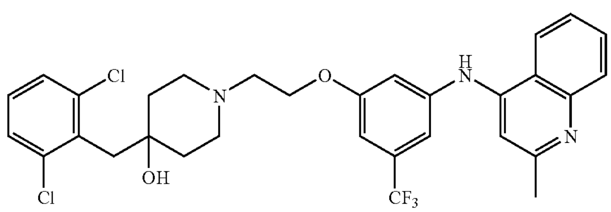 | 4-(2,6-dichlorobenzyl)-1-{2-[3-(2-methylquinolin-4-ylamino)-5-trifluoromethyl phenoxy]ethyl}piperidin-4-ol | pale yellow solid[b] | 604.38 |
| 256 | 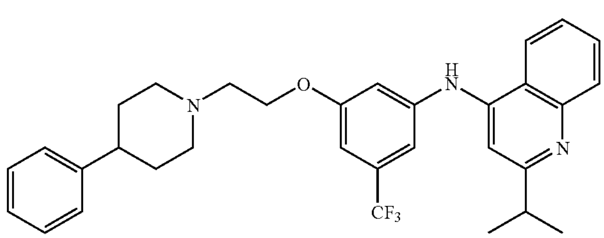 | {3-[2-(4-phenylpiperidin-1-yl)ethoxy]-5-trifluoromethylphenyl}(2-isopropylquinolin-4-yl)amine | off-white solid | 534.45 |
| 257 | 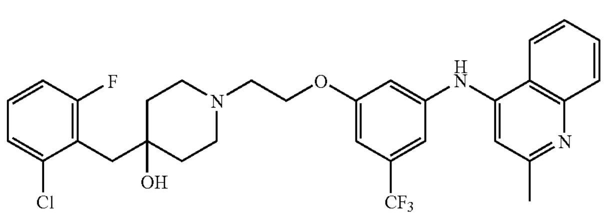 | 4-(2-chloro-6-fluorobenzyl)-1-{2-[3-(2-methylquinolin-4-yl amino)-5-trifluoromethyl phenoxy]ethyl}piperidin-4-ol | yellow solid | 586.23 |

-continued

| Example # | structure | chemical name | physical description[a] | [M + H]+ |
|---|---|---|---|---|
| 258 | 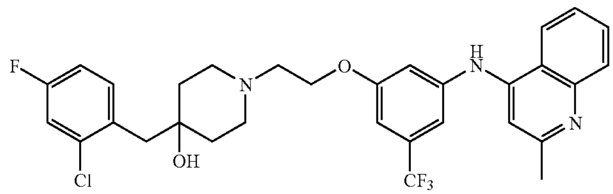 | 4-(2-chloro-4-fluorobenzyl)-1-{2-[3-(2-methylquinolin-4-ylamino)-5-trifluoromethylphenoxy]ethyl}piperidin-4-ol | pale yellow solid[b] | 588.18 |
| 259 | 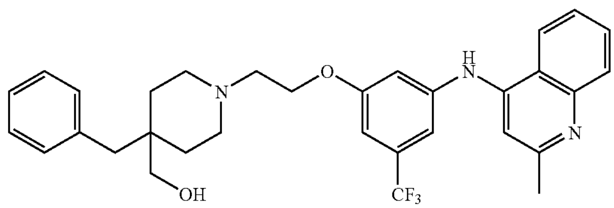 | (4-benzyl-1-{2-[3-(2-methylquinolin-4-ylamino)-5-trifluoromethylphenoxy]ethyl}piperidin-4-yl)methanol | white solid | 550.23 |
| 260 | 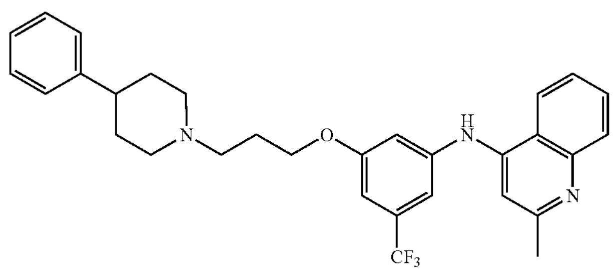 | (2-methylquinolin-4-yl)-{3-[3-(4-phenylpiperidin-1-yl)propoxy]-5-trifluoromethylphenyl}amine | off-white solid | 520.21 |
| 261 | 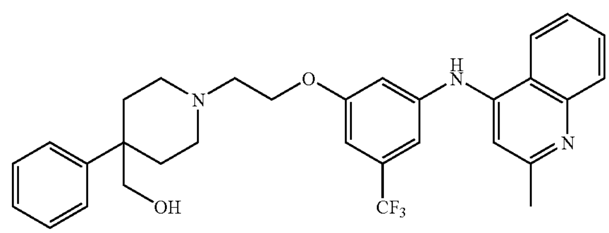 | (1-{2-[3-(2-methylquinolin-4-ylamino)-5-trifluoromethylphenoxy]ethyl}-4-phenylpiperidin-4-yl)methanol | yellow powder | 536.23 |
| 262 | 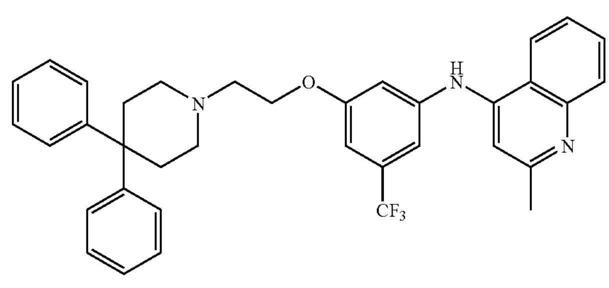 | {3-[2-(4,4-diphenylpiperidin-1-yl)ethoxy]-5-trifluoromethylphenyl}(2-methylquinolin-4-yl)amine | off-white solid | 582.24 |
| 263 | 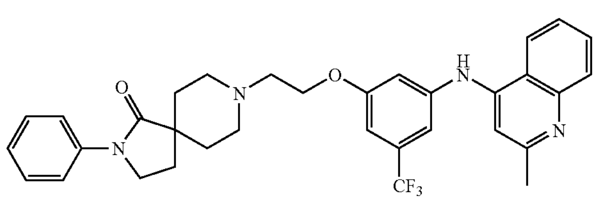 | 8-{2-[3-(2-methylquinolin-4-ylamino)-5-trifluoromethylphenoxy]ethyl}-2-phenyl-2,8-diazaspiro[4.5]decan-1-one | white solid | 575.23 |

| Example # | structure | chemical name | physical description[a] | [M + H]+ |
|---|---|---|---|---|
| 264 | 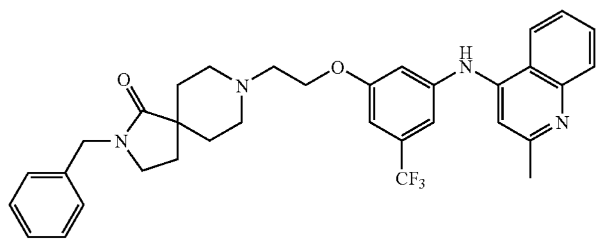 | 2-benzyl-8-{2-[3-(2-methyl quinolin-4-ylamino)-5-trifluoro methylphenoxy]ethyl}-2,8-diazaspiro[4.5]decan-1-one | white solid | 589.58 |
| 265 | 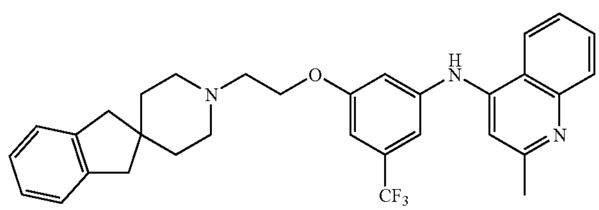 | (2-methylquinolin-4-yl){3-[2-(4-spiroindanepiperidin-1-yl)ethoxy]-5-trifluoromethylphenyl}amine | pale yellow solid | 532.16 |
| 266 | 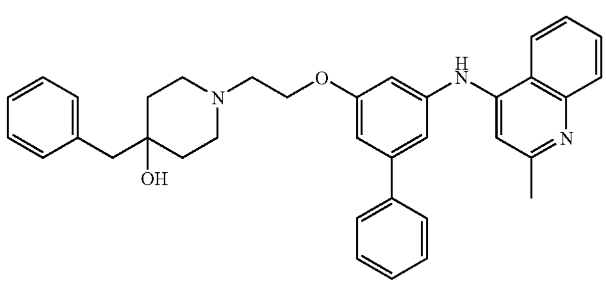 | 4-benzyl-1-{2-[5-(2-methyl quinolin-4-ylamino)biphenyl-3-yloxy]ethyl}piperidin-4-ol | pale yellow solid [b] | 544.28 |
| 267 | 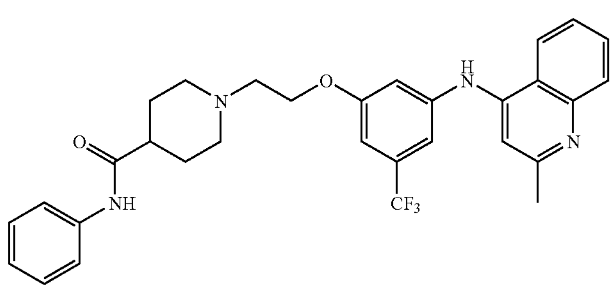 | 1-{2-[3-(2-methylquinolin-4-yl amino)-trifluoromethyl phenoxy]ethyl}-N-phenyl piperidine-4-carboxamide | light yellow solid | 549.21 |
| 268 | 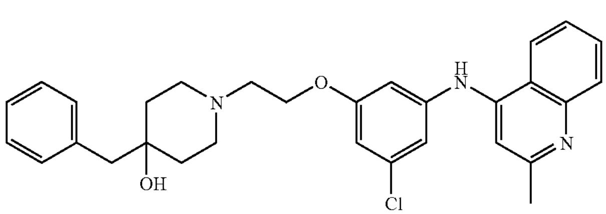 | 4-benzyl-1-{2-[3-chloro-5-(2-methylquinolin-4-ylamino) phenoxy]ethyl}piperidin-4-ol | pale yellow solid | 502.33 |

| Example # | structure | chemical name | physical description[a] | [M + H]+ |
|---|---|---|---|---|
| 269 | 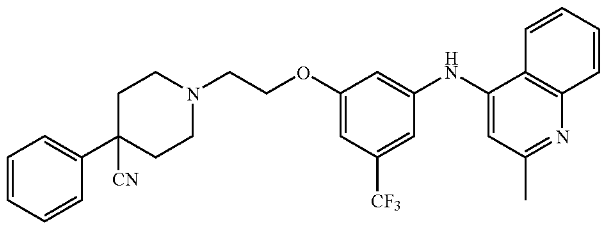 | 1-{2-[3-(2-methylquinolin-4-yl amino)-5-trifluoromethylphenoxy]ethyl}-4-phenylpiperidine-4-carbonitrile | pale yellow solid[b] | 531.34 |

[a] diHCl salt unless otherwise noted
[b] parent compound
[c] sodium salt
[d] triHCl salt
[e] $(M + 2H)^{2+}/2$ The compounds of Examples 270 and 271 were synthesized in the same manner as for Example 45.

The compound of Example 272 was synthesized in the same manner as for Example 71.

The compound of Example 273 was synthesized in the same manner as for Example 276 (vid infra).

The compound of Example 274. (2-Methylquinolin-4-yl)(3-{2-[4-(3-trifluoromethylbenzyl)piperazin-1-yl]ethoxy}phenyl)amine.

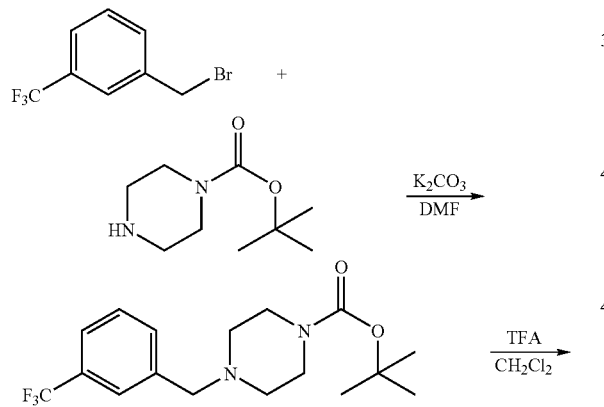

Step 1. tert-Butyl 4-(3-trifluoromethylbenzyl)piperazine-1-carboxylate.

To a solution of tert-butyl-1-piperzinecarboxylate (0.8 g, 4.2 mmol) in DMF (15 ml) were sequentially added K₂CO₃ (1.2 g, 8.5 mmol) and 3-trifluoromethylbenzylbromide (0.68 g, 4.2 mmol) and the reaction mixture was stirred at room temperature overnight. The reaction mixture was treated with water (20 ml), brine (5.0 ml), and extracted with EtOAc (3×20 ml).

The combined organic layers were dried (MgSO₄) and concentrated under reduced pressure to give product 139 as an off-white solid (1.47 g, 99%).

Step 2. 1-(3-Trifluoromethylbenzyl)piperazine.

To a solution of 139 (1.4 g, 4.2 mmol) in CH₂Cl₂ (15 ml) was added TFA (1.3 ml, 17 mmol) and the reaction mixture was stirred at room temperature for 2 hours. The reaction was mixed with water (10 ml), brine (3.0 ml), made basic with 2N NaOH (2.0 ml), and extracted with CH₂Cl₂ (3×20 ml). The combined organic layers were dried (MgSO₄) and concentrated under reduced pressure to give product 140 as an off-white solid (0.5 g, 50%).

Step 3. (2-Methylquinolin-4-yl)(3-{2-[4-(3-trifluoromethylbenzyl)piperazin-1-yl]ethoxy}phenyl)amine.

The title compound was synthesized in the same procedure of Example 248, last step.

The compound of Example 275 was synthesized in the same manner as for Example 274.

EXAMPLE 276

(3-{2-[2S,4S-5-(3-Chlorobenzyl)-2,5-diazabicyclo[2.2.1]hept-2-yl]ethoxy}-5-trifluoromethylphenyl)(2-methylquinolin-4-yl)amine

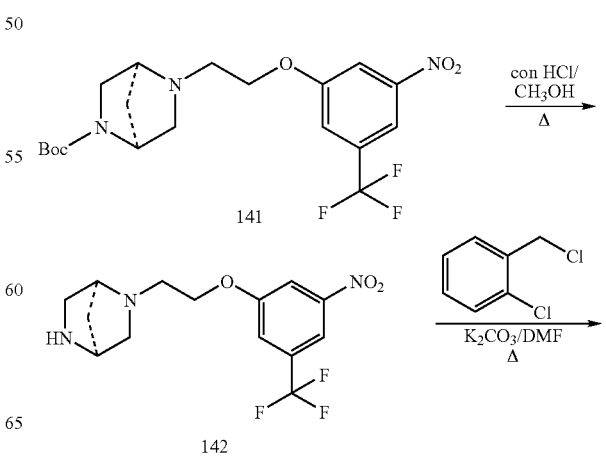

-continued

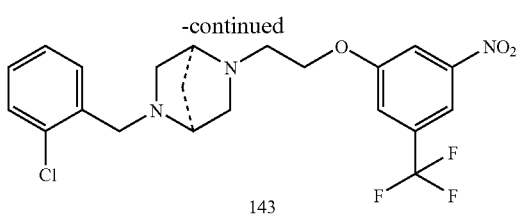

143

Step 1. tert-Butyl 5-[2-(3-nitro-5-trifluoromethylphenoxy) ethyl]-2,5-diazabicyclo[2.2.1]heptane-2-carboxylate.

The title compound was synthesized in the same manner as for Example 67, Step 3, ii).

Step 2. 2-(2-Chlorobenzyl)-5-[2-(3-nitro-5-trifluoromethylphenoxy)ethyl]-2,5-diazabicyclo[2.2.1]heptane.

A mixture of 2-chlorobenzyl chloride (82 mg, 0.51 mmol), 20 (168 mg, 0.51 mmol), and $K_2CO_3$ (84 mg, 0.615 mmol) in dry DMF (3 ml) was heated at 90° C. overnight. The mixture was partitioned between $H_2O$ (50 ml) and EtOAc (50 ml). The organic layer was washed with brine, dried over $MgSO_4$, and concentrated on a rotavap to give the desired crude compound 143 as a brown oil (256 mg, ~100%).

Step 3. (3-{2-[2S,4S-5-(3-Chlorobenzyl)-2,5-diazabicyclo[2.2.1]hept-2-yl]ethoxy}-5-trifluoromethylphenyl)(2-methylquinolin-4-yl)amine.

The title compound was synthesized using a sequence of reduction/coupling as illustrated by Steps 4-5 for Example 67.

The compound of Example 277 was synthesized in the same manner as for Example 274.

The compounds of Examples 278 and 279 were synthesized in the same manner as for Example 276.

The compounds of Examples 280 and 281 were synthesized in the same manner as for Example 274.

The compounds of Examples 282 and 283 were synthesized in the same manner as for Example 276.

The compound of Example 284 was synthesized in the same manner as for Example 274.

The compound of Example 285 was synthesized in the same manner as for Example 276.

The compound of Example 286 was synthesized in the same manner as for Example 67, Steps 3-5.

The compounds of Examples 287 and 288 were synthesized in the same manner as for Example 274 using 3,5-difluorobenzyl bromide and 3-pyridiylmethyl bromide, respectively, instead of 3-trifluoromethylbenzyl bromide.

The compound of Example 289 was synthesized in the same manner as for Example 276 except that tert-butyl [1,4]diazepane-1-carboxylate was used instead of tert-butyl 2,5-diazabicyclo[2.2.1]heptane-2-carboxylate.

The compounds of Examples 290 and 291 were synthesized in the same manner as for Example 274.

The compounds of Examples 292 and 293 were synthesized in the same manner as for Example 276.

The compounds of Examples 294 and 295 were synthesized in the same manner as for Example 67, Steps 3-5.

EXAMPLE 296

1-Benzyl-4-{2-[3-(2-methylquinolin-4-ylamino)-5-trifluoromethylphenoxy]ethyl}piperazin-2-one

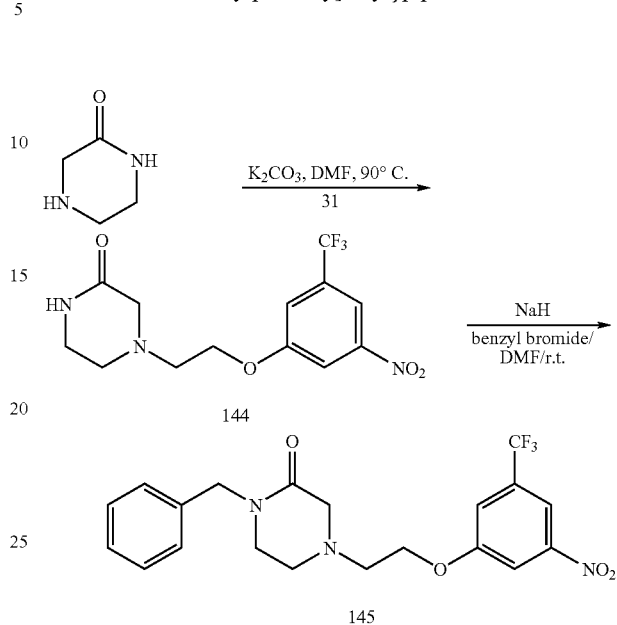

Step 1. 4-[2-(3-Nitro-5-trifluoromethylphenoxy)ethyl]piperazin-2-one.

See Example 67, Step 3, ii).

Step 2. 1-Benzyl-4-[2-(3-nitro-5-trifluoromethylphenoxy)ethyl]piperazin-2-one

To a solution of A (0.10 g, 0.31 mmol) in anhydrous DMF (5 ml) was added NaH (60% disperse in mineral oil, 0.02 g, 0.46 mmol) at room temperature. After 10 minutes stirring at room temperature, benzyl bromide (0.06 g, 0.34 mmol) was added. The resulting mixture was stirred at room temperature overnight before the reaction was quenched with water and brought into EtOAc (60 ml). The organic layer was washed with water (50 ml), brine (50 ml), and dried over $Na_2SO_4$. The organic layer was concentrated on a rotavap and the residue was chromatographed on silica gel to give product 145 as a yellow oil (46 mg, 35%).

Step 3. 1-Benzyl-4-{2-[3-(2-methylquinolin-4-ylamino)-5-trifluoromethylphenoxy]ethyl}piperazin-2-one The title compound was synthesized in the same manner as for Example 67, last 3 steps.

The compound of Example 297 was synthesized in the same manner as for Example 276.

The compound of Example 298 was synthesized in the same manner as for Example 274.

The compounds of Examples 299 and 300 were synthesized in the same manner as for Example 288.

The compound of Example 301 was synthesized in the same manner as for Example 274 except that benzenesulfonyl chloride was used instead of 3-trifluoromethylbenzyl bromide.

The compound of Example 302 was synthesized in the same manner as for Example 248, last step, except 1-(3-thienyl-methyl)piperazine was used.

The compound of Example 303 was synthesized in the same manner as for Example 274 except that 2-chloro-5-chloromethylpyridine was used instead of 3-trifluoromethylbenzyl bromide.

EXAMPLE 304

{3-[2-(4-Benzyl-3,5-dimethylpiperazin-1-yl)-ethoxy]-5-trifluoromethylphenyl}(2-methyl-quinolin-4-yl)amine

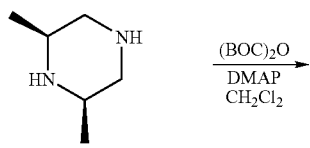

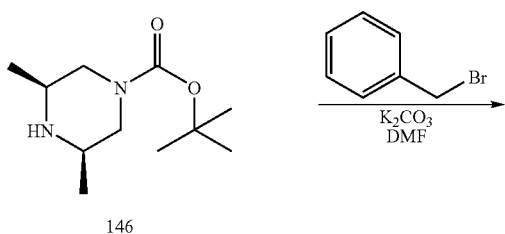

146

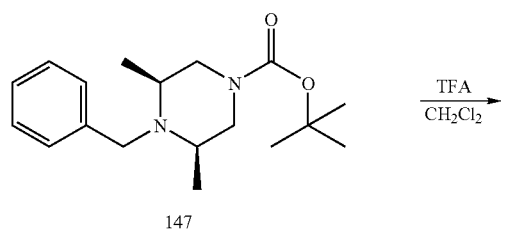

147

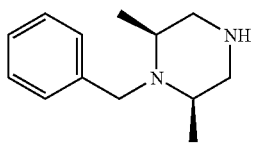

148

Step 1. tert-Butyl 3,5-dimethylpiperazine-1-carboxylate.

To a solution of 2,6-cis-dimethylpiperazine (2.0 g, 17 mmol) in CH$_2$Cl$_2$ (60 ml) were sequentially added di-tert-butyl dicarbonate (3.8 g, 17 mmol) and a catalytic amount of DMAP. The reaction mixture was stirred at room temperature overnight before it was washed with water (50 ml), brine (10 ml), and extracted with CH$_2$Cl$_2$ (3×30 ml). The extracts were dried (MgSO$_4$) and concentrated under reduced pressure to give product 146 as colorless oil (3.95, ~100%).

Step 2. tert-Butyl 4-benzyl-3,5-dimethylpiperazine-1-carboxylate.

To a solution of amine 146 (0.8 g, 3.7 mmol) in DMF (15 ml) were added K$_2$CO$_3$ (1.0 g, 7.4 mmol), benzyl bromide (0.45 ml, 3.7 mmol), and the reaction mixture was stirred at room temperature overnight. The reaction mixture was diluted with water (15 ml), brine (5.0 ml), and extracted with EtOAc (3×20 ml). The combined organic layers were dried (MgSO$_4$) and concentrated under reduced pressure to give product 147 as colorless oil (1.0 g, 88%).

Step 3. 1-Benzyl-2,6-dimethylpiperazine.

To a solution of 147 (1.0 g, 3.3 mmol) in CH$_2$Cl$_2$ (15 ml) was added TFA (2.2 ml, 19 mmol) and the reaction mixture was stirred at room temperature for 2 hours. The reaction mixture was washed with water (15 ml), saturated NaCl solution (5.0 ml), made basic with 2N NaOH (2.0 ml), and extracted with CH$_2$Cl$_2$ (3×20 ml). The combined organic layers were dried (MgSO$_4$) and concentrated under reduced pressure to give product 148 as a white solid (0.86 g, 95%).

Step 4. {3-[2-(4-Benzyl-3,5-dimethylpiperazin-1-yl)-ethoxy]-5-trifluoromethylphenyl}(2-methyl-quinolin-4-yl)amine.

The title compound was synthesized in the same manner as for Example 248, last step.

The compound of Example 305 was synthesized in the same manner as for Example 274 except that 4-methylsulphonylbenzyl bromide was used instead of 3-trifluoromethylbenzyl bromide.

The compound of Example 306 was synthesized in the same manner as for Example 276 except that benzenesulfonyl chloride was used instead of 2-chlorobenzyl chloride.

The compound of Example 307 was synthesized in the same manner as for Example 239 except that 3-chloro-5-(2-methylquinolin-4-ylamino)phenol and 2-benzyl-2,5-diazabicyclo[2.2.1]heptane were used instead of 3-(2-methylquinolin-4-ylamino)phenol and 4-(3-methylbenzyl)piperidin-4-ol, respectively.

The compounds of Examples 308 and 309 were synthesized in the same manner as for Example 276.

The compound of Example 310 was synthesized in the same manner as for Example 276 except that benzoyl chloride was used instead of 2-chlorobenzyl chloride.

| Example # | structure | chemical name | physical description[a] | [M + H]+ |
|---|---|---|---|---|
| 270 | 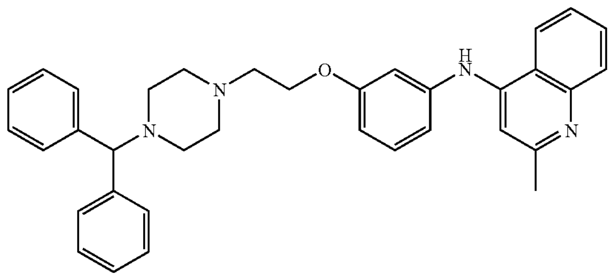 | {3-[2-(4-benzhydrylpiperazin-1-yl)ethoxy]phenyl}(2-methylquinolin-4-yl)amine | yellow solid | 529.17 |
| 271 | 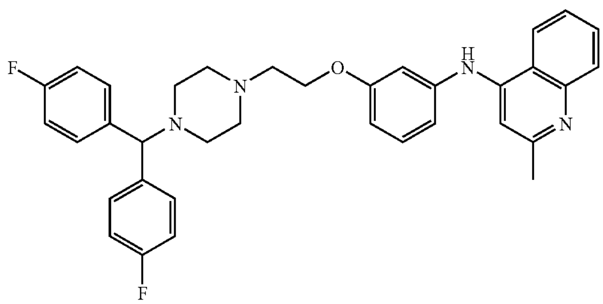 | [3-(2-{4-[bis(4-fluorophenyl)methyl]piperazin-1-yl}ethoxy)phenyl](2-methylquinolin-4-yl)amine | yellow solid | 565.22 |
| 272 | 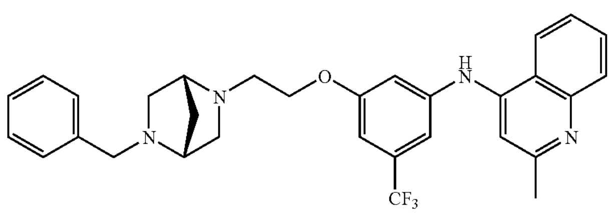 | {-[2-(2R,5R-5-benzyl-2,5-diazabicyclo[2.2.1]hept-2-yl)ethoxy]-5-trifluoromethylphenyl}(2-methylquinolin-4-yl)amine | yellowish solid[d] | 533.44 |
| 273 | 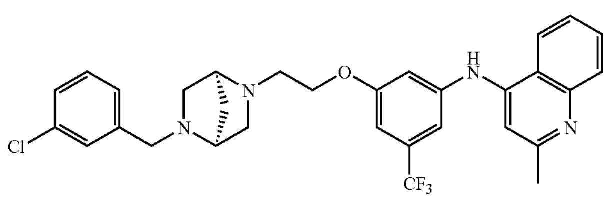 | (3-{2-[2S,4S-5-(3-chlorobenzyl)-2,5-diazabicyclo[2.2.1]hept-2-yl]ethoxy}-5-trifluoromethylphenyl)(2-methylquinolin-4-yl)amine | yellowish solid[d] | 567.19 |
| 274 | 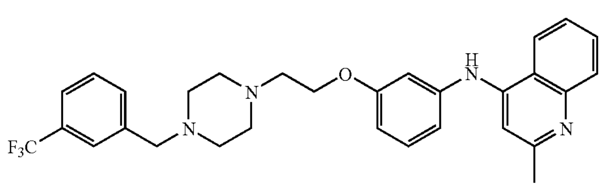 | (2-methylquinolin-4-yl)(3-{2-[4-(3-trifluoromethylbenzyl)piperazin-1-yl]ethoxy}phenyl)amine | pale yellow solid[d] | 531.23 |
| 275 | 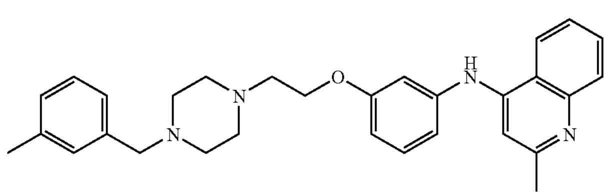 | (2-methylquinolin-4-yl)(3-{2-[4-(3-methylbenzyl)piperazin-1-yl]ethoxy}phenyl)amine | pale yellow solid[d] | 467.30 |

| Example # | structure | chemical name | physical description[a] | [M + H]+ |
|---|---|---|---|---|
| 276 | 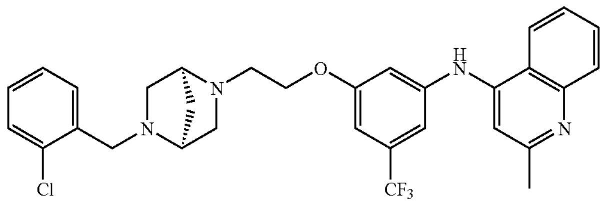 | (3-{2-[2S,4S-5-(2-chlorobenzyl)-2,5-diazabicyclo[2.2.1]hept-2-yl]ethoxy}-5-trifluoromethylphenyl)(2-methylquinolin-4-yl)amine | yellow solid[d] | 467.48 |
| 277 | 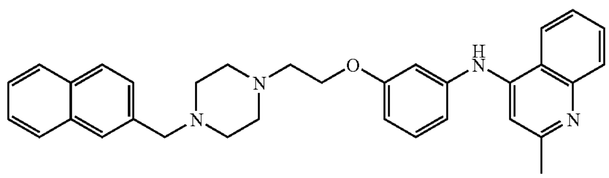 | (2-methylquinolin-4-yl)-{3-[2-(4-naphthalen-2-ylmethylpiperazin-1-yl)ethoxy]phenyl}amine | off-white solid[d] | 503.44 |
| 278 | 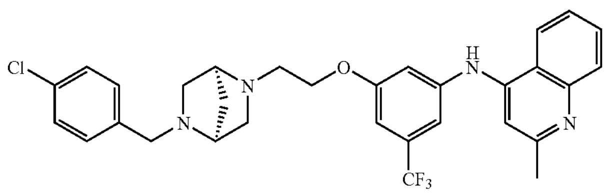 | (3-{2-[2S,4S-5-(4-chlorobenzyl)-2,5-diazabicyclo[2.2.1]hept-2-yl]ethoxy}-5-trifluoromethylphenyl)(2-methylquinolin-4-yl)amine | yellow solid[d] | 567.16 |
| 279 | 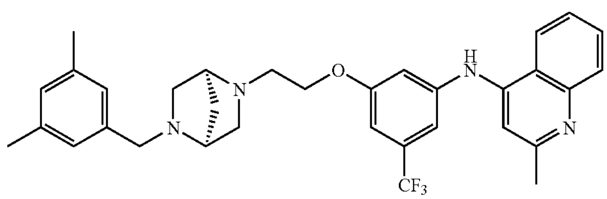 | (3-{2-[2S,4S-5-(3,5-dimethylbenzyl)-2,5-diazabicyclo[2.2.1]hept-2-yl]ethoxy}-5-trifluoromethylphenyl)(2-methylquinolin-4-yl)amine | yellow solid[d] | 561.26 |
| 280 | 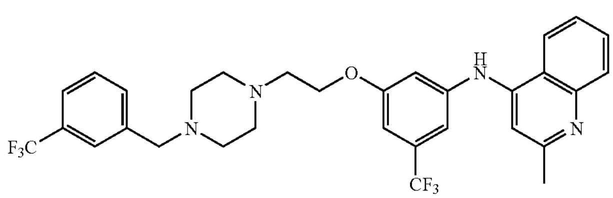 | (2-methylquinolin-4-yl)(3-trifluoromethyl-5-{2-[4-(3-trifluoromethylbenzyl)piperazin-1-yl]ethoxy)phenyl)amine | pale yellow solid[d] | 589.41 |
| 281 | 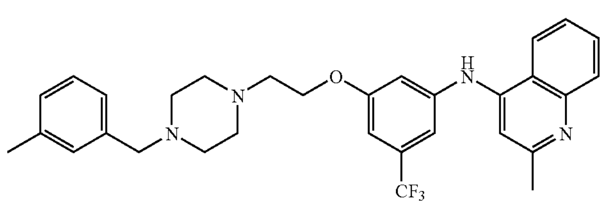 | (2-methylquinolin-4-yl)(3-{2-[4-(3-methylbenzyl)piperazin-1-yl]-ethoxy}-5-trifluoromethylphenyl)amine | pale yellow solid[d] | 535.59 |
| 282 | 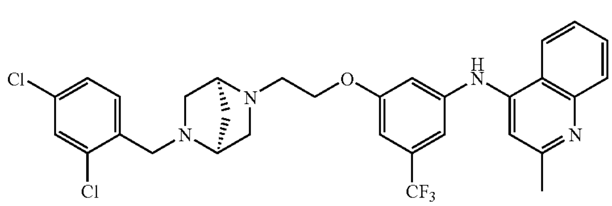 | (3-{2-[2S,4S-5-(2,4-dichlorobenzyl)-2,5-diazabicyclo[2.2.1]hept-2-yl]ethoxy}-5-trifluoromethylphenyl)(2-methylquinolin-4-yl)amine | yellow solid[d] | 601.40 |

-continued

| Example # | structure | chemical name | physical description[a] | [M + H]+ |
|---|---|---|---|---|
| 283 | 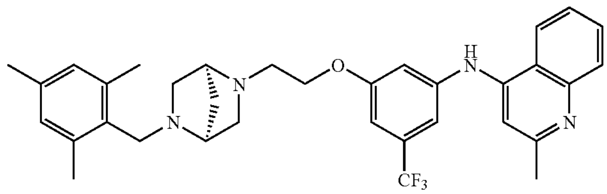 | (3-{2-[2S,4S-5-(2,4,6-trimethylbenzyl)-2,5-diazabicyclo[2.2.1]hept-2-yl]ethoxy}-5-trifluoromethylphenyl)(2-methylquinolin-4-yl)amine | yellow solid[d] | 575.51 |
| 284 | 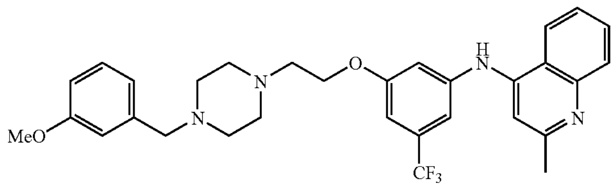 | (2-methylquinolin-4-yl)(3-{2-[4-(3-methoxybenzyl)piperazin-1-yl]-ethoxy}-5-trifluoro methylphenyl)amine | pale yellow solid[d] | 551.40 |
| 285 | 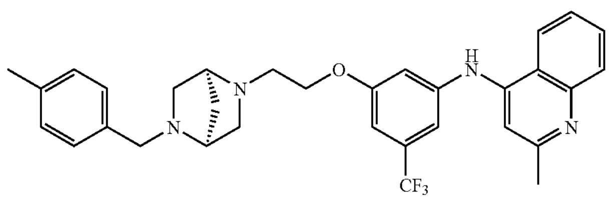 | (3-{2-[2S,4S-5-(4-methylbenzyl)-2,5-diazabicyclo[2.2.1]hept-2-yl]ethoxy}-5-trifluoromethylphenyl)(2-methylquinolin-4-yl)amine | yellow solid[d] | 547.46 |
| 286 | 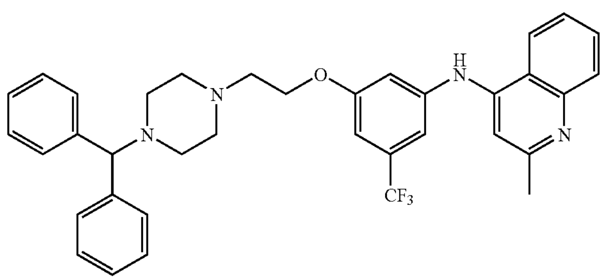 | {3-[2-(4-benzhydrylpiperazin-1-yl)ethoxy]-5-trifluoromethylphenyl}(2-methylquinolin-4-yl)amine | yellow solid[d] | 597.45 |
| 287 | 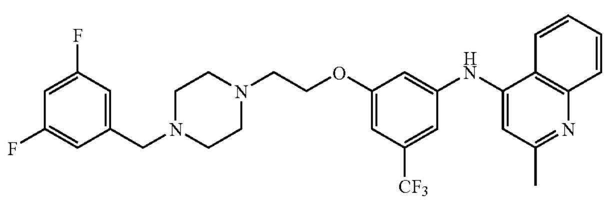 | (2-methylquinolin-4-yl)(3-{2-[4-(3,5-difluorobenzyl)piperazin-1-yl]ethoxy}-5-trifluoro methylphenyl)amine | yellow solid[d] | 557.38 |
| 288 | 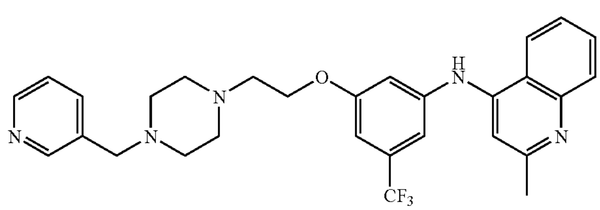 | (2-methylquinolin-4-yl)(3-{2-[4-(pyridin-3-yl)piperazin-1-yl]-ethoxy}-5-trifluoro methylphenyl)amine | off-white solid[b] | 522.41 |
| 289 | 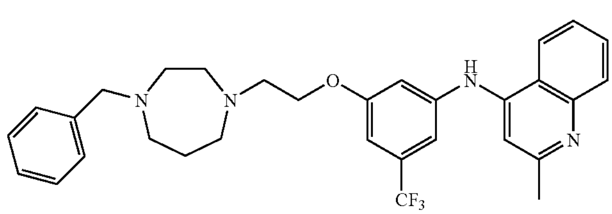 | {3-[2-(4-benzyl[1,4]diazepan-1-yl)ethoxy]-5-trifluoromethyl phenyl}(2-methyl quinolin-4-yl)amine | yellow solid[d] | 535.47 |

-continued

| Example # | structure | chemical name | physical description[a] | [M + H]+ |
|---|---|---|---|---|
| 290 | 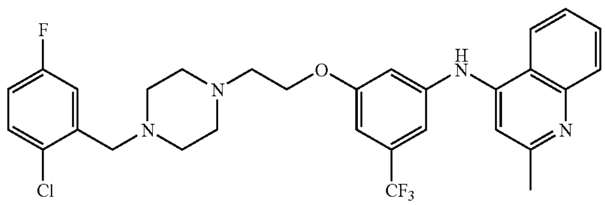 | (3-{2-[4-(2-chloro-5-fluoro benzyl)piperazin-1-yl]-ethoxy}-5-trifluoro methylphenyl)(2-methyl quinolin-4-yl)amine | yellow solid[b] | 573.33 |
| 291 | 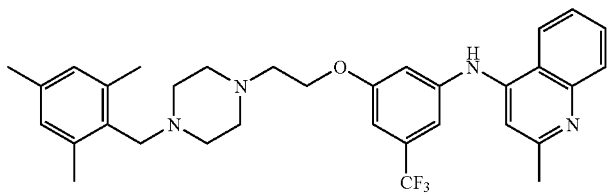 | (2-methylquinolin-4-yl) (3-trifluoromethyl-5-{2-[4-(2,4,6-trimethylbenzyl)piperazin-1-yl]ethoxy}phenyl)amine | yellow solid[b] | 563.45 |
| 292 | 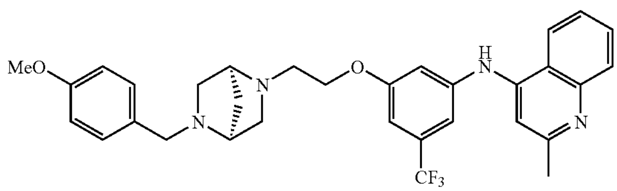 | (3-{2-[2S,4S-5-(4-methoxybenzyl)-2,5-diazabicyclo[2.2.1]hept-2-yl]ethoxy}-5-trifluoromethylphenyl)(2-methylquinolin-4-yl)amine | yellow solid[d] | 563.44 |
| 293 | 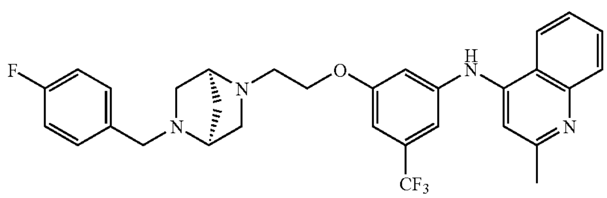 | (3-{2-[2S,4S-5-(4-fluorobenzyl)-2,5-diazabicyclo[2.2.1]hept-2-yl]ethoxy}-5-trifluoromethylphenyl)(2-methylquinolin-4-yl)amine | yellow solid[d] | 551.45 |
| 294 | 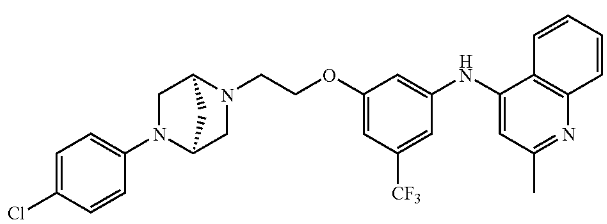 | (3-{2-[2S,4S-5-(4-chlorophenyl)-2,5-diazabicyclo[2.2.1]hept-2-yl]ethoxy}-5-trifluoromethylphenyl)(2-methylquinolin-4-yl)amine | off-white solid[d] | 553.37 |
| 295 | 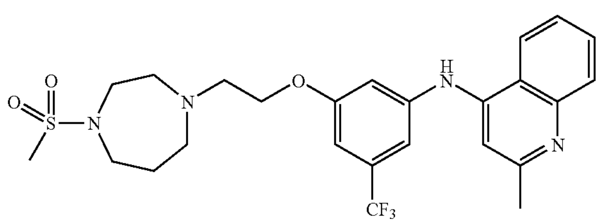 | {3-[2-(4-methanesulfonyl[1,4]diazepan-1-yl)ethoxy]-5-trifluoromethylphenyl}(2-methyl quinolin-4-yl)amine | yellow solid | 523.34 |
| 296 | 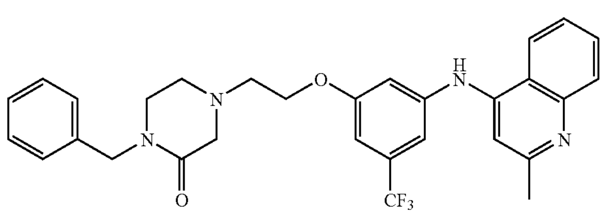 | 1-benzyl-4-{2-[3-(2-methyl quinolin-4-ylamino)-5-trifluoromethylphenoxy]ethyl}piperazin-2-one | light yellow solid | 535.41 |

-continued

| Example # | structure | chemical name | physical description[a] | [M + H]+ |
|---|---|---|---|---|
| 297 | 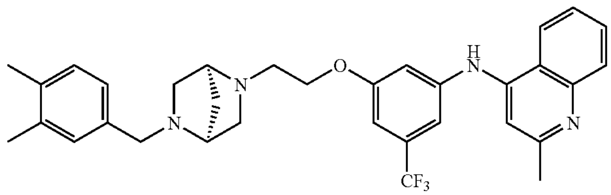 | (3-{2-[2S,4S-5-(3,4-dimethylbenzyl)-2,5-diazabicyclo[2.2.1]hept-2-yl]ethoxy}-5-trifluoromethylphenyl)(2-methylquinolin-4-yl)amine | yellow solid[d] | 561.43 |
| 298 | 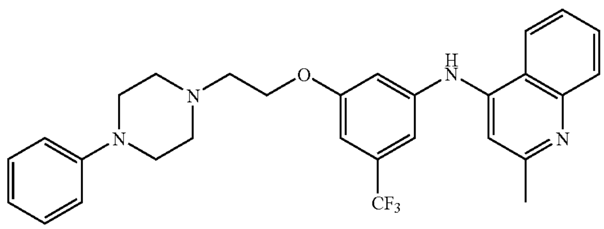 | (3-{2-[4-phenylpiperazin-1-yl]-ethoxy}-5-trifluoro methylphenyl)(2-methyl quinolin-4-yl)amine | pale yellow solid[b] | 507.39 |
| 299 | 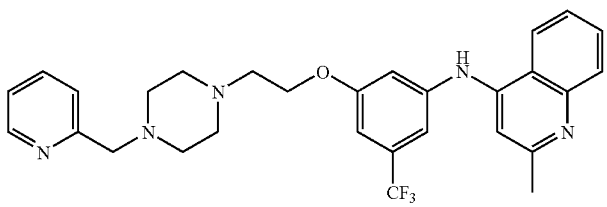 | (3-{2-[4-pyridin-2-ylpiperazin-1-yl]-ethoxy}-5-trifluoro methylphenyl)(2-methyl quinolin-4-yl)amine | pale yellow solid[b] | 522.40 |
| 300 | 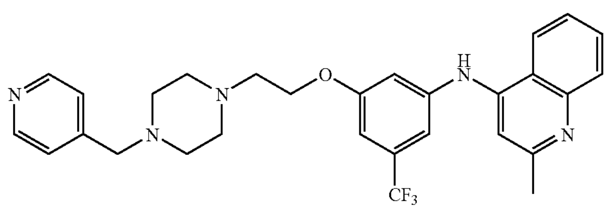 | (3-{2-[4-pyridin-4-ylpiperazin-1-yl]-ethoxy}-5-trifluoro methylphenyl)(2-methyl quinolin-4-yl)amine | pale yellow solid[b] | 522.39 |
| 301 | 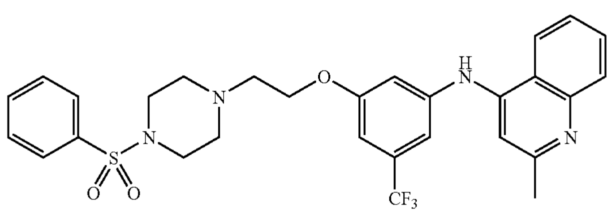 | {3-[2-(4-benzenesulfonylpiperazin-1-yl)ethoxy]-5-trifluoromethylphenyl}(2-methylquinolin-4-yl)amine | off-white solid[b] | 571.32 |
| 302 | 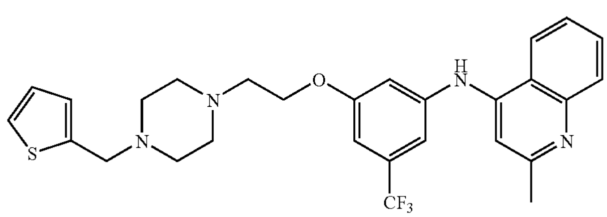 | (2-methylquinolin-4-yl)-{3-[2-(4-thiophen-3-ylmethyl piperazin-1-yl)ethoxy]-5-trifluoromethylphenyl}amine | off-white solid[b] | 527.18 |
| 303 | 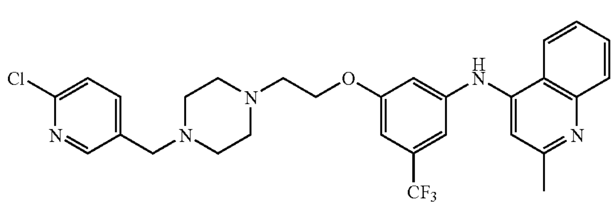 | (3-{2-[4-(6-chloropyridin-3-ylmethyl)piperazin-1-yl]ethoxy}-5-trifluoromethyl phenyl)-(2-methylquinolin-4-yl)amine | pale yellow solid[b] | 556.18 |

-continued

| Example # | structure | chemical name | physical description[a] | [M + H]+ |
|---|---|---|---|---|
| 304 | 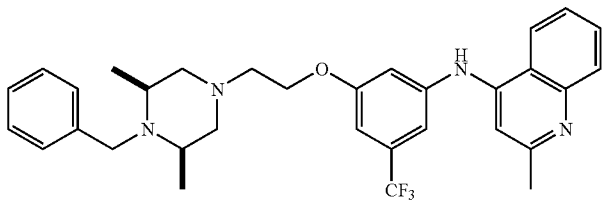 | {3-[2-(4-benzyl-3,5-dimethyl piperazin-1-yl)-ethoxy]-5-trifluoromethylphenyl}-(2-methyl-quinolin-4-yl)amine | pale yellow solid[d] | 549.19 |
| 305 | 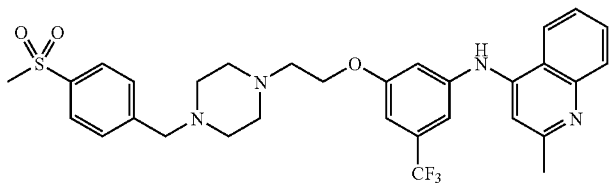 | (3-{2-[4-(4-methanesulfonyl benzyl)piperazin-1-yl]ethoxy}-5-trifluoromethylphenyl)(2-methyl quinolin-4-yl)amine | pale yellow solid[d] | 599.24 |
| 306 | 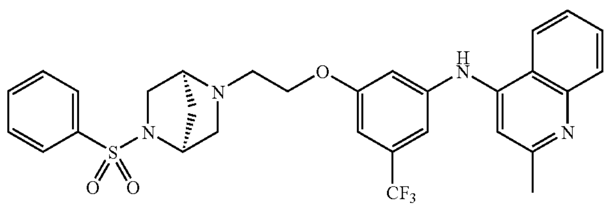 | {3-[2-(5-benzenesulfonyl-1S,4S-2,5-diazabicyclo[2.2.1]hept-2-yl)ethoxy]-5-trifluoromethyl-henyl}(2-methyl quinolin-4-yl)amine | yellow solid | 583.23 |
| 307 | 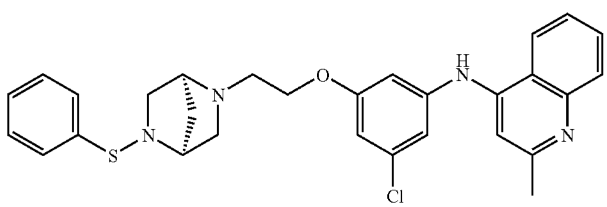 | {3-[2-(1S,4S-5-benzyl-2,5-diazabicyclo[2.2.1]hept-2-yl)ethoxy]-5-chlorophenyl}(2-methyl quinolin-4-yl)amine | pale yellow solid | 499.33 |
| 308 | 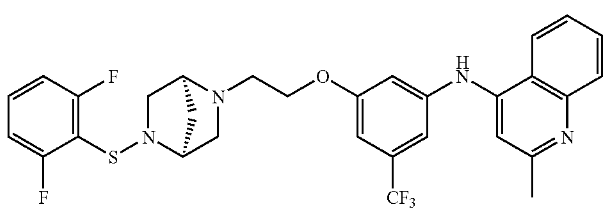 | (3-{2-[2S,4S-5-(2,6-difluoro benzyl)-2,5-diazabicyclo[2.2.1] hept-2-yl]ethoxy}-5-trifluoro methylphenyl)(2-methyl quinolin-4-yl)amine | yellow solid | 569.26 |
| 309 | 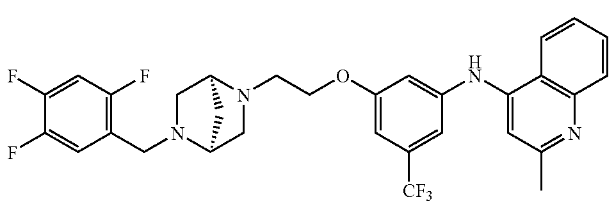 | (3-{2-[2S,4S-5-(2,4,5-trifluoro benzyl)-2,5-diazabicyclo[2.2.1] hept-2-yl]ethoxy}-5-trifluoro methylphenyl)(2-methyl quinolin-4-yl)amine | yellow solid | 587.24 |
| 310 | 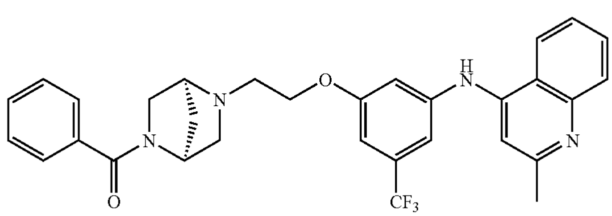 | (3-{2-[2S,4S-5-acetyl-2,5-diazabicyclo[2.2.1] hept-2-yl]ethoxy}-5-trifluoro methylphenyl)(2-methyl quinolin-4-yl)amine | yellow solid | 547.35 |

[a] diHCl salt unless otherwise noted
[b] parent compound
[c] sodium salt
[d] triHCl salt The compounds of Examples 311 and 312 were synthesized in the same manner as for Example 214.

The compounds of Examples 313 and 314 were synthesized in the same manner as for Example 274 except that 1-bromo-3-methylbutane and cyclohexanemethyl bromide were used instead of 3-trifluoromethylbenzyl bromide.

The compounds of Examples 315 and 317 were synthesized in the same manner as for Example 67.

The compound of Example 318 was synthesized in the same manner as for Example 214.

The compounds of Examples 319 and 320 were synthesized in the same manner as for Example 276.

The compound of Example 321 was synthesized in the same manner as for Example 67.

The compounds of Examples 322 to 324 were synthesized in the same manner as for Example 248, last step.

The compound of Example 325 was synthesized in the same manner as for Example 67.

The compound of Example 326 was synthesized in the same manner as for Example 248, last step.

EXAMPLE 327

[3-Chloro-5-(3-piperidin-1-ylpropoxy)phenyl](2-methylquinolin-4-yl)amine

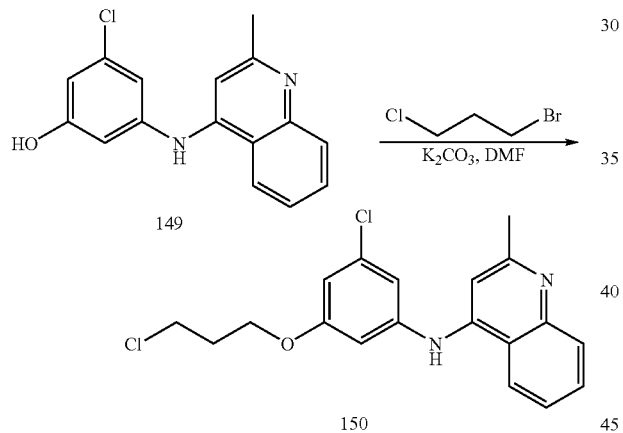

Step 1. [3-Chloro-5-(3-chloropropoxy)phenyl](2-methylquinolin-4-yl)amine.

Compound 149 was synthesized in the same manner as for 116 from 138 (see Example 222).

To a solution of the 149 (1.14 g, 4 mmol) in DMF (20 ml) were sequentially added 1-bromo-3-chloropropane (1.36 g, 15 mmol), potassium carbonate (2.1 g, 15 mmol), and the mixture was heated at 100° C. for 4 hours. The reaction was mixed with water (80 ml) then extracted with methylene chloride (3×20 ml). The extracts were combined, washed with water (50 ml), brine (50 ml), then dried (MgSO$_4$) and concentrated. The residue was purified by flash chromatography (SiO$_2$, gradient 3:1 hexane/ethyl acetate to 7:3 methylene chloride/methanol) to give the desired product 150 as an off-white solid (350 mg, 20%).

Step 2. [3-Chloro-5-(3-piperidin-1-ylpropoxy)phenyl](2-methylquinolin-4-yl)amine.

The title compound was synthesized in the same manner as for Example 248, last step using 149 and piperidine.

EXAMPLE 328

4-Methyl-1-{3-[3-(2-methylquinolin-4-ylamino)-5-trifluoromethylphenoxy]propyl}piperidin-4-ol

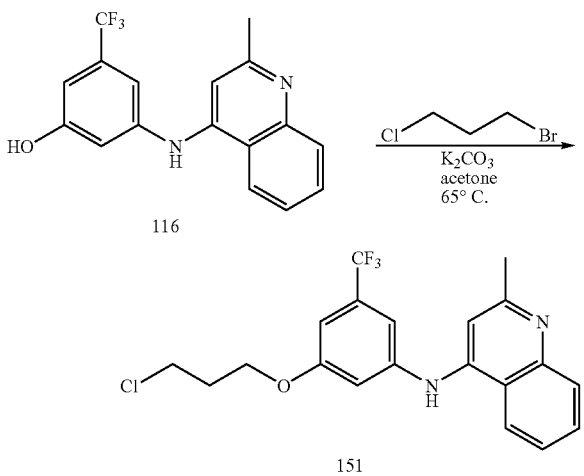

Step 1. [3-(3-Chloropropoxy)-5-trifluoromethylphenyl](2-methylquinolin-4-yl)amine.

See Example 327, Step 1.

Step 2. 4-Methyl-1-{3-[3-(2-methylquinolin-4-ylamino)-5-trifluoromethylphenoxy]propyl}piperidin-4-ol.

The title compound was synthesized in the same manner as for Example 248, last step using 151 and 4-methylpiperidin-4-ol.

The compounds of Examples 329 and 330 were synthesized in the same manner as for Example 328.

The compound of Example 331 was synthesized in the same manner as for Example 67.

EXAMPLE 332

(3-{3-[4-(3-Methylbutyl)piperazin-1-yl]propoxy}-5-trifluoromethylphenyl)-(2-methylquinolin-4-yl)amine

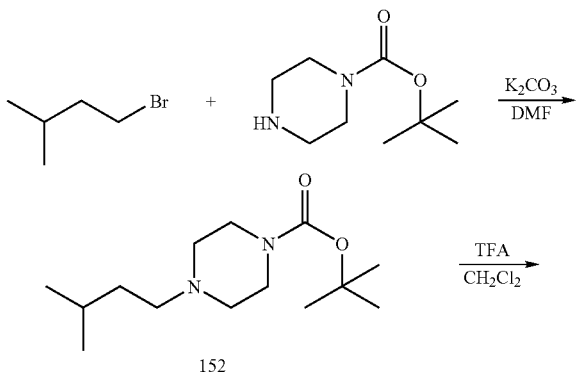

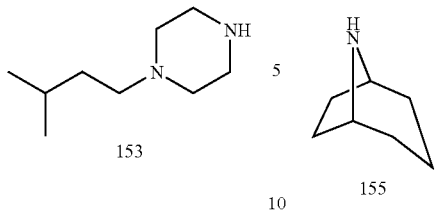

153

Step 1. tert-Butyl 4-(3-methylbutyl)piperazine-1-carboxylate.

To a solution of tert-butyl-1-piperzinecarboxylate (0.8 g, 4.2 mmol) in DMF (20 ml) were sequentially added K$_2$CO$_3$ (1.8 g, 12 mmol), 1-bromo-3-methylbutane (0.8 ml, 4.2 mmol), and the reaction mixture was stirred at room temperature overnight. The reaction mixture was diluted with water (20 ml), brine (4 ml), and extracted with EtOAc (3×20 ml). The combined organic layers were dried (MgSO$_4$) and concentrated under reduced pressure to give product 152 as a white solid (0.82 g, 60%).

Step 2. 1-(3-Methylbutyl)piperazine.

To a solution of 152 (0.82 g, 3.1 mmol) in CH$_2$Cl$_2$ (12 ml) was added TTA (1.4 ml, 19 mmol) and the reaction mixture was stirred at room temperature for 4 hours. The reaction mixture was washed with water (10 ml), brine (3 ml), made basic with 2N NaOH (3.0 ml), and extracted with 7:3 CH$_2$Cl$_2$/MeOH (3×5.0 ml). The organic layers were combined, dried (K$_2$CO$_3$), and then concentrated under reduced pressure to give 153 as an off-white solid (0.41 g, 82%).

Step 3. (3-{3-[4-(3-Methylbutyl)piperazin-1-yl]propoxy}-5-trifluoromethylphenyl)-(2-methylquinolin-4-yl)amine.

The title compound was synthesized in the same manner as for Example 248, last step using amine 153 and chloride 151.

EXAMPLE 333

{3-[3-(8-Azabicyclo[3.2.1]oct-8-yl)propoxy]-5-trifluoromethylphenyl}(2-methylquinolin-4-yl)amine

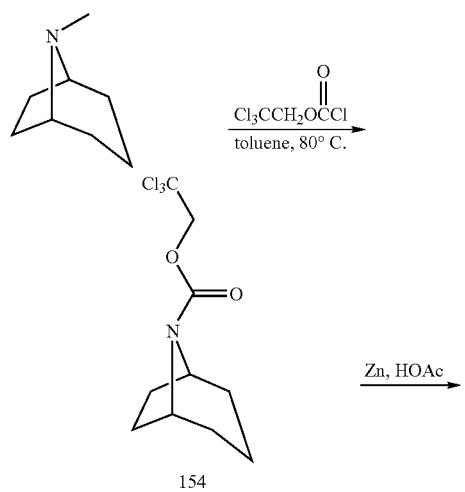

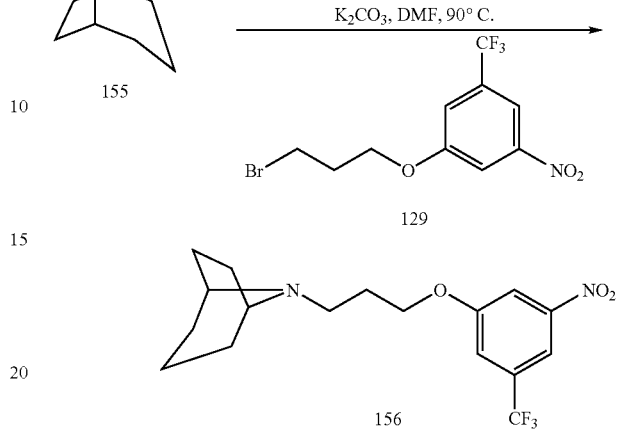

Step 1. 2,2,2-Trichloroethyl 8-azabicyclo[3.2.1]octane-8-carboxylate.

To a solution of tropane (0.50 g, 3.99 mmol) in anhydrous toluene (10 ml) was added trichloroethane chloroformate (0.93 g, 4.38 mmol) at room temperature. The resulting solution was heated at 80° C. for 2 hours before it was partitioned between Et$_2$O (80 ml) and water (50 ml). The organic layer was washed subsequently with 1N NaOH (2×50 ml), brine (50 ml), dried over Na$_2$SO$_4$ and concentrated on a rotavap to give the desired carbamate 154 as white solid (0.94 g, 82%).

Step 2. 8-Azabicyclo[3.2.1]octane.

To a solution of carbamate 154 (0.94 g, 3.28 mmol) in HOAc (10 ml) was added zinc (0.64 g, 9.84 mmol). The resulting mixture was stirred at room temperature overnight before excess zinc was removed by filtration. The filtrate was brought into EtOAc (80 ml) which was then washed with dilute NaOH (2×50 ml) and brine. The organic layer was dried over Na$_2$SO$_4$ and concentrated on a rotavap to give the desired product 155 as an orange oil (0.06 g, 16%).

Step 3. {3-[3-(8-Azabicyclo[3.2.1]oct-8-yl)propoxy]-5-trifluoromethylphenyl}(2-methylquinolin-4-yl)amine.

The title compound was synthesized in the same manner as for Example 67 using the amine 155 and 1-(3-bromopropoxy)-3-nitro-5-trifluoromethyl-benzene (129).

Examples 334 and 335 were synthesized in the same manner as for Example 67 using 129 instead of 31.

The compounds of Examples 336 to 338 were synthesized in the same manner as for Example 248.

The compound of Example 339 was synthesized in the same manner as for Example 214.

The compounds of Examples 340 and 341 were synthesized in the same manner as for Example 67 using 129 instead of 31.

| Example # | structure | chemical name | physical description[a] | [M + H]+ |
|---|---|---|---|---|
| 311 | 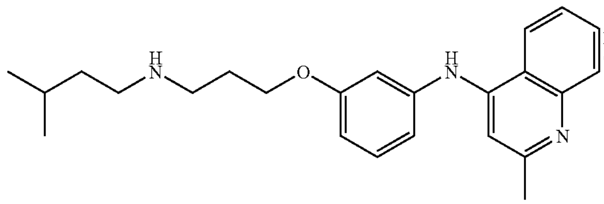 | {3-[3-(3-methylbutylamino)propoxy]phenyl}(2-methylquinolin-4-yl)amine | pale yellow solid | 378.24 |
| 312 | 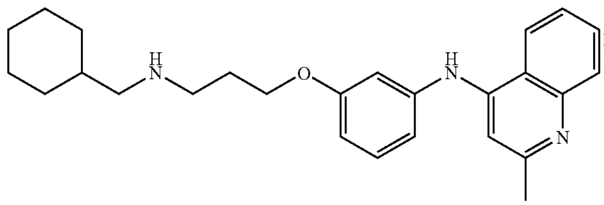 | {3-[3-(cyclohexylmethylamino)propoxy]phenyl}(2-methylquinolin-4-yl)amine | pale yellow solid | 404.32 |
| 313 | 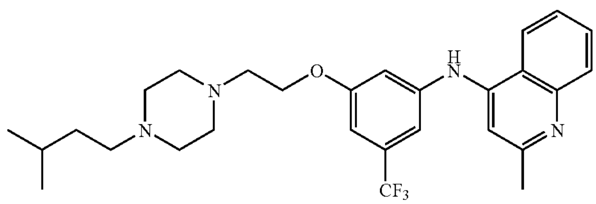 | (3-{2-[4-(3-methylbutyl)piperazin-1-yl]ethoxy}-5-trifluoromethylphenyl)(2-methylquinolin-4-yl)amine | pale yellow solid[d] | 501.39 |
| 314 | 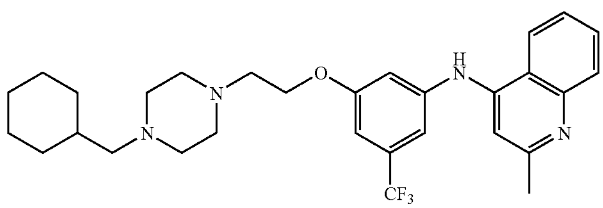 | (3-{2-[4-cyclohexylmethylpiperazin-1-yl]ethoxy}-5-trifluoromethylphenyl)(2-methylquinolin-4-yl)amine | pale yellow solid[d] | 527.33 |
| 315 | 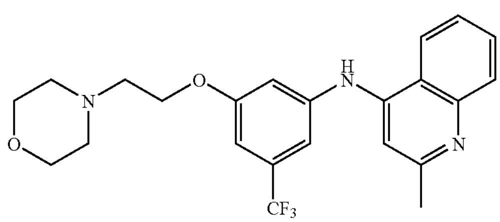 | (2-methylquinolin-4-yl)[3-(2-morpholin-4-ylethoxy)-5-trifluoromethylphenyl]amine | yellow solid | 432.24 |
| 316 | 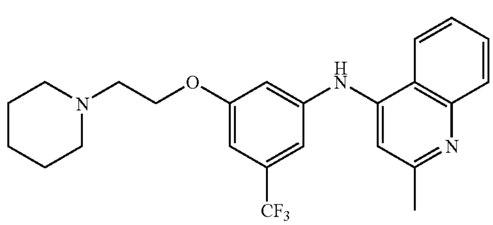 | (2-methylquinolin-4-yl)[3-(2-piperidin-1-ylethoxy)-5-trifluoromethylphenyl]amine | yellow solid | 430.30 |
| 317 | 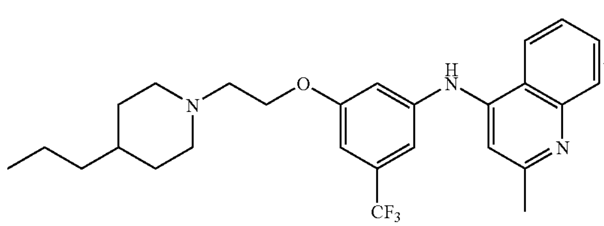 | (2-methylquinolin-4-yl)[3-(2-(4-propylpiperidin-1-yl)ethoxy)-5-trifluoromethylphenyl]amine | yellow solid | 472.30 |

-continued

| Example # | structure | chemical name | physical description[a] | [M + H]+ |
|---|---|---|---|---|
| 318 | 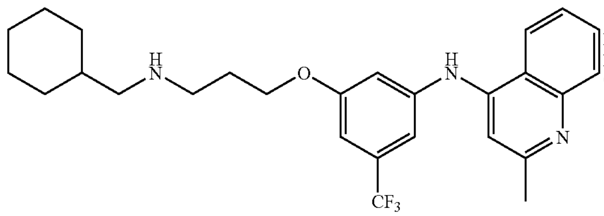 | {3-[3-(cyclohexylmethylamino) propoxy]-5-trifluoromethyl phenyl}(2-methyl quinolin-4-yl)amine | white solid | 472.23 |
| 319 | 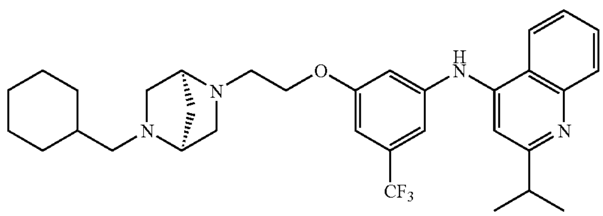 | {3-[2-(5-cyclohexylmethyl-2,5-diazabicyclo[2.21] hept-2-yl)ethoxy]-5-trifluoro methylphenyl}(2-isopropyl quinolin-4-yl)amine | brown solid[d] | 567.35 |
| 320 | 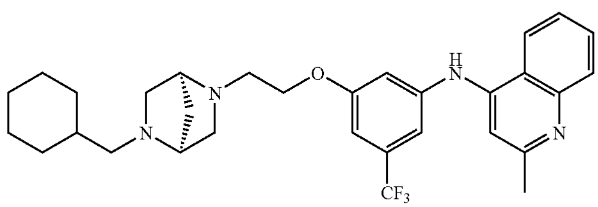 | {3-[2-(5-cyclohexylmethyl-2,5-diazabicyclo[2.2.1] hept-2-yl)ethoxy]-5-trifluoro methylphenyl}(2-methyl quinolin-4-yl)amine | yellow solid[d] | 539.28 |
| 321 | 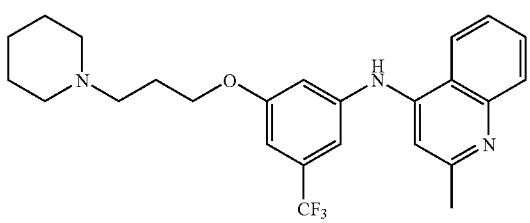 | (2-methylquinolin-4-yl)-[3-(3-piperidin-1-ylpropoxy)-5-trifluoromethylphenyl]amine | yellow solid | 444.21 |
| 322 | 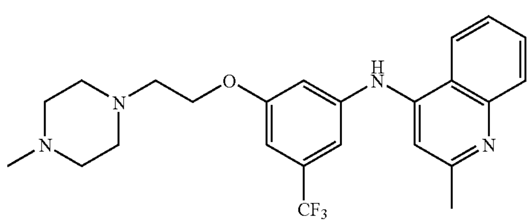 | (3-{2-[4-methylpiperazin-1-yl] ethoxy}-5-trifluoromethyl phenyl)-(2-methyl quinolin-4-yl)amine | yellow solid[d] | 445.18 |
| 323 | 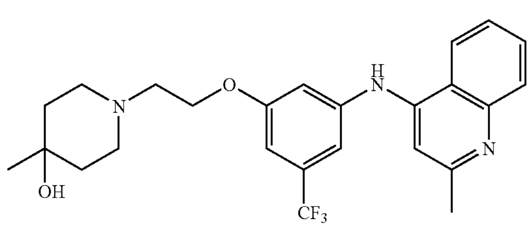 | 4-methyl-1-{2-[3-(2-methylquinolin-4-ylamino)-5-trifluoromethylphenoxy]-ethyl}piperidin-4-ol | pale yellow solid | 460.21 |
| 324 | 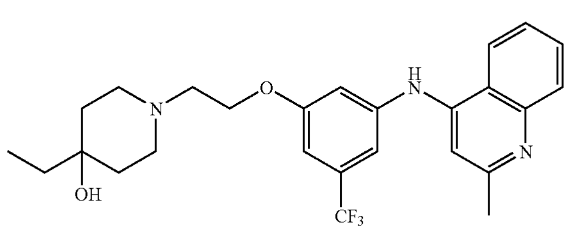 | 4-ethyl-1-{2-[3-(2-methylquinolin-4-ylamino)-5-trifluoromethylphenoxy]-ethyl}piperidin-4-ol | pale yellow solid[b] | 473.29 |

-continued

| Example # | structure | chemical name | physical description[a] | [M + H]+ |
|---|---|---|---|---|
| 325 | 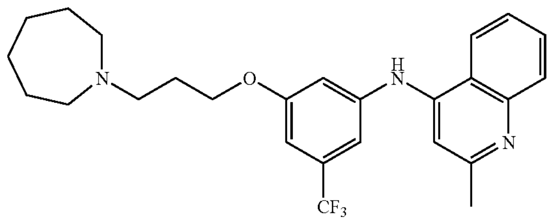 | [3-(3-azepan-1-yl-propoxy)-5-trifluoromethyl-phenyl]-(2-methyl-quinolin-4-yl)-amine | pale yellow solid | 458.27 |
| 326 | 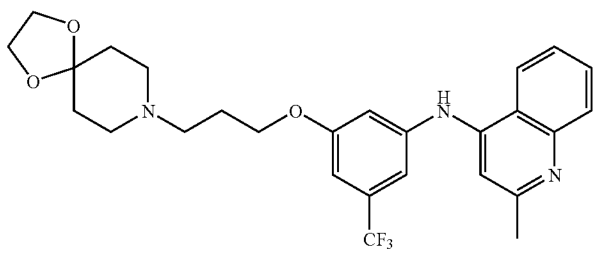 | {3-[3-(1,4-dioxa-8-azaspiro[4.5]dec-8-yl)propoxy]-5-trifluoromethylphenyl}(2-methylquinolin-4-yl)amine | pale yellow solid | 502.39 |
| 327 | 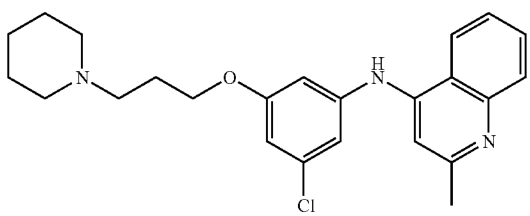 | [3-chloro-5-(3-piperidin-1-ylpropoxy)phenyl](2-methylquinolin-4-yl)amine | pale yellow solid | 410.31 |
| 328 | 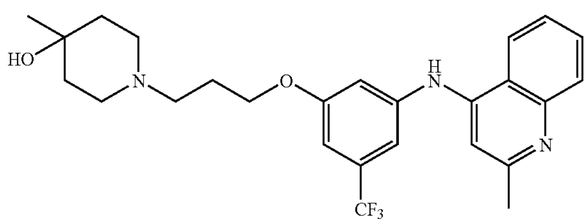 | 4-methyl-1-{3-[3-(2-methyl quinolin-4-ylamino)-5-trifluoromethylphenoxy]propyl}piperidin-4-ol | pale yellow solid[b] | 474.32 |
| 329 | 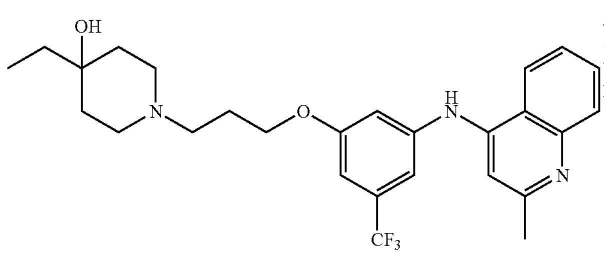 | 4-ethyl-1-{3-[3-(2-methyl quinolin-4-ylamino)-5-trifluoromethylphenoxy]propyl}piperidin-4-ol | pale yellow solid | 486.26 |
| 330 | 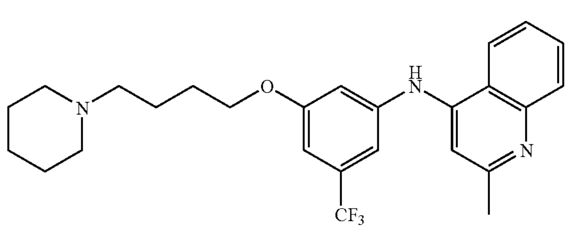 | (2-methylquinolin-4-yl)[3-(4-piperidin-1-yl-butoxy)-5-trifluoromethylphenyl]amine | pale yellow solid[b] | 458.39 |

-continued

| Example # | structure | chemical name | physical description[a] | [M + H]+ |
|---|---|---|---|---|
| 331 | 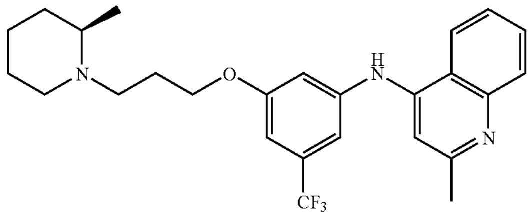 | {3-[3-(2R-2-methylpiperidin-1-yl)propoxy]-5-trifluoromethyl phenyl}-(2-methyl quinolin-4-yl)amine | pale yellow solid | 458.53 |
| 332 | 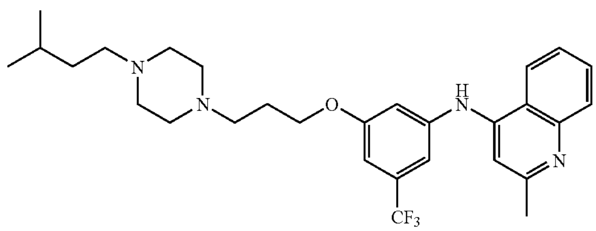 | (3-(3-[4-(3-methylbutyl) piperazin-1-yl]propoxy)-5-trifluoromethylphenyl)-(2-methylquinolin-4-yl)amine | pale yellow solid[d] | 515.40 |
| 333 | 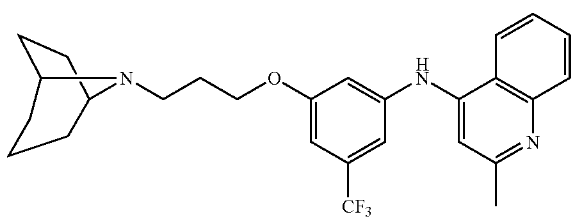 | {3-[3-(8-azabicyclo[3.2.1] oct-8-yl)propoxy]-5-trifluoromethylphenyl}(2-methylquinolin-4-yl)amine | off-white solid | 470.40 |
| 334 | 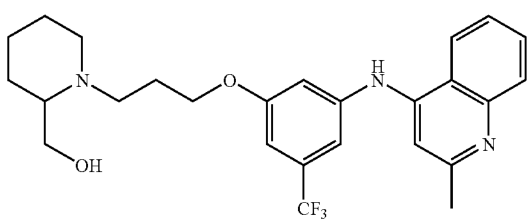 | (1-{3-[3-(2-methylquinolin-4-ylamino)-5-trifluoromethyl phenoxy]propyl}piperidin-2-yl)methanol | pale yellow solid | 474.23 |
| 335 | 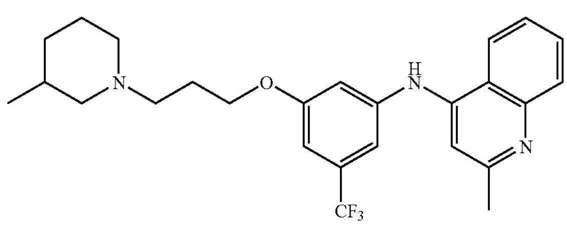 | {3-[3-(3-methylpiperidin-1-yl)propoxy]-5-trifluoromethyl phenyl}-(2-methyl quinolin-4-yl)amine | pale yellow solid | 458.39 |
| 336 | 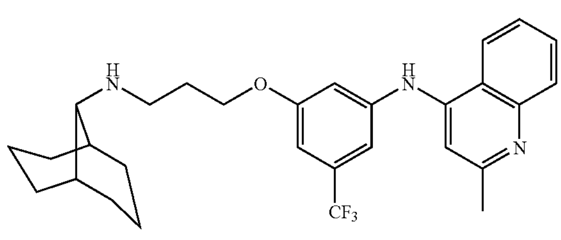 | {3-[3-(bicyclo[3.3.1]non-9-ylamino)propoxy]-5-trifluoromethylphenyl}(2-methylquinolin-4-yl)amine | off-white solid | 498.29 |

-continued

| Example # | structure | chemical name | physical description[a] | [M + H]+ |
|---|---|---|---|---|
| 337 | 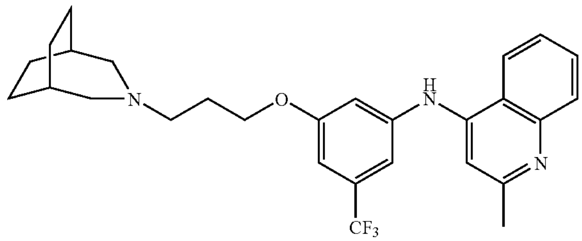 | {3-[3-(3-azabicyclo[3.2.2]non-3-yl)propoxy]-5-trifluoromethylphenyl}(2-methylquinolin-4-yl)amine | pale yellow solid | 484.26 |
| 338 | 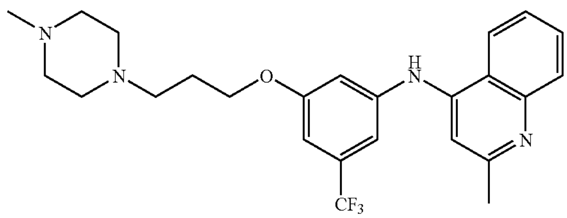 | (3-{3-[4-methylpiperazin-1-yl]propoxy}-5-trifluoro methylphenyl)-(2-methyl quinolin-4-yl)amine | pale yellow solid[b] | 459.22 |
| 339 | 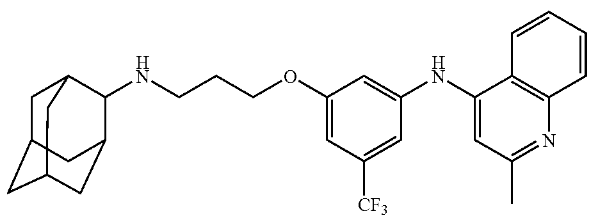 | {3-[3-(adamantan-2-ylamino)-propoxy]-5-trifluoromethyl-phenyl}-(2-methyl-quinolin-4-yl)-amine | pale yellow solid | 510.40 |
| 340 | 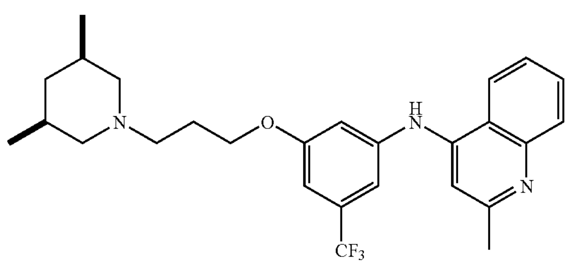 | {3-[3-(cis-3,5-dimethylpiperidin-1-yl)propoxy]-5-trifluoromethyl phenyl}-(2-methyl quinolin-4-yl)amine | pale yellow solid | 472.30 |
| 341 | 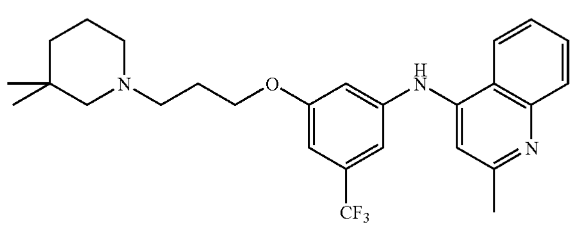 | {3-[3-(3,3-dimethylpiperidin-1-yl)propoxy]-5-trifluoromethyl phenyl}-(2-methyl quinolin-4-yl)amine | pale yellow solid | 472.25 |

[a]diHCl salt unless otherwise noted
[b]parent compound
[c]sodium salt
[d]triHCl salt

EXAMPLE 342

N-[2-(3,4-Dihydro-1H-isoquinolin-2-yl)ethyl]-3-(5-methoxyquinolin-8-ylamino)benzamide

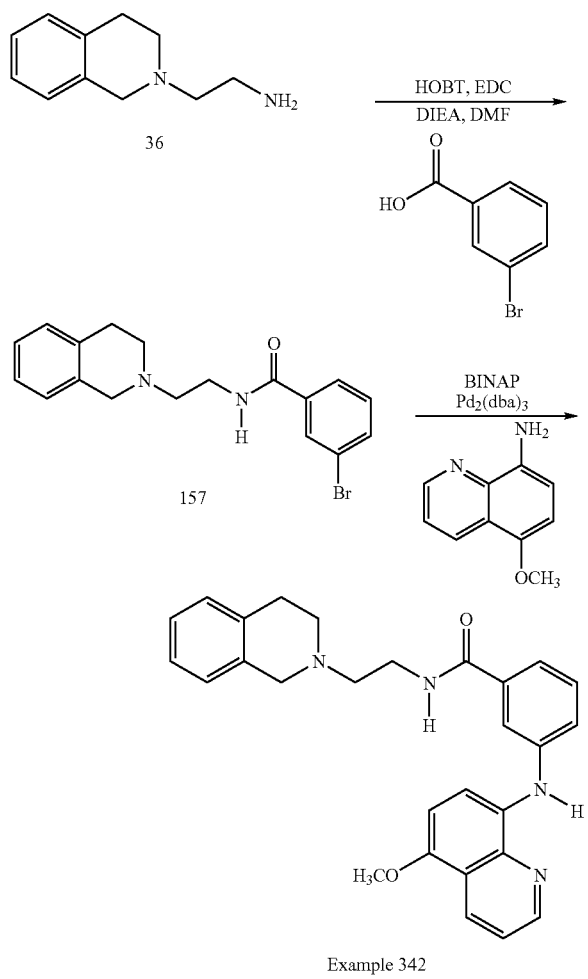

Example 342

Step 1. 3-Bromo-N-[2-(3,4-dihydro-1H-isoquinolin-2-yl)ethyl]benzamide.

To a solution of N-2-aminoethyl tetrahydroisoquinoline (0.53 g, 3 mmol) in DMF (12 ml) were sequentially added 1-[3-(dimethylamino)propyl]-3-ethyl carbodiimide HCl (0.58 g, 3 mmol), 1-hydroxybenzotriazole hydrate (0.41 g, 3 mmol), diisopropylethyl amine (1.1 ml, 6.1 mmol) then 3-bromobenzoic acid (0.6 g, 3 mmol). The mixture was stirred at room temperature for 24 hours, then water (100 ml) was added, and the mixture was extracted with ethyl acetate (3×10 ml). The organic materials were combined, dried (MgSO₄) then concentrated under reduced pressure. The residue was purified by flash chromatography (silica gel, gradient 3:1 hexane/ethyl acetate to 7:3 methylene chloride/methanol) to give amide 157 as an orange oil (0.91 g, 85%).

Step 2. N-[2-(3,4-Dihydro-1H-isoquinolin-2-yl)ethyl]-3-(5-methoxyquinolin-8-ylamino)benzamide.

To a solution of the amide 157 (300 mg, 0.835 mmol) and 8-amino-5-methoxyquinoline (204 mg, 1.17 mmol) in toluene (8 ml), were sequentially added BINAP (78 mg, 15 mol %), potassium tert-butoxide (141 mg, 1.25 mmol), and tris(dibenzylidene acetone)dipalladium (0) (38 mg). The mixture was purged with nitrogen and heated under reflux for 14 hours, then mixed with water (10 ml) and extracted with ethyl acetate (3×5 ml). The organic materials were combined, dried (MgSO₄) and concentrated under reduced pressure. The residue was purified by reverse phase HPLC (5-70% aq acetonitrile) to give the desired product as an orange solid (217 mg, 58%).

The compound of Example 343 was synthesized in the same manner as for Example 342 using 1-amino-3-methylnaphthalene instead of 5-methoxyquinolin-8-ylamine. 1-Amino-3-methylnaphthalene was synthesized from 1-amino-3-methylnaphthalene-2-carbonitrile (Kobayashi, K. et al. J. Org. Chem. 1997, 62, 664) using a literature procedure (Mirek, J., is Sepiol, J. Ange. Chemie Int. Ed. Eng. 1973, 12, 837).

EXAMPLE 344

N-[2-(4-benzylpiperidin-1-yl)ethyl]-N-[3-(2-methylquinolin-4-ylamino)phenyl]methanesulfonamide

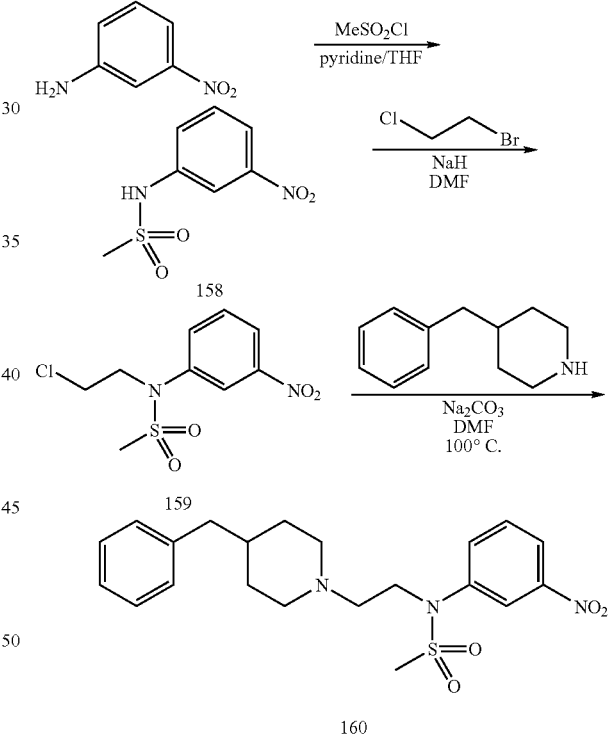

Step 1. N-(3-Nitrophenyl)methanesulfonamide.

To a solution of 3-nitroaniline (3.00 g, 21.72 mmol) in THF (75 mL) were sequentially added pyridine (4.29 g, 54.30 mmol) and methanesulfonyl chloride (6.20 g, 54.14 mmol) at room temperature. The resulting mixture was stirred at room temperature for 16 hours before the reaction was quenched with water (50 mL). The mixture was extracted with ethyl acetate (100 mL) and washed with water (100 mL). The organic layer was dried over MgSO₄ and concentrated on a rotavap to afford the desired 158 as a yellow solid (3.94 g, 84% yield).

Step 2. N-(2-Chloroethyl)-N-(3-nitrophenyl)methanesulfonamide.

To a solution of 158 (1.023 g, 4.73 mmol) in DMF (19 mL) were sequentially added NaH (60% dispersion in mineral oil, 290 mg, 7.25 mmol) and 1-bromo-2-chloroethane (1.361 g, 9.49 mmol) at room temperature. The resulting mixture was stirred at room temperature for 89 hours before the reaction was quenched with water (40 mL). The mixture was acidified with conc. HCl (1 mL), extracted with ethyl acetate (50 mL), and washed with water (2×40 mL). The organic layer was dried over MgSO$_4$ and concentrated on a rotavap to give a 1:1 mixture of product 158 and the desired product 159 as a mixture (805 mg, 30% yield).

Step 3. N-[2-(4-Benzylpiperidin-1-yl)ethyl]-N-(3-nitrophenyl)methanesulfonamide.

To a solution of the 1:1 mixture of 158 and 159 (805 mg) in DMF (5.1 mL) were sequentially added Na$_2$CO$_3$ (218 mg, 2.06 mmol) and 4-benzylpiperidine (197 mg, 1.12 mmol) at room temperature. The resulting mixture was heated at 100° C. for 53 hours before the reaction was diluted with EtOAc (50 mL). The mixture was extracted with ethyl acetate (2×50 mL) and washed with water (2×40 mL). The organic layer was dried over MgSO$_4$, concentrated on a rotavap, and the residue chromatographed on silica gel (1:1 to >1:6 hexanes/ethyl acetate) to afford the desired product 160 as a yellow oil (238 mg, 51%).

Step 4. N-[2-(4-benzylpiperidin-1-yl)ethyl]-N-[3-(2-methylquinolin-4-ylamino)phenyl]methanesulfonamide.

The title compound was synthesized in the same manner as for Example 67, Steps 4 and 5 using 160.

EXAMPLE 345

3-(4-Benzylpiperidin-1-YL)-1-[3-(2-methylquinolin-4-ylamino)phenyl]propan-1-ol

To a solution of Example 209 (0.15 g, 0.32 mmol) in THF (5.0 ml) was added LAH (1.0 M in THF, 0.66 ml, 0.66 mmol) at 0° C. The mixture was stirred at room temperature overnight before it was quenched with Na$_2$SO$_4$.10H$_2$O (pellets) until no further bubbles was observed.

The mixture was diluted with ethyl acetate and the solids filtered. The filtrate was washed with water (50 ml), brine (50 ml), dried over MgSO$_4$ and concentrated on a rotovap to give the desired alcohol as a yellow solid (0.04 g, 27%).

EXAMPLE 346

N-[2-(3,4-Dihydro-1H-isoquinolin-2-yl)ethyl]-3-(2-methylquinolin-4-yloxy)benzamide

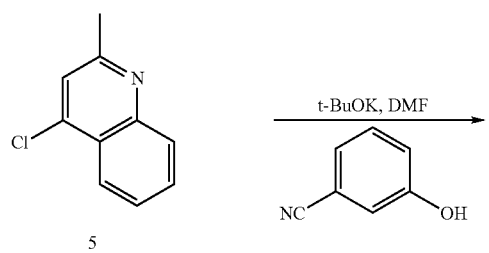

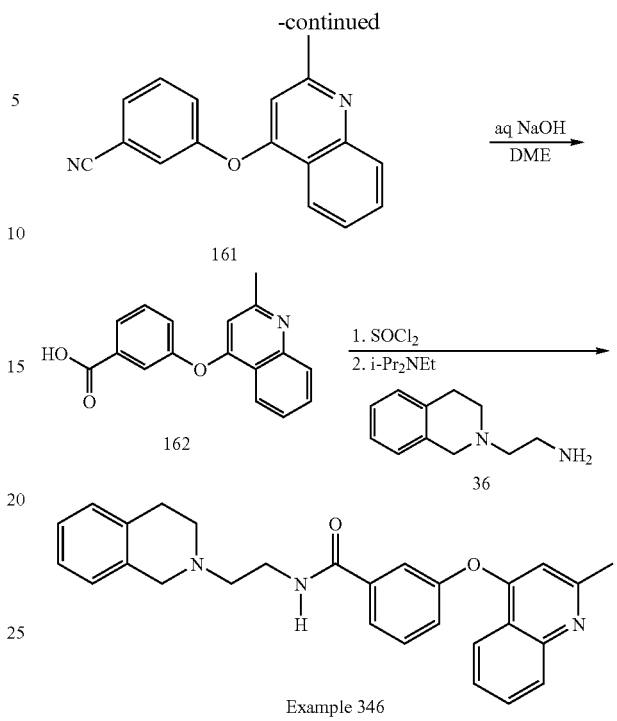

Example 346

Step 1. 4-(3-Isocyanophenoxy)-2-methylquinoline.

To a solution of 4-chloroquinolidine (5) (1.18 g, 10 mmol) and 3-cyanophenol (1.19 g, 10 mmol) in DMF (50 ml) was added potassium tert-butoxide (1.23 g, 11 mmol). The mixture was heated under reflux for 18 hours, then mixed with water (200 ml). The mixture was extracted with methylene chloride (3×15 ml), and the extracts were combined, washed with water (50 ml), brine (50 ml), and dried (MgSO$_4$). The solution was concentrated under reduced pressure, and the residue was purified by flash chromatography (SiO$_2$, gradient hexane to 2:1 hexane/ethyl acetate) to give product 161 as a pale yellow oil (1.9 g, 73%).

Step 2. 3-(2-Methylquinolin-4-yloxy)benzoic acid.

To a solution of nitrile 161 (1.9 g, 7.29 mmol) in 1,2-dimethoxyethane (10 ml) was added 4 M NaOH (2 ml). The mixture was heated under reflux for 18 hours, then cooled and neutralized (to pH 7) by the addition of concentrated HCl. The solids were collected by filtration, and dried under vacuum to give product 162 as a white solid (1.4 g, 69%) which was used without further purification.

Step 3. N-[2-(3,4-Dihydro-1H-isoquinolin-2-yl)ethyl]-3-(2-methylquinolin-4-yloxy)benzamide.

Carboxylic acid 162 (264 mg, 0.95 mmol) was dissolved in 1,2-dichloroethane (1 ml) and thionyl chloride (0.1 ml, 1.1 mmol) was added. The mixture was warmed at 60° C. for 10 min, then concentrated under reduced pressure. The residue was mixed with 1,2-dichloroethane (2 ml) then treated with a solution of N-2-aminoethyltetrahydroisoquinoline (36) (100 mg, 0.56 mmol) and N,N-diisopropyl-ethylamine (0.11 ml, 0.6 mmol) in 1,2-dichloroethane (1 ml). The mixture was stirred at room temperature overnight, then washed with water (10 ml), then saturated sodium chloride solution (10 ml) and dried (MgSO$_4$). The solution was concentrated under reduced pressure, and a portion of the residue was

EXAMPLE 347

(3-{2-[2-(4-Benzylpiperidin-1-yl)ethyl][1,3]dioxan-2-yl}phenyl)(2-methylquinolin-4-yl)amine To the mixture of the compound of Example 209 (0.31 g, 0.67 mmol) in toluene/propane-1,3-diol (7 ml/7 ml) was added p-TsOH (0.32 g, 1.68 mmol) at room temperature. The resulting mixture was heated under reflux in a Dean-Stark setup overnight before the reaction was diluted with EtOAc (80 ml). The mixture was washed with 1 N NaOH (2×50 ml) and brine (50 ml). The organic layer was dried over $Na_2SO_4$ and concentrated on a rotavap to dryness.

The residue was purified by reverse phase HPLC to afford the desired product as an off-white solid (74 mg, 42% with 50% starting material recovered).

The compound of Example 348 was synthesized in the same manner as for Example 191 using 1-benzylpiperazine instead of compound 36.

EXAMPLE 349 trans-[3-(4-Benzylaminocyclohexyloxy)phenyl](2-methylquinolin-4-yl)amine

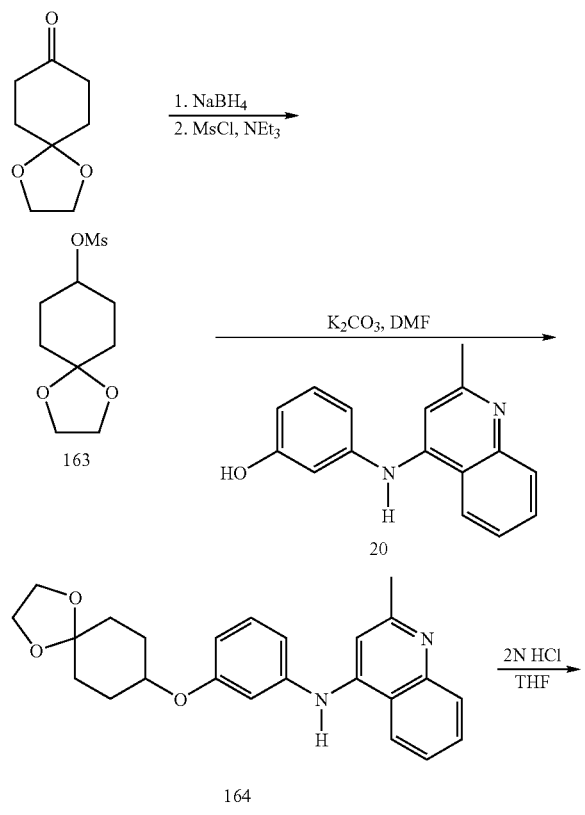

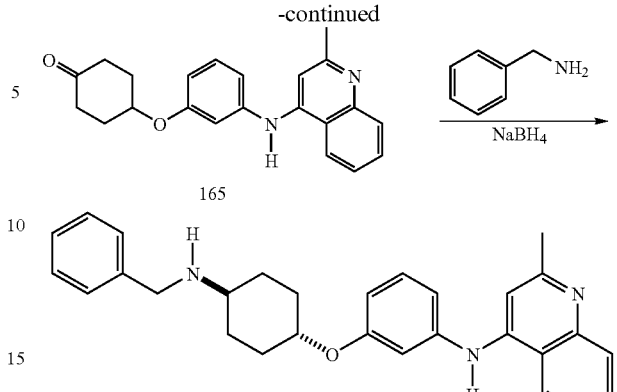

Example 349

Step 1. 1,4-Dioxa-spiro[4.5]dec-8-yl methanesulfonate.

To a solution of 1,4-cyclohexandione monoethylene ketal (1.0 g, 6.4 mmol) in ethanol (30 ml) was added sodium borohydride (0.4 g, 10 mmol) in small portions at 0° C. and the mixture was stirred at room temperature overnight. The reaction was then quenched by the cautious addition of glacial acetic acid (~2 ml) and the mixture was stirred an additional 30 minutes, then concentrated under reduced pressure. The residue was mixed with ethyl acetate (20 ml) and brine (20 ml), then the organic materials were separated, dried ($MgSO_4$) and concentrated under reduced pressure. To a solution of the residue in methylene chloride (30 ml) were sequentially added triethylamine (1.67 ml, 12 mmol) and methane sulfonyl chloride (0.74 g, 6.5 mmol) at 0° C. The reaction mixture was stirred at room temperature overnight and mixed with water (30 ml). The organic layer was separated, dried ($MgSO_4$) then concentrated under reduced pressure to give product 163 as a clear oil (1.33 g, 89%).

Step 2. [3-(1,4-Dioxaspiro[4.5]dec-8-yloxy)phenyl](2-methylquinolin-4-yl)amine.

To a solution of 3-(2-methylquinolin-4-ylamino)phenol (20) (0.5 g, 2 mmol) in DMF (8 ml) were sequentially added $K_2CO_3$ (0.55 g, 4 mmol) and a solution of 1,4-dioxaspiro[4,5]dec-8-yl methanesulfonate (163, 0.47 g, 2 mmol) in DMF (2 ml). The mixture was heated at 80° C. under nitrogen for 24 hours, then cooled and diluted with water (30 ml). The mixture was extracted with ethyl acetate (3×5 ml) and the organic materials were combined, dried ($MgSO_4$) then concentrated under reduced pressure to give product 164 as a pale yellow oil (0.75 g, 98%).

Step 3. 4-[3-(2-Methylquinolin-4-ylamino)phenoxy]cyclohexanone.

Compound 164 was dissolved in THF (10 ml) and acetone (3 ml), then 2 N aqueous HCl (5 ml) was added and the mixture was stirred at 50° C. overnight. The reaction was cooled to room temperature and neutralized (pH 7) with 2 N NaOH, then extracted with 7:3 methylene chloride/methanol (3×8 ml). The extracts were combined, washed with saturated sodium bicarbonate (15 ml) then dried ($K_2CO_3$) and concentrated under reduced pressure. The residue was purified by flash chromatography ($SiO_2$, gradient elution 3:1 hexane/ethyl acetate to 7:3 methylene chloride/methanol) to give 165 170 mg (25%).

Step 4. trans-[3-(4-Benzylaminocyclohexyloxy)phenyl](2-methylquinolin-4-yl)amine.

The ketone 165 obtained in the previous step was mixed with ethanol (1 ml), benzylamine (56 mg, 0.52 mmol) and 4 Å molecular sieves (25 mg), and the mixture was heated under reflux overnight. The solution was then cooled to room temperature and sodium borohydride (40 mg, 1.06 mmol) was added, and the reaction was stirred at room temperature overnight before it was quenched by the addition of glacial acetic acid (0.5 ml). The mixture was concentrated under reduced pressure and the residue was partitioned between water (1.5 ml) and 7:3 methylene chloride/methanol (1.5 ml). The organic material was separated, concentrated and a portion was purified by reverse-phase HPLC (10-70% aq. acetonitrile) to give the desired product as a pale yellow solid (35 mg).

EXAMPLE 350

1-Benzylamino-3-[3-(2-methylquinolin-4-ylamino)-5-trifluoromethylphenoxy]-2S-propan-2-ol

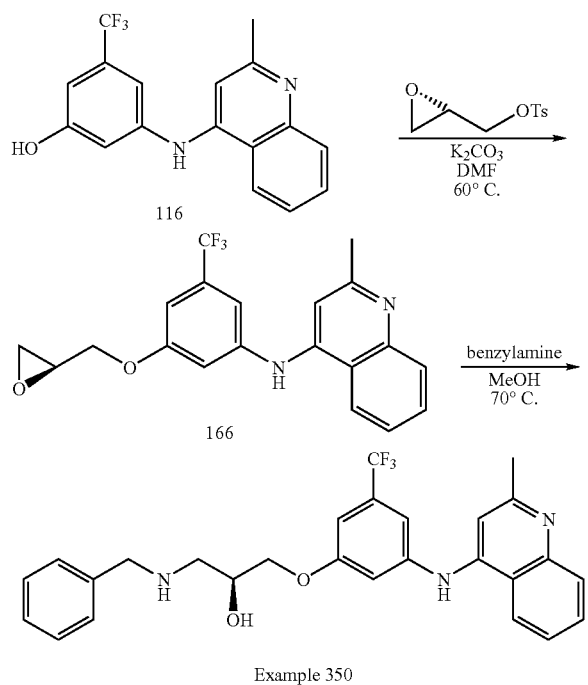

Example 350

Step 1. (2-Methylquinolin-4-yl)(3-oxiranylmethoxy-5-trifluoromethylphenyl)amine.

To a solution of 116 (467 mg, 1.47 mmol) in DMF (9.7 mL) were sequentially added K$_2$CO$_3$ (509 mg, 3.68 mmol) and (2S)-(+)-glycidyl tosylate (497 mg, 2.18 mmol) at room temperature. The resulting mixture was stirred at 60° C. for 7 hours before the reaction was diluted with ethyl acetate (20 mL). The mixture was extracted with ethyl acetate (2×50 mL) and washed with water (2×30 mL). The organic layer was dried over MgSO$_4$ and concentrated on a rotavap to give the desired 166 as a pale yellow solid (124 mg, 23%).

Step 2. 1-Benzylamino-3-[3-(2-methylquinolin-4-ylamino)-5-trifluoromethylphenoxy]-2S-propan-2-ol.

To a solution of 166 (114 mg, 0.305 mmol) in methanol (3.1 mL) was added benzylamine (39 mg, 0.366 mmol) at room temperature. The resulting mixture was heated at 70° C. for 17 hours before the solvent was evaporated. The residue was chromatographed on silica gel (1:4 hexanes/ethyl acetate to >4/1 dichloromethane/methanol), then further purified on reversed-phase HPLC (20% to >50% 95:5 acetonitrile:water) to afford the desired produect as a colorless film (5.5 mg, 4%).

The compounds of Examples 351 to 353 were synthesized in the same manner as for Example 350.

EXAMPLE 354

[3-(1-Benzylpyrrolidin-3R-3-yloxy)-5-trifluoromethylphenyl](2-methylquinolin-4-yl)amine

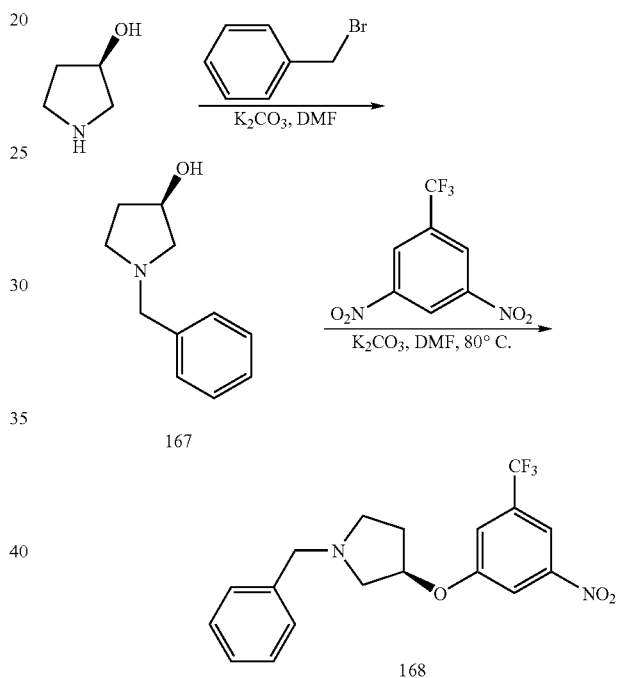

Step 1. 1-Benzylpyrrolidin-3-ol.

To a solution of (R)-pyrrolidine-3-ol (0.24 g, 2.75 mmol) and benzyl bromide (0.56 g, 3.28 mmol) in DMF (10 ml) was added K$_2$CO$_3$ (0.49 g, 3.54 mmol, 1.3 equiv.) at room temperature. The resulting mixture was stirred at room temperature overnight before it was diluted with EtOAc (80 ml). The organic layer was washed with water (3×50 ml), brine (50 ml), dried over Na$_2$SO$_4$ and concentrated on a rotavap to give the desired product 167 as a yellow oil 0.15 g, 32%).

Step 2. 1-Benzyl-3R-3-(3-nitro-5-trifluoromethylphenoxy)pyrrolidine.

To a solution of 167 (0.15 g, 0.85 mmol) and 1,3-dinitro-5-trifluoromethylbenzene (0.19 g, 0.85 mmol) in DMF (5 ml) was added K$_2$CO$_3$ (0.23 g, 1.70 mmol) at room temperature. The resulting mixture was heated at 80° C. overnight before the reaction was diluted with EtOAc (60 ml). The organic layer was washed with water (30 ml), brine (30 ml), dried over Na$_2$SO$_4$ and concentrated on a rotavap. The residue was chromatographed on silica gel to give the desired product 168 as a yellow oil (0.11 g, 37%).

Step 3. [3-(1-Benzylpyrrolidin-3R-3-yloxy)-5-trifluoromethylphenyl](2-methylquinolin-4-yl)amine.

The title compound was synthesized in the same manner as for Example 67, last 3 steps using 168.

The compound of Example 355 was synthesized in the same manner as for Example 350.

The compound of Example 356 was synthesized in the same manner as for Example 354.

The compound of Example 357 was synthesized in the same manner as for Example 350.

| Example # | structure | chemical name | physical description[a] | [M + H]+ |
|---|---|---|---|---|
| 342 | 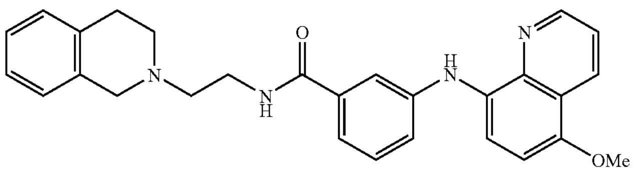 | N-[2-(3,4-dihydro-1H-isoquinolin-2-yl)ethyl]-3-(5-methoxyquinolin-8-ylamino)benzamide | orange solid[b] | 453.18 |
| 343 | 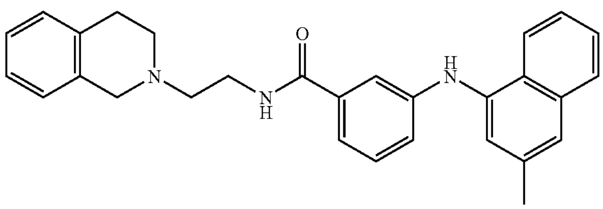 | N-[2-(3,4-dihydro-1H-isoquinolin-2-yl)ethyl]-3-(3-methylnaphthalen-1-ylamino)benzamide | orange solid[b] | 436.20 |
| 344 | 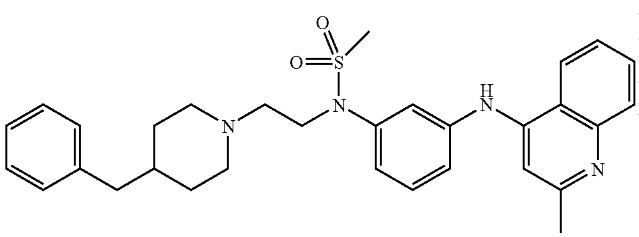 | N-[2-(4-benzylpiperidin-1-yl)ethyl]-N-[3-(2-methylquinolin-4-ylamino)-phenyl]methanesulfonamide | pale yellow solid[b] | 529.21 |
| 345 | 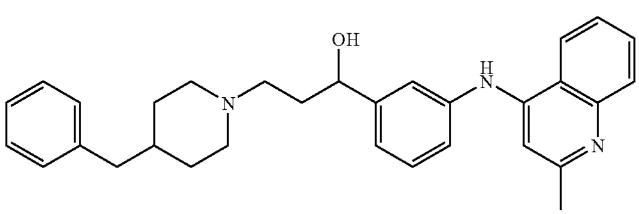 | 3-(4-benzylpiperidin-1-yl)-1-[3-(2-methylquinolin-4-yl amino)phenyl]propan-1-ol | pale yellow solid | 466.27 |
| 346 | 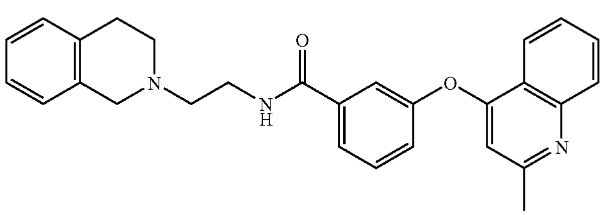 | N-[2-(3,4-dihydro-1H-isoquinolin-2-yl)ethyl]-3-(2-methylquinolin-4-yl oxy)benzamide | orange solid[b] | 438.15 |
| 347 | 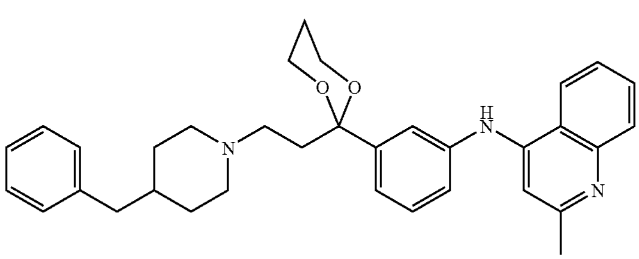 | (3-{2-[2-(4-benzylpiperidin-1-yl)ethyl][1,3]dioxan-2-yl}phenyl)(2-methylquinolin-4-yl)amine | light yellow solid | 522.18 |

-continued

| Example # | structure | chemical name | physical description[a] | [M + H]+ |
|---|---|---|---|---|
| 348 | 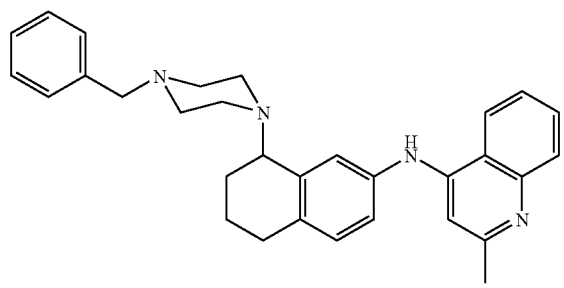 | [8-(4-benzylpiperazin-1-yl)-5,6,7,8-tetrahydronaphthalen-2-yl] (2-methylquinolin-4-yl)amine | yellow solid[d] | 463.21 |
| 349 | 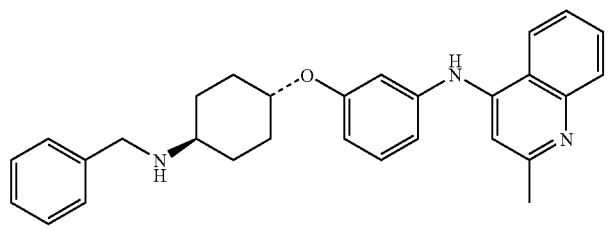 | trans-[3-(4-benzylaminocyclohexyloxy)phenyl](2-methylquinolin-4-yl)amine | pale yellow solid[b] | 438.44 |
| 350 | 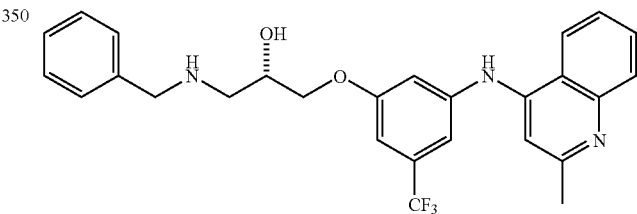 | 1-benzylamino-3-[3-(2-methyl quinolin-4-ylamino)-5-trifluoromethylphenoxy]-2S-propan-2-ol | pale yellow solid | 482.30 |
| 351 | 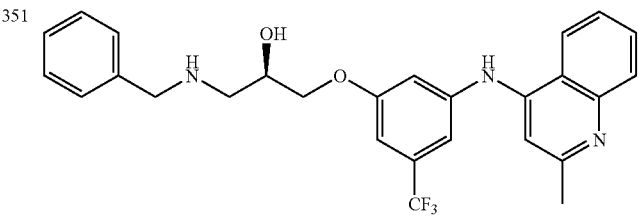 | 1-benzylamino-3-[3-(2-methyl quinolin-4-ylamino)-5-trifluoromethylphenoxy]-2R-propan-2-ol | pale yellow solid[b] | 482.17 |
| 352 | 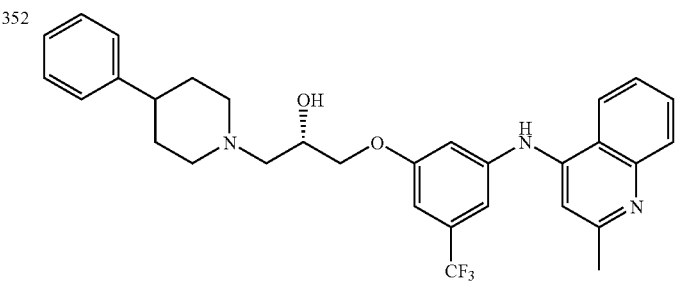 | 1-[3-(2-methylquinolin-4-ylamino)-5-trifluoromethylphenoxy]-3-(4-phenylpiperidin-1-yl)-2S-propan-2-ol | white solid[b] | |

-continued

| Example # | structure | chemical name | physical description[a] | [M + H]+ |
|---|---|---|---|---|
| 353 | 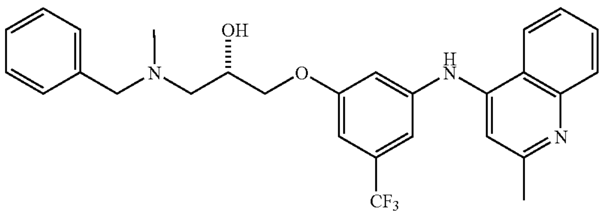 | 1-(Benzyl-methyl-amino)-3-[3-(2-methyl-quinolin-4-ylamino)-5-trifluoromethyl-phenoxy]-2S-propan-2-ol | yellow solid[b] | 496.15 |
| 354 | 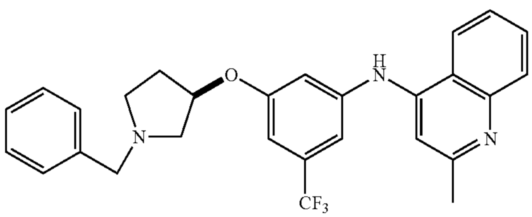 | [3-(1-benzylpyrrolidin-3R-3-yloxy)-5-trifluoromethylphenyl](2-methyl quinolin-4-yl)amine | light yellow solid | 478.08 |
| 355 | 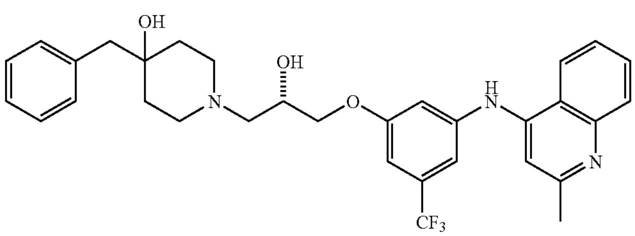 | 4-benzyl-1-{2S-2-hydroxy-3-[3-(2-methylquinolin-4-ylamino)-5-trifluoromethylphenoxy]propyl}piperidin-4-ol | pale yellow solid[b] | 566.26 |
| 356 | 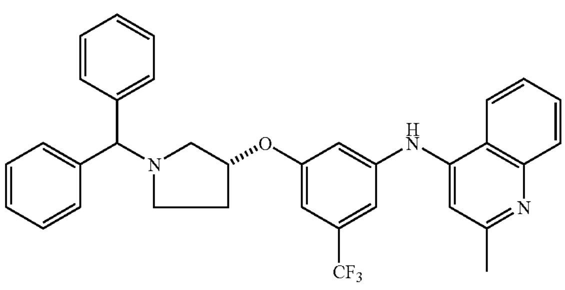 | [3-(1-benzhydrylpyrrolidin-3R-3-yloxy)-5-trifluoromethylphenyl](2-methyl quinolin-4-yl)amine | light yellow solid | 554.18 |
| 357 | 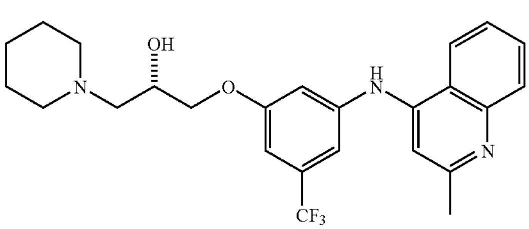 | 1-[3-(2-methylquinolin-4-yl amino)-5-trifluoromethyl phenoxy]-3-piperidin-1-yl-2S-propan-2-ol | pale yellow solid[b] | |

[a] diHCl salt unless otherwise noted
[b] parent compound
[c] sodium salt
[d] triHCl salt The compound of Example 358 was synthesized in the same manner as for Example 68.

The compounds of Examples 359 to 362 were synthesized in the same manner as for Example 67.

EXAMPLE 363

Ethyl 4-phenyl-1-{2-[3-(2-methylquinolin-4-ylamino)-5-trifluoromethylphenoxy]ethyl}piperidine-4-carboxylate

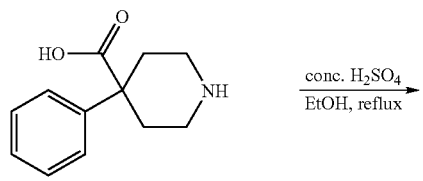

169

Step 1. Ethyl 4-phenylpiperidine-4-carboxylate.

To a solution of 4-phenylpiperidine-4-carboxylic acid p-toluenesulfonate (0.94 g, 2.49 mmol) in EtOH (10 ml) was added conc. $H_2SO_4$ (5 drops). The resulting solution was heated under reflux overnight before the solvent was removed on a rotavap. The residue was brought into EtOAc (80 ml) which was washed with 1N NaOH (3×60 ml) and brine (50 ml). The organic layer was dried over $Na_2SO_4$ and concentrated on a rotavap to give the desired product 169 as colorless oil (0.40 g, 69%).

Step 2. Ethyl 4-phenyl-1-{2-[3-(2-methylquinolin-4-ylamino)-5-trifluoromethylphenoxy]ethyl}piperidine-4-carboxylate.

The title compound was synthesized in the same manner as for Example 67, see last 3 steps using 169.

The compound of Example 364 was synthesized in the same manner as for Example 68 using the product of Example 363.

The compound of Example 365 was synthesized in the same manner as for Example 67.

The compound of Example 366 was synthesized in the same manner as for Example 68.

The compound of Example 367 was synthesized in the same manner as for Example 67.

The compound of Example 368 was synthesized in the same manner as for Example 68.

EXAMPLE 369

1-{2-[3-chloro-5-(2-methylquinolin-4-ylamino)phenoxy]ethyl}-4-phenylpiperidine-4-carboxylic acid Step 1. Ethyl 1-{2-[3-chloro-5-(2-methylquinolin-4-ylamino)phenoxy]ethyl}-4-phenylpiperidine-4-carboxylic acid.

See Step 4 in Example 268.

Step 2. -{2-[3-Chloro-5-(2-methylquinolin-4-ylamino)phenoxy]ethyl}-4-phenylpiperidine-4-carboxylic acid.

The title compound was synthesized in the same manner as for Example 68.

The compound of Example 370 was synthesized in the same manner as for Example 67.

The compound of Example 371 was synthesized in the same manner as for Example 68.

EXAMPLE 372

1-{2-[3-Fluoro-5-(2-methylquinolin-4-ylamino)phenoxy]ethyl}-4-phenylpiperidine-4-carboxylic acid

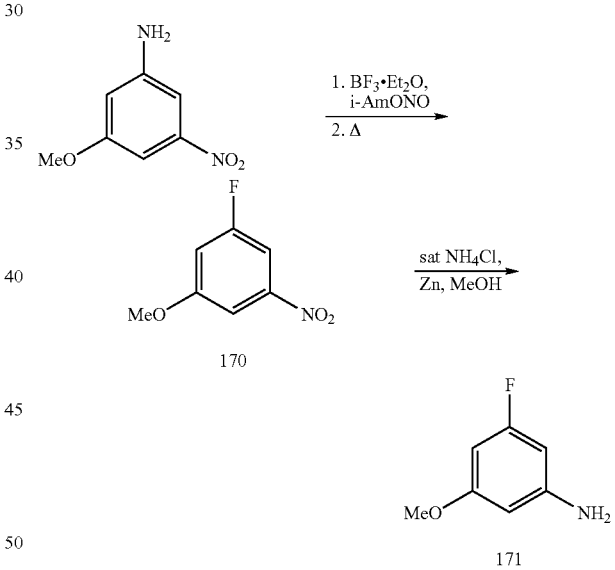

Step 1. 1-Fluoro-3-methoxy-5-nitrobenzene.

In a 100 ml flask, boron trifluoride etherate (1.63 ml, 12.93 mmol) was cooled in an ice bath and a solution of 3-methoxy-5-nitrophenylamine (1.45 g, 8.62 mmol) in DME (25 ml) was added slowly. The mixture was stirred for 5 minutes then a solution of i-amyl nitrite (1.4 ml, 10.3 mmol) in DME (20 ml) was added slowly while the temperature was maintained below 5° C. The thick slurry was stirred for an additional hour before the solids were collected by filtration and washed with cold DME (10 ml) and dried under vacuum. The resulting diazonium tetrafluoroborate salt was pyrolyzed under a slight stream of nitrogen which gave 3-fluoro-5-nitroanisole (170) as a dark solid (0.9 g, 61%).

Step 2. 3-Fluoro-5-methoxyphenylamine.

Compound 170 was dissolved in methanol (25 ml) and was treated with zinc powder (1.96 g, 30 mmol) then saturated ammonium chloride solution (20 ml) in small portions. The mixture was stirred vigorously for 5 hours then filtered through a pad of Celite® and concentrated under reduced pressure. The residue was partitioned between ethyl acetate (25 ml) and brine (20 ml). The organic material was separated, dried (MgSO$_4$) then concentrated under reduced pressure. The residue was flushed through a pad of silica gel with 3:1 hexane/ethyl acetate to give 3-fluoro-5-methoxyaniline (171) as a yellow solid (0.404 g, 54%).

Step 3. 1-{2-[3-Fluoro-5-(2-methylquinolin-4-ylamino)phenoxy]ethyl}-4-phenyl-piperidine-4carboxylic acid.

The title compound was synthesized in the same manner as for Example 369 using 3-fluoro-oxyphenylamine 5-methoxyphenylamine (171) instead of 3-chloro-5-methoxyphenylamine.

| Example # | structure | chemical name | physical description[a] | [M + H]$^+$ |
|---|---|---|---|---|
| 358 | 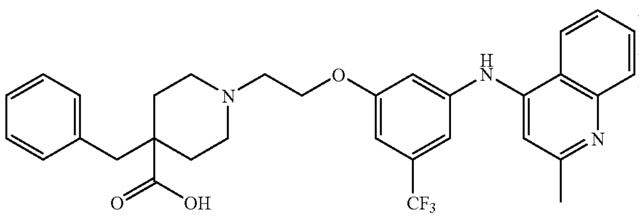 | 4-benzyl-1-{2-[3-(2-methyl quinolin-4-ylamino)-5-trifluoromethyl phenoxy}ethyl)piperidine-4-carboxylic acid | yellow solid | 464.42 |
| 359 | 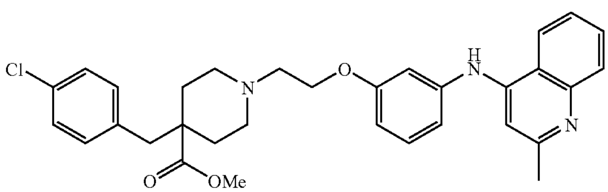 | methyl 4-(4-chlorobenzyl)-1-{2-[3-(2-methyl-quinolin-4-ylamino)phenoxy]ethyl} piperidine-4-carboxylate | pale yellow solid | 544.22 |
| 360 | 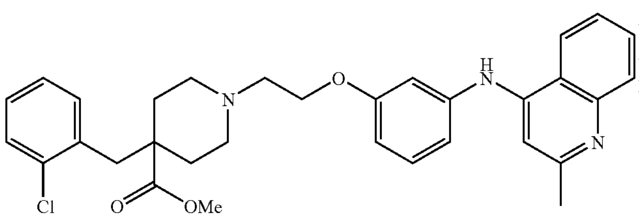 | methyl 4-(2-chlorobenzyl)-1-{2-[3-(2-methyl-quinolin-4-ylamino)phenoxy]ethyl} piperidine-4-carboxylate | pale yellow solid | 544.20 |
| 361 | 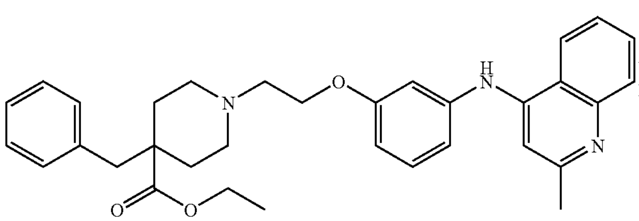 | ethyl 4-benzyl-1-{2-[3-(2-methyl-quinolin-4-ylamino)phenoxy]ethyl} piperidine-4-carboxylate | pale yellow solid | 524.27 |
| 362 | 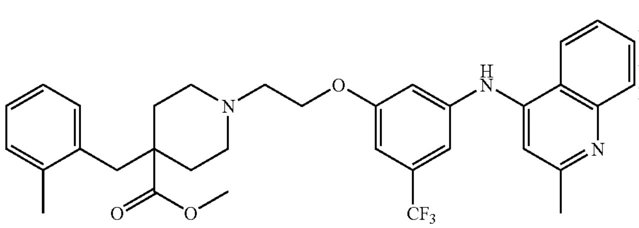 | methyl 4-(2-methylbenzyl)-1-{2-(3-(2-methylquinolin-4-ylamino)-5-trifluoromethyl phenoxy]ethyl]piperidine-4-carboxylate | off-white solid | 592.40 |

| Example # | structure | chemical name | physical description[a] | [M + H]+ |
|---|---|---|---|---|
| 363 | 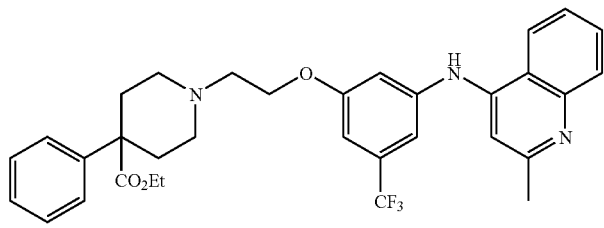 | ethyl 4-phenyl-1-{2-[3-(2-methylquinolin-4-ylamino)-5-trifluoromethyl phenoxy]ethyl}piperidine-4-carboxylate | off-white solid | 578.27 |
| 364 | 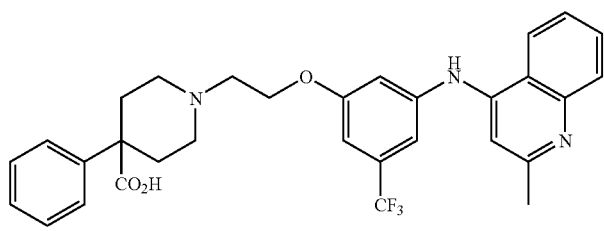 | 4-phenyl-1-{2-[3-(2-methylquinolin-4-ylamino)-5-trifluoromethyl phenoxy]ethyl}piperidine-4-carboxylic acid | off-white solid | 550.25 |
| 365 | 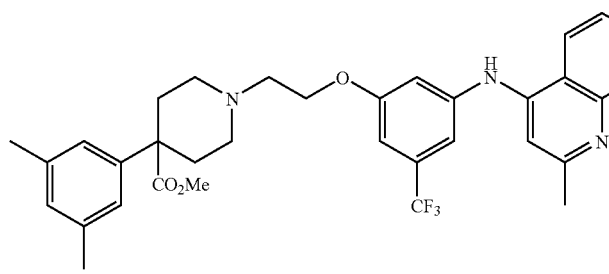 | methyl 4-(3,5-dimethylphenyl)-1-{2-[3-(2-methylquinolin-4-ylamino)-5-trifluoromethyl phenoxy]ethyl}piperidine-4-carboxylate | white foam[b] | 592.16 |
| 366 | 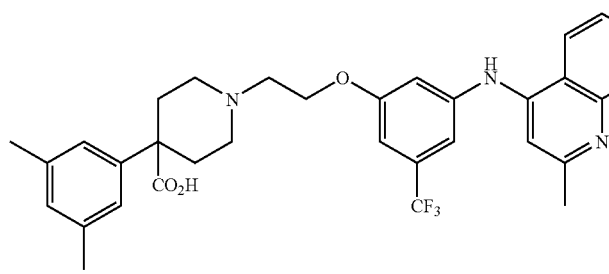 | 4-(3,5-dimethylphenyl)-1-{2-[3-(2-methylquinolin-4-ylamino)-5-trifluoromethyl phenoxy]ethyl}piperidine-4-carboxylic acid | off-white solid | 578.27 |
| 367 | 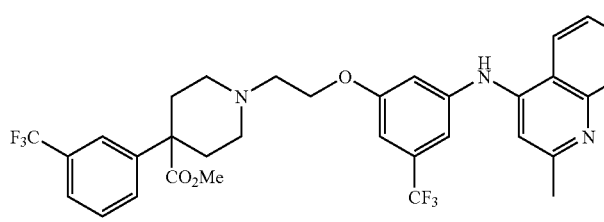 | methyl 1-{2-[3-(2-methyl quinolin-4-ylamino)-5-trifluoro methylphenoxy]ethyl}-4-(3-trifluoromethylphenyl)-piperidine-4-carboxylate | yellowish solid[b] | 632.27 |

| Example # | structure | chemical name | physical description[a] | [M + H]+ |
|---|---|---|---|---|
| 368 | 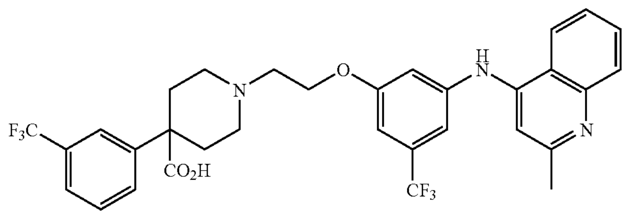 | 1-{2-[3-(2-methyl quinolin-4-ylamino)-5-trifluoro methylphenoxy]ethyl}-4-(3-trifluoromethylphenyl)-piperidine-4-carboxylic acid | yellowish solid | 618.18 |
| 369 | 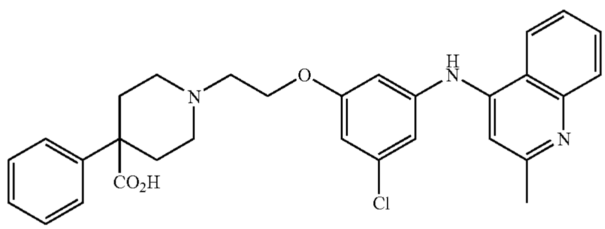 | 1-{2-[3-chloro-5-(2-methyl quinolin-4-ylamino)phenoxy] ethyl)-4-phenyl piperidine-4-carboxylic acid | pale yellow solid | 516.36 |
| 370 | 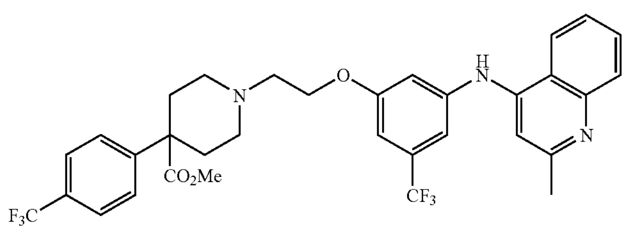 | methyl 1-{2-[3-(2-methyl quinolin-4-ylamino)-5-trifluoro methylphenoxy]ethyl}-4-(4-trifluoromethylphenyl)-piperidine-4-carboxylate | yellowish solid[b] | 632.31 |
| 371 | 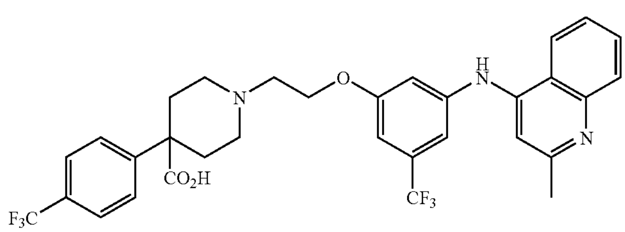 | 1-{2-[3-(2-methyl quinolin-4-ylamino)-5-trifluoro methylphenoxy]ethyl}-4-(4-trifluoromethylphenyl)-piperidine-4-carboxylic acid | yellow solid | 618.31 |
| 372 | 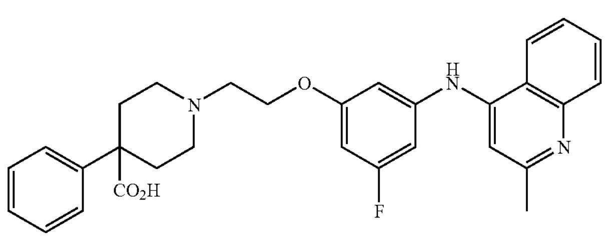 | 1-{2-[3-fluoro-5-(2-methyl quinolin-4-ylamino) phenoxy]ethyl}-4-phenyl-piperidine-4-carboxylic acid | pale yellow solid | 500.23 |

[a]diHCl salt unless otherwise noted
[b]parent compound
[c]sodium salt
[d]triHCl salt Representative additional analogs of compounds of the present invention include:
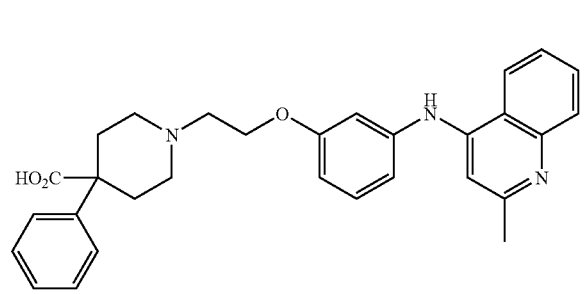
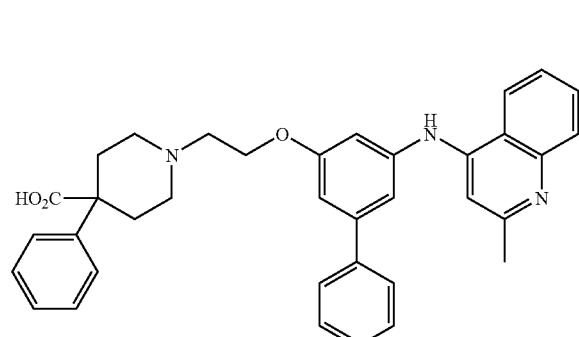
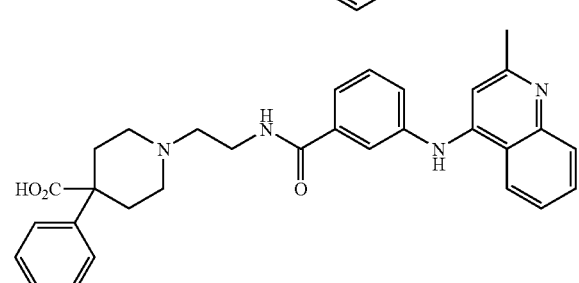
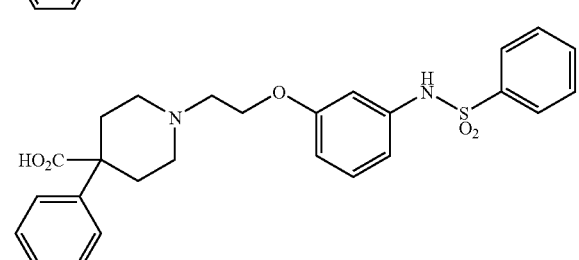
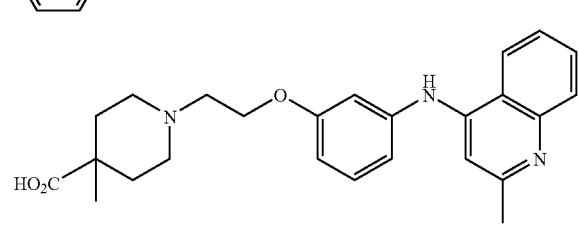
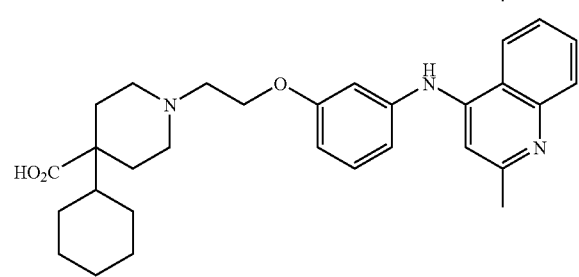
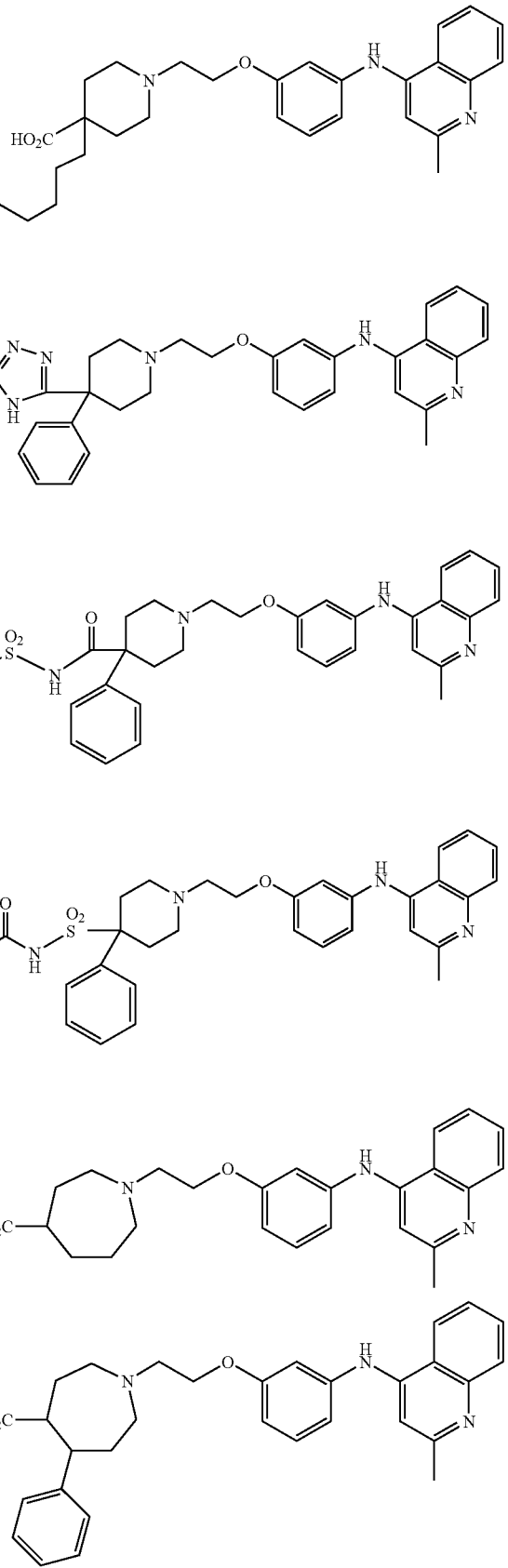

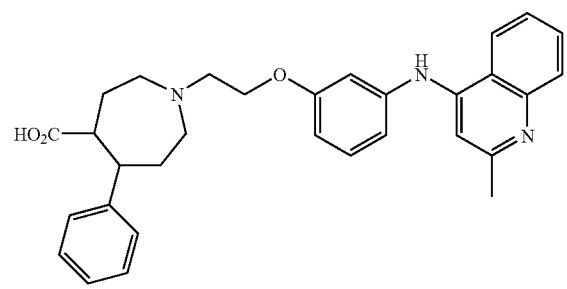
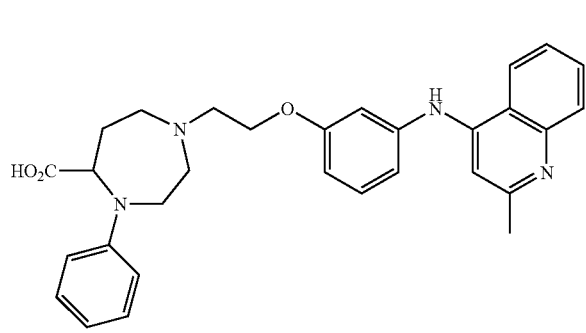
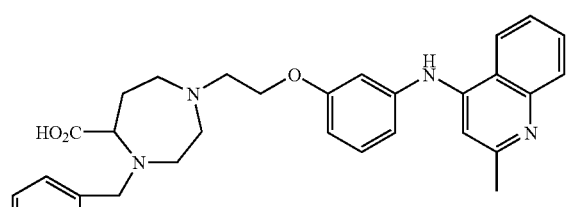
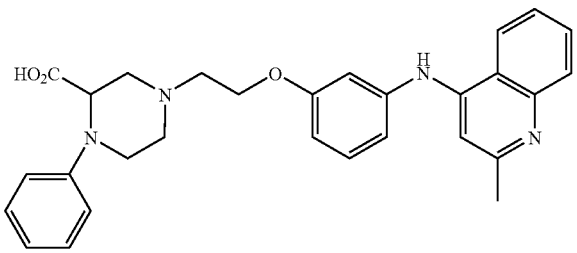
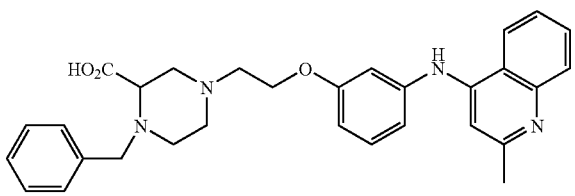
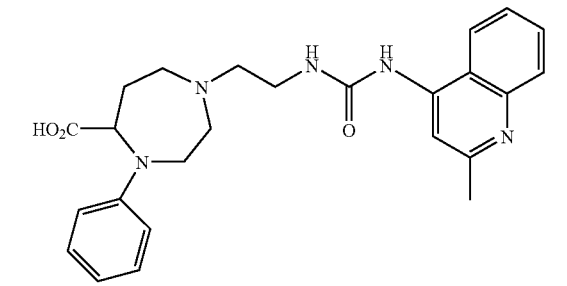
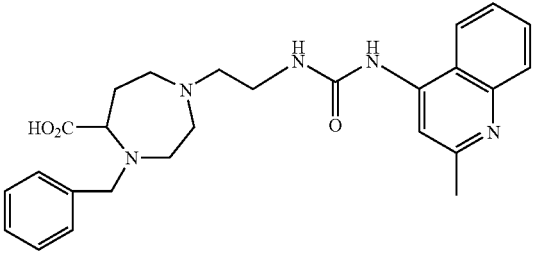
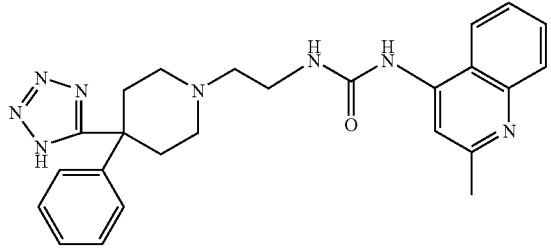
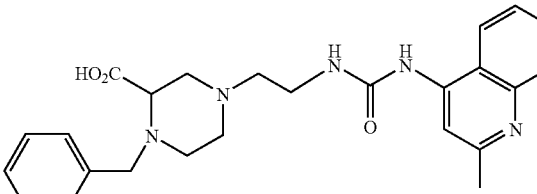
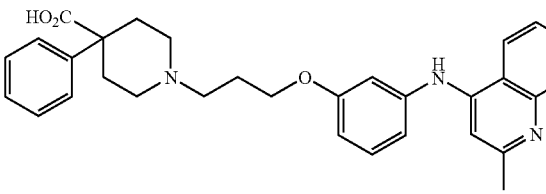
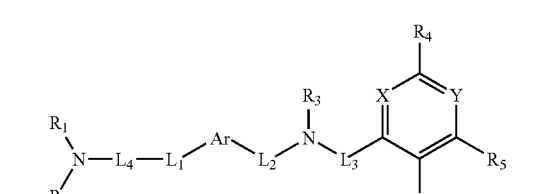
The invention claimed is:
1. A compound of the formula
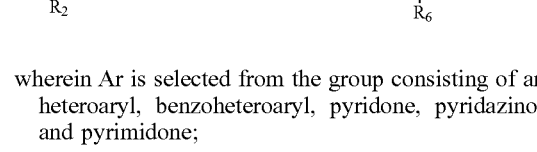
wherein Ar is selected from the group consisting of aryl, heteroaryl, benzoheteroaryl, pyridone, pyridazinone, and pyrimidone;

R₁ and R₂ are independently H, alkyl, cycloalkyl, bicyclic alkyl, adamantyl, aralkyl, aryl, R₇CO, or R₈OCO;
R₃ is H, alkyl or aralkyl;
X is C;
Y is N;
R₄ is selected from the group consisting of H, alkyl, aralkyl, aryl, heteroaryl, benzoheteroaryl, hydroxyl, halo, haloalkyl, alkoxy, aminocarbonyl and aminosulfonyl;
R₅ and R₆ together form a 5-6 membered aromatic ring or a 5-7 membered aliphatic ring;
L₁ is O;
L₂ and L₃ are single bond;
L₄ is (Z)$_n$ where each Z is CH₂; n is an integer from 1 to 6; and
R₇ and R₈ are independently selected from the group consisting of H, alkyl, aryl and aralkyl, or a pharmaceutically acceptable salt thereof.

2. The compound of claim 1 of the formula:

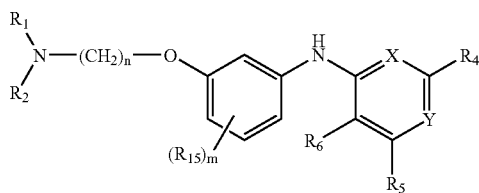

wherein each R₁₅ is independently H, alkyl, aralkyl, haloalkyl, aryl, heteroaryl, benzoheteroaryl, alkoxy, aminocarbonyl or aminosulfonyl and two of R₁₅ can form a 5-6 membered aromatic ring or a 5-7 member aliphatic ring;
m is 0-3; and
R₁, R₂, R₄, R₅, R₆, n and X are as defined in claim 1, or a pharmaceutically acceptable salt thereof.

3. The compound of claim 1 selected from the group consisting of:
{3-[2-(Benzylmethylamino)ethoxy]phenyl}-(2-methylquinolin-4-yl)amine;
{3-[2-(1-Methyl-1-phenylethylamino)ethoxy]phenyl}-(2-methylquinolin-4-yl)amine;
[3-(2-Benzylaminoethoxy)phenyl]-(2-methylquinolin-4-yl)amine;
[3-(3-Benzylaminopropoxy)phenyl]-(2-methylquinolin-4-yl)amine;
{3-[3-(1-Methyl-1-phenylethylamino)propoxy]phenyl}-(2-methylquinolin-4-yl)amine; and
{3-[3-(adamantan-2-ylamino)propoxy]-5-trifluoromethyl-phenyl}-(2-methylquinolin-4-yl)amine.

4. A pharmaceutical composition comprising a compound of claim 1 and a pharmaceutically acceptable carrier or excipient.

* * * * *